(12) United States Patent
Campana et al.

(10) Patent No.: US 10,144,770 B2
(45) Date of Patent: Dec. 4, 2018

(54) CHIMERIC RECEPTORS AND USES THEREOF IN IMMUNE THERAPY

(71) Applicants: National University of Singapore, Singapore (SG); St. Jude Children's Research Hospital, Memphis, TN (US); Unum Therapeutics Inc., Cambridge, MA (US)

(72) Inventors: Dario Campana, Singapore (SG); Ko Kudo, Shizuoka (JP); Charles Wilson, Cambridge, MA (US); Kathleen McGinness, Cambridge, MA (US)

(73) Assignees: National University of Singapore, Singapore (SG); St. Jude Children's Research Hospital, Memphis, TN (US); Unum Therapeutics Inc., Cambridge, MA (US)

( * ) Notice: Subject to any disclaimer, the term of this patent is extended or adjusted under 35 U.S.C. 154(b) by 377 days.

(21) Appl. No.: 14/516,880

(22) Filed: Oct. 17, 2014

(65) Prior Publication Data
US 2015/0139943 A1 May 21, 2015

Related U.S. Application Data

(60) Provisional application No. 62/047,916, filed on Sep. 9, 2014, provisional application No. 62/026,243, filed on Jul. 18, 2014, provisional application No. 61/892,218, filed on Oct. 17, 2013.

(51) Int. Cl.
| | |
|---|---|
| C07K 14/735 | (2006.01) |
| C07K 16/28 | (2006.01) |
| C07K 16/30 | (2006.01) |
| C07K 16/32 | (2006.01) |
| C07K 14/705 | (2006.01) |
| C07K 14/725 | (2006.01) |
| A61K 39/395 | (2006.01) |
| A61K 35/17 | (2015.01) |
| A61K 39/00 | (2006.01) |
| A61K 38/00 | (2006.01) |

(52) U.S. Cl.
CPC ........ *C07K 14/70535* (2013.01); *A61K 35/17* (2013.01); *A61K 39/39558* (2013.01); *C07K 14/7051* (2013.01); *C07K 14/70517* (2013.01); *C07K 14/70578* (2013.01); *C07K 16/2887* (2013.01); *C07K 16/3084* (2013.01); *C07K 16/32* (2013.01); *A61K 38/00* (2013.01); *A61K 2039/515* (2013.01); *A61K 2039/572* (2013.01); *C07K 2319/00* (2013.01); *C07K 2319/02* (2013.01); *C07K 2319/03* (2013.01); *C07K 2319/32* (2013.01); *C07K 2319/90* (2013.01); *C12N 2740/13043* (2013.01)

(58) Field of Classification Search
CPC ............................................... C07K 14/70535
See application file for complete search history.

(56) References Cited

U.S. PATENT DOCUMENTS

| | | |
|---|---|---|
| 5,843,728 A | 12/1998 | Seed et al. |
| 8,399,645 B2 | 3/2013 | Campana et al. |
| 8,450,112 B2 | 5/2013 | Li et al. |
| 9,212,229 B2 | 12/2015 | Schonfeld et al. |
| 9,605,049 B2 | 3/2017 | Campana et al. |
| 2008/0003225 A1 | 1/2008 | Vie et al. |
| 2010/0135974 A1 | 6/2010 | Eshhar et al. |
| 2011/0123440 A1 | 5/2011 | Hansen et al. |
| 2012/0070819 A1* | 3/2012 | Hengel ............ C07K 14/70535 435/5 |
| 2012/0213783 A1 | 8/2012 | Rosenberg et al. |
| 2013/0225668 A1 | 8/2013 | Rosenberg et al. |
| 2013/0266551 A1 | 10/2013 | Campana et al. |
| 2013/0280285 A1 | 10/2013 | Schonfeld et al. |
| 2013/0287748 A1 | 10/2013 | June et al. |

(Continued)

FOREIGN PATENT DOCUMENTS

| | | | | |
|---|---|---|---|---|
| WO | WO 2005/044996 A2 * | 5/2005 | ............. | C07K 16/46 |
| WO | WO 2012/021648 A2 * | 2/2012 | ............. | G01N 33/53 |

(Continued)

OTHER PUBLICATIONS

Gattinoni et al. (J. Clin. Investigation Jun. 2005 115:1616) (Year: 2005).*
Morgan et al. (Mol. Therapy Apr. 2010 18:843) (Year: 2010).*
Dusseaux et al. (Haematologica Jun. 2016 101 (Suppl.1): 122-123, Ab/ No. P365) (Year: 2016).*
Weissmann et al. (T-cell receptor zeta chain: GenBank: AAA60394. 1. Jan. 13, 1995) (Year: 1995).*
Deford-Watts (J. Immunology, 2011 186:6839-6847) (Year: 2011).*
Moritz et al. (Gene Therapy Oct. 1995 2(8): 539-46), "Moritz" (Year: 1995).*

(Continued)

*Primary Examiner* — Peter J Reddig
(74) *Attorney, Agent, or Firm* — Wolf, Greenfield & Sacks, P.C.

(57) ABSTRACT

Disclosed herein are chimeric receptors comprising an extracellular domain with affinity and specific for the Fc portion of an immunoglobulin molecule (Ig) (e.g., an extracellular ligand-binding domain of F158 FCGR3A or V158 FCGR3A variant); a transmembrane domain (e.g., a transmembrane domain of CD8α); at least one co-stimulatory signaling domain (e.g., a co-stimulatory signaling domain of 4-1BB); and a cytoplasmic signaling domain comprising an immunoreceptor tyrosine-based activation motif (ITAM) (e.g., a cytoplasmic signaling domain of CD3ζ). Also provided herein are nucleic acids encoding such chimeric receptors and immune cells expressing the chimeric receptors. Such immune cells can be used to enhance antibody-dependent cell-mediated cytotoxicity and/or to enhance antibody-based immunotherapy, such as cancer immunotherapy.

31 Claims, 22 Drawing Sheets
Specification includes a Sequence Listing.

(56) References Cited

U.S. PATENT DOCUMENTS

| | | | |
|---|---|---|---|
| 2014/0099309 | A1 | 4/2014 | Powell et al. |
| 2014/0099340 | A1 | 4/2014 | June et al. |
| 2014/0322183 | A1 | 10/2014 | Milone et al. |
| 2014/0328812 | A1 | 11/2014 | Campana et al. |
| 2014/0341869 | A1 | 11/2014 | Campana et al. |
| 2015/0139943 | A1 | 5/2015 | Campana et al. |
| 2016/0009784 | A1* | 1/2016 | Campana ........... C07K 16/2866 435/243 |
| 2017/0281682 | A1 | 10/2017 | Wilson et al. |

FOREIGN PATENT DOCUMENTS

| | | | | |
|---|---|---|---|---|
| WO | WO 2012/079000 | A1 * | 6/2012 | ............. A61K 39/00 |
| WO | WO 2013/040557 | A2 | 3/2013 | |
| WO | WO 2013/044225 | A1 | 3/2013 | |
| WO | WO 2013/126712 | A1 | 8/2013 | |
| WO | WO 2013/126726 | A1 | 8/2013 | |
| WO | WO 2013/126733 | A1 | 8/2013 | |
| WO | WO 2014/165707 | A2 | 10/2014 | |
| WO | WO 2015/058018 | A1 | 4/2015 | |
| WO | WO 2016/040441 | A1 | 3/2016 | |

OTHER PUBLICATIONS

[No Author Listed] Database UniProt, Accession No. M9MML0. Sep. 18, 2013. URL<http://www.uniprot/M9MML0>, [retrieved on Jan. 8, 2015]. 2 pages.

[No Author Listed] Database UniProt, Accession No. P08637. Sep. 18, 2013. URL<http://www.uniprot/P08637>, [retrieved on Jan. 8, 2015]. 5 pages.

Baessler et al., CD137 ligand mediates opposite effects in human and mouse NK cells and impairs NK-cell reactivity against human acute myeloid leukemia cells. Blood. Apr. 15, 2010;115(15):3058-69. doi: 10.1182/blood-2009-06-227934. Epub Dec. 14, 2009.

Buechele et al., 4-1BB ligand modulates direct and Rituximab-induced NK-cell reactivity in chronic lymphocytic leukemia. Eur J Immunol. Mar. 2012;42(3):737-48. doi: 10.1002/eji.201141920. Epub Dec. 20, 2011.

Campana et al., 4-1 BB Chimeric Antigen Receptors. The Cancer Journal. 2014;20(2):134-40.

Choi et al., Peripheral 4-1BB signaling negatively regulates NK cell development through IFN-gamma. J Immunol. Aug. 1, 2010;185(3):1404-11. doi: 10.4049/jimmunol.1000850. Epub Jul. 7, 2010.

Clemenceau et al., Antibody-dependent cellular cytotoxicity (ADCC) is mediated by genetically modified antigen-specific human T lymphocytes. Blood. 2006;107:4669-77.

Eshhar et al., The emergence of T-bodies/CAR T cells. Cancer J. Mar.-Apr. 2014;20(2):123-6. doi: 10.1097/PPO.0000000000000027.

Milone et al., Chimeric Receptors Containing CD 137 Signal Transduction Domains Mediate Enhanced Survival of T Cells and Increased Antileukemic Efficacy In Vivo. Molecular Therapy. 2009;17(8):1453-64.

Ochi et al., Gene-modified human α/β-T cells expressing a chimeric CD16-CD3ζ receptor as adoptively transferable effector cells for anticancer monoclonal antibody therapy. Cancer Immunol Research Mar. 2014;2(3):249-62. doi: 10.1158/2326-6066.CIR-13-0099-T. Epub Jan. 3, 2014.

Vivier et al., Signaling function of reconstituted CD16: zeta: gamma receptor complex isoforms. Int Immunol. Nov. 1992;4(11):1313-23.

Wirthmueller et al., Signal transduction by Fc gamma RIII (CD 16) is mediated through the gamma chain. J Exp Med. May 1, 1992;175(5):1381-90.

Abken et al., Chimeric T-cell receptors: highly specific tools to target cytotoxic T-lymphocytes to tumour cells. Cancer Treat Rev. Mar. 1997;23(2):97-112.

Alderson et al., Molecular and biological characterization of human 4-1BB and its ligand. Eur J Immunol. Sep. 1994;24(9):2219-27.

Allison et al., Structure, function, and serology of the T-cell antigen receptor complex. Annu Rev Immunol. 1987;5:503-40.

Barrett et al., Chimeric antigen receptor therapy for cancer. Annu Rev Med. 2014;65:333-47.doi:10.1146/annurev-med-060512-150254. Epub Nov. 20, 2013.

Bridgeman et al., Building better chimeric antigen receptors for adoptive T cell therapy. Curr Gene Ther. Apr. 2010;10(2):77-90.

Bukczynski et al., Costimulation of human CD28− T cells by 4-1BB ligand. Eur J Immunol. Feb. 2003;33(2):446-54.

Campana et al., Immunophenotyping of leukemia. J Immunol Methods. Sep. 21, 2000;243(1-2):59-75.

Champlin, T-cell depletion to prevent graft-versus-host disease after bone marrow transplantation. Hematol Oncol Clin North Am. Jun. 1990;4(3):687-98.

Debenedette et al., Costimulation of CD28− T lymphocytes by 4-1BB ligand. J Immunol. Jan. 15, 1997;158(2):551-9.

Debenedette et al., Role of 4-1BB ligand in costimulation of T lymphocyte growth and its upregulation on M12 B lymphomas by cAMP. J Exp Med. Mar. 1, 1995;181(3):985-92.

Eshhar et al., Functional expression of chimeric receptor genes in human T cells. J Immunol Methods. Feb. 1, 2001;248(1-2):67-76.

Finney et al., Chimeric receptors providing both primary and costimulatory signaling in T cells from a single gene product. J Immunol. Sep. 15, 1998;161(6):2791-7.

Goodwin et al. Molecular cloning of a ligand for the inducible T cell gene 4-1BB: a member of an emerging family of cytokines with homology to tumor necrosis factor. Eur J Immunol. Oct. 1993;23(10):2631-41.

Grupp et al., Chimeric antigen receptor-modified T cells for acute lymphoid leukemia. N Engl J Med. Apr. 18, 2013;368(16):1509-18. doi: 10.1056/NEJMoa1215134. Epub Mar. 25, 2013.

Hombach et al., T cell activation by recombinant FcεRI γ-chain immune receptors: an extracellular spacer domain impairs antigen dependent T cell activation but not antigen recognition, Gene Therapy.2000;7:1067-1075.

Hurtado et al., Potential role of 4-1BB in T cell activation. Comparison with the costimulatory molecule CD28, J Immunol, Oct. 1995, 155(7): 3360-7.

Hurtado et al., Signals through 4-1 BB are costimulatory to previously activated splenic T cells and inhibit activation-induced cell death. J Immunol. Mar. 15, 1997; 158(6):2600-2609.

Imai et al., Chimeric receptors with 4-1BB signaling capacity provoke potent cytotoxicity against acute lymphoblastic leukemia, Leukemia. Feb. 12, 2004; 18(4):676-684.

Imai et al., T-cell immunotherapy for B-lineage acute lymphoblastic leukemia using chimeric antigen receptors that deliver 4-1 BB-mediated co stimulatory signals, Blood. Nov. 16, 2003; 102(11):66a-67a. Abstract 223.

Kalos et al, T Cells with Chimeric Antigen Receptors Have Potent Antitumor Effects and Can 180. Establish Memory in Patients with Advanced Leukemia, Sci Transl Med. Aug. 10, 2011;3(95):95ra73; 1-11.

Kim et al., Human 4-1 BB regulates CD28 co-stimulation to promote Th1 cell responses. Eur J Immunol, Mar. 1998; 28(3):881-890.

Kim et al., Novel T cell antigen 4-1 BB associates with the protein tyrosine kinase p56lck1 , J Immunol.Aug. 1, 1993; 151(3):1255-1262.

Kudo et al., T lymphocytes expressing a CD16 signaling receptor exert antibody-dependent cancer cell killing. Cancer Res. Jan. 1, 2014;74(1):93-103. doi:10.1158/0008-5472.CAN-13-1365. Epub Nov. 6, 2013.

Liq et al., Polarization effects of 4-1 BB during CD28 costimulation in generating tumor-reactive T cells for cancer immunotherapy, Cancer Res. May 15, 2003; 63(10):2546-2552.

Maude et al., Chimeric antigen receptor T cells for sustained remissions in leukemia. N Engl J Med. Oct. 16, 2014;371(16):1507-17. doi: 10.1056/NEJMoa1407222.

May et al., Anti-4-1 BB monoclonal antibody enhances rejection of large tumor burden by 230. promoting survival but not clonal expansion of tumor-specific CDS+ T cells, Cancer Res. 2002;62(12):3459-3465.

(56) References Cited

OTHER PUBLICATIONS

Melero et al., Amplification of tumor immunity by gene transfer of the co-stimulatory 4-1 BB ligand: synergy with the CD2S co-stimulatory pathway. Eur J Immunol., 1998, 28(3):1116-1121.

Melero et al., Monoclonal antibodies against the 4-1BB T-cell activation molecule eradicate established tumors, Nat. Med., 1997, 3(6): 682-685.

Melero et al., NK1 .1 cells express 4-1BB(CDw137) costimulatory molecule and are required for tumor immunity elicited by anti-4-1 BB monoclonal antibodies. Cell Immunol., 1998;190(2):167172.

Mogi et al., Tumour rejection by gene transfer of 4-1BB ligand and into a CD80(+) murine squamous cell carcinoma and the requirements of co-stimulatory molecules on tumour and host cells, Immunology, Dec. 2000, 101(4): 541-7.

Pollok et al., Inducible T cell antigen 4-1 BB Analysis of expression and function, J Immunol. 1993;150(3):771-781.

Pollok et al., Regulation of 4-1BB expression by cell-cell interactions and the cytokines, interleukin-2 and interleukin-4. Eur J Immunol. Feb. 1995;25(2):488-94.

Robertson et al., Costimulation of human natural killer cell proliferation: role of accessory cytokines and cell contact-dependent signals. Nat Immun. 1996-1997; 15(5):213-226.

Shuford et al., 4-1BB costimulatory signals preferentially induce CDS+ T cell 318. proliferation and lead to the amplification in vivo of cytotoxic T cell responses, J Exp Med. Jul. 7, 1997; 186(1):47-55.

Sica et al., Modulation of the immune response through 4-1BB. In: Habib N, ed. Cancer gene therapy: past achievements and future challenges. New York: Kluwer Academic/Plenum Publishers;355-362 (2000).

Takahashi et al., Cutting edge: 4-1 BB is a bona fide CDS T cell survival signal, J Immunol. May 1, 1999; 162(9):5037-5040.

Vinay et al., Role of 4-1 BB in immune responses. Semin Immunol. Dec. 1998; 10(6):481-489.

\* cited by examiner

A

B

C

SEQUENCE LISTING

```
<160> NUMBER OF SEQ ID NOS: 84

<210> SEQ ID NO 1
<211> LENGTH: 436
<212> TYPE: PRT
<213> ORGANISM: Artificial Sequence
<220> FEATURE:
```

<223> OTHER INFORMATION: Synthetic Polypeptide

<400> SEQUENCE: 1

```
Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Lys Arg Gly Arg Lys Lys
        275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
    370                 375                 380

Glu Leu Gln Lys Asp Lys Met Ala Glu Ala Tyr Ser Glu Ile Gly Met
385                 390                 395                 400
```

```
Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 2
<211> LENGTH: 442
<212> TYPE: PRT
<213> ORGANISM: Artificial Sequence
<220> FEATURE:
<223> OTHER INFORMATION: Synthetic Polypeptide

<400> SEQUENCE: 2

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Ile Ser Phe Phe Leu Ala Leu Thr Ser Thr Ala Leu Leu
            260                 265                 270

Phe Leu Leu Phe Phe Leu Thr Leu Arg Phe Ser Val Val Lys Arg Gly
        275                 280                 285

Lys Arg Gly Arg Lys Lys Leu Leu Tyr Ile Phe Lys Gln Pro Phe Met
    290                 295                 300

Arg Pro Val Gln Thr Thr Gln Glu Glu Asp Gly Cys Ser Cys Arg Phe
305                 310                 315                 320
```

-continued

```
Pro Glu Glu Glu Gly Gly Cys Glu Leu Arg Val Lys Phe Ser Arg
                325                 330                 335

Ser Ala Asp Ala Pro Ala Tyr Gln Gln Gly Gln Asn Gln Leu Tyr Asn
            340                 345                 350

Glu Leu Asn Leu Gly Arg Arg Glu Glu Tyr Asp Val Leu Asp Lys Arg
            355                 360                 365

Arg Gly Arg Asp Pro Glu Met Gly Gly Lys Pro Arg Arg Lys Asn Pro
            370                 375                 380

Gln Glu Gly Leu Tyr Asn Glu Leu Gln Lys Asp Lys Met Ala Glu Ala
385                 390                 395                 400

Tyr Ser Glu Ile Gly Met Lys Gly Glu Arg Arg Arg Gly Lys Gly His
                405                 410                 415

Asp Gly Leu Tyr Gln Gly Leu Ser Thr Ala Thr Lys Asp Thr Tyr Asp
            420                 425                 430

Ala Leu His Met Gln Ala Leu Pro Pro Arg
            435                 440

<210> SEQ ID NO 3
<211> LENGTH: 442
<212> TYPE: PRT
<213> ORGANISM: Artificial Sequence
<220> FEATURE:
<223> OTHER INFORMATION: Synthetic Polypeptide

<400> SEQUENCE: 3

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240
```

Arg Pro Ala Ala Gly Gly Ala Val His Thr Arg Gly Leu Asp Phe Ala
            245                 250                 255

Cys Asp Phe Trp Val Leu Val Val Gly Gly Val Leu Ala Cys Tyr
            260                 265                 270

Ser Leu Leu Val Thr Val Ala Phe Ile Ile Phe Trp Val Arg Ser Lys
            275                 280                 285

Lys Arg Gly Arg Lys Lys Leu Leu Tyr Ile Phe Lys Gln Pro Phe Met
            290                 295                 300

Arg Pro Val Gln Thr Thr Gln Glu Glu Asp Gly Cys Ser Cys Arg Phe
305                 310                 315                 320

Pro Glu Glu Glu Glu Gly Gly Cys Glu Leu Arg Val Lys Phe Ser Arg
                    325                 330                 335

Ser Ala Asp Ala Pro Ala Tyr Gln Gln Gly Gln Asn Gln Leu Tyr Asn
            340                 345                 350

Glu Leu Asn Leu Gly Arg Arg Glu Glu Tyr Asp Val Leu Asp Lys Arg
            355                 360                 365

Arg Gly Arg Asp Pro Glu Met Gly Gly Lys Pro Arg Arg Lys Asn Pro
            370                 375                 380

Gln Glu Gly Leu Tyr Asn Glu Leu Gln Lys Asp Lys Met Ala Glu Ala
385                 390                 395                 400

Tyr Ser Glu Ile Gly Met Lys Gly Glu Arg Arg Arg Gly Lys Gly His
                    405                 410                 415

Asp Gly Leu Tyr Gln Gly Leu Ser Thr Ala Thr Lys Asp Thr Tyr Asp
            420                 425                 430

Ala Leu His Met Gln Ala Leu Pro Pro Arg
            435                 440

<210> SEQ ID NO 4
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 4

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
            50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                    85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
            130                 135                 140

Thr Tyr Leu Gln Asn Gly Lys Gly Arg Lys Tyr Phe His His Asn Ser
145                 150                 155                 160

```
Asp Phe Tyr Ile Pro Lys Ala Thr Leu Lys Asp Ser Gly Ser Tyr Phe
            165                 170                 175

Cys Arg Gly Leu Val Gly Ser Lys Asn Val Ser Ser Glu Thr Val Asn
        180                 185                 190

Ile Thr Ile Thr Gln Gly Leu Ala Val Ser Thr Ile Ser Ser Phe Phe
    195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Leu Ile Ala Leu Val Thr Ser Gly Ala Leu Leu Ala Val Leu
            260                 265                 270

Gly Ile Thr Gly Tyr Phe Leu Met Asn Arg Lys Arg Gly Arg Lys Lys
        275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
            435

<210> SEQ ID NO 5
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 5

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80
```

Ile Asp Ala Ala Thr Val Asp Asp Ser Gly Glu Tyr Arg Cys Gln Thr
            85                  90                  95

Asn Leu Ser Thr Leu Ser Asp Pro Val Gln Leu Glu Val His Ile Gly
        100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
        210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Leu Leu Ala Ala Leu Leu Ala Leu Ala Ala Leu Leu Ala
            260                 265                 270

Leu Leu Ala Ala Leu Leu Ala Arg Ser Lys Lys Arg Gly Arg Lys Lys
        275                 280                 285

Leu Leu Tyr Ile Phe Lys Gln Pro Phe Met Arg Pro Val Gln Thr Thr
        290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
        370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
            435

<210> SEQ ID NO 6
<211> LENGTH: 428
<212> TYPE: PRT
<213> ORGANISM: Artificial Sequence
<220> FEATURE:
<223> OTHER INFORMATION: Synthetic Polypeptide

<400> SEQUENCE: 6

-continued

```
Met Ala Leu Pro Val Thr Ala Leu Leu Leu Pro Leu Ala Leu Leu Leu
1               5                   10                  15

His Ala Ala Arg Pro Gln Ala Ala Pro Pro Lys Ala Val Leu Lys
            20                  25                  30

Leu Glu Pro Pro Trp Ile Asn Val Leu Gln Glu Asp Ser Val Thr Leu
                35                  40                  45

Thr Cys Gln Gly Ala Arg Ser Pro Glu Ser Asp Ser Ile Gln Trp Phe
    50                  55                  60

His Asn Gly Asn Leu Ile Pro Thr His Thr Gln Pro Ser Tyr Arg Phe
65                  70                  75                  80

Lys Ala Asn Asn Asn Asp Ser Gly Glu Tyr Thr Cys Gln Thr Gly Gln
                85                  90                  95

Thr Ser Leu Ser Asp Pro Val His Leu Thr Val Leu Ser Glu Trp Leu
            100                 105                 110

Val Leu Gln Thr Pro His Leu Glu Phe Gln Glu Gly Glu Thr Ile Met
        115                 120                 125

Leu Arg Cys His Ser Trp Lys Asp Lys Pro Leu Val Lys Val Thr Phe
    130                 135                 140

Phe Gln Asn Gly Lys Ser Gln Lys Phe Ser His Leu Asp Pro Thr Phe
145                 150                 155                 160

Ser Ile Pro Gln Ala Asn His Ser His Ser Gly Asp Tyr His Cys Thr
                165                 170                 175

Gly Asn Ile Gly Tyr Thr Leu Phe Ser Ser Lys Pro Val Thr Ile Thr
            180                 185                 190

Val Gln Val Pro Ser Met Gly Ser Ser Pro Met Gly Thr Thr Thr
        195                 200                 205

Pro Ala Pro Arg Pro Pro Thr Pro Ala Pro Thr Ile Ala Ser Gln Pro
210                 215                 220

Leu Ser Leu Arg Pro Glu Ala Cys Arg Pro Ala Ala Gly Gly Ala Val
225                 230                 235                 240

His Thr Arg Gly Leu Asp Phe Ala Cys Asp Ile Tyr Ile Trp Ala Pro
                245                 250                 255

Leu Ala Gly Thr Cys Gly Val Leu Leu Leu Ser Leu Val Ile Thr Leu
            260                 265                 270

Tyr Cys Lys Arg Gly Arg Lys Lys Leu Leu Tyr Ile Phe Lys Gln Pro
    275                 280                 285

Phe Met Arg Pro Val Gln Thr Thr Gln Glu Glu Asp Gly Cys Ser Cys
290                 295                 300

Arg Phe Pro Glu Glu Glu Glu Gly Gly Cys Glu Leu Arg Val Lys Phe
305                 310                 315                 320

Ser Arg Ser Ala Asp Ala Pro Ala Tyr Gln Gln Gly Gln Asn Gln Leu
                325                 330                 335

Tyr Asn Glu Leu Asn Leu Gly Arg Arg Glu Glu Tyr Asp Val Leu Asp
            340                 345                 350

Lys Arg Arg Gly Arg Asp Pro Glu Met Gly Gly Lys Pro Arg Arg Lys
        355                 360                 365

Asn Pro Gln Glu Gly Leu Tyr Asn Glu Leu Gln Lys Asp Lys Met Ala
    370                 375                 380

Glu Ala Tyr Ser Glu Ile Gly Met Lys Gly Glu Arg Arg Arg Gly Lys
385                 390                 395                 400

Gly His Asp Gly Leu Tyr Gln Gly Leu Ser Thr Ala Thr Lys Asp Thr
                405                 410                 415

Tyr Asp Ala Leu His Met Gln Ala Leu Pro Pro Arg
```

```
            420             425
```

<210> SEQ ID NO 7
<211> LENGTH: 435
<212> TYPE: PRT
<213> ORGANISM: Artificial Sequence
<220> FEATURE:
<223> OTHER INFORMATION: Synthetic Polypeptide

<400> SEQUENCE: 7

```
Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Arg Ser Lys Arg Ser Arg
        275                 280                 285

Leu Leu His Ser Asp Tyr Met Asn Met Thr Pro Arg Arg Pro Gly Pro
    290                 295                 300

Thr Arg Lys His Tyr Gln Pro Tyr Ala Pro Pro Arg Asp Phe Ala Ala
305                 310                 315                 320

Tyr Arg Ser Arg Val Lys Phe Ser Arg Ser Ala Asp Ala Pro Ala Tyr
                325                 330                 335

Gln Gln Gly Gln Asn Gln Leu Tyr Asn Glu Leu Asn Leu Gly Arg Arg
            340                 345                 350

Glu Glu Tyr Asp Val Leu Asp Lys Arg Arg Gly Arg Asp Pro Glu Met
```

```
                355                 360                 365
Gly Gly Lys Pro Arg Arg Lys Asn Pro Gln Glu Gly Leu Tyr Asn Glu
            370                 375                 380
Leu Gln Lys Asp Lys Met Ala Glu Ala Tyr Ser Glu Ile Gly Met Lys
385                 390                 395                 400
Gly Glu Arg Arg Arg Gly Lys Gly His Asp Gly Leu Tyr Gln Gly Leu
                405                 410                 415
Ser Thr Ala Thr Lys Asp Thr Tyr Asp Ala Leu His Met Gln Ala Leu
            420                 425                 430
Pro Pro Arg
        435

<210> SEQ ID NO 8
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 8

Met Ala Leu Pro Val Thr Ala Leu Leu Leu Pro Leu Ala Leu Leu Leu
1               5                   10                  15
His Ala Ala Arg Pro Gly Met Arg Thr Glu Asp Leu Pro Lys Ala Val
            20                  25                  30
Val Phe Leu Glu Pro Gln Trp Tyr Arg Val Leu Glu Lys Asp Ser Val
        35                  40                  45
Thr Leu Lys Cys Gln Gly Ala Tyr Ser Pro Glu Asp Asn Ser Thr Gln
    50                  55                  60
Trp Phe His Asn Glu Ser Leu Ile Ser Ser Gln Ala Ser Ser Tyr Phe
65                  70                  75                  80
Ile Asp Ala Ala Thr Val Asp Asp Ser Gly Glu Tyr Arg Cys Gln Thr
                85                  90                  95
Asn Leu Ser Thr Leu Ser Asp Pro Val Gln Leu Glu Val His Ile Gly
            100                 105                 110
Trp Leu Leu Leu Gln Ala Pro Arg Trp Val Phe Lys Glu Glu Asp Pro
        115                 120                 125
Ile His Leu Arg Cys His Ser Trp Lys Asn Thr Ala Leu His Lys Val
    130                 135                 140
Thr Tyr Leu Gln Asn Gly Lys Gly Arg Lys Tyr Phe His His Asn Ser
145                 150                 155                 160
Asp Phe Tyr Ile Pro Lys Ala Thr Leu Lys Asp Ser Gly Ser Tyr Phe
                165                 170                 175
Cys Arg Gly Leu Val Gly Ser Lys Asn Val Ser Ser Glu Thr Val Asn
            180                 185                 190
Ile Thr Ile Thr Gln Gly Leu Ala Val Ser Thr Ile Ser Ser Phe Phe
        195                 200                 205
Pro Pro Gly Tyr Gln Thr Thr Pro Ala Pro Arg Pro Pro Thr Pro
    210                 215                 220
Ala Pro Thr Ile Ala Ser Gln Pro Leu Ser Leu Arg Pro Glu Ala Cys
225                 230                 235                 240
Arg Pro Ala Ala Gly Gly Ala Val His Thr Arg Gly Leu Asp Phe Ala
                245                 250                 255
Cys Asp Ile Tyr Ile Trp Ala Pro Leu Ala Gly Thr Cys Gly Val Leu
            260                 265                 270
Leu Leu Ser Leu Val Ile Thr Leu Tyr Cys Ala Leu Tyr Leu Leu Arg
```

```
                  275                 280                 285
Arg Asp Gln Arg Leu Pro Pro Asp Ala His Lys Pro Pro Gly Gly Gly
290                 295                 300

Ser Phe Arg Thr Pro Ile Gln Glu Glu Gln Ala Asp Ala His Ser Thr
305                 310                 315                 320

Leu Ala Lys Ile Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
                340                 345                 350

Arg Glu Glu Tyr Asp Val Leu Asp Lys Arg Arg Gly Arg Asp Pro Glu
            355                 360                 365

Met Gly Gly Lys Pro Arg Arg Lys Asn Pro Gln Glu Gly Leu Tyr Asn
        370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
                420                 425                 430

Leu Pro Pro Arg
        435

<210> SEQ ID NO 9
<211> LENGTH: 477
<212> TYPE: PRT
<213> ORGANISM: Artificial Sequence
<220> FEATURE:
<223> OTHER INFORMATION: Synthetic Polypeptide

<400> SEQUENCE: 9

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
        130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
```

```
              195                 200                 205
Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Ala Val His Thr Arg Gly Leu Asp Phe Ala
                245                 250                 255

Cys Asp Ile Tyr Ile Trp Ala Pro Leu Ala Gly Thr Cys Gly Val Leu
                260                 265                 270

Leu Leu Ser Leu Val Ile Thr Leu Tyr Cys Arg Ser Lys Arg Ser Arg
                275                 280                 285

Leu Leu His Ser Asp Tyr Met Asn Met Thr Pro Arg Arg Pro Gly Pro
                290                 295                 300

Thr Arg Lys His Tyr Gln Pro Tyr Ala Pro Pro Arg Asp Phe Ala Ala
305                 310                 315                 320

Tyr Arg Ser Lys Arg Gly Arg Lys Lys Leu Leu Tyr Ile Phe Lys Gln
                325                 330                 335

Pro Phe Met Arg Pro Val Gln Thr Thr Gln Glu Glu Asp Gly Cys Ser
                340                 345                 350

Cys Arg Phe Pro Glu Glu Glu Gly Gly Cys Glu Leu Arg Val Lys
                355                 360                 365

Phe Ser Arg Ser Ala Asp Ala Pro Ala Tyr Gln Gln Gly Gln Asn Gln
370                 375                 380

Leu Tyr Asn Glu Leu Asn Leu Gly Arg Arg Glu Glu Tyr Asp Val Leu
385                 390                 395                 400

Asp Lys Arg Arg Gly Arg Asp Pro Glu Met Gly Gly Lys Pro Arg Arg
                405                 410                 415

Lys Asn Pro Gln Glu Gly Leu Tyr Asn Glu Leu Gln Lys Asp Lys Met
                420                 425                 430

Ala Glu Ala Tyr Ser Glu Ile Gly Met Lys Gly Glu Arg Arg Arg Gly
                435                 440                 445

Lys Gly His Asp Gly Leu Tyr Gln Gly Leu Ser Thr Ala Thr Lys Asp
                450                 455                 460

Thr Tyr Asp Ala Leu His Met Gln Ala Leu Pro Pro Arg
465                 470                 475

<210> SEQ ID NO 10
<211> LENGTH: 391
<212> TYPE: PRT
<213> ORGANISM: Artificial Sequence
<220> FEATURE:
<223> OTHER INFORMATION: Synthetic Polypeptide

<400> SEQUENCE: 10

Met Ala Leu Pro Val Thr Ala Leu Leu Leu Pro Leu Ala Leu Leu Leu
1               5                   10                  15

His Ala Ala Arg Pro Gly Met Thr Glu Asp Leu Pro Lys Ala Val
                20                  25                  30

Val Phe Leu Glu Pro Gln Trp Tyr Arg Val Leu Glu Lys Asp Ser Val
                35                  40                  45

Thr Leu Lys Cys Gln Gly Ala Tyr Ser Pro Glu Asp Asn Ser Thr Gln
                50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
```

```
            85                  90                  95
Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
            130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
                195                 200                 205

Pro Pro Gly Tyr Gln Ile Tyr Ile Trp Ala Pro Leu Ala Gly Thr Cys
                210                 215                 220

Gly Val Leu Leu Leu Ser Leu Val Ile Thr Leu Tyr Cys Lys Arg Gly
225                 230                 235                 240

Arg Lys Lys Leu Leu Tyr Ile Phe Lys Gln Pro Phe Met Arg Pro Val
                245                 250                 255

Gln Thr Thr Gln Glu Glu Asp Gly Cys Ser Cys Arg Phe Pro Glu Glu
                260                 265                 270

Glu Glu Gly Gly Cys Glu Leu Arg Val Lys Phe Ser Arg Ser Ala Asp
                275                 280                 285

Ala Pro Ala Tyr Gln Gln Gly Gln Asn Gln Leu Tyr Asn Glu Leu Asn
                290                 295                 300

Leu Gly Arg Arg Glu Glu Tyr Asp Val Leu Asp Lys Arg Arg Gly Arg
305                 310                 315                 320

Asp Pro Glu Met Gly Gly Lys Pro Arg Arg Lys Asn Pro Gln Glu Gly
                325                 330                 335

Leu Tyr Asn Glu Leu Gln Lys Asp Lys Met Ala Glu Ala Tyr Ser Glu
                340                 345                 350

Ile Gly Met Lys Gly Glu Arg Arg Arg Gly Lys Gly His Asp Gly Leu
                355                 360                 365

Tyr Gln Gly Leu Ser Thr Ala Thr Lys Asp Thr Tyr Asp Ala Leu His
                370                 375                 380

Met Gln Ala Leu Pro Pro Arg
385                 390

<210> SEQ ID NO 11
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 11

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
```

```
                50             55             60
Trp Phe His Asn Glu Ser Leu Ile Ser Ser Gln Ala Ser Ser Tyr Phe
 65              70              75              80

Ile Asp Ala Ala Thr Val Asp Asp Ser Gly Glu Tyr Arg Cys Gln Thr
                 85              90              95

Asn Leu Ser Thr Leu Ser Asp Pro Val Gln Leu Glu Val His Ile Gly
                100             105             110

Trp Leu Leu Leu Gln Ala Pro Arg Trp Val Phe Lys Glu Glu Asp Pro
                115             120             125

Ile His Leu Arg Cys His Ser Trp Lys Asn Thr Ala Leu His Lys Val
130             135             140

Thr Tyr Leu Gln Asn Gly Lys Gly Arg Lys Tyr Phe His His Asn Ser
145             150             155             160

Asp Phe Tyr Ile Pro Lys Ala Thr Leu Lys Asp Ser Gly Ser Tyr Phe
                165             170             175

Cys Arg Gly Leu Val Gly Ser Lys Asn Val Ser Ser Glu Thr Val Asn
                180             185             190

Ile Thr Ile Thr Gln Gly Leu Ala Val Ser Thr Ile Ser Ser Phe Phe
                195             200             205

Pro Pro Gly Tyr Gln Gly Gly Ser Pro Ala Gly Ser Pro Thr Ser Thr
210             215             220

Glu Glu Gly Thr Ser Glu Ser Ala Thr Pro Glu Ser Gly Pro Gly Thr
225             230             235             240

Ser Thr Glu Pro Ser Glu Gly Ser Ala Pro Gly Ser Pro Ala Gly Ser
                245             250             255

Pro Thr Ile Tyr Ile Trp Ala Pro Leu Ala Gly Thr Cys Gly Val Leu
                260             265             270

Leu Leu Ser Leu Val Ile Thr Leu Tyr Cys Lys Arg Gly Arg Lys Lys
                275             280             285

Leu Leu Tyr Ile Phe Lys Gln Pro Phe Met Arg Pro Val Gln Thr Thr
                290             295             300

Gln Glu Glu Asp Gly Cys Ser Cys Arg Phe Pro Glu Glu Glu Glu Gly
305             310             315             320

Gly Cys Glu Leu Arg Val Lys Phe Ser Arg Ser Ala Asp Ala Pro Ala
                325             330             335

Tyr Gln Gln Gly Gln Asn Gln Leu Tyr Asn Glu Leu Asn Leu Gly Arg
                340             345             350

Arg Glu Glu Tyr Asp Val Leu Asp Lys Arg Arg Gly Arg Asp Pro Glu
                355             360             365

Met Gly Gly Lys Pro Arg Arg Lys Asn Pro Gln Glu Gly Leu Tyr Asn
370             375             380

Glu Leu Gln Lys Asp Lys Met Ala Glu Ala Tyr Ser Glu Ile Gly Met
385             390             395             400

Lys Gly Glu Arg Arg Arg Gly Lys Gly His Asp Gly Leu Tyr Gln Gly
                405             410             415

Leu Ser Thr Ala Thr Lys Asp Thr Tyr Asp Ala Leu His Met Gln Ala
                420             425             430

Leu Pro Pro Arg
                435

<210> SEQ ID NO 12
<211> LENGTH: 435
<212> TYPE: PRT
<213> ORGANISM: Artificial Sequence
```

<220> FEATURE:
<223> OTHER INFORMATION: Synthetic Polypeptide

<400> SEQUENCE: 12

```
Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Arg Ser Lys Arg Ser Arg
        275                 280                 285

Gly Gly His Ser Asp Tyr Met Asn Met Thr Pro Arg Arg Pro Gly Pro
290                 295                 300

Thr Arg Lys His Tyr Gln Pro Tyr Ala Pro Pro Arg Asp Phe Ala Ala
305                 310                 315                 320

Tyr Arg Ser Arg Val Lys Phe Ser Arg Ser Ala Asp Ala Pro Ala Tyr
                325                 330                 335

Gln Gln Gly Gln Asn Gln Leu Tyr Asn Glu Leu Asn Leu Gly Arg Arg
            340                 345                 350

Glu Glu Tyr Asp Val Leu Asp Lys Arg Arg Gly Arg Asp Pro Glu Met
        355                 360                 365

Gly Gly Lys Pro Arg Arg Lys Asn Pro Gln Glu Gly Leu Tyr Asn Glu
370                 375                 380

Leu Gln Lys Asp Lys Met Ala Glu Ala Tyr Ser Glu Ile Gly Met Lys
385                 390                 395                 400
```

```
Gly Glu Arg Arg Arg Gly Lys Gly His Asp Gly Leu Tyr Gln Gly Leu
            405                 410                 415

Ser Thr Ala Thr Lys Asp Thr Tyr Asp Ala Leu His Met Gln Ala Leu
            420                 425                 430

Pro Pro Arg
        435

<210> SEQ ID NO 13
<211> LENGTH: 477
<212> TYPE: PRT
<213> ORGANISM: Artificial Sequence
<220> FEATURE:
<223> OTHER INFORMATION: Synthetic Polypeptide

<400> SEQUENCE: 13

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Arg Ser Lys Arg Ser Arg
        275                 280                 285

Gly Gly His Ser Asp Tyr Met Asn Met Thr Pro Arg Arg Pro Gly Pro
    290                 295                 300

Thr Arg Lys His Tyr Gln Pro Tyr Ala Pro Pro Arg Asp Phe Ala Ala
305                 310                 315                 320
```

```
Tyr Arg Ser Lys Arg Gly Arg Lys Leu Leu Tyr Ile Phe Lys Gln
            325                 330                 335

Pro Phe Met Arg Pro Val Gln Thr Thr Gln Glu Asp Gly Cys Ser
            340                 345                 350

Cys Arg Phe Pro Glu Glu Glu Gly Gly Cys Glu Leu Arg Val Lys
            355                 360                 365

Phe Ser Arg Ser Ala Asp Ala Pro Ala Tyr Gln Gln Gly Gln Asn Gln
    370                 375                 380

Leu Tyr Asn Glu Leu Asn Leu Gly Arg Arg Glu Glu Tyr Asp Val Leu
385                 390                 395                 400

Asp Lys Arg Arg Gly Arg Asp Pro Glu Met Gly Gly Lys Pro Arg Arg
                405                 410                 415

Lys Asn Pro Gln Glu Gly Leu Tyr Asn Glu Leu Gln Lys Asp Lys Met
            420                 425                 430

Ala Glu Ala Tyr Ser Glu Ile Gly Met Lys Gly Glu Arg Arg Arg Gly
            435                 440                 445

Lys Gly His Asp Gly Leu Tyr Gln Gly Leu Ser Thr Ala Thr Lys Asp
    450                 455                 460

Thr Tyr Asp Ala Leu His Met Gln Ala Leu Pro Pro Arg
465                 470                 475

<210> SEQ ID NO 14
<211> LENGTH: 437
<212> TYPE: PRT
<213> ORGANISM: Artificial Sequence
<220> FEATURE:
<223> OTHER INFORMATION: Synthetic Polypeptide

<400> SEQUENCE: 14

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65              70                  75                  80

Ile Asp Ala Ala Thr Val Asp Asp Ser Gly Glu Tyr Arg Cys Gln Thr
            85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
            165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205
```

```
Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Met Ala Leu Ile Val Leu Gly Gly Val Ala Gly Leu Leu Leu
            260                 265                 270

Phe Ile Gly Leu Gly Ile Phe Phe Cys Val Arg Lys Arg Gly Arg Lys
        275                 280                 285

Lys Leu Leu Tyr Ile Phe Lys Gln Pro Phe Met Arg Pro Val Gln Thr
    290                 295                 300

Thr Gln Glu Glu Asp Gly Cys Ser Cys Arg Phe Pro Glu Glu Glu Glu
305                 310                 315                 320

Gly Gly Cys Glu Leu Arg Val Lys Phe Ser Arg Ser Ala Asp Ala Pro
                325                 330                 335

Ala Tyr Gln Gln Gly Gln Asn Gln Leu Tyr Asn Glu Leu Asn Leu Gly
            340                 345                 350

Arg Arg Glu Glu Tyr Asp Val Leu Asp Lys Arg Arg Gly Arg Asp Pro
        355                 360                 365

Glu Met Gly Gly Lys Pro Arg Arg Lys Asn Pro Gln Glu Gly Leu Tyr
    370                 375                 380

Asn Glu Leu Gln Lys Asp Lys Met Ala Glu Ala Tyr Ser Glu Ile Gly
385                 390                 395                 400

Met Lys Gly Glu Arg Arg Arg Gly Lys Gly His Asp Gly Leu Tyr Gln
                405                 410                 415

Gly Leu Ser Thr Ala Thr Lys Asp Thr Tyr Asp Ala Leu His Met Gln
            420                 425                 430

Ala Leu Pro Pro Arg
            435

<210> SEQ ID NO 15
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 15

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125
```

```
Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Met Ala Leu Ile Val Leu Gly Val Ala Gly Leu Leu Leu
            260                 265                 270

Phe Ile Gly Leu Gly Ile Phe Phe Cys Val Arg Arg Ser Lys Arg Ser
        275                 280                 285

Arg Gly Gly His Ser Asp Tyr Met Asn Met Thr Pro Arg Arg Pro Gly
    290                 295                 300

Pro Thr Arg Lys His Tyr Gln Pro Tyr Ala Pro Pro Arg Asp Phe Ala
305                 310                 315                 320

Ala Tyr Arg Ser Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
    435

<210> SEQ ID NO 16
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 16

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45
```

```
Thr Leu Lys Cys Gln Gly Ala Tyr Ser Pro Glu Asp Asn Ser Thr Gln
 50                  55                  60

Trp Phe His Asn Glu Ser Leu Ile Ser Ser Gln Ala Ser Ser Tyr Phe
 65                  70                  75                  80

Ile Asp Ala Ala Thr Val Asp Asp Ser Gly Glu Tyr Arg Cys Gln Thr
                 85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Leu Cys Tyr Ile Leu Asp Ala Ile Leu Phe Leu Tyr Gly Ile
            260                 265                 270

Val Leu Thr Leu Leu Tyr Cys Arg Leu Lys Arg Gly Arg Lys Lys
        275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
    370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
            435

<210> SEQ ID NO 17
<211> LENGTH: 436
```

<212> TYPE: PRT
<213> ORGANISM: Artificial Sequence
<220> FEATURE:
<223> OTHER INFORMATION: Synthetic Polypeptide

<400> SEQUENCE: 17

```
Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Leu Leu Leu Ile Leu Leu Gly Val Leu Ala Gly Val Leu Ala
            260                 265                 270

Thr Leu Ala Ala Leu Leu Ala Arg Ser Lys Lys Arg Gly Arg Lys Lys
        275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
    370                 375                 380
```

```
Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
            405                 410                 415

Leu Ser Thr Ala Thr Lys Asp Thr Tyr Asp Ala Leu His Met Gln Ala
        420                 425                 430

Leu Pro Pro Arg
        435

<210> SEQ ID NO 18
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 18

Met Ala Leu Pro Val Thr Ala Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Thr Leu Gly Leu Val Ala Gly Val Leu Val Leu Leu
            260                 265                 270

Val Ser Leu Gly Val Ala Ile His Leu Cys Lys Arg Gly Arg Lys Lys
        275                 280                 285

Leu Leu Tyr Ile Phe Lys Gln Pro Phe Met Arg Pro Val Gln Thr Thr
290                 295                 300
```

```
Gln Glu Glu Asp Gly Cys Ser Cys Arg Phe Pro Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Gly Arg Asp Pro Glu
        355                 360                 365

Met Gly Gly Lys Pro Arg Arg Lys Asn Pro Gln Glu Gly Leu Tyr Asn
    370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
            435

<210> SEQ ID NO 19
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 19

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220
```

```
Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
            245                 250                 255

Cys Asp Val Ser Phe Cys Leu Val Met Val Leu Leu Phe Ala Val Asp
            260                 265                 270

Thr Gly Leu Tyr Phe Ser Val Lys Thr Asn Lys Arg Gly Arg Lys Lys
            275                 280                 285

Leu Leu Tyr Ile Phe Lys Gln Pro Phe Met Arg Pro Val Gln Thr Thr
            290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
                340                 345                 350

Arg Glu Glu Tyr Asp Val Leu Asp Lys Arg Arg Gly Arg Asp Pro Glu
                355                 360                 365

Met Gly Gly Lys Pro Arg Arg Lys Asn Pro Gln Glu Gly Leu Tyr Asn
370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
                420                 425                 430

Leu Pro Pro Arg
            435

<210> SEQ ID NO 20
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 20

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
        130                 135                 140
```

-continued

```
Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
            165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
            195                 200                 205

Pro Pro Gly Tyr Gln Thr Thr Thr Pro Ala Pro Arg Pro Pro Thr Pro
            210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
            245                 250                 255

Cys Asp Val Ala Ala Ile Leu Gly Leu Gly Leu Val Leu Gly Leu Leu
            260                 265                 270

Gly Pro Leu Ala Ile Leu Leu Ala Leu Tyr Lys Arg Gly Arg Lys Lys
            275                 280                 285

Leu Leu Tyr Ile Phe Lys Gln Pro Phe Met Arg Pro Val Gln Thr Thr
290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
            325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
            355                 360                 365

Met Gly Gly Lys Pro Arg Arg Lys Asn Pro Gln Glu Gly Leu Tyr Asn
            370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
            405                 410                 415

Leu Ser Thr Ala Thr Lys Asp Thr Tyr Asp Ala Leu His Met Gln Ala
            420                 425                 430

Leu Pro Pro Arg
            435

<210> SEQ ID NO 21
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 21

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
50                  55                  60
```

```
Trp Phe His Asn Glu Ser Leu Ile Ser Ser Gln Ala Ser Ser Tyr Phe
 65                  70                  75                  80

Ile Asp Ala Ala Thr Val Asp Asp Ser Gly Glu Tyr Arg Cys Gln Thr
                 85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Leu Cys Tyr Leu Leu Asp Gly Ile Leu Phe Ile Tyr Gly Val
            260                 265                 270

Ile Leu Thr Ala Leu Phe Leu Arg Val Lys Lys Arg Gly Arg Lys Lys
        275                 280                 285

Leu Leu Tyr Ile Phe Lys Gln Pro Phe Met Arg Pro Val Gln Thr Thr
290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Gly Arg Asp Pro Glu
        355                 360                 365

Met Gly Gly Lys Pro Arg Arg Lys Asn Pro Gln Glu Gly Leu Tyr Asn
370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 22
<211> LENGTH: 441
<212> TYPE: PRT
<213> ORGANISM: Artificial Sequence
<220> FEATURE:
<223> OTHER INFORMATION: Synthetic Polypeptide
```

<400> SEQUENCE: 22

Met Ala Leu Pro Val Thr Ala Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Val Met Ser Val Ala Thr Ile Val Ile Val Asp Ile Cys Ile
            260                 265                 270

Thr Gly Gly Leu Leu Leu Leu Val Tyr Tyr Trp Ser Lys Asn Arg Lys
        275                 280                 285

Arg Gly Arg Lys Lys Leu Leu Tyr Ile Phe Lys Gln Pro Phe Met Arg
    290                 295                 300

Pro Val Gln Thr Thr Gln Glu Glu Asp Gly Cys Ser Cys Arg Phe Pro
305                 310                 315                 320

Glu Glu Glu Glu Gly Gly Cys Glu Leu Arg Val Lys Phe Ser Arg Ser
                325                 330                 335

Ala Asp Ala Pro Ala Tyr Gln Gln Gly Gln Asn Gln Leu Tyr Asn Glu
            340                 345                 350

Leu Asn Leu Gly Arg Arg Glu Glu Tyr Asp Val Leu Asp Lys Arg Arg
        355                 360                 365

Gly Arg Asp Pro Glu Met Gly Gly Lys Pro Arg Arg Lys Asn Pro Gln
    370                 375                 380

Glu Gly Leu Tyr Asn Glu Leu Gln Lys Asp Lys Met Ala Glu Ala Tyr
385                 390                 395                 400

Ser Glu Ile Gly Met Lys Gly Glu Arg Arg Arg Gly Lys Gly His Asp

```
                    405                 410                 415
Gly Leu Tyr Gln Gly Leu Ser Thr Ala Thr Lys Asp Thr Tyr Asp Ala
                420                 425                 430

Leu His Met Gln Ala Leu Pro Pro Arg
        435                 440

<210> SEQ ID NO 23
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 23

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65              70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Gly Phe Leu Phe Ala Glu Ile Val Ser Ile Phe Val Leu Ala
            260                 265                 270

Val Gly Val Tyr Phe Ile Ala Gly Gln Asp Lys Arg Gly Arg Lys Lys
        275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
```

```
                      325                 330                 335
Tyr Gln Gln Gly Gln Asn Gln Leu Tyr Asn Glu Leu Asn Leu Gly Arg
                340                 345                 350

Arg Glu Glu Tyr Asp Val Leu Asp Lys Arg Arg Gly Arg Asp Pro Glu
            355                 360                 365

Met Gly Gly Lys Pro Arg Arg Lys Asn Pro Gln Glu Gly Leu Tyr Asn
        370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
            435

<210> SEQ ID NO 24
<211> LENGTH: 437
<212> TYPE: PRT
<213> ORGANISM: Artificial Sequence
<220> FEATURE:
<223> OTHER INFORMATION: Synthetic Polypeptide

<400> SEQUENCE: 24

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
```

```
                245                 250                 255
Cys Asp Gly Ile Ile Val Thr Asp Val Ile Ala Thr Leu Leu Leu Ala
            260                 265                 270

Leu Gly Val Phe Cys Phe Ala Gly His Glu Thr Lys Arg Gly Arg Lys
        275                 280                 285

Lys Leu Leu Tyr Ile Phe Lys Gln Pro Phe Met Arg Pro Val Gln Thr
    290                 295                 300

Thr Gln Glu Glu Asp Gly Cys Ser Cys Arg Phe Pro Glu Glu Glu
305                 310                 315                 320

Gly Gly Cys Glu Leu Arg Val Lys Phe Ser Arg Ser Ala Asp Ala Pro
                325                 330                 335

Ala Tyr Gln Gln Gly Gln Asn Gln Leu Tyr Asn Glu Leu Asn Leu Gly
            340                 345                 350

Arg Arg Glu Glu Tyr Asp Val Leu Asp Lys Arg Arg Gly Arg Asp Pro
        355                 360                 365

Glu Met Gly Gly Lys Pro Arg Arg Lys Asn Pro Gln Glu Gly Leu Tyr
    370                 375                 380

Asn Glu Leu Gln Lys Asp Lys Met Ala Glu Ala Tyr Ser Glu Ile Gly
385                 390                 395                 400

Met Lys Gly Glu Arg Arg Arg Gly Lys Gly His Asp Gly Leu Tyr Gln
                405                 410                 415

Gly Leu Ser Thr Ala Thr Lys Asp Thr Tyr Asp Ala Leu His Met Gln
            420                 425                 430

Ala Leu Pro Pro Arg
            435

<210> SEQ ID NO 25
<211> LENGTH: 435
<212> TYPE: PRT
<213> ORGANISM: Artificial Sequence
<220> FEATURE:
<223> OTHER INFORMATION: Synthetic Polypeptide

<400> SEQUENCE: 25

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
```

165                 170                 175
Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
            195                 200                 205

Pro Pro Gly Tyr Gln Thr Thr Thr Pro Ala Pro Arg Pro Pro Thr Pro
            210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
            245                 250                 255

Cys Asp Val Ile Gly Phe Arg Ile Leu Leu Leu Lys Val Ala Gly Phe
            260                 265                 270

Asn Leu Leu Met Thr Leu Arg Leu Trp Lys Arg Gly Arg Lys Lys Leu
            275                 280                 285

Leu Tyr Ile Phe Lys Gln Pro Phe Met Arg Pro Val Gln Thr Thr Gln
            290                 295                 300

Glu Glu Asp Gly Cys Ser Cys Arg Phe Pro Glu Glu Glu Glu Gly Gly
305                 310                 315                 320

Cys Glu Leu Arg Val Lys Phe Ser Arg Ser Ala Asp Ala Pro Ala Tyr
            325                 330                 335

Gln Gln Gly Gln Asn Gln Leu Tyr Asn Glu Leu Asn Leu Gly Arg Arg
            340                 345                 350

Glu Glu Tyr Asp Val Leu Asp Lys Arg Arg Gly Arg Asp Pro Glu Met
            355                 360                 365

Gly Gly Lys Pro Arg Arg Lys Asn Pro Gln Glu Gly Leu Tyr Asn Glu
            370                 375                 380

Leu Gln Lys Asp Lys Met Ala Glu Ala Tyr Ser Glu Ile Gly Met Lys
385                 390                 395                 400

Gly Glu Arg Arg Arg Gly Lys Gly His Asp Gly Leu Tyr Gln Gly Leu
            405                 410                 415

Ser Thr Ala Thr Lys Asp Thr Tyr Asp Ala Leu His Met Gln Ala Leu
            420                 425                 430

Pro Pro Arg
        435

<210> SEQ ID NO 26
<211> LENGTH: 438
<212> TYPE: PRT
<213> ORGANISM: Artificial Sequence
<220> FEATURE:
<223> OTHER INFORMATION: Synthetic Polypeptide

<400> SEQUENCE: 26

Met Ala Leu Pro Val Thr Ala Leu Leu Leu Pro Leu Ala Leu Leu Leu
1               5                   10                  15

His Ala Ala Arg Pro Gly Met Thr Glu Asp Leu Pro Lys Ala Val
            20                  25                  30

Val Phe Leu Glu Pro Gln Trp Tyr Arg Val Leu Glu Lys Asp Ser Val
                35                  40                  45

Thr Leu Lys Cys Gln Gly Ala Tyr Ser Pro Glu Asp Asn Ser Thr Gln
            50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr

```
                    85                  90                  95
Asn Leu Ser Thr Leu Ser Asp Pro Val Gln Leu Glu Val His Ile Gly
                100                 105                 110

Trp Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
            130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
                195                 200                 205

Pro Pro Gly Tyr Gln Thr Thr Thr Pro Ala Pro Arg Pro Pro Thr Pro
                210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Ile Val Ala Val Val Ile Ala Thr Ala Val Ala Ala Ile
                260                 265                 270

Val Ala Ala Val Val Ala Leu Ile Tyr Cys Arg Lys Lys Arg Gly Arg
                275                 280                 285

Lys Lys Leu Leu Tyr Ile Phe Lys Gln Pro Phe Met Arg Pro Val Gln
                290                 295                 300

Thr Thr Gln Glu Glu Asp Gly Cys Ser Cys Arg Phe Pro Glu Glu Glu
305                 310                 315                 320

Glu Gly Gly Cys Glu Leu Arg Val Lys Phe Ser Arg Ser Ala Asp Ala
                325                 330                 335

Pro Ala Tyr Gln Gln Gly Gln Asn Gln Leu Tyr Asn Glu Leu Asn Leu
                340                 345                 350

Gly Arg Arg Glu Glu Tyr Asp Val Leu Asp Lys Arg Arg Gly Arg Asp
                355                 360                 365

Pro Glu Met Gly Gly Lys Pro Arg Arg Lys Asn Pro Gln Glu Gly Leu
                370                 375                 380

Tyr Asn Glu Leu Gln Lys Asp Lys Met Ala Glu Ala Tyr Ser Glu Ile
385                 390                 395                 400

Gly Met Lys Gly Glu Arg Arg Arg Gly Lys Gly His Asp Gly Leu Tyr
                405                 410                 415

Gln Gly Leu Ser Thr Ala Thr Lys Asp Thr Tyr Asp Ala Leu His Met
                420                 425                 430

Gln Ala Leu Pro Pro Arg
                435

<210> SEQ ID NO 27
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 27

Met Ala Leu Pro Val Thr Ala Leu Leu Leu Pro Leu Ala Leu Leu Leu
```

-continued

```
1               5                   10                  15
His Ala Ala Arg Pro Gly Met Arg Thr Glu Asp Leu Pro Lys Ala Val
                20                  25                  30
Val Phe Leu Glu Pro Gln Trp Tyr Arg Val Leu Glu Lys Asp Ser Val
                35                  40                  45
Thr Leu Lys Cys Gln Gly Ala Tyr Ser Pro Glu Asp Asn Ser Thr Gln
    50                  55                  60
Trp Phe His Asn Glu Ser Leu Ile Ser Ser Gln Ala Ser Ser Tyr Phe
65                  70                  75                  80
Ile Asp Ala Ala Thr Val Asp Asp Ser Gly Glu Tyr Arg Cys Gln Thr
                85                  90                  95
Asn Leu Ser Thr Leu Ser Asp Pro Val Gln Leu Glu Val His Ile Gly
                100                 105                 110
Trp Leu Leu Leu Gln Ala Pro Arg Trp Val Phe Lys Glu Glu Asp Pro
                115                 120                 125
Ile His Leu Arg Cys His Ser Trp Lys Asn Thr Ala Leu His Lys Val
                130                 135                 140
Thr Tyr Leu Gln Asn Gly Lys Gly Arg Lys Tyr Phe His His Asn Ser
145                 150                 155                 160
Asp Phe Tyr Ile Pro Lys Ala Thr Leu Lys Asp Ser Gly Ser Tyr Phe
                165                 170                 175
Cys Arg Gly Leu Val Gly Ser Lys Asn Val Ser Ser Glu Thr Val Asn
                180                 185                 190
Ile Thr Ile Thr Gln Gly Leu Ala Val Ser Thr Ile Ser Ser Phe Phe
                195                 200                 205
Pro Pro Gly Tyr Gln Thr Thr Thr Pro Ala Pro Arg Pro Pro Thr Pro
                210                 215                 220
Ala Pro Thr Ile Ala Ser Gln Pro Leu Ser Leu Arg Pro Glu Ala Cys
225                 230                 235                 240
Arg Pro Ala Ala Gly Gly Ala Val His Thr Arg Gly Leu Asp Phe Ala
                245                 250                 255
Cys Asp Val Leu Phe Tyr Leu Ala Val Gly Ile Met Phe Leu Val Asn
                260                 265                 270
Thr Val Leu Trp Val Thr Ile Arg Lys Glu Lys Arg Gly Arg Lys Lys
                275                 280                 285
Leu Leu Tyr Ile Phe Lys Gln Pro Phe Met Arg Pro Val Gln Thr Thr
                290                 295                 300
Gln Glu Glu Asp Gly Cys Ser Cys Arg Phe Pro Glu Glu Glu Glu Gly
305                 310                 315                 320
Gly Cys Glu Leu Arg Val Lys Phe Ser Arg Ser Ala Asp Ala Pro Ala
                325                 330                 335
Tyr Gln Gln Gly Gln Asn Gln Leu Tyr Asn Glu Leu Asn Leu Gly Arg
                340                 345                 350
Arg Glu Glu Tyr Asp Val Leu Asp Lys Arg Arg Gly Arg Asp Pro Glu
                355                 360                 365
Met Gly Gly Lys Pro Arg Arg Lys Asn Pro Gln Glu Gly Leu Tyr Asn
                370                 375                 380
Glu Leu Gln Lys Asp Lys Met Ala Glu Ala Tyr Ser Glu Ile Gly Met
385                 390                 395                 400
Lys Gly Glu Arg Arg Arg Gly Lys Gly His Asp Gly Leu Tyr Gln Gly
                405                 410                 415
Leu Ser Thr Ala Thr Lys Asp Thr Tyr Asp Ala Leu His Met Gln Ala
                420                 425                 430
```

Leu Pro Pro Arg
        435

<210> SEQ ID NO 28
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 28

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Ile Ile Leu Val Gly Thr Ala Val Ile Ala Met Phe Phe
            260                 265                 270

Trp Leu Leu Leu Val Ile Ile Leu Arg Thr Lys Arg Gly Arg Lys Lys
        275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

```
Arg Glu Glu Tyr Asp Val Leu Asp Lys Arg Gly Arg Asp Pro Glu
        355                 360                 365

Met Gly Gly Lys Pro Arg Arg Lys Asn Pro Gln Glu Gly Leu Tyr Asn
370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
        405                 410                 415

Leu Ser Thr Ala Thr Lys Asp Thr Tyr Asp Ala Leu His Met Gln Ala
        420                 425                 430

Leu Pro Pro Arg
        435

<210> SEQ ID NO 29
<211> LENGTH: 432
<212> TYPE: PRT
<213> ORGANISM: Artificial Sequence
<220> FEATURE:
<223> OTHER INFORMATION: Synthetic Polypeptide

<400> SEQUENCE: 29

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Leu Gly Trp Leu Cys Leu Leu Leu Pro Ile Pro Leu Ile
            260                 265                 270
```

```
Val Trp Val Lys Arg Lys Arg Gly Arg Lys Lys Leu Leu Tyr Ile
        275                 280                 285

Phe Lys Gln Pro Phe Met Arg Pro Val Gln Thr Thr Gln Glu Glu Asp
290                 295                 300

Gly Cys Ser Cys Arg Phe Pro Glu Glu Glu Gly Gly Cys Glu Leu
305                 310                 315                 320

Arg Val Lys Phe Ser Arg Ser Ala Asp Ala Pro Ala Tyr Gln Gln Gly
                325                 330                 335

Gln Asn Gln Leu Tyr Asn Glu Leu Asn Leu Gly Arg Arg Glu Glu Tyr
                340                 345                 350

Asp Val Leu Asp Lys Arg Arg Gly Arg Asp Pro Glu Met Gly Gly Lys
                355                 360                 365

Pro Arg Arg Lys Asn Pro Gln Glu Gly Leu Tyr Asn Glu Leu Gln Lys
                370                 375                 380

Asp Lys Met Ala Glu Ala Tyr Ser Glu Ile Gly Met Lys Gly Glu Arg
385                 390                 395                 400

Arg Arg Gly Lys Gly His Asp Gly Leu Tyr Gln Gly Leu Ser Thr Ala
                405                 410                 415

Thr Lys Asp Thr Tyr Asp Ala Leu His Met Gln Ala Leu Pro Pro Arg
                420                 425                 430

<210> SEQ ID NO 30
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 30

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
            195                 200                 205
```

```
Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Ala Ile Tyr Cys Ile Gly Val Phe Leu Ile Ala Cys Met
            260                 265                 270

Val Val Thr Val Ile Leu Cys Arg Met Lys Lys Arg Gly Arg Lys Lys
        275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
    370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 31
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 31

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125
```

```
Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Phe Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Lys Arg Gly Arg Lys Lys
        275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
    370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 32
<211> LENGTH: 476
<212> TYPE: PRT
<213> ORGANISM: Artificial Sequence
<220> FEATURE:
<223> OTHER INFORMATION: Synthetic Polypeptide

<400> SEQUENCE: 32

Met Ala Leu Pro Val Thr Ala Leu Leu Leu Pro Leu Ala Leu Leu Leu
1               5                   10                  15

His Ala Ala Arg Pro Gln Val Asp Thr Thr Lys Ala Val Ile Thr Leu
            20                  25                  30

Gln Pro Pro Trp Val Ser Val Phe Gln Glu Glu Thr Val Thr Leu His
        35                  40                  45
```

```
Cys Glu Val Leu His Leu Pro Gly Ser Ser Thr Gln Trp Phe Leu
     50                  55                  60

Asn Gly Thr Ala Thr Gln Thr Ser Thr Pro Ser Tyr Arg Ile Thr Ser
 65                  70                  75                  80

Ala Ser Val Asn Asp Ser Gly Glu Tyr Arg Cys Gln Arg Gly Leu Ser
                 85                  90                  95

Gly Arg Ser Asp Pro Ile Gln Leu Glu Ile His Arg Gly Trp Leu Leu
            100                 105                 110

Leu Gln Val Ser Ser Arg Val Phe Thr Glu Gly Glu Pro Leu Ala Leu
        115                 120                 125

Arg Cys His Ala Trp Lys Asp Lys Leu Val Tyr Asn Val Leu Tyr Tyr
    130                 135                 140

Arg Asn Gly Lys Ala Phe Lys Phe Phe His Trp Asn Ser Asn Leu Thr
145                 150                 155                 160

Ile Leu Lys Thr Asn Ile Ser His Asn Gly Thr Tyr His Cys Ser Gly
                165                 170                 175

Met Gly Lys His Arg Tyr Thr Ser Ala Gly Ile Ser Val Thr Val Lys
            180                 185                 190

Glu Leu Phe Pro Ala Pro Val Leu Asn Ala Ser Val Thr Ser Pro Leu
        195                 200                 205

Leu Glu Gly Asn Leu Val Thr Leu Ser Cys Glu Thr Lys Leu Leu Leu
    210                 215                 220

Gln Arg Pro Gly Leu Gln Leu Tyr Phe Ser Phe Tyr Met Gly Ser Lys
225                 230                 235                 240

Thr Leu Arg Gly Arg Asn Thr Ser Ser Glu Tyr Gln Ile Leu Thr Ala
                245                 250                 255

Arg Arg Glu Asp Ser Gly Leu Tyr Trp Cys Glu Ala Ala Thr Glu Asp
            260                 265                 270

Gly Asn Val Leu Lys Arg Ser Pro Glu Leu Glu Leu Gln Val Leu Gly
        275                 280                 285

Leu Gln Leu Pro Thr Pro Val Trp Phe His Ile Tyr Ile Trp Ala Pro
    290                 295                 300

Leu Ala Gly Thr Cys Gly Val Leu Leu Leu Ser Leu Val Ile Thr Leu
305                 310                 315                 320

Tyr Cys Lys Arg Gly Arg Lys Lys Leu Leu Tyr Ile Phe Lys Gln Pro
                325                 330                 335

Phe Met Arg Pro Val Gln Thr Thr Gln Glu Glu Asp Gly Cys Ser Cys
            340                 345                 350

Arg Phe Pro Glu Glu Glu Glu Gly Gly Cys Glu Leu Arg Val Lys Phe
        355                 360                 365

Ser Arg Ser Ala Asp Ala Pro Ala Tyr Gln Gln Gly Gln Asn Gln Leu
    370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
            420                 425                 430

Glu Ala Tyr Ser Glu Ile Gly Met Lys Gly Glu Arg Arg Arg Gly Lys
        435                 440                 445

Gly His Asp Gly Leu Tyr Gln Gly Leu Ser Thr Ala Thr Lys Asp Thr
    450                 455                 460
```

Tyr Asp Ala Leu His Met Gln Ala Leu Pro Pro Arg
465                 470                 475

<210> SEQ ID NO 33
<211> LENGTH: 623
<212> TYPE: PRT
<213> ORGANISM: Artificial Sequence
<220> FEATURE:
<223> OTHER INFORMATION: Synthetic Polypeptide

<400> SEQUENCE: 33

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Ile Tyr Ile
        435                 440                 445

Trp Ala Pro Leu Ala Gly Thr Cys Gly Val Leu Leu Leu Ser Leu Val
    450                 455                 460

Ile Thr Leu Tyr Cys Lys Arg Gly Arg Lys Lys Leu Leu Tyr Ile Phe
465                 470                 475                 480

Lys Gln Pro Phe Met Arg Pro Val Gln Thr Thr Gln Glu Glu Asp Gly
                485                 490                 495

Cys Ser Cys Arg Phe Pro Glu Glu Glu Glu Gly Gly Cys Glu Leu Arg
            500                 505                 510

Val Lys Phe Ser Arg Ser Ala Asp Ala Pro Ala Tyr Gln Gln Gly Gln
        515                 520                 525

Asn Gln Leu Tyr Asn Glu Leu Asn Leu Gly Arg Arg Glu Glu Tyr Asp
    530                 535                 540

Val Leu Asp Lys Arg Arg Gly Arg Asp Pro Glu Met Gly Gly Lys Pro
545                 550                 555                 560

Arg Arg Lys Asn Pro Gln Glu Gly Leu Tyr Asn Glu Leu Gln Lys Asp
                565                 570                 575

Lys Met Ala Glu Ala Tyr Ser Glu Ile Gly Met Lys Gly Glu Arg Arg
            580                 585                 590

Arg Gly Lys Gly His Asp Gly Leu Tyr Gln Gly Leu Ser Thr Ala Thr
        595                 600                 605

Lys Asp Thr Tyr Asp Ala Leu His Met Gln Ala Leu Pro Pro Arg
    610                 615                 620

<210> SEQ ID NO 34
<211> LENGTH: 510
<212> TYPE: PRT
<213> ORGANISM: Artificial Sequence
<220> FEATURE:
<223> OTHER INFORMATION: Synthetic Polypeptide

<400> SEQUENCE: 34

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

```
Asn Leu Ser Thr Leu Ser Asp Pro Val Gln Leu Glu Val His Ile Gly
                100                 105                 110
Trp Leu Leu Leu Gln Ala Pro Arg Trp Val Phe Lys Glu Glu Asp Pro
            115                 120                 125
Ile His Leu Arg Cys His Ser Trp Lys Asn Thr Ala Leu His Lys Val
        130                 135                 140
Thr Tyr Leu Gln Asn Gly Lys Gly Arg Lys Tyr Phe His His Asn Ser
145                 150                 155                 160
Asp Phe Tyr Ile Pro Lys Ala Thr Leu Lys Asp Ser Gly Ser Tyr Phe
                165                 170                 175
Cys Arg Gly Leu Val Gly Ser Lys Asn Val Ser Ser Glu Thr Val Asn
            180                 185                 190
Ile Thr Ile Thr Gln Gly Leu Ala Val Ser Thr Ile Ser Ser Phe Phe
        195                 200                 205
Pro Pro Gly Tyr Gln Glu Pro Lys Ser Cys Asp Lys Thr His Thr Cys
210                 215                 220
Pro Gly Gln Pro Arg Glu Pro Gln Val Tyr Thr Leu Pro Pro Ser Arg
225                 230                 235                 240
Asp Glu Leu Thr Lys Asn Gln Val Ser Leu Thr Cys Leu Val Lys Gly
                245                 250                 255
Phe Tyr Pro Ser Asp Ile Ala Val Glu Trp Glu Ser Asn Gly Gln Pro
            260                 265                 270
Glu Asn Asn Tyr Lys Thr Thr Pro Pro Val Leu Asp Ser Asp Gly Ser
        275                 280                 285
Phe Phe Leu Tyr Ser Lys Leu Thr Val Asp Lys Ser Arg Trp Gln Gln
290                 295                 300
Gly Asn Val Phe Ser Cys Ser Val Met His Glu Ala Leu His Asn His
305                 310                 315                 320
Tyr Thr Gln Lys Ser Leu Ser Leu Ser Pro Gly Lys Ile Tyr Ile Trp
                325                 330                 335
Ala Pro Leu Ala Gly Thr Cys Gly Val Leu Leu Leu Ser Leu Val Ile
            340                 345                 350
Thr Leu Tyr Cys Lys Arg Gly Arg Lys Lys Leu Leu Tyr Ile Phe Lys
        355                 360                 365
Gln Pro Phe Met Arg Pro Val Gln Thr Thr Gln Glu Glu Asp Gly Cys
370                 375                 380
Ser Cys Arg Phe Pro Glu Glu Glu Glu Gly Gly Cys Glu Leu Arg Val
385                 390                 395                 400
Lys Phe Ser Arg Ser Ala Asp Ala Pro Ala Tyr Gln Gln Gly Gln Asn
                405                 410                 415
Gln Leu Tyr Asn Glu Leu Asn Leu Gly Arg Arg Glu Glu Tyr Asp Val
            420                 425                 430
Leu Asp Lys Arg Arg Gly Arg Asp Pro Glu Met Gly Gly Lys Pro Arg
        435                 440                 445
Arg Lys Asn Pro Gln Glu Gly Leu Tyr Asn Glu Leu Gln Lys Asp Lys
450                 455                 460
Met Ala Glu Ala Tyr Ser Glu Ile Gly Met Lys Gly Glu Arg Arg Arg
465                 470                 475                 480
Gly Lys Gly His Asp Gly Leu Tyr Gln Gly Leu Ser Thr Ala Thr Lys
                485                 490                 495
Asp Thr Tyr Asp Ala Leu His Met Gln Ala Leu Pro Pro Arg
            500                 505                 510
```

<210> SEQ ID NO 35
<211> LENGTH: 403
<212> TYPE: PRT
<213> ORGANISM: Artificial Sequence
<220> FEATURE:
<223> OTHER INFORMATION: Synthetic Polypeptide

<400> SEQUENCE: 35

```
Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Glu Pro Lys Ser Cys Asp Lys Thr His Thr Cys
    210                 215                 220

Pro Ile Tyr Ile Trp Ala Pro Leu Ala Gly Thr Cys Gly Val Leu Leu
225                 230                 235                 240

Leu Ser Leu Val Ile Thr Leu Tyr Cys Lys Arg Gly Arg Lys Lys Leu
                245                 250                 255

Leu Tyr Ile Phe Lys Gln Pro Phe Met Arg Pro Val Gln Thr Thr Gln
            260                 265                 270

Glu Glu Asp Gly Cys Ser Cys Arg Phe Pro Glu Glu Glu Glu Gly Gly
        275                 280                 285

Cys Glu Leu Arg Val Lys Phe Ser Arg Ser Ala Asp Ala Pro Ala Tyr
    290                 295                 300

Gln Gln Gly Gln Asn Gln Leu Tyr Asn Glu Leu Asn Leu Gly Arg Arg
305                 310                 315                 320

Glu Glu Tyr Asp Val Leu Asp Lys Arg Arg Gly Arg Asp Pro Glu Met
                325                 330                 335

Gly Gly Lys Pro Arg Arg Lys Asn Pro Gln Glu Gly Leu Tyr Asn Glu
            340                 345                 350

Leu Gln Lys Asp Lys Met Ala Glu Ala Tyr Ser Glu Ile Gly Met Lys
        355                 360                 365

Gly Glu Arg Arg Arg Gly Lys Gly His Asp Gly Leu Tyr Gln Gly Leu
```

```
                    370                 375                 380
Ser Thr Ala Thr Lys Asp Thr Tyr Asp Ala Leu His Met Gln Ala Leu
385                 390                 395                 400

Pro Pro Arg

<210> SEQ ID NO 36
<211> LENGTH: 421
<212> TYPE: PRT
<213> ORGANISM: Artificial Sequence
<220> FEATURE:
<223> OTHER INFORMATION: Synthetic Polypeptide

<400> SEQUENCE: 36

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Phe
225                 230                 235                 240

Ala Cys Asp Ile Tyr Ile Trp Ala Pro Leu Ala Gly Thr Cys Gly Val
                245                 250                 255

Leu Leu Leu Ser Leu Val Ile Thr Leu Tyr Cys Lys Arg Gly Arg Lys
            260                 265                 270

Lys Leu Leu Tyr Ile Phe Lys Gln Pro Phe Met Arg Pro Val Gln Thr
        275                 280                 285

Thr Gln Glu Glu Asp Gly Cys Ser Cys Arg Phe Pro Glu Glu Glu Glu
290                 295                 300

Gly Gly Cys Glu Leu Arg Val Lys Phe Ser Arg Ser Ala Asp Ala Pro
305                 310                 315                 320

Ala Tyr Gln Gln Gly Gln Asn Gln Leu Tyr Asn Glu Leu Asn Leu Gly
                325                 330                 335
```

```
Arg Arg Glu Glu Tyr Asp Val Leu Asp Lys Arg Arg Gly Arg Asp Pro
            340                 345                 350

Glu Met Gly Gly Lys Pro Arg Arg Lys Asn Pro Gln Glu Gly Leu Tyr
        355                 360                 365

Asn Glu Leu Gln Lys Asp Lys Met Ala Glu Ala Tyr Ser Glu Ile Gly
370                 375                 380

Met Lys Gly Glu Arg Arg Arg Gly Lys Gly His Asp Gly Leu Tyr Gln
385                 390                 395                 400

Gly Leu Ser Thr Ala Thr Lys Asp Thr Tyr Asp Ala Leu His Met Gln
                405                 410                 415

Ala Leu Pro Pro Arg
            420

<210> SEQ ID NO 37
<211> LENGTH: 406
<212> TYPE: PRT
<213> ORGANISM: Artificial Sequence
<220> FEATURE:
<223> OTHER INFORMATION: Synthetic Polypeptide

<400> SEQUENCE: 37

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Phe Ala Cys Asp Ile Tyr Ile Trp Ala Pro Leu Ala Gly Thr Cys Gly
225                 230                 235                 240

Val Leu Leu Leu Ser Leu Val Ile Thr Leu Tyr Cys Lys Arg Gly Arg
                245                 250                 255

Lys Lys Leu Leu Tyr Ile Phe Lys Gln Pro Phe Met Arg Pro Val Gln
            260                 265                 270
```

```
Thr Thr Gln Glu Glu Asp Gly Cys Ser Cys Arg Phe Pro Glu Glu Glu
        275                 280                 285

Glu Gly Gly Cys Glu Leu Arg Val Lys Phe Ser Arg Ser Ala Asp Ala
    290                 295                 300

Pro Ala Tyr Gln Gln Gly Gln Asn Gln Leu Tyr Asn Glu Leu Asn Leu
305                 310                 315                 320

Gly Arg Arg Glu Glu Tyr Asp Val Leu Asp Lys Arg Gly Arg Asp
                325                 330                 335

Pro Glu Met Gly Gly Lys Pro Arg Arg Lys Asn Pro Gln Glu Gly Leu
                340                 345                 350

Tyr Asn Glu Leu Gln Lys Asp Lys Met Ala Glu Ala Tyr Ser Glu Ile
                355                 360                 365

Gly Met Lys Gly Glu Arg Arg Arg Gly Lys Gly His Asp Gly Leu Tyr
    370                 375                 380

Gln Gly Leu Ser Thr Ala Thr Lys Asp Thr Tyr Asp Ala Leu His Met
385                 390                 395                 400

Gln Ala Leu Pro Pro Arg
                405

<210> SEQ ID NO 38
<211> LENGTH: 406
<212> TYPE: PRT
<213> ORGANISM: Artificial Sequence
<220> FEATURE:
<223> OTHER INFORMATION: Synthetic Polypeptide

<400> SEQUENCE: 38

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
            195                 200                 205

Pro Pro Gly Tyr Gln Gly Gly Gly Gly Ser Gly Gly Gly Gly Ser Gly
    210                 215                 220
```

```
Gly Gly Gly Ser Ile Tyr Ile Trp Ala Pro Leu Ala Gly Thr Cys Gly
225                 230                 235                 240

Val Leu Leu Leu Ser Leu Val Ile Thr Leu Tyr Cys Lys Arg Gly Arg
                245                 250                 255

Lys Lys Leu Leu Tyr Ile Phe Lys Gln Pro Phe Met Arg Pro Val Gln
                260                 265                 270

Thr Thr Gln Glu Glu Asp Gly Cys Ser Cys Arg Phe Pro Glu Glu Glu
                275                 280                 285

Glu Gly Gly Cys Glu Leu Arg Val Lys Phe Ser Arg Ser Ala Asp Ala
                290                 295                 300

Pro Ala Tyr Gln Gln Gly Gln Asn Gln Leu Tyr Asn Glu Leu Asn Leu
305                 310                 315                 320

Gly Arg Arg Glu Glu Tyr Asp Val Leu Asp Lys Arg Arg Gly Arg Asp
                325                 330                 335

Pro Glu Met Gly Gly Lys Pro Arg Arg Lys Asn Pro Gln Glu Gly Leu
                340                 345                 350

Tyr Asn Glu Leu Gln Lys Asp Lys Met Ala Glu Ala Tyr Ser Glu Ile
                355                 360                 365

Gly Met Lys Gly Glu Arg Arg Arg Gly Lys Gly His Asp Gly Leu Tyr
                370                 375                 380

Gln Gly Leu Ser Thr Ala Thr Lys Asp Thr Tyr Asp Ala Leu His Met
385                 390                 395                 400

Gln Ala Leu Pro Pro Arg
                405

<210> SEQ ID NO 39
<211> LENGTH: 421
<212> TYPE: PRT
<213> ORGANISM: Artificial Sequence
<220> FEATURE:
<223> OTHER INFORMATION: Synthetic Polypeptide

<400> SEQUENCE: 39

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
                35                  40                  45

Thr Leu Lys Cys Gln Gly Ala Tyr Ser Pro Glu Asp Asn Ser Thr Gln
            50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
                130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175
```

```
Cys Arg Gly Leu Val Gly Ser Lys Asn Val Ser Ser Glu Thr Val Asn
                180                 185                 190
Ile Thr Ile Thr Gln Gly Leu Ala Val Ser Thr Ile Ser Ser Phe Phe
            195                 200                 205
Pro Pro Gly Tyr Gln Gly Gly Gly Ser Gly Gly Gly Gly Ser Gly
210                 215                 220
Gly Gly Gly Ser Gly Gly Gly Gly Ser Gly Gly Gly Gly Ser Gly Gly
225                 230                 235                 240
Gly Gly Ser Ile Tyr Ile Trp Ala Pro Leu Ala Gly Thr Cys Gly Val
                245                 250                 255
Leu Leu Leu Ser Leu Val Ile Thr Leu Tyr Cys Lys Arg Gly Arg Lys
260                 265                 270
Lys Leu Leu Tyr Ile Phe Lys Gln Pro Phe Met Arg Pro Val Gln Thr
            275                 280                 285
Thr Gln Glu Glu Asp Gly Cys Ser Cys Arg Phe Pro Glu Glu Glu Glu
        290                 295                 300
Gly Gly Cys Glu Leu Arg Val Lys Phe Ser Arg Ser Ala Asp Ala Pro
305                 310                 315                 320
Ala Tyr Gln Gln Gly Gln Asn Gln Leu Tyr Asn Glu Leu Asn Leu Gly
                325                 330                 335
Arg Arg Glu Glu Tyr Asp Val Leu Asp Lys Arg Arg Gly Arg Asp Pro
            340                 345                 350
Glu Met Gly Gly Lys Pro Arg Arg Lys Asn Pro Gln Glu Gly Leu Tyr
        355                 360                 365
Asn Glu Leu Gln Lys Asp Lys Met Ala Glu Ala Tyr Ser Glu Ile Gly
    370                 375                 380
Met Lys Gly Glu Arg Arg Arg Gly Lys Gly His Asp Gly Leu Tyr Gln
385                 390                 395                 400
Gly Leu Ser Thr Ala Thr Lys Asp Thr Tyr Asp Ala Leu His Met Gln
                405                 410                 415
Ala Leu Pro Pro Arg
                420

<210> SEQ ID NO 40
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 40

Met Ala Leu Pro Val Thr Ala Leu Leu Leu Pro Leu Ala Leu Leu Leu
1               5                   10                  15
His Ala Ala Arg Pro Gly Met Arg Thr Glu Asp Leu Pro Lys Ala Val
                20                  25                  30
Val Phe Leu Glu Pro Gln Trp Tyr Arg Val Leu Glu Lys Asp Ser Val
            35                  40                  45
Thr Leu Lys Cys Gln Gly Ala Tyr Ser Pro Glu Asp Asn Ser Thr Gln
        50                  55                  60
Trp Phe His Asn Glu Ser Leu Ile Ser Ser Gln Ala Ser Ser Tyr Phe
65                  70                  75                  80
Ile Asp Ala Ala Thr Val Asp Asp Ser Gly Glu Tyr Arg Cys Gln Thr
                85                  90                  95
Asn Leu Ser Thr Leu Ser Asp Pro Val Gln Leu Glu Val His Ile Gly
            100                 105                 110
```

```
Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Gly Gly Gly Ser Gly Gly Gly Ser Gly
    210                 215                 220

Gly Gly Gly Ser Gly Gly Gly Ser Gly Gly Gly Ser Gly Gly
225                 230                 235                 240

Gly Gly Ser Gly Gly Gly Ser Gly Gly Gly Ser Gly Gly Gly
            245                 250                 255

Gly Ser Ile Tyr Ile Trp Ala Pro Leu Ala Gly Thr Cys Gly Val Leu
        260                 265                 270

Leu Leu Ser Leu Val Ile Thr Leu Tyr Cys Lys Arg Gly Arg Lys Lys
        275                 280                 285

Leu Leu Tyr Ile Phe Lys Gln Pro Phe Met Arg Pro Val Gln Thr Thr
        290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
            325                 330                 335

Tyr Gln Gln Gly Gln Asn Gln Leu Tyr Asn Glu Leu Asn Leu Gly Arg
                340                 345                 350

Arg Glu Glu Tyr Asp Val Leu Asp Lys Arg Arg Gly Arg Asp Pro Glu
            355                 360                 365

Met Gly Gly Lys Pro Arg Arg Lys Asn Pro Gln Glu Gly Leu Tyr Asn
    370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 41
<211> LENGTH: 451
<212> TYPE: PRT
<213> ORGANISM: Artificial Sequence
<220> FEATURE:
<223> OTHER INFORMATION: Synthetic Polypeptide

<400> SEQUENCE: 41

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30
```

```
Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
        130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
        195                 200                 205

Pro Pro Gly Tyr Gln Gly Gly Gly Ser Gly Gly Gly Ser Gly
        210                 215                 220

Gly Gly Gly Ser Gly Gly Gly Gly Ser Gly Gly Gly Gly Ser Gly Gly
225                 230                 235                 240

Gly Gly Ser Gly Gly Gly Gly Ser Gly Gly Gly Gly Ser Gly Gly Gly
                245                 250                 255

Gly Ser Gly Gly Gly Gly Ser Gly Gly Gly Gly Ser Gly Gly Gly Gly
        260                 265                 270

Ser Ile Tyr Ile Trp Ala Pro Leu Ala Gly Thr Cys Gly Val Leu Leu
        275                 280                 285

Leu Ser Leu Val Ile Thr Leu Tyr Cys Lys Arg Gly Arg Lys Lys Leu
        290                 295                 300

Leu Tyr Ile Phe Lys Gln Pro Phe Met Arg Pro Val Gln Thr Thr Gln
305                 310                 315                 320

Glu Glu Asp Gly Cys Ser Cys Arg Phe Pro Glu Glu Glu Glu Gly Gly
                325                 330                 335

Cys Glu Leu Arg Val Lys Phe Ser Arg Ser Ala Asp Ala Pro Ala Tyr
                340                 345                 350

Gln Gln Gly Gln Asn Gln Leu Tyr Asn Glu Leu Asn Leu Gly Arg Arg
                355                 360                 365

Glu Glu Tyr Asp Val Leu Asp Lys Arg Gly Arg Asp Pro Glu Met
            370                 375                 380

Gly Gly Lys Pro Arg Arg Lys Asn Pro Gln Glu Gly Leu Tyr Asn Glu
385                 390                 395                 400

Leu Gln Lys Asp Lys Met Ala Glu Ala Tyr Ser Glu Ile Gly Met Lys
                405                 410                 415

Gly Glu Arg Arg Arg Gly Lys Gly His Asp Gly Leu Tyr Gln Gly Leu
                420                 425                 430

Ser Thr Ala Thr Lys Asp Thr Tyr Asp Ala Leu His Met Gln Ala Leu
                435                 440                 445
```

```
Pro Pro Arg
    450
```

<210> SEQ ID NO 42
<211> LENGTH: 451
<212> TYPE: PRT
<213> ORGANISM: Artificial Sequence
<220> FEATURE:
<223> OTHER INFORMATION: Synthetic Polypeptide

<400> SEQUENCE: 42

```
Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
 50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Gly Gly Ser Pro Ala Gly Ser Pro Thr Ser Thr
210                 215                 220

Glu Glu Gly Thr Ser Glu Ser Ala Thr Pro Glu Ser Gly Pro Gly Thr
225                 230                 235                 240

Ser Thr Glu Pro Ser Glu Gly Ser Ala Pro Gly Ser Pro Ala Gly Ser
                245                 250                 255

Pro Thr Ser Thr Glu Glu Gly Thr Ser Thr Glu Pro Ser Glu Gly Ser
            260                 265                 270

Ala Ile Tyr Ile Trp Ala Pro Leu Ala Gly Thr Cys Gly Val Leu Leu
        275                 280                 285

Leu Ser Leu Val Ile Thr Leu Tyr Cys Lys Arg Gly Arg Lys Lys Leu
290                 295                 300

Leu Tyr Ile Phe Lys Gln Pro Phe Met Arg Pro Val Gln Thr Thr Gln
305                 310                 315                 320

Glu Glu Asp Gly Cys Ser Cys Arg Phe Pro Glu Glu Glu Glu Gly Gly
                325                 330                 335

Cys Glu Leu Arg Val Lys Phe Ser Arg Ser Ala Asp Ala Pro Ala Tyr
            340                 345                 350
```

```
Gln Gln Gly Gln Asn Gln Leu Tyr Asn Glu Leu Asn Leu Gly Arg Arg
            355                 360                 365

Glu Glu Tyr Asp Val Leu Asp Lys Arg Gly Arg Asp Pro Glu Met
370                 375                 380

Gly Gly Lys Pro Arg Arg Lys Asn Pro Gln Glu Gly Leu Tyr Asn Glu
385                 390                 395                 400

Leu Gln Lys Asp Lys Met Ala Glu Ala Tyr Ser Glu Ile Gly Met Lys
            405                 410                 415

Gly Glu Arg Arg Arg Gly Lys Gly His Asp Gly Leu Tyr Gln Gly Leu
                420                 425                 430

Ser Thr Ala Thr Lys Asp Thr Tyr Asp Ala Leu His Met Gln Ala Leu
            435                 440                 445

Pro Pro Arg
    450

<210> SEQ ID NO 43
<211> LENGTH: 421
<212> TYPE: PRT
<213> ORGANISM: Artificial Sequence
<220> FEATURE:
<223> OTHER INFORMATION: Synthetic Polypeptide

<400> SEQUENCE: 43

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Gly Ser Pro Ala Gly Ser Pro Thr Ser Thr
            210                 215                 220

Glu Glu Gly Thr Ser Glu Ser Ala Thr Pro Glu Ser Gly Pro Gly Thr
225                 230                 235                 240

Ser Thr Glu Ile Tyr Ile Trp Ala Pro Leu Ala Gly Thr Cys Gly Val
                245                 250                 255
```

Leu Leu Leu Ser Leu Val Ile Thr Leu Tyr Cys Lys Arg Gly Arg Lys
            260                 265                 270

Lys Leu Leu Tyr Ile Phe Lys Gln Pro Phe Met Arg Pro Val Gln Thr
        275                 280                 285

Thr Gln Glu Glu Asp Gly Cys Ser Cys Arg Phe Pro Glu Glu Glu Glu
    290                 295                 300

Gly Gly Cys Glu Leu Arg Val Lys Phe Ser Arg Ser Ala Asp Ala Pro
305                 310                 315                 320

Ala Tyr Gln Gln Gly Gln Asn Gln Leu Tyr Asn Glu Leu Asn Leu Gly
                325                 330                 335

Arg Arg Glu Glu Tyr Asp Val Leu Asp Lys Arg Arg Gly Arg Asp Pro
            340                 345                 350

Glu Met Gly Gly Lys Pro Arg Arg Lys Asn Pro Gln Glu Gly Leu Tyr
                355                 360                 365

Asn Glu Leu Gln Lys Asp Lys Met Ala Glu Ala Tyr Ser Glu Ile Gly
            370                 375                 380

Met Lys Gly Glu Arg Arg Arg Gly Lys Gly His Asp Gly Leu Tyr Gln
385                 390                 395                 400

Gly Leu Ser Thr Ala Thr Lys Asp Thr Tyr Asp Ala Leu His Met Gln
                405                 410                 415

Ala Leu Pro Pro Arg
            420

<210> SEQ ID NO 44
<211> LENGTH: 406
<212> TYPE: PRT
<213> ORGANISM: Artificial Sequence
<220> FEATURE:
<223> OTHER INFORMATION: Synthetic Polypeptide

<400> SEQUENCE: 44

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

```
Ile Thr Ile Thr Gln Gly Leu Ala Val Ser Thr Ile Ser Ser Phe Phe
        195                 200                 205

Pro Pro Gly Tyr Gln Gly Gly Ser Pro Ala Gly Ser Pro Thr Ser Thr
210                 215                 220

Glu Glu Gly Thr Ile Tyr Ile Trp Ala Pro Leu Ala Gly Thr Cys Gly
225                 230                 235                 240

Val Leu Leu Leu Ser Leu Val Ile Thr Leu Tyr Cys Lys Arg Gly Arg
                245                 250                 255

Lys Lys Leu Leu Tyr Ile Phe Lys Gln Pro Phe Met Arg Pro Val Gln
                260                 265                 270

Thr Thr Gln Glu Glu Asp Gly Cys Ser Cys Arg Phe Pro Glu Glu Glu
            275                 280                 285

Glu Gly Gly Cys Glu Leu Arg Val Lys Phe Ser Arg Ser Ala Asp Ala
        290                 295                 300

Pro Ala Tyr Gln Gln Gly Gln Asn Gln Leu Tyr Asn Glu Leu Asn Leu
305                 310                 315                 320

Gly Arg Arg Glu Glu Tyr Asp Val Leu Asp Lys Arg Arg Gly Arg Asp
                325                 330                 335

Pro Glu Met Gly Gly Lys Pro Arg Arg Lys Asn Pro Gln Glu Gly Leu
            340                 345                 350

Tyr Asn Glu Leu Gln Lys Asp Lys Met Ala Glu Ala Tyr Ser Glu Ile
355                 360                 365

Gly Met Lys Gly Glu Arg Arg Arg Gly Lys Gly His Asp Gly Leu Tyr
        370                 375                 380

Gln Gly Leu Ser Thr Ala Thr Lys Asp Thr Tyr Asp Ala Leu His Met
385                 390                 395                 400

Gln Ala Leu Pro Pro Arg
                405

<210> SEQ ID NO 45
<211> LENGTH: 433
<212> TYPE: PRT
<213> ORGANISM: Artificial Sequence
<220> FEATURE:
<223> OTHER INFORMATION: Synthetic Polypeptide

<400> SEQUENCE: 45

Met Leu Arg Leu Leu Leu Ala Leu Asn Leu Phe Pro Ser Ile Gln Val
1               5                   10                  15

Thr Gly Gly Met Arg Thr Glu Asp Leu Pro Lys Ala Val Val Phe Leu
                20                  25                  30

Glu Pro Gln Trp Tyr Arg Val Leu Glu Lys Asp Ser Val Thr Leu Lys
            35                  40                  45

Cys Gln Gly Ala Tyr Ser Pro Glu Asp Asn Ser Thr Gln Trp Phe His
    50                  55                  60

Asn Glu Ser Leu Ile Ser Ser Gln Ala Ser Ser Tyr Phe Ile Asp Ala
65                  70                  75                  80

Ala Thr Val Asp Asp Ser Gly Glu Tyr Arg Cys Gln Thr Asn Leu Ser
                85                  90                  95

Thr Leu Ser Asp Pro Val Gln Leu Glu Val His Ile Gly Trp Leu Leu
                100                 105                 110

Leu Gln Ala Pro Arg Trp Val Phe Lys Glu Glu Asp Pro Ile His Leu
            115                 120                 125

Arg Cys His Ser Trp Lys Asn Thr Ala Leu His Lys Val Thr Tyr Leu
    130                 135                 140
```

Gln Asn Gly Lys Gly Arg Lys Tyr Phe His His Asn Ser Asp Phe Tyr
145                 150                 155                 160

Ile Pro Lys Ala Thr Leu Lys Asp Ser Gly Ser Tyr Phe Cys Arg Gly
            165                 170                 175

Leu Val Gly Ser Lys Asn Val Ser Ser Glu Thr Val Asn Ile Thr Ile
            180                 185                 190

Thr Gln Gly Leu Ala Val Ser Thr Ile Ser Ser Phe Phe Pro Pro Gly
            195                 200                 205

Tyr Gln Thr Thr Thr Pro Ala Pro Arg Pro Pro Thr Pro Ala Pro Thr
            210                 215                 220

Ile Ala Ser Gln Pro Leu Ser Leu Arg Pro Glu Ala Cys Arg Pro Ala
225                 230                 235                 240

Ala Gly Gly Ala Val His Thr Arg Gly Leu Asp Phe Ala Cys Asp Ile
            245                 250                 255

Tyr Ile Trp Ala Pro Leu Ala Gly Thr Cys Gly Val Leu Leu Leu Ser
            260                 265                 270

Leu Val Ile Thr Leu Tyr Cys Lys Arg Gly Arg Lys Lys Leu Leu Tyr
            275                 280                 285

Ile Phe Lys Gln Pro Phe Met Arg Pro Val Gln Thr Thr Gln Glu Glu
290                 295                 300

Asp Gly Cys Ser Cys Arg Phe Pro Glu Glu Glu Glu Gly Gly Cys Glu
305                 310                 315                 320

Leu Arg Val Lys Phe Ser Arg Ser Ala Asp Ala Pro Ala Tyr Gln Gln
            325                 330                 335

Gly Gln Asn Gln Leu Tyr Asn Glu Leu Asn Leu Gly Arg Arg Glu Glu
            340                 345                 350

Tyr Asp Val Leu Asp Lys Arg Gly Arg Asp Pro Glu Met Gly Gly
            355                 360                 365

Lys Pro Arg Arg Lys Asn Pro Gln Glu Gly Leu Tyr Asn Glu Leu Gln
            370                 375                 380

Lys Asp Lys Met Ala Glu Ala Tyr Ser Glu Ile Gly Met Lys Gly Glu
385                 390                 395                 400

Arg Arg Arg Gly Lys Gly His Asp Gly Leu Tyr Gln Gly Leu Ser Thr
            405                 410                 415

Ala Thr Lys Asp Thr Tyr Asp Ala Leu His Met Gln Ala Leu Pro Pro
            420                 425                 430

Arg

<210> SEQ ID NO 46
<211> LENGTH: 436
<212> TYPE: PRT
<213> ORGANISM: Artificial Sequence
<220> FEATURE:
<223> OTHER INFORMATION: Synthetic Polypeptide

<400> SEQUENCE: 46

Met Glu Thr Asp Thr Leu Leu Leu Trp Val Leu Leu Leu Trp Val Pro
1               5                   10                  15

Gly Ser Thr Gly Asp Gly Met Arg Thr Glu Asp Leu Pro Lys Ala Val
            20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe 65                  70                  75                  80
Ile Asp Ala Ala Thr Val Asp Asp Ser Gly Glu Tyr Arg Cys Gln Thr
                    85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
                115                 120                 125

Ile His Leu Arg Cys His Ser Trp Lys Asn Thr Ala Leu His Lys Val
            130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
            195                 200                 205

Pro Pro Gly Tyr Gln Thr Thr Thr Pro Ala Pro Arg Pro Pro Thr Pro
        210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
                260                 265                 270

Leu Leu Ser Leu Val Ile Thr Leu Tyr Cys Lys Arg Gly Arg Lys Lys
            275                 280                 285

Leu Leu Tyr Ile Phe Lys Gln Pro Phe Met Arg Pro Val Gln Thr Thr
        290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
                340                 345                 350

Arg Glu Glu Tyr Asp Val Leu Asp Lys Arg Arg Gly Arg Asp Pro Glu
            355                 360                 365

Met Gly Gly Lys Pro Arg Arg Lys Asn Pro Gln Glu Gly Leu Tyr Asn
        370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
                420                 425                 430

Leu Pro Pro Arg
        435

<210> SEQ ID NO 47
<211> LENGTH: 431
<212> TYPE: PRT
<213> ORGANISM: Artificial Sequence
<220> FEATURE:
<223> OTHER INFORMATION: Synthetic Polypeptide -continued

```
<400> SEQUENCE: 47

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Phe Pro Pro Gly Tyr Gln
            195                 200                 205

Thr Thr Thr Pro Ala Pro Arg Pro Pro Thr Pro Ala Pro Thr Ile Ala
    210                 215                 220

Ser Gln Pro Leu Ser Leu Arg Pro Glu Ala Cys Arg Pro Ala Ala Gly
225                 230                 235                 240

Gly Ala Val His Thr Arg Gly Leu Asp Phe Ala Cys Asp Ile Tyr Ile
                245                 250                 255

Trp Ala Pro Leu Ala Gly Thr Cys Gly Val Leu Leu Leu Ser Leu Val
            260                 265                 270

Ile Thr Leu Tyr Cys Lys Arg Gly Arg Lys Lys Leu Leu Tyr Ile Phe
        275                 280                 285

Lys Gln Pro Phe Met Arg Pro Val Gln Thr Thr Gln Glu Glu Asp Gly
290                 295                 300

Cys Ser Cys Arg Phe Pro Glu Glu Glu Glu Gly Gly Cys Glu Leu Arg
305                 310                 315                 320

Val Lys Phe Ser Arg Ser Ala Asp Ala Pro Ala Tyr Gln Gln Gly Gln
                325                 330                 335

Asn Gln Leu Tyr Asn Glu Leu Asn Leu Gly Arg Arg Glu Glu Tyr Asp
            340                 345                 350

Val Leu Asp Lys Arg Arg Gly Arg Asp Pro Glu Met Gly Gly Lys Pro
        355                 360                 365

Arg Arg Lys Asn Pro Gln Glu Gly Leu Tyr Asn Glu Leu Gln Lys Asp
    370                 375                 380

Lys Met Ala Glu Ala Tyr Ser Glu Ile Gly Met Lys Gly Glu Arg Arg
385                 390                 395                 400

Arg Gly Lys Gly His Asp Gly Leu Tyr Gln Gly Leu Ser Thr Ala Thr
                405                 410                 415
```

```
Lys Asp Thr Tyr Asp Ala Leu His Met Gln Ala Leu Pro Pro Arg
            420                 425                 430

<210> SEQ ID NO 48
<211> LENGTH: 432
<212> TYPE: PRT
<213> ORGANISM: Artificial Sequence
<220> FEATURE:
<223> OTHER INFORMATION: Synthetic Polypeptide

<400> SEQUENCE: 48

Met Ala Leu Pro Val Thr Ala Leu Leu Leu Pro Leu Ala Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Cys Trp Leu Thr Lys Lys
        275                 280                 285

Lys Tyr Ser Ser Ser Val His Asp Pro Asn Gly Glu Tyr Met Phe Met
290                 295                 300

Arg Ala Val Asn Thr Ala Lys Lys Ser Arg Leu Thr Asp Val Thr Leu
305                 310                 315                 320

Arg Val Lys Phe Ser Arg Ser Ala Asp Ala Pro Ala Tyr Gln Gln Gly
                325                 330                 335

Gln Asn Gln Leu Tyr Asn Glu Leu Asn Leu Gly Arg Arg Glu Glu Tyr
            340                 345                 350
```

```
Asp Val Leu Asp Lys Arg Arg Gly Arg Asp Pro Glu Met Gly Gly Lys
            355                 360                 365

Pro Arg Arg Lys Asn Pro Gln Glu Gly Leu Tyr Asn Glu Leu Gln Lys
    370                 375                 380

Asp Lys Met Ala Glu Ala Tyr Ser Glu Ile Gly Met Lys Gly Glu Arg
385                 390                 395                 400

Arg Arg Gly Lys Gly His Asp Gly Leu Tyr Gln Gly Leu Ser Thr Ala
                405                 410                 415

Thr Lys Asp Thr Tyr Asp Ala Leu His Met Gln Ala Leu Pro Pro Arg
            420                 425                 430

<210> SEQ ID NO 49
<211> LENGTH: 442
<212> TYPE: PRT
<213> ORGANISM: Artificial Sequence
<220> FEATURE:
<223> OTHER INFORMATION: Synthetic Polypeptide

<400> SEQUENCE: 49

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
    195                 200                 205

Pro Pro Gly Tyr Gln Thr Thr Thr Pro Ala Pro Arg Pro Pro Thr Pro
        210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Gln Arg Arg Lys Tyr Arg
        275                 280                 285
```

Ser Asn Lys Gly Glu Ser Pro Val Glu Pro Ala Glu Pro Cys Arg Tyr
            290                 295                 300

Ser Cys Pro Arg Glu Glu Gly Ser Thr Ile Pro Ile Gln Glu Asp
305                 310                 315                 320

Tyr Arg Lys Pro Glu Pro Ala Cys Ser Pro Arg Val Lys Phe Ser Arg
                325                 330                 335

Ser Ala Asp Ala Pro Ala Tyr Gln Gln Gly Gln Asn Gln Leu Tyr Asn
            340                 345                 350

Glu Leu Asn Leu Gly Arg Arg Glu Glu Tyr Asp Val Leu Asp Lys Arg
                355                 360                 365

Arg Gly Arg Asp Pro Glu Met Gly Gly Lys Pro Arg Arg Lys Asn Pro
            370                 375                 380

Gln Glu Gly Leu Tyr Asn Glu Leu Gln Lys Asp Lys Met Ala Glu Ala
385                 390                 395                 400

Tyr Ser Glu Ile Gly Met Lys Gly Glu Arg Arg Arg Gly Lys Gly His
                405                 410                 415

Asp Gly Leu Tyr Gln Gly Leu Ser Thr Ala Thr Lys Asp Thr Tyr Asp
            420                 425                 430

Ala Leu His Met Gln Ala Leu Pro Pro Arg
            435                 440

<210> SEQ ID NO 50
<211> LENGTH: 452
<212> TYPE: PRT
<213> ORGANISM: Artificial Sequence
<220> FEATURE:
<223> OTHER INFORMATION: Synthetic Polypeptide

<400> SEQUENCE: 50

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
                260                 265                 270

Leu Leu Ser Leu Val Ile Thr Leu Tyr Cys Gln Leu Gly Leu His Ile
                275                 280                 285

Trp Gln Leu Arg Ser Gln Cys Met Trp Pro Arg Glu Thr Gln Leu Leu
                290                 295                 300

Leu Glu Val Pro Pro Ser Thr Glu Asp Ala Arg Ser Cys Gln Phe Pro
305                 310                 315                 320

Glu Glu Glu Arg Gly Glu Arg Ser Ala Glu Glu Lys Gly Arg Leu Gly
                325                 330                 335

Asp Leu Trp Val Arg Val Lys Phe Ser Arg Ser Ala Asp Ala Pro Ala
                340                 345                 350

Tyr Gln Gln Gly Gln Asn Gln Leu Tyr Asn Glu Leu Asn Leu Gly Arg
                355                 360                 365

Arg Glu Glu Tyr Asp Val Leu Asp Lys Arg Arg Gly Arg Asp Pro Glu
                370                 375                 380

Met Gly Gly Lys Pro Arg Arg Lys Asn Pro Gln Glu Gly Leu Tyr Asn
385                 390                 395                 400

Glu Leu Gln Lys Asp Lys Met Ala Glu Ala Tyr Ser Glu Ile Gly Met
                405                 410                 415

Lys Gly Glu Arg Arg Arg Gly Lys Gly His Asp Gly Leu Tyr Gln Gly
                420                 425                 430

Leu Ser Thr Ala Thr Lys Asp Thr Tyr Asp Ala Leu His Met Gln Ala
                435                 440                 445

Leu Pro Pro Arg
    450

<210> SEQ ID NO 51
<211> LENGTH: 454
<212> TYPE: PRT
<213> ORGANISM: Artificial Sequence
<220> FEATURE:
<223> OTHER INFORMATION: Synthetic Polypeptide

<400> SEQUENCE: 51

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
                35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
        130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
            245                 250                 255

Cys Asp Ile Tyr Ile Trp Ala Pro Leu Ala Gly Thr Cys Gly Val Leu
        260                 265                 270

Leu Leu Ser Leu Val Ile Thr Leu Tyr Cys Cys Val Lys Arg Arg Lys
    275                 280                 285

Pro Arg Gly Asp Val Val Lys Val Ile Val Ser Val Gln Arg Lys Arg
    290                 295                 300

Gln Glu Ala Glu Gly Glu Ala Thr Val Ile Glu Ala Leu Gln Ala Pro
305                 310                 315                 320

Pro Asp Val Thr Thr Val Ala Val Glu Glu Thr Ile Pro Ser Phe Thr
                325                 330                 335

Gly Arg Ser Pro Asn His Arg Val Lys Phe Ser Arg Ser Ala Asp Ala
            340                 345                 350

Pro Ala Tyr Gln Gln Gly Gln Asn Gln Leu Tyr Asn Glu Leu Asn Leu
        355                 360                 365

Gly Arg Arg Glu Glu Tyr Asp Val Leu Asp Lys Arg Arg Gly Arg Asp
    370                 375                 380

Pro Glu Met Gly Gly Lys Pro Arg Arg Lys Asn Pro Gln Glu Gly Leu
385                 390                 395                 400

Tyr Asn Glu Leu Gln Lys Asp Lys Met Ala Glu Ala Tyr Ser Glu Ile
                405                 410                 415

Gly Met Lys Gly Glu Arg Arg Arg Gly Lys Gly His Asp Gly Leu Tyr
            420                 425                 430

Gln Gly Leu Ser Thr Ala Thr Lys Asp Thr Tyr Asp Ala Leu His Met
        435                 440                 445

Gln Ala Leu Pro Pro Arg
    450

<210> SEQ ID NO 52
<211> LENGTH: 442
<212> TYPE: PRT
<213> ORGANISM: Artificial Sequence
<220> FEATURE:
<223> OTHER INFORMATION: Synthetic Polypeptide

<400> SEQUENCE: 52

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
 50                  55                  60

Trp Phe His Asn Glu Ser Leu Ile Ser Ser Gln Ala Ser Ser Tyr Phe
 65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Lys Lys Tyr Phe Phe Lys
        275                 280                 285

Lys Glu Val Gln Gln Leu Ser Val Ser Phe Ser Ser Leu Gln Ile Lys
290                 295                 300

Ala Leu Gln Asn Ala Val Glu Lys Glu Val Gln Ala Glu Asp Asn Ile
305                 310                 315                 320

Tyr Ile Glu Asn Ser Leu Tyr Ala Thr Asp Arg Val Lys Phe Ser Arg
                325                 330                 335

Ser Ala Asp Ala Pro Ala Tyr Gln Gln Gly Gln Asn Gln Leu Tyr Asn
            340                 345                 350

Glu Leu Asn Leu Gly Arg Arg Glu Glu Tyr Asp Val Leu Asp Lys Arg
        355                 360                 365

Arg Gly Arg Asp Pro Glu Met Gly Gly Lys Pro Arg Arg Lys Asn Pro
370                 375                 380

Gln Glu Gly Leu Tyr Asn Glu Leu Gln Lys Asp Lys Met Ala Glu Ala
385                 390                 395                 400

Tyr Ser Glu Ile Gly Met Lys Gly Glu Arg Arg Arg Gly Lys Gly His
                405                 410                 415

Asp Gly Leu Tyr Gln Gly Leu Ser Thr Ala Thr Lys Asp Thr Tyr Asp
            420                 425                 430

```
Ala Leu His Met Gln Ala Leu Pro Arg
        435             440
```

<210> SEQ ID NO 53
<211> LENGTH: 453
<212> TYPE: PRT
<213> ORGANISM: Artificial Sequence
<220> FEATURE:
<223> OTHER INFORMATION: Synthetic Polypeptide

<400> SEQUENCE: 53

```
Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Tyr Lys Val Gly Phe Phe
        275                 280                 285

Lys Arg Asn Leu Lys Glu Lys Met Glu Ala Gly Arg Gly Val Pro Asn
    290                 295                 300

Gly Ile Pro Ala Glu Asp Ser Glu Gln Leu Ala Ser Gly Gln Glu Ala
305                 310                 315                 320

Gly Asp Pro Gly Cys Leu Lys Pro Leu His Glu Lys Asp Ser Glu Ser
                325                 330                 335

Gly Gly Gly Lys Asp Arg Val Lys Phe Ser Arg Ser Ala Asp Ala Pro
            340                 345                 350
```

Ala Tyr Gln Gln Gly Gln Asn Gln Leu Tyr Asn Glu Leu Asn Leu Gly
                355                 360                 365

Arg Arg Glu Glu Tyr Asp Val Leu Asp Lys Arg Arg Gly Arg Asp Pro
            370                 375                 380

Glu Met Gly Gly Lys Pro Arg Arg Lys Asn Pro Gln Glu Gly Leu Tyr
385                 390                 395                 400

Asn Glu Leu Gln Lys Asp Lys Met Ala Glu Ala Tyr Ser Glu Ile Gly
                405                 410                 415

Met Lys Gly Glu Arg Arg Arg Gly Lys Gly His Asp Gly Leu Tyr Gln
            420                 425                 430

Gly Leu Ser Thr Ala Thr Lys Asp Thr Tyr Asp Ala Leu His Met Gln
                435                 440                 445

Ala Leu Pro Pro Arg
    450

<210> SEQ ID NO 54
<211> LENGTH: 510
<212> TYPE: PRT
<213> ORGANISM: Artificial Sequence
<220> FEATURE:
<223> OTHER INFORMATION: Synthetic Polypeptide

<400> SEQUENCE: 54

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

```
Cys Asp Ile Tyr Ile Trp Ala Pro Leu Ala Gly Thr Cys Gly Val Leu
             260                 265                 270

Leu Leu Ser Leu Val Ile Thr Leu Tyr Cys Lys Arg Lys Lys Gln Arg
        275                 280                 285

Ser Arg Arg Asn Asp Glu Glu Leu Glu Thr Arg Ala His Arg Val Ala
    290                 295                 300

Thr Glu Glu Arg Gly Arg Lys Pro His Gln Ile Pro Ala Ser Thr Pro
305                 310                 315                 320

Gln Asn Pro Ala Thr Ser Gln His Pro Pro Pro Pro Gly His Arg
                325                 330                 335

Ser Gln Ala Pro Ser His Arg Pro Pro Pro Gly His Arg Val Gln
            340                 345                 350

His Gln Pro Gln Lys Arg Pro Pro Ala Pro Ser Gly Thr Gln Val His
        355                 360                 365

Gln Gln Lys Gly Pro Pro Leu Pro Arg Pro Arg Val Gln Pro Lys Pro
    370                 375                 380

Pro His Gly Ala Ala Glu Asn Ser Leu Ser Pro Ser Ser Asn Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510

<210> SEQ ID NO 55
<211> LENGTH: 365
<212> TYPE: PRT
<213> ORGANISM: Artificial Sequence
<220> FEATURE:
<223> OTHER INFORMATION: Synthetic Polypeptide

<400> SEQUENCE: 55

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110
```

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
        130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Pro Gln Leu Cys Tyr Ile Leu Asp Ala Ile Leu Phe Leu Tyr
            260                 265                 270

Gly Ile Val Leu Thr Leu Leu Tyr Cys Arg Leu Lys Ile Gln Val Arg
        275                 280                 285

Lys Ala Ala Ile Thr Ser Tyr Glu Lys Ser Asp Gly Val Tyr Thr Gly
    290                 295                 300

Leu Ser Thr Arg Asn Gln Glu Thr Tyr Glu Thr Leu Lys His Glu Lys
305                 310                 315                 320

Pro Pro Gln Lys Arg Gly Arg Lys Lys Leu Leu Tyr Ile Phe Lys Gln
                325                 330                 335

Pro Phe Met Arg Pro Val Gln Thr Thr Gln Glu Glu Asp Gly Cys Ser
            340                 345                 350

Cys Arg Phe Pro Glu Glu Glu Glu Gly Gly Cys Glu Leu
        355                 360                 365

<210> SEQ ID NO 56
<211> LENGTH: 366
<212> TYPE: PRT
<213> ORGANISM: Artificial Sequence
<220> FEATURE:
<223> OTHER INFORMATION: Synthetic Polypeptide

<400> SEQUENCE: 56

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
    195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Lys Arg Gly Arg Lys Lys
    275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Leu Lys Ile Gln Val Arg Lys Ala Ala Ile Thr
                325                 330                 335

Ser Tyr Glu Lys Ser Asp Gly Val Tyr Thr Gly Leu Ser Thr Arg Asn
            340                 345                 350

Gln Glu Thr Tyr Glu Thr Leu Lys His Glu Lys Pro Pro Gln
    355                 360                 365

<210> SEQ ID NO 57
<211> LENGTH: 192
<212> TYPE: PRT
<213> ORGANISM: Artificial Sequence
<220> FEATURE:
<223> OTHER INFORMATION: Synthetic Polypeptide

<400> SEQUENCE: 57

Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Leu Ile Ser Ser Gln Ala Ser Ser Tyr Phe Ile Asp Ala Ala Thr
    50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
            115                 120                 125

Gly Lys Gly Arg Lys Tyr Phe His His Asn Ser Asp Phe Tyr Ile Pro
        130                 135                 140

Lys Ala Thr Leu Lys Asp Ser Gly Ser Tyr Phe Cys Arg Gly Leu Val
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Ser Phe Phe Pro Pro Gly Tyr Gln
            180                 185                 190

<210> SEQ ID NO 58
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 58

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 59
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 59

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 60
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 60

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys

```
                50                  55                  60
Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110

<210> SEQ ID NO 61
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 61

Met Ala Leu Pro Val Thr Ala Leu Leu Leu Pro Leu Ala Leu Leu Leu
 1               5                  10                  15

His Ala Ala Arg Pro
             20

<210> SEQ ID NO 62
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 62
cttctgcagg gggcttgttg ggagtaaaaa tgtgtc                            36

<210> SEQ ID NO 63
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 63
gacacatttt tactcccaac aagcccctg cagaag                             36

<210> SEQ ID NO 64
<211> LENGTH: 1311
<212> TYPE: DNA
<213> ORGANISM: Artificial Sequence
<220> FEATURE:
<223> OTHER INFORMATION: Synthetic Polynucleotide

<400> SEQUENCE: 64
atggccttac cagtgaccgc cttgctcctg ccgctggcct tgctgctcca cgccgccagg    60
ccgggcatgc ggactgaaga tctcccaaag gctgtggtgt cctggagcc tcaatggtac    120 agggtgctcg agaaggacag tgtgactctg aagtgccagg agcctactc ccctgaggac    180 aattccacac agtggtttca caatgagagc ctcatctcaa gccaggcctc gagctacttc    240
attgacgctg ccacagtcga cgacagtgga gagtacaggt gccagacaaa cctctccacc    300
ctcagtgacc cggtgcagct agaagtccat atcggctggc tgttgctcca ggcccctcgg    360
tgggtgttca aggaggaaga ccctattcac ctgaggtgtc acagctggaa gaacactgct    420
ctgcataagg tcacatattt cagaatggca aaggcagga agtatttcca tcataattct    480
gacttctaca ttccaaaagc cacactcaaa gacagcggct cctacttctg cagggggctt    540
```

```
gttgggagta aaaatgtgtc ttcagagact gtgaacatca ccatcactca aggtttggca      600
gtgtcaacca tctcatcatt ctttccacct gggtaccaaa ccacgacgcc agcgccgcga      660
ccaccaacac cggcgcccac catcgcgtcg cagcccctgt ccctgcgccc agaggcgtgc      720
cggccagcgg cgggggggcgc agtgcacacg aggggggctgg acttcgcctg tgatatctac    780
atctgggcgc ccttggccgg gacttgtggg gtccttctcc tgtcactggt tatcacccctt    840 tactgcaaac ggggcagaaa gaaactcctg tatatattca acaaccatt tatgagacca      900 gtacaaacta ctcaagagga gatggctgt agctgccgat tccagaaga agaagaagga       960 ggatgtgaac tgagagtgaa gttcagcagg agcgcagacg ccccgcgta ccagcagggc     1020 cagaaccagc tctataacga gctcaatcta ggacgaagag aggagtacga tgttttggac    1080
aagagacgtg gccgggaccc tgagatgggg ggaaagccga aaggaagaa ccctcaggaa     1140 ggcctgtaca atgaactgca gaaagataag atggcggagg cctacagtga gattgggatg    1200
aaaggcgagc gccggagggg caaggggcac gatggccttt accagggtct cagtacagcc    1260
accaaggaca cctacgacgc ccttcacatg caggccctgc ccctcgcta a              1311

<210> SEQ ID NO 65
<211> LENGTH: 576
<212> TYPE: DNA
<213> ORGANISM: Artificial Sequence
<220> FEATURE:
<223> OTHER INFORMATION: Synthetic Polynucleotide

<400> SEQUENCE: 65
ggcatgcgga ctgaagatct cccaaaggct gtggtgttcc tggagcctca atggtacagg     60
gtgctcgaga aggacagtgt gactctgaag tgccagggag cctactcccc tgaggacaat    120
tccacacagt ggtttcacaa tgagagcctc atctcaagcc aggcctcgag ctacttcatt    180
gacgctgcca cagtcgacga cagtggagag tacaggtgcc agacaaacct ctccacctc    240 agtgacccgg tgcagctaga agtccatatc ggctggctgt tgctccaggc ccctcggtgg    300
gtgttcaagg aggaagaccc tattcacctg aggtgtcaca gctggaagaa cactgctctg    360
cataaggtca catatttaca gaatggcaaa ggcaggaagt attttcatca taattctgac    420
ttctacattc caaaagccac actcaaagac agcggctcct acttctgcag ggggcttgtt    480
gggagtaaaa atgtgtcttc agagactgtg aacatcacca tcactcaagg tttggcagtg    540
tcaaccatct catcattctt tccacctggg taccaa                              576

<210> SEQ ID NO 66
<211> LENGTH: 207
<212> TYPE: DNA
<213> ORGANISM: Artificial Sequence
<220> FEATURE:
<223> OTHER INFORMATION: Synthetic Polynucleotide

<400> SEQUENCE: 66
accacgacgc cagcgccgcg accaccaaca ccggcgccca ccatcgcgtc gcagcccctg     60
tccctgcgcc cagaggcgtg ccggccagcg gcgggggggcg cagtgcacac gagggggctg   120
gacttcgcct gtgatatcta catctgggcg cccttggccg ggacttgtgg ggtccttctc   180
ctgtcactgg ttatcaccct ttactgc                                        207

<210> SEQ ID NO 67
<211> LENGTH: 126
<212> TYPE: DNA
<213> ORGANISM: Artificial Sequence
```

```
<220> FEATURE:
<223> OTHER INFORMATION: Synthetic Polynucleotide

<400> SEQUENCE: 67
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 68
<211> LENGTH: 339
<212> TYPE: DNA
<213> ORGANISM: Artificial Sequence
<220> FEATURE:
<223> OTHER INFORMATION: Synthetic Polynucleotide

<400> SEQUENCE: 68
agagtgaagt tcagcaggag cgcagacgcc ccgcgtacc agcagggcca gaaccagctc      60
tataacgagc tcaatctagg acgaagagag gagtacgatg ttttggacaa gagacgtggc    120
cgggaccctg agatggggg aaagccgaga aggaagaacc ctcaggaagg cctgtacaat     180
gaactgcaga agataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgctaa                            339

<210> SEQ ID NO 69
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 69
atggccttac cagtgaccgc cttgctcctg ccgctggcct tgctgctcca cgccgccagg      60
ccg                                                                    63

<210> SEQ ID NO 70
<211> LENGTH: 192
<212> TYPE: PRT
<213> ORGANISM: Artificial Sequence
<220> FEATURE:
<223> OTHER INFORMATION: Synthetic Polypeptide

<400> SEQUENCE: 70

Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Leu Ile Ser Ser Gln Ala Ser Ser Tyr Phe Ile Asp Ala Ala Thr
    50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
```

```
                115             120             125
Gly Lys Gly Arg Lys Tyr Phe His His Asn Ser Asp Phe Tyr Ile Pro
        130                 135                 140

Lys Ala Thr Leu Lys Asp Ser Gly Ser Tyr Phe Cys Arg Gly Leu Phe
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Ser Phe Phe Pro Pro Gly Tyr Gln
        180                 185                 190
```

<210> SEQ ID NO 71
<211> LENGTH: 1311
<212> TYPE: DNA
<213> ORGANISM: Artificial Sequence
<220> FEATURE:
<223> OTHER INFORMATION: Synthetic Polynucleotide

<400> SEQUENCE: 71

```
atggccttac cagtgaccgc cttgctcctg ccgctggcct tgctgctcca cgccgccagg    60
ccgggcatgc ggactgaaga tctcccaaag gctgtggtgt tcctggagcc tcaatggtac   120
agggtgctcg agaaggacag tgtgactctg aagtgccagg gagcctactc ccctgaggac   180
aattccacac agtggtttca caatgagagc ctcatctcaa gccaggcctc gagctacttc   240
attgacgctg ccacagtcga cgacagtgga gagtacaggt gccagacaaa cctctccacc   300
ctcagtgacc cggtgcagct agaagtccat atcggctggc tgttgctcca ggcccctcgg   360
tgggtgttca aggaggaaga ccctattcac ctgaggtgtc acagctggaa gaacactgct   420
ctgcataagg tcacatattt cagaatggc aaaggcagga agtattttca tcataattct   480
gacttctaca ttccaaaagc cacactcaaa gacagcggct cctacttctg caggggcttt   540
tttggagta aaaatgtgtc ttcagagact gtgaacatca ccatcactca aggtttggca   600
gtgtcaacca tctcatcatt cttccacct gggtaccaaa ccacgacgcc agcgccgcga   660
ccaccaacac cggcgcccac catcgcgtcg cagcccctgt ccctgcgccc agaggcgtgc   720
cggccagcgg cgggggggcgc agtgcacacg aggggggctgg acttcgcctg tgatatctac   780
atctgggcgc ccttggccgg gacttgtggg gtccttctcc tgtcactggt tatcaccctt   840
tactgcaaac ggggcagaaa gaaactcctg tatatattca acaaccatt tatgagacca   900
gtacaaacta ctcaagagga gatggctgt agctgccgat tccagaaga agaagaagga   960
ggatgtgaac tgagagtgaa gttcagcagg agcgcagacg cccccgcgta ccagcagggc  1020
cagaaccagc tctataacga gctcaatcta ggacgaagag aggagtacga tgttttggac  1080
aagagacgtg gccgggaccc tgagatgggg ggaaagccga aaggaagaa ccctcaggaa  1140
ggcctgtaca atgaactgca gaaagataag atggcggagg cctacagtga gattgggatg  1200
aaaggcgagc gccggagggg caaggggcac gatggccttt accagggtct cagtacagcc  1260
accaaggaca cctacgacgc ccttcacatg caggccctgc ccctcgcta a             1311
```

<210> SEQ ID NO 72
<211> LENGTH: 576
<212> TYPE: DNA
<213> ORGANISM: Artificial Sequence
<220> FEATURE:
<223> OTHER INFORMATION: Synthetic Polynucleotide

<400> SEQUENCE: 72

```
ggcatgcgga ctgaagatct cccaaaggct gtggtgttcc tggagcctca atggtacagg    60
```

```
gtgctcgaga aggacagtgt gactctgaag tgccagggag cctactcccc tgaggacaat    120
tccacacagt ggtttcacaa tgagagcctc atctcaagcc aggcctcgag ctacttcatt    180
gacgctgcca cagtcgacga cagtggagag tacaggtgcc agacaaacct ctccaccctc    240
agtgacccgg tgcagctaga agtccatatc ggctggctgt tgctccaggc ccctcggtgg    300
gtgttcaagg aggaagaccc tattcacctg aggtgtcaca gctggaagaa cactgctctg    360
cataaggtca catatttaca gaatggcaaa ggcaggaagt attttcatca taattctgac    420
ttctacattc caaaagccac actcaaagac agcggctcct acttctgcag ggggcttttt    480
gggagtaaaa atgtgtcttc agagactgtg aacatcacca tcactcaagg tttggcagtg    540
tcaaccatct catcattctt tccacctggg taccaa                              576
```

<210> SEQ ID NO 73
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 73

```
cttctgcagg gggcttgttg ggagtaaaaa tgtgtc                               36
```

<210> SEQ ID NO 74
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 74

```
gacacatttt tactcccaac aagcccctg cagaag                                36
```

<210> SEQ ID NO 75
<211> LENGTH: 254
<212> TYPE: PRT
<213> ORGANISM: Artificial Sequence
<220> FEATURE:
<223> OTHER INFORMATION: Synthetic Polypeptide

<400> SEQUENCE: 75

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
            165                 170                 175

Gly Ser Lys Asn Val Ser Ser Glu Thr Val Asn Ile Thr Ile Thr Gln
        180                 185                 190

Gly Leu Ala Val Ser Thr Ile Ser Ser Phe Phe Pro Pro Gly Tyr Gln
    195                 200                 205

Val Ser Phe Cys Leu Val Met Val Leu Leu Phe Ala Val Asp Thr Gly
210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 76
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 76

Gly Gly Gly Gly Ser
1               5

<210> SEQ ID NO 77
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 77

Gly Gly Gly Gly Ser Gly Gly Gly Gly Ser Gly Gly Gly Gly Ser
1               5                   10                  15

<210> SEQ ID NO 78
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 78

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 79
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 79

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Ser Gly Gly Gly Gly Ser
         35                  40                  45

<210> SEQ ID NO 80
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 80

Gly Gly Gly Gly Ser Gly Gly Gly Ser Gly Gly Gly Gly Ser Gly
1               5                   10                  15

Gly Gly Ser Gly Gly Gly Gly Ser Gly Gly Gly Ser Gly Gly
            20                  25                  30

Gly Gly Ser Gly Gly Gly Gly Ser Gly Gly Gly Ser Gly Gly
            35                  40                  45

Gly Ser Gly Gly Gly Gly Ser Gly Gly Gly Gly Ser
        50                  55                  60

<210> SEQ ID NO 81
<211> LENGTH: 75
<212> TYPE: PRT
<213> ORGANISM: Artificial Sequence
<220> FEATURE:
<223> OTHER INFORMATION: Synthetic Polypeptide

<400> SEQUENCE: 81

Gly Gly Gly Gly Ser Gly Gly Gly Gly Ser Gly Gly Gly Ser Gly
1               5                   10                  15

Gly Gly Ser Gly Gly Gly Gly Ser Gly Gly Gly Ser Gly Gly Gly
            20                  25                  30

Gly Gly Ser Gly Gly Gly Gly Ser Gly Gly Gly Ser Gly Gly Gly
            35                  40                  45

Gly Ser Gly Gly Gly Gly Ser Gly Gly Gly Ser Gly Gly Gly Gly
        50                  55                  60

Ser Gly Gly Gly Gly Ser Gly Gly Gly Gly Ser
65                  70                  75

<210> SEQ ID NO 82
<211> LENGTH: 150
<212> TYPE: PRT
<213> ORGANISM: Artificial Sequence
<220> FEATURE:
<223> OTHER INFORMATION: Synthetic Polypeptide

<400> SEQUENCE: 82

Gly Gly Gly Gly Ser Gly Gly Gly Gly Ser Gly Gly Gly Ser Gly
1               5                   10                  15

Gly Gly Gly Ser Gly Gly Gly Ser Gly Gly Gly Ser Gly Gly Gly
            20                  25                  30

Gly Gly Ser Gly Gly Gly Gly Ser Gly Gly Gly Ser Gly Gly Gly
            35                  40                  45

Gly Ser Gly Gly Gly Gly Ser Gly Gly Gly Ser Gly Gly Gly Gly
        50                  55                  60

Ser Gly Gly Gly Gly Ser Gly Gly Gly Gly Ser Gly Gly Gly Ser
65                  70                  75                  80

Gly Gly Gly Gly Ser Gly Gly Gly Gly Ser Gly Gly Gly Ser Gly
                85                  90                  95

Gly Gly Gly Ser Gly Gly Gly Gly Ser Gly Gly Gly Ser Gly Gly
            100                 105                 110

Gly Gly Ser Gly Gly Gly Ser Gly Gly Gly Ser Gly Gly Gly
        115                 120                 125

Gly Ser Gly Gly Gly Ser Gly Gly Gly Ser Gly Gly Gly Gly
    130                 135                 140

Ser Gly Gly Gly Gly Ser
145                 150

<210> SEQ ID NO 83
<211> LENGTH: 225
<212> TYPE: PRT
<213> ORGANISM: Artificial Sequence
<220> FEATURE:
<223> OTHER INFORMATION: Synthetic Polypeptide

<400> SEQUENCE: 83

Gly Gly Gly Gly Ser Gly Gly Gly Ser Gly Gly Gly Ser Gly
1               5                   10                  15

Gly Gly Gly Ser Gly Gly Gly Gly Ser Gly Gly Gly Ser Gly Gly
            20                  25                  30

Gly Gly Ser Gly Gly Gly Ser Gly Gly Gly Ser Gly Gly Gly
        35                  40                  45

Gly Ser Gly Gly Gly Ser Gly Gly Gly Ser Gly Gly Gly Gly
    50                  55                  60

Ser Gly Gly Gly Gly Ser Gly Gly Gly Ser Gly Gly Gly Ser
65                  70                  75                  80

Gly Gly Gly Gly Ser Gly Gly Gly Ser Gly Gly Gly Ser Gly
                85                  90                  95

Gly Gly Gly Ser Gly Gly Gly Ser Gly Gly Gly Ser Gly Gly
            100                 105                 110

Gly Gly Ser Gly Gly Gly Ser Gly Gly Gly Ser Gly Gly Gly
        115                 120                 125

Gly Ser Gly Gly Gly Ser Gly Gly Gly Ser Gly Gly Gly Gly
    130                 135                 140

Ser Gly Gly Gly Ser Gly Gly Gly Ser Gly Gly Gly Gly Ser
145                 150                 155                 160

Gly Gly Gly Gly Ser Gly Gly Gly Ser Gly Gly Gly Ser Gly
                165                 170                 175

Gly Gly Gly Ser Gly Gly Gly Ser Gly Gly Gly Ser Gly Gly
            180                 185                 190

Gly Gly Ser Gly Gly Gly Ser Gly Gly Gly Ser Gly Gly Gly
        195                 200                 205

Gly Ser Gly Gly Gly Ser Gly Gly Gly Ser Gly Gly Gly Gly
    210                 215                 220

Ser
225

<210> SEQ ID NO 84
<211> LENGTH: 300
<212> TYPE: PRT
<213> ORGANISM: Artificial Sequence
<220> FEATURE:
<223> OTHER INFORMATION: Synthetic Polypeptide

<400> SEQUENCE: 84

Gly Gly Gly Gly Ser Gly Gly Gly Gly Ser Gly Gly Gly Ser Gly
1               5                   10                  15

-continued

```
Gly Gly Gly Ser Gly Gly Gly Ser Gly Gly Gly Ser Gly Gly
            20              25              30
Gly Gly Ser Gly Gly Gly Gly Ser Gly Gly Gly Gly Ser Gly Gly Gly
        35                  40                  45
Gly Ser Gly Gly Gly Gly Ser Gly Gly Gly Gly Ser Gly Gly Gly Gly
    50                  55                  60
Ser Gly Gly Gly Gly Ser Gly Gly Gly Gly Ser Gly Gly Gly Gly Ser
65                  70                  75                  80
Gly Gly Gly Gly Ser Gly Gly Gly Gly Ser Gly Gly Gly Gly Ser Gly
            85                  90                  95
Gly Gly Gly Ser Gly Gly Gly Gly Ser Gly Gly Gly Gly Ser Gly Gly
            100                 105                 110
Gly Gly Ser Gly Gly Gly Gly Ser Gly Gly Gly Gly Ser Gly Gly Gly
        115                 120                 125
Gly Ser Gly Gly Gly Gly Ser Gly Gly Gly Gly Ser Gly Gly Gly Gly
    130                 135                 140
Ser Gly Gly Gly Gly Ser Gly Gly Gly Gly Ser Gly Gly Gly Gly Ser
145                 150                 155                 160
Gly Gly Gly Gly Ser Gly Gly Gly Gly Ser Gly Gly Gly Gly Ser Gly
            165                 170                 175
Gly Gly Gly Ser Gly Gly Gly Gly Ser Gly Gly Gly Gly Ser Gly Gly
            180                 185                 190
Gly Gly Ser Gly Gly Gly Gly Ser Gly Gly Gly Gly Ser Gly Gly Gly
        195                 200                 205
Gly Ser Gly Gly Gly Gly Ser Gly Gly Gly Gly Ser Gly Gly Gly Gly
    210                 215                 220
Ser Gly Gly Gly Gly Ser Gly Gly Gly Gly Ser Gly Gly Gly Gly Ser
225                 230                 235                 240
Gly Gly Gly Gly Ser Gly Gly Gly Gly Ser Gly Gly Gly Gly Ser Gly
            245                 250                 255
Gly Gly Gly Ser Gly Gly Gly Gly Ser Gly Gly Gly Gly Ser Gly Gly
            260                 265                 270
Gly Gly Ser Gly Gly Gly Gly Ser Gly Gly Gly Gly Ser Gly Gly Gly
        275                 280                 285
Gly Ser Gly Gly Gly Gly Ser Gly Gly Gly Gly Ser
    290                 295                 300
```

CHIMERIC RECEPTORS AND USES THEREOF IN IMMUNE THERAPY

CROSS REFERENCE TO RELATED APPLICATIONS

This application claims the benefit of U.S. Provisional Application No. 61/892,218, filed Oct. 17, 2013, U.S. Provisional Application No. 62/026,243, filed Jul. 18, 2014, and U.S. Provisional Application No. 62/047,916, filed Sep. 9, 2014, under 35 U.S.C. § 119. The entire content of all prior applications is herein incorporated by reference.

SEQUENCE LISTING

The instant application contains a Sequence Listing which has been submitted in ASCII format via EFS-Web and is hereby incorporated by reference in its entirety. Said ASCII copy, created on Oct. 17, 2014, is named U119970000US01-SEQ-YJC.txt and is 241,271 bytes in size.

BACKGROUND OF DISCLOSURE

Cancer immunotherapy, including cell-based therapy, antibody therapy and cytokine therapy, is used to provoke immune responses attacking tumor cells while sparing normal tissues. It is a promising option for treating various types of cancer because of its potential to evade genetic and cellular mechanisms of drug resistance, and to target tumor cells while sparing normal tissues. T-lymphocytes can exert major anti-tumor effects as demonstrated by results of allogeneic hematopoietic stem cell transplantation (HSCT) for hematologic malignancies, where T-cell-mediated graft-versus-host disease (GvHD) is inversely associated with disease recurrence, and immunosuppression withdrawal or infusion of donor lymphocytes can contain relapse. Weiden et al., *N Engl J Med.* 1979; 300(19):1068-1073; Porter et al., *N Engl J Med.* 1994; 330(2):100-106; Kolb et al., *Blood.* 1995; 86(5):2041-2050; Slavin et al., *Blood.* 1996; 87(6): 2195-2204; and Appelbaum, *Nature.* 2001; 411(6835):385-389.

Cell-based therapy may involve cytotoxic T cells having reactivity skewed toward cancer cells. Eshhar et al., *Proc. Natl. Acad. Sci. U.S.A.;* 1993; 90(2):720-724; Geiger et al., *J Immunol.* 1999; 162(10):5931-5939; Brentjens et al., *Nat. Med.* 2003; 9(3):279-286; Cooper et al., *Blood.* 2003; 101 (4):1637-1644; and Imai et al., *Leukemia.* 2004; 18:676-684. One approach is to express a chimeric antigen receptor having an antigen-binding domain fused to one or more T cell activation signaling domains. Binding of a cancer antigen via the antigen-binding domain results in T cell activation and triggers cytotoxicity. Recent results of clinical trials with infusions of chimeric receptor-expressing autologous T lymphocytes provided compelling evidence of their clinical potential. Pule et al., *Nat. Med.* 2008; 14(11):1264-1270; Porter et al., *N Engl J Med;* 2011; 25; 365(8):725-733; Brentjens et al., *Blood.* 2011; 118(18):4817-4828; Till et al., *Blood.* 2012; 119(17):3940-3950; Kochenderfer et al., *Blood.* 2012; 119(12):2709-2720; and Brentjens et al., *Sci Transl Med.* 2013; 5(177):177ra138.

Antibody-based immunotherapies, such as monoclonal antibodies, antibody-fusion proteins, and antibody drug conjugates (ADCs) are used to treat a wide variety of diseases, including many types of cancer. Such therapies may depend on recognition of cell surface molecules that are differentially expressed on cells for which elimination is desired (e.g., target cells such as cancer cells) relative to normal cells (e.g., non-cancer cells). Binding of an antibody-based immunotherapy to a cancer cell can lead to cancer cell death via various mechanisms, e.g., antibody-dependent cell-mediated cytotoxicity (ADCC), complement-dependent cytotoxicity (CDC), or direct cytotoxic activity of the payload from an antibody-drug conjugate (ADC).

SUMMARY OF DISCLOSURE

The present disclosure is based on the design of chimeric receptors comprising an extracellular domain with affinity and specificity for the Fc portion of an IgG antibody, a transmembrane domain, at least one co-stimulatory signaling domain, and a cytoplasmic signaling domain that comprises an immunoreceptor tyrosine-based activation motif (ITAM). Immune cells expressing such a chimeric receptor construct would enhance efficacy of immune therapy such as antibody-based immunotherapies via, e.g., enhancing ADCC activity.

Accordingly, one aspect of the present disclosure features a chimeric receptor that comprises (a) an extracellular domain that binds to the Fc portion of an immunoglobulin gamma chain (IgG); (b) a transmembrane domain; (c) at least one co-stimulatory signaling domain; and (d) a cytoplasmic signaling domain that comprises an ITAM. Either the at least one co-stimulatory signaling domain or the cytoplasmic signaling domain that comprises an ITAM can be localized at the C-terminus of a chimeric receptor construct as described herein. In some embodiments, the ITAM-containing cytoplasmic signaling domain is located at the C-terminus of a chimeric receptor construct. In some embodiments, (a) is an extracellular ligand-binding domain of CD16 (e.g., CD16A or CD16B) and (d) does not comprise an ITAM of an Fc receptor. In some embodiments, (d) is a cytoplasmic signaling domain of CD3ζ or FcεR1γ. The chimeric receptors described herein may further comprise (e) a hinge domain, which can be located at the C-terminus of (a) and the N-terminus of (b).

In some embodiments, (a) of the chimeric receptor construct described herein is an extracellular ligand-binding domain of an Fc receptor such as Fc-gamma receptor, an Fc-alpha receptor, or an Fc-epsilon receptor. For example, (a) can be an extracellular ligand-binding domain of CD16 (e.g., CD16A or CD16B), CD32 (e.g., CD32A, or CD32B), or CD64 (e.g., CD64A, CD64B, or CD64C). In some examples, (a) is not the extracellular ligand-binding domain of CD16.

In other embodiments, (a) is of a non-Fc receptor naturally-occurring protein capable of binding to the Fc portion of an IgG molecule. For example, (a) may be all or part of protein A or protein G. Alternatively, (a) may be an antibody fragment that binds the Fc portion of an IgG molecule, including, but not limited to a single-chain variable fragment (scFv), or a domain antibody, a nanobody.

In yet other embodiments, (a) is a designed (e.g., non-naturally occurring) peptide capable of binding to the Fc portion of an IgG molecule, including a Kunitz domain peptide, a small modular immunopharmaceutical (SMIP), an adnectin, an avimer, an affibody, a DARPin, or an anticalin.

Alternatively or in addition, the transmembrane domain of the chimeric receptor is of a single-pass membrane protein, including, but not limited to, CD8α, CD8β, 4-1BB, CD28, CD34, CD4, FcεRIγ, CD16 (e.g., CD16A or CD16B), OX40, CD3ζ, CD3ε, CD3γ, CD3δ, TCRα, CD32 (e.g., CD32A or CD32B), CD64 (e.g., CD64A, CD64B, or CD64C), VEGFR2, FAS, and FGFR2B. In some examples, the membrane protein is not CD8α. The transmembrane domain may also be a non-naturally occurring hydrophobic protein segment.

In any of the chimeric receptor constructs described herein, the at least one co-stimulatory signaling domain of the chimeric receptor described herein may be of a co-stimulatory molecule such as 4-1BB (also known as CD137), CD28, CD28$_{LL\_GG}$ variant, OX40, ICOS, CD27, GITR, HVEM, TIM1, LFA1, or CD2. In some examples, the at least one co-stimulatory signaling domain is not from 4-1BB. In some examples, the chimeric receptor comprises two co-stimulatory signaling domains, e.g., CD28 and 4-1BB, or CD28$_{LL\_GG}$ variant and 4-1BB.

In any of the chimeric receptors described herein, the hinge domain can be of a protein such as CD8α, or IgG. For example, the hinge domain can be a fragment of the transmembrane or hinge domain of CD8α. In some examples, the hinge domain is not the hinge domain of CD8α. In some examples, the hinge domain is a non-naturally occurring peptide, such as an polypeptide consisting of hydrophilic residues of varying length (XTEN) or a (Gly$_4$Ser)$_n$ polypeptide, in which n is an integer of 3-12, inclusive.

In some embodiments, any of the chimeric receptors described herein may further comprise a signal peptide at its N-terminus.

Examples of the chimeric receptors described herein may comprise components (a)-(e) as shown in Table 3, Table 4, and Table 5. In some examples, the chimeric receptor comprises the amino acid sequence selected from SEQ ID NOs:2-30 and 32-56, or a fragment thereof which excludes the signal peptide of a reference sequence.

In specific embodiments, the present disclosure provides chimeric receptors comprising (a) an extracellular ligand-binding domain of F158 FCGR3A or V158 FCGR3A variant, (b) a hinge and transmembrane domain of CD8α, (c) a co-stimulatory signaling domain of 4-1BB, and (d) a cytoplasmic signaling domain of CD3ζ. Optionally, such a chimeric receptor may further comprise a signal peptide of CD8α. In some examples, the extracellular domain of F158 FCGR3A and V158 FCGR3A variant consist of the amino acid sequences of SEQ ID NO:70 and SEQ ID NO:57, respectively. In some examples, the hinge and transmembrane domains of CD8α consist of the amino acid sequence of SEQ ID NO: 58. In some examples, the co-stimulatory signaling domain of 4-1BB consists of the amino acid sequence of SEQ ID NO: 59. In some examples, the cytoplasmic signaling domain of CD3ζ consists of the amino acid sequence of SEQ ID NO: 60. Alternatively or in addition, the signal peptide of CD8α consists of the amino acid sequence of SEQ ID NO: 61. The chimeric receptor may comprise the amino acid sequence of residues 22 to 436 of SEQ ID NO: 1, or residues 22 to 436 of SEQ ID NO: 31. In some examples, it may comprise the amino acid sequence of SEQ ID NO: 1 or SEQ ID NO:31.

In another aspect, the present disclosure features a nucleic acid (e.g., a DNA molecule or an RNA molecule) comprising a nucleotide sequence encoding any of the chimeric receptors described herein; vectors (e.g., expression vectors) comprising the nucleic acid; and host cells (e.g., immune cells such as natural killer cells, macrophages, neutrophils, eosinophils, and T cells). In some embodiments, the vector is a viral vector, e.g., a lentiviral vector or a retroviral vector. In some embodiments, the vector is a transposon or contains a transposon.

In some embodiments, the nucleic acid as described herein comprises a nucleotide sequence that encodes the amino acid sequence of residues 22 to 436 of SEQ ID NO:1, or residues 22 to 436 of SEQ ID NO: 31. In one example, the nucleotide sequence encodes the amino acid sequence of SEQ ID NO:1 or SEQ ID NO: 31. In some examples, the nucleotide sequence comprises SEQ ID NO: 64 or SEQ ID NO: 71.

In some embodiments, the host cell as described herein is a T lymphocyte or an NK cell., both of which may be activated and/or expanded ex vivo. In some examples, the T lymphocyte or NK cell is an autologous T lymphocyte or an autologous NK cell isolated from a patient having a cancer. In some examples, the T lymphocyte or NK cell is an allogenic T lymphocyte or an allogenic NK cell. The T lymphocyte may be an allogeneic T lymphocyte, in which the expression of the endogenous T cell receptor has been inhibited or eliminated. Alternatively or in addition, the T lymphocyte is activated in the presence of one or more agents selected from the group consisting of anti-CD3/CD28, IL-2, and phytohemoagglutinin. The NK cell is activated in the presence of one or more agents selected from the group consisting of CD137 ligand protein, CD137 antibody, IL-15 protein, IL-15 receptor antibody, IL-2 protein, IL-12 protein, IL-21 protein, and K562 cell line.

In yet another aspect, described herein are pharmaceutical compositions that comprise (a) any of the nucleic acids or host cells described herein, and (b) a pharmaceutically acceptable carrier. In some examples, the composition may further comprise an Fc-containing protein such as an antibody or an Fc-fusion protein. In some examples, the antibody is cytotoxic to cancer cells. Such an antibody may comprise a human or humanized Fc portion which binds to human CD16 (FCGR3A). Therapeutic antibody, including, but not limited to, Adalimumab, Ado-Trastuzumab emtansine, Alemtuzumab, Basiliximab, Bevacizumab, Belimumab, Brentuximab, Canakinumab, Cetuximab, Daclizumab, Denosumab, Dinutuximab, Eculizumab, Efalizumab, Epratuzumab, Gemtuzumab, Golimumab, Infliximab, Ipilimumab, Labetuzumab, Natalizumab, Obinutuzumab, Ofatumumab, Omalizumab, Palivizumab, Panitumumab, Pertuzumab, Ramucirumab, Ritutimab, Tocilizumab, Tratuzumab, Ustekinumab, or Vedolizumab.

Also provided herein are kits comprising (a) a first pharmaceutical composition that comprises any of the nucleic acids or host cells described herein, and a pharmaceutically acceptable carrier; and (b) a second pharmaceutical composition that comprises an Fc-containing protein such as an antibody or an Fc-fusion protein (e.g., those described herein) and a pharmaceutically acceptable carrier.

Further, the present disclosure provides methods for enhancing antibody-dependent cell-mediated cytotoxicity (ADCC) in a subject. The method comprises administering to a subject in need of the treatment (e.g., a human cancer patient) an effective amount of host cells that express any of the chimeric receptors provided herein. In some embodiments, the host cells are immune cells such as natural killer cells, macrophages, neutrophils, eosinophils, T cells, or a combination thereof. In some examples, the host immune cells are autologous. In other examples, the host immune cells are allogeneic. Any of the host immune cells may be activated, expanded, or both ex vivo.

The subject may be subjected to treatment by an anti-cancer antibody, which may comprise a human or humanized Fc portion that binds to human CD16. The subject may be a patient having a cancer, such as carcinoma, lymphoma, sarcoma, blastomas, and leukemia. For example, the patient may have a cancer of B-cell origin, breast cancer, gastric cancer, neuroblastoma, osteosarcoma, lung cancer, melanoma, prostate cancer, colon cancer, renal cell carcinoma, ovarian cancer, rhabdomyosarcoma, leukemia, and Hodgkin's lymphoma. Cancers of B-cell origin include, but not limited to, B-lineage acute lymphoblastic leukemia, B-cell chronic lymphocytic leukemia, and B-cell non-Hodgkin's lymphoma.

In another aspect, the present disclosure is related to methods for enhancing efficacy of an antibody-based immunotherapy. The method comprises administering an effective amount of host cells that express any of the chimeric receptors provided herein to a subject who has been treated or is being treated with a therapeutic antibody (e.g., any of the therapeutic antibodies described herein). Exemplary host immune cells include, but are not limited to, natural killer cells, macrophages, neutrophils, eosinophils, T cells, or a combination thereof. In some examples, the host immune cells are autologous. In other examples, the host immune cells are allogeneic. Any of the host immune cells may be activated, expanded, or both ex vivo.

In some examples, the host cells bearing the chimeric receptor are co-administered with an Fc-containing protein, e.g., those described herein. In some examples, host cells bearing the chimeric receptor are administered before or after the Fc-containing protein. In some examples, host cells bearing the chimeric receptor are administered first and Fc-containing protein is subsequently administered stepwise to increase concentration until a therapeutic response is observed.

In any of the methods provided herein, the subject may be a human patient suffering from a cancer and the therapeutic antibody is for treating the cancer. In some examples, the cancer is lymphoma, breast cancer, gastric cancer, neuroblastoma, osteosarcoma, lung cancer, skin cancer, prostate cancer, colon cancer, renal cell carcinoma, ovarian cancer, rhabdomyosarcoma, leukemia, mesothelioma, pancreatic cancer, head and neck cancer, retinoblastoma, glioma, glioblastoma, or thyroid cancer.

Also within the scope of the present disclosure are (a) pharmaceutical compositions for use in enhancing ADCC activity and/or enhancing efficacy of antibody therapy of a cancer, the pharmaceutical composition comprising immune cells as described herein that express any of the chimeric receptor constructs described herein and a pharmaceutically acceptable carrier; and (b) use of such immune cells for manufacturing a medicament for use in the intended treatment.

Further, present disclosure provides methods for preparing immune cells expressing a chimeric receptor as described herein. The method comprises (i) providing a population of immune cells; (ii) introducing into the immune cells a vector (e.g., a viral vector such as a lentiviral vector or a retroviral vector, a transposon or a vector that contains a transposon sequence) or a naked nucleic acid (e.g., an mRNA) encoding any of the chimeric receptors provided herein; and (iii) culturing the immune cells under conditions allowing for expression of the chimeric receptor. Such a method may further comprise (iv) activating the immune cells expressing the chimeric receptor. In examples in which the immune cells comprise T cells, the T cells may be activated in the presence of one or more of anti-CD3 antibody, anti-CD28 antibody, IL-2, and phytohemoagglutinin. In examples in which the immune cells comprise natural killer cells, the natural killer cells may be activated in the presence of one or more of 4-1BB ligand, anti-4-1BB antibody, anti-IL-15 receptor antibody, IL-2, IL-12, IL-21 and K562 cells.

In some embodiments, the population of immune cells is derived from peripheral blood mononuclear cells (PBMC). Exemplary immune cells include, but are not limited to, natural killer cells, macrophages, neutrophils, eosinophils, T cells, or a combination thereof. In some embodiments, the immune cells (e.g., PBMCs) are derived from a human cancer patient. In some embodiments, the immune cells are derived from a human donor. In some embodiments, the immune cells are differentiated from stem cells or stem-like cells derived from a human patient or a human donor. In some embodiments, the immune cells are established cell lines such as NK-92 cells.

In any of the methods provided herein, the vector may be introduced into the immune cells by lentiviral transduction, retroviral transduction, DNA electroporation, or RNA electroporation.

The details of one of more embodiments of the disclosure are set forth in the description below. Other features or advantages of the present disclosure will be apparent from the detailed description of several embodiments and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

DETAILED DESCRIPTION OF DISCLOSURE

Figure 1:
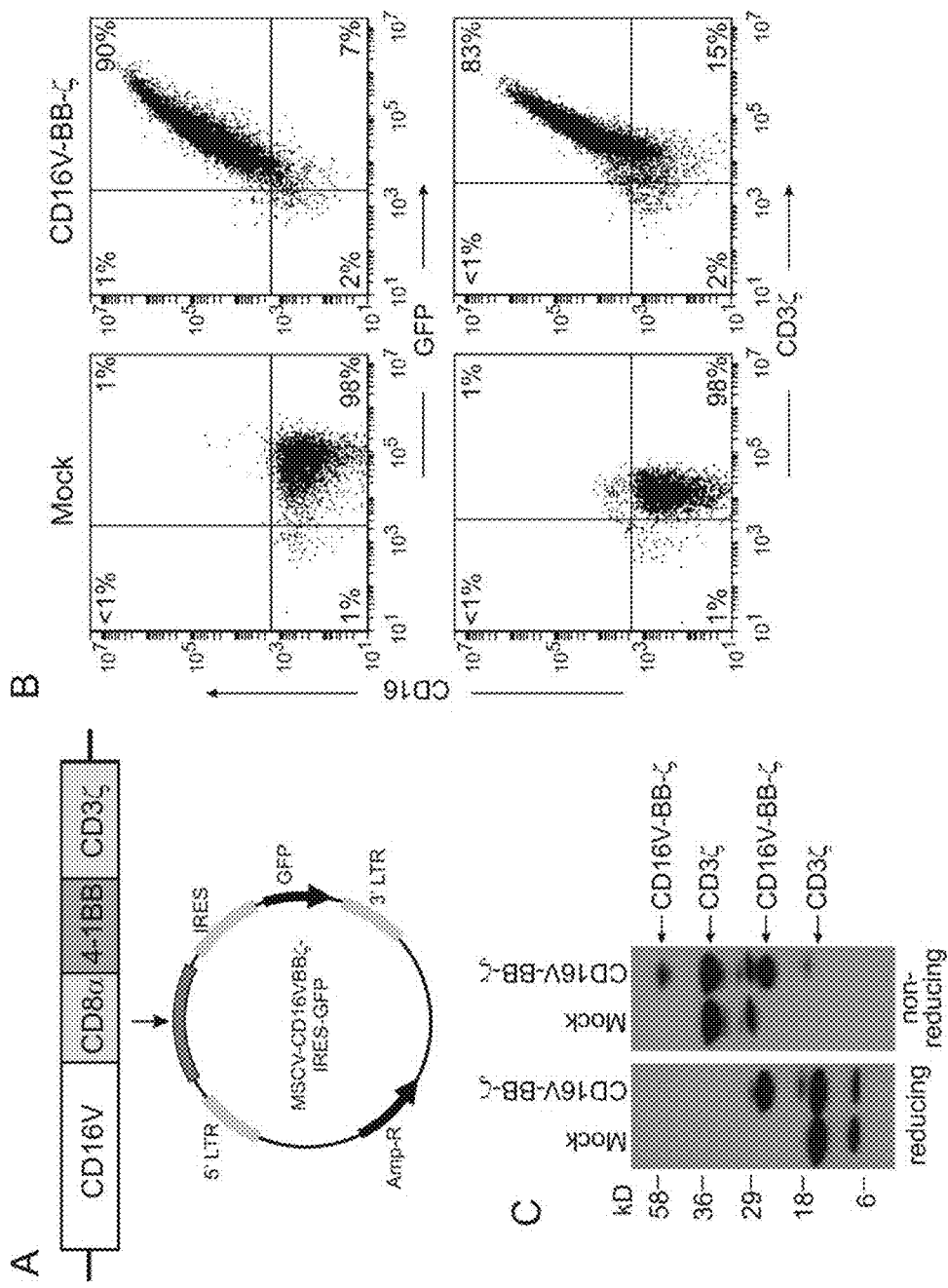
FIG. 1 is a diagram demonstrating expression of CD16V-BB-ζ receptors in T cells. A: a schematic representation of the CD16V-BB-ζ receptor construct. B: graphs showing expression of CD16V-BB-ζ receptors in peripheral blood T lymphocytes. Flow cytometric dot plots illustrate expression of CD16 (B73.1 antibody) in combination with GFP or CD3ζ in activated T lymphocytes transduced with a vector containing GFP alone (Mock) or GFP and CD16V-BB-ζ. Percentage of positive cells in each quadrant is shown. C: a photo showing a representative Western blot of cell lysates from T lymphocytes transduced with GFP alone or CD16V-BB-ζ. The membranes were probed with an anti-CD3ζ antibody.

Antibody-based immunotherapies are used to treat a wide variety of diseases, including many types of cancer. Such a therapy often depends on recognition of cell surface molecules that are differentially expressed on cells for which elimination is desired (e.g., target cells such as cancer cells) relative to normal cells (e.g., non-cancer cells) (Weiner et al. Cell (2012) 148(6): 1081-1084). Several antibody-based immunotherapies have been shown in vitro to facilitate antibody-dependent cell-mediated cytotoxicity of target cells (e.g. cancer cells), and for some it is generally considered that this is the mechanism of action in vivo, as well. ADCC is a cell-mediated innate immune mechanism whereby an effector cell of the immune system, such as natural killer (NK) cells, T cells, monocyte cells, macrophages, or eosinophils, actively lyses target cells (e.g., cancer cells) recognized by specific antibodies.

The present disclosure provides chimeric receptors capable of binding to Fc-containing molecules (e.g., antibodies or Fc fusion proteins), immune cells expressing such, and methods of using the immune cells to enhance ADCC effects against target cells (e.g., cancer cells). As used herein, a chimeric receptor refers to a non-naturally occurring molecule that can be expressed on the surface of a host cell and comprises an extracellular domain capable of binding to a target molecule containing an Fc portion and one or more cytoplasmic signaling domains for triggering effector functions of the immune cell expressing the chimeric receptor, wherein at least two domains of the chimeric receptor are derived from different molecules.

Fc-containing molecules such as antibodies proteins can bind to a target such as a cell surface molecule, receptor, or carbohydrate on the surface of a target cell (e.g., a cancer cell). Immune cells that express receptors capable of binding such Fc-containing molecules, for example the chimeric receptor molecules described herein, recognize the target cell-bound antibodies and this receptor/antibody engagement stimulates the immune cell to perform effector functions such as release of cytotoxic granules or expression of cell-death-inducing molecules, leading to cell death of the target cell recognized by the Fc-containing molecules.

The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

In the context of the present disclosure insofar as it relates to any of the disease conditions recited herein, the terms "treat", "treatment", and the like mean to relieve or alleviate at least one symptom associated with such condition, or to slow or reverse the progression of such condition. Within the meaning of the present disclosure, the term "treat" also denotes to arrest, delay the onset (i.e., the period prior to clinical manifestation of a disease) and/or reduce the risk of developing or worsening a disease. For example, in connection with cancer the term "treat" may mean eliminate or reduce a patient's tumor burden, or prevent, delay or inhibit metastasis, etc.

As used herein the term "therapeutically effective" applied to dose or amount refers to that quantity of a compound or pharmaceutical composition (e.g., a composition comprising immune cells such as T lymphocytes and/or NK cells) comprising a chimeric receptor of the disclosure, and optionally further comprising a tumor-specific cytotoxic monoclonal antibody or another anti-tumor molecule comprising the Fc portion (e.g., a composite molecule constituted by a ligand (e.g., cytokine, immune cell receptor) binding a tumor surface receptor combined with the Fc-portion of an immunoglobulin or Fc-containing DNA or RNA)) that is sufficient to result in a desired activity upon administration to a subject in need thereof. Within the context of the present disclosure, the term "therapeutically effective" refers to that quantity of a compound or pharmaceutical composition that is sufficient to delay the manifestation, arrest the progression, relieve or alleviate at least one symptom of a disorder treated by the methods of the present disclosure. Note that when a combination of active ingredients is administered the effective amount of the combination may or may not include amounts of each ingredient that would have been effective if administered individually.

The phrase "pharmaceutically acceptable", as used in connection with compositions of the present disclosure, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "subject" refers to any mammal. In a preferred embodiment, the subject is human.

As used in this specification and the appended claims, the singular forms "a," "an," and "the" include plural references unless the context clearly dictates otherwise.

I. Chimeric Receptors

The chimeric receptors described herein comprise an extracellular domain with binding affinity and specificity for the Fc portion of an immunoglobulin ("Fc binder"), a transmembrane domain, at least one co-stimulatory signaling domain, and a cytoplasmic signaling domain comprising an ITAM. The chimeric receptors are configured such that, when expressed on a host cell, the extracellular ligand-binding domain is located extracellularly for binding to a target molecule (e.g., an antibody or a Fc-fusion protein) and the co-stimulatory signaling domain and the ITAM-containing cytoplasmic signaling domain are located in the cytoplasm for triggering activation and/or effector signaling. In some embodiments, a chimeric receptor construct as described herein comprises, from N-terminus to C-terminus, the Fc binder, the transmembrane domain, the at least one co-stimulatory signaling domain, and the ITAM-containing cytoplasmic signaling domain. In other embodiments, a chimeric receptor construct as described herein comprises, from N-terminus to C-terminus, the Fc binder, the transmembrane domain, the ITAM-containing cytoplasmic signaling domains, and the at least one co-stimulatory signaling domain.

Any of the chimeric receptors described herein may further comprise a hinge domain, which may be located at the C-terminus of the Fc binder and the N-terminus of the transmembrane domain. Alternatively or in addition, the chimeric receptor constructs described herein may contain two or more co-stimulatory signaling domains, which may link to each other or be separated by the ITAM-containing cytoplasmic signaling domain. The extracellular Fc binder, transmembrane domain, co-stimulatory signaling domain(s), and ITAM-containing cytoplasmic signaling domain in a chimeric receptor construct may be linked to each other directly, or via a peptide linker.

A. Fc Binders

The chimeric receptor constructs described herein comprises an extracellular domain that is an Fc binder, i.e., capable of binding to the Fc portion of an immunoglobulin (e.g., IgG, IgA, IgM, or IgE) of a suitable mammal (e.g., human, mouse, rat, goat, sheep, or monkey). Suitable Fc binders may be derived from naturally occurring proteins such as mammalian Fc receptors or certain bacterial proteins (e.g., protein A, protein G). Additionally, Fc binders may be synthetic polypeptides engineered specifically to bind the Fc portion of any of the Ig molecules described herein with high affinity and specificity. For example, such an Fc binder can be an antibody or an antigen-binding fragment thereof that specifically binds the Fc portion of an immunoglobulin. Examples include, but are not limited to, a single-chain variable fragment (scFv), a domain antibody, or a nanobody. Alternatively, an Fc binder can be a synthetic peptide that specifically binds the Fc portion, such as a Kunitz domain, a small modular immunopharmaceutical (SMIP), an adnectin, an avimer, an affibody, a DARPin, or an anticalin, which may be identified by screening a peptide combinatory library for binding activities to Fc.

In some embodiments, the Fc binder is an extracellular ligand-binding domain of a mammalian Fc receptor. As used herein, an "Fc receptor" is a cell surface bound receptor that is expressed on the surface of many immune cells (including B cells, dendritic cells, natural killer (NK) cells, macrophage, neutorphils, mast cells, and eosinophils) and exhibits binding specificity to the Fc domain of an antibody. Fc receptors are typically comprised of at least 2 immunoglobulin (Ig)-like domains with binding specificity to an Fc (fragment crystallizable) portion of an antibody. In some instances, binding of an Fc receptor to an Fc portion of the antibody may trigger antibody dependent cell-mediated cytotoxicity (ADCC) effects. The Fc receptor used for constructing a chimeric receptor as described herein may be a naturally-occurring polymorphism variant (e.g., the CD16 V158 variant), which may have increased or decreased affinity to Fc as compared to a wild-type counterpart. Alternatively, the Fc receptor may be a functional variant of a wild-type counterpart, which carry one or more mutations (e.g., up to 10 amino acid residue substitutions) that alter the binding affinity to the Fc portion of an Ig molecule. In some instances, the mutation may alter the glycosylation pattern of the Fc receptor and thus the binding affinity to Fc.

The table below lists a number of exemplary polymorphisms in Fc receptor extracellular domains (see, e.g., Kim et al., *J. Mol. Evol.* 53:1-9, 2001):

TABLE 1

Exemplary Polymorphisms in Fc Receptors

| Amino Acid Number | 19 | 48 | 65 | 89 | 105 | 130 | 134 | 141 | 142 | 158 |
|---|---|---|---|---|---|---|---|---|---|---|
| FCR10 | R | S | D | I | D | G | F | Y | T | V |
| P08637 | R | S | D | I | D | G | F | Y | I | F |
| S76824 | R | S | D | I | D | G | F | Y | I | V |
| J04162 | R | N | D | V | D | D | F | H | I | V |
| M31936 | S | S | N | I | D | D | F | H | I | V |
| M24854 | S | S | N | I | E | D | S | H | I | V |
| X07934 | R | S | N | I | D | D | F | H | I | V |
| X14356 (FcγRII) | N | N | N | S | E | S | S | S | I | I |
| M31932 (FcγRI) | S | T | N | R | E | A | F | T | I | G |
| X06948 (FcαεI) | R | S | E | S | Q | S | E | S | I | V |

Fc receptors are classified based on the isotype of the antibody to which it is able to bind. For example, Fc-gamma receptors (FcγR) generally bind to IgG antibodies, such as one or more subtype thereof (i.e., IgG1, IgG2, IgG3, IgG4); Fc-alpha receptors (FcαR) generally bind to IgA antibodies; and Fc-epsilon receptors (FcεR) generally bind to IgE antibodies. In some embodiments, the Fc receptor is an Fc-gamma receptor, an Fc-alpha receptor, or an Fc-epsilon receptor. Examples of Fc-gamma receptors include, without limitation, CD64A, CD64B, CD64C, CD32A, CD32B, CD16A, and CD16B. An example of an Fc-alpha receptor is FcαR1/CD89. Examples of Fc-epsilon receptors include, without limitation, FcεRI and FcεRII/CD23. The table below lists exemplary Fc receptors for use in constructing the chimeric receptors described herein and their binding activity to corresponding Fc domains:

TABLE 2

Exemplary Fc Receptors

| Receptor name | Principal antibody ligand | Affinity for ligand |
|---|---|---|
| FcγRI (CD64) | IgG1 and IgG3 | High (Kd~$10^{-9}$ M) |
| FcγRIIA (CD32) | IgG | Low (Kd > $10^{-7}$ M) |
| FcγRIIB1 (CD32) | IgG | Low (Kd > $10^{-7}$ M) |
| FcγRIIB2 (CD32) | IgG | Low (Kd > $10^{-7}$ M) |
| FcγRIIIA (CD16a) | IgG | Low (Kd > $10^{-6}$ M) |
| FcγRIIIB (CD16b) | IgG | Low (Kd > $10^{-6}$ M) |
| FcεRI | IgE | High (Kd~$10^{-10}$ M) |
| FcεRII (CD23) | IgE | Low (Kd > $10^{-7}$ M) |
| FcαRI (CD89) | IgA | Low (Kd > $10^{-6}$ M) |
| Fcα/μR | IgA and IgM | High for IgM, Mid for IgA |
| FcRn | IgG | |

Selection of the ligand binding domain of an Fc receptor for use in the chimeric receptors described herein will be apparent to one of skill in the art. For example, it may depend on factors such as the isotype of the antibody to which binding of the Fc receptor is desired and the desired affinity of the binding interaction.

In some examples, (a) is the extracellular ligand-binding domain of CD16 incorporating a naturally occurring polymorphism that may modulate affinity for Fc. In some examples, (a) is the extracellular ligand-binding domain of CD16 incorporating a polymorphism at position 158 (e.g., valine or phenylalanine). In some embodiments, (a) is produced under conditions that alter its glycosylation state and its affinity for Fc.

In some embodiments, (a) is the extracellular ligand-binding domain of CD16 incorporating modifications that render the chimeric receptor incorporating it specific for a subset of IgG antibodies. For example, mutations that increase or decrease the affinity for an IgG subtype (e.g., IgG1) may be incorporated.

In other embodiments, the Fc binder is derived from a naturally occurring bacterial protein that is capable of binding to the Fc portion of an IgG molecule. A Fc binder for use in constructing a chimeric receptor as described herein can be a full-length protein or a functional fragment thereof. Protein A is a 42 kDa surface protein originally found in the cell wall of the bacterium Staphylococcus aureus. It is composed of five domains that each fold into a three-helix bundle and are able to bind IgG through interactions with the Fc region of most antibodies as well as the Fab region of human VH3 family antibodies. Protein G is an approximately 60-kDa protein expressed in group C and G Streptococcal bacteria that binds to both the Fab and Fc region of mammalian IgGs. While native protein G also binds albumin, recombinant variants have been engineered that eliminate albumin binding.

Fc binders for use in chimeric receptors may also be created de novo using combinatorial biology or directed evolution methods. Starting with a protein scaffold (e.g., an scFv derived from IgG, a Kunitz domain derived from a Kunitz-type protease inhibitor, an ankyrin repeat, the Z domain from protein A, a lipocalin, a fibronectin type III domain, an SH3 domain from Fyn, or others), amino acid side chains for a set of residues on the surface may be randomly substituted in order to create a large library of variant scaffolds. From large libraries it is possible to isolate rare variants with affinity for a target like the Fc domain by first selecting for binding, followed by amplification by phage, ribosome or cell display. Repeated rounds of selection and amplification can be used to isolate those proteins with the highest affinity for the target.

Any of the Fc binders described herein may have a suitable binding affinity for the Fc portion of a therapeutic antibody. As used herein, "binding affinity" refers to the apparent association constant or $K_A$. The $K_A$ is the reciprocal of the dissociation constant, $K_D$. The extracellular ligand-binding domain of an Fc receptor domain of the chimeric receptors described herein may have a binding affinity $K_D$ of at least $10^{-5}$, $10^{-6}$, $10^{-7}$, $10^{-8}$, $10^{-9}$, $10^{-10}$M or lower for the Fc portion of antibody. In some embodiments, the Fc binder has a high binding affinity for antibody, isotype of antibodies, or subtype(s) thereof, as compared to the binding affinity of the Fc binder to another antibody, isotype of antibodies or subtypes thereof. In some embodiments, the extracellular ligand-binding domain of an Fc receptor has specificity for an antibody, isotype of antibodies, or subtype(s) thereof, as compared to binding of the extracellular ligand-binding domain of an Fc receptor to another antibody, isotype of antibodies, or subtypes thereof. Fc-gamma receptors with high affinity binding include CD64A, CD64B, and CD64C. Fc-gamma receptors with low affinity binding include CD32A, CD32B, CD16A, and CD16B. An Fc-epsilon receptor with high affinity binding is FcεRI, and an Fc-epsilon receptor with low affinity binding is FcεRII/CD23.

The binding affinity or binding specificity for an Fc receptor or a chimeric receptor comprising an Fc binder (e.g., an extracellular ligand-binding domain of an Fc receptor) can be determined by a variety of methods including equilibrium dialysis, equilibrium binding, gel filtration, ELISA, surface plasmon resonance, or spectroscopy.

In some embodiments, the extracellular ligand-binding domain of an Fc receptor comprises an amino acid sequence that is at least 90% (e.g., 91, 92, 93, 94, 95, 96, 97, 98, 99%) identical to the amino acid sequence of the extracellular ligand-binding domain of a naturally-occurring Fc-gamma receptor, an Fc-alpha receptor, or an Fc-epsilon receptor. The "percent identity" of two amino acid sequences can be determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of the disclosure. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

Also within the scope of the present disclosure are variants of the extracellular ligand-binding domains of Fc receptors, such as those described herein. In some embodiments, the variant extracellular ligand-binding domain may comprise up to 10 amino acid residue variations (e.g., 1, 2, 3, 4, or 5) relative to the amino acid sequence of the reference extracellular ligand-binding domain. In some embodiments, the variant can be a naturally-occurring variant due to gene polymorphism. In other embodiments, the variant can be a non-naturally occurring modified molecule. For examples, mutations may be introduced into the extracellular ligand-binding domain of an Fc receptor to alter its glycosylation pattern and thus its binding affinity to the corresponding Fc domain.

In some examples, the Fc receptor can be CD16A, CD16B, CD32A, CD32B, CD32C, CD64A, CD64B, CD64C, or a variant thereof as described herein. The extracellular ligand-binding domain of an Fc receptor may comprise up to 10 amino acid residue variations (e.g., 1, 2, 3, 4, 5, or 8) relative to the amino acid sequence of the extracellular ligand-binding domain of CD16A, CD16B, CD32A, CD32B, CD32C, CD64A, CD64B, CD64C as described herein. Such Fc domains comprising one or more amino acid variations may be referred to as a variant. Mutation of amino acid residues of the extracellular ligand-binding domain of an Fc receptor may result in an increase in binding affinity for the Fc receptor domain to bind to an antibody, isotype of antibodies, or subtype(s) thereof relative to Fc receptor domains that do not comprise the mutation. For example, mutation of residue 158 of the Fc-gamma receptor CD16A may result in an increase in binding affinity of the Fc receptor to an Fc portion of an antibody. In some embodiments, the mutation is a substitution of a phenylalanine to a valine at residue 158 of the Fc-gamma receptor CD16A, referred to as a CD16A V158 variant. The amino acid sequence of human CD16A V158 variant is provided below with the V158 residue highlighted in bold/face (signal peptide italicized):

```
                                                    (SEQ ID NO: 75)
MWQLLLPTALLLLVSAGMRTEDLPKAVVFLEPQWYRVLEKDSVTLKCQGA

YSPEDNSTQWFHNESLISSQASSYFIDAATVDDSGEYRCQTNLSTLSDPV

QLEVHIGWLLLQAPRWVFKEEDPIHLRCHSWKNTALHKVTYLQNGKGRKY

FHHNSDFYIPKATLKDSGSYFCRGLVGSKNVSSETVNITITQGLAVSTIS

SFFPPGYQVSFCLVMVLLFAVDTGLYFSVKTNIRSSTRDWKDHKFKWRKD

PQDK
```

Alternative or additional mutations that can be made in the extracellular ligand-binding domain of an Fc receptor that may enhance or reduce the binding affinity to an Fc portion of a molecule such as an antibody will be evident to one of ordinary skill in the art. In some embodiments, the Fc receptor is CD16A, CD16A V158 variant, CD16B, CD32A, CD32B, CD32C, CD64A, CD64B, or CD64C. In some embodiments, the extracellular ligand-binding domain of the chimeric receptor constructs described herein is not the extracellular ligand-binding domain of CD16A or CD16A V158 variant.

B. Transmembrane Domain

The transmembrane domain of the chimeric receptors described herein can be in any form known in the art. As used herein, a "transmembrane domain" refers to any protein structure that is thermodynamically stable in a cell membrane, preferably a eukaryotic cell membrane. Transmembrane domains compatible for use in the chimeric receptors used herein may be obtained from a naturally occurring protein. Alternatively, it can be a synthetic, non-naturally occurring protein segment, e.g., a hydrophobic protein segment that is thermodynamically stable in a cell membrane.

Transmembrane domains are classified based on the three dimensional structure of the transmembrane domain. For example, transmembrane domains may form an alpha helix, a complex of more than one alpha helix, a beta-barrel, or any other stable structure capable of spanning the phospholipid bilayer of a cell. Furthermore, transmembrane domains may also or alternatively be classified based on the transmembrane domain topology, including the number of passes that the transmembrane domain makes across the membrane and the orientation of the protein. For example, single-pass membrane proteins cross the cell membrane once, and multi-pass membrane proteins cross the cell membrane at least twice (e.g., 2, 3, 4, 5, 6, 7 or more times).

Membrane proteins may be defined as Type I, Type II or Type III depending upon the topology of their termini and membrane-passing segment(s) relative to the inside and outside of the cell. Type I membrane proteins have a single membrane-spanning region and areoriented such that the N-terminus of the protein is present on the extracellular side of the lipid bilayer of the cell and the C-terminus of the protein is present on the cytoplasmic side. Type II membrane proteins also have a single membrane-spanning region but are oriented such that the C-terminus of the protein is present on the extracellular side of the lipid bilayer of the cell and the N-terminus of the protein is present on the cytoplasmic side. Type III membrane proteins have multiple membrane-spanning segments and may be further sub-classified based on the number of transmembrane segments and the location of N- and C-termini.

In some embodiments, the transmembrane domain of the chimeric receptor described herein is derived from a Type I single-pass membrane protein. Single-pass membrane proteins include, but are not limited to, CD8α, CD8β, 4-1BB/CD137, CD28, CD34, CD4, FcεRIγ, CD16, OX40/CD134, CD3ζ, CD3ε, CD3γ, CD3δ, TCRα, TCRβ, TCRζ, CD32, CD64, CD64, CD45, CD5, CD9, CD22, CD37, CD80, CD86, CD40, CD40L/CD154, VEGFR2, FAS, and FGFR2B. In some embodiments, the transmembrane domain is from a membrane protein selected from the following: CD8α, CD8β, 4-1BB/CD137, CD28, CD34, CD4, FcεRIγ, CD16, OX40/CD134, CD3ζ, CD3ε, CD3γ, CD3δ, TCRα, CD32, CD64, VEGFR2, FAS, and FGFR2B. In some examples, the transmembrane domain is of CD8α. In some examples, the transmembrane domain is of 4-1BB/CD137. In other examples, the transmembrane domain is of CD28 or CD34. In yet other examples, the transmembrane domain is not derived from human CD8α. In some embodiments, the transmembrane domain of the chimeric receptor is a single-pass alpha helix.

Transmembrane domains from multi-pass membrane proteins may also be compatible for use in the chimeric receptors described herein. Multi-pass membrane proteins may comprise a complex (at least 2, 3, 4, 5, 6, 7 or more) alpha helices or a beta sheet structure. Preferably, the N-terminus and the C-terminus of a multi-pass membrane protein are present on opposing sides of the lipid bilayer, e.g., the N-terminus of the protein is present on the cytoplasmic side of the lipid bilayer and the C-terminus of the protein is present on the extracellular side. Either one or multiple helix passes from a multi-pass membrane protein can be used for constructing the chimeric receptor described herein.

Transmembrane domains for use in the chimeric receptors described herein can also comprise at least a portion of a synthetic, non-naturally occurring protein segment. In some embodiments, the transmembrane domain is a synthetic, non-naturally occurring alpha helix or beta sheet. In some embodiments, the protein segment is at least approximately 20 amino acids, e.g., at least 18, 19, 20, 21, 22, 23, 24, 25, 26, 27, 28, 29, 30, or more amino acids. Examples of synthetic transmembrane domains are known in the art, for example in U.S. Pat. No. 7,052,906 B1 and PCT Publication No. WO 2000/032776 A2, the relevant disclosures of which are incorporated by reference herein.

In some embodiments, the amino acid sequence of the transmembrane domain does not comprise cysteine residues. In some embodiments, the amino acid sequence of the transmembrane domain comprises one cysteine residue. In some embodiments, the amino acid sequence of the transmembrane domain comprises two cysteine residues. In some embodiments, the amino acid sequence of the transmembrane domain comprises more than two cysteine residues (e.g., 3, 4, 5 or more).

The transmembrane domain may comprise a transmembrane region and a cytoplasmic region located at the C-terminal side of the transmembrane domain. The cytoplasmic region of the transmembrane domain may comprise three or more amino acids and, in some embodiments, helps to orient the transmembrane domain in the lipid bilayer. In some embodiments, one or more cysteine residues are present in the transmembrane region of the transmembrane domain. In some embodiments, one or more cysteine residues are present in the cytoplasmic region of the transmembrane domain. In some embodiments, the cytoplasmic region of the transmembrane domain comprises positively charged amino acids. In some embodiments, the cytoplasmic region of the transmembrane domain comprises the amino acids arginine, serine, and lysine.

In some embodiments, the transmembrane region of the transmembrane domain comprises hydrophobic amino acid residues. In some embodiments, the transmembrane region comprises mostly hydrophobic amino acid residues, such as alanine, leucine, isoleucine, methionine, phenylalanine, tryptophan, or valine. In some embodiments, the transmembrane region is hydrophobic. In some embodiments, the transmembrane region comprises a poly-leucine-alanine sequence.

The hydropathy, or hydrophobic or hydrophilic characteristics of a protein or protein segment, can be assessed by any method known in the art, for example the Kyte and Doolittle hydropathy analysis.

C. Co-Stimulatory Signaling Domains

Many immune cells require co-stimulation, in addition to stimulation of an antigen-specific signal, to promote cell proliferation, differentiation and survival, as well as to activate effector functions of the cell. The chimeric receptors described herein comprise at least one co-stimulatory signaling domain. The term "co-stimulatory signaling domain," as used herein, refers to at least a portion of a protein that mediates signal transduction within a cell to induce an immune response such as an effector function. The co-stimulatory signaling domain of the chimeric receptor described herein can be a cytoplasmic signaling domain from a co-stimulatory protein, which transduces a signal and modulates responses mediated by immune cells, such as T cells, NK cells, macrophages, neutrophils, or eosinophils.

Activation of a co-stimulatory signaling domain in a host cell (e.g., an immune cell) may induce the cell to increase or decrease the production and secretion of cytokines, phagocytic properties, proliferation, differentiation, survival, and/or cytotoxicity. The co-stimulatory signaling domain of any co-stimulatory molecule may be compatible for use in the chimeric receptors described herein. The type(s) of co-stimulatory signaling domain is selected based on factors such as the type of the immune cells in which the chimeric receptors would be expressed (e.g., T cells, NK cells, macrophages, neutrophils, or eosinophils) and the desired immune effector function (e.g., ADCC effect). Examples of co-stimulatory signaling domains for use in the chimeric receptors can be the cytoplasmic signaling domain of co-stimulatory proteins, including, without limitation, members of the B7/CD28 family (e.g., B7-1/CD80, B7-2/CD86, B7-H1/PD-L1, B7-H2, B7-H3, B7-H4, B7-H6, B7-H7, BTLA/CD272, CD28, CTLA-4, Gi24/VISTA/B7-H5, ICOS/CD278, PD-1, PD-L2/B7-DC, and PDCD6); members of the TNF superfamily (e.g., 4-1BB/TNFSF9/CD137, 4-1BB Ligand/TNFSF9, BAFF/BLyS/TNFSF13B, BAFF R/TNFRSF13C, CD27/TNFRSF7, CD27 Ligand/TNFSF7, CD30/TNFRSF8, CD30 Ligand/TNFSF8, CD40/TNFRSF5, CD40/TNFSF5, CD40 Ligand/TNFSF5, DR3/TNFRSF25, GITR/TNFRSF18, GITR Ligand/TNFSF18, HVEM/TNFRSF14, LIGHT/TNFSF14, Lymphotoxin-alpha/TNF-beta, OX40/TNFRSF4, OX40 Ligand/TNFSF4, RELT/TNFRSF19L, TACI/TNFRSF13B, TL1A/TNFSF15, TNF-alpha, and TNF RII/TNFRSF1B); members of the SLAM family (e.g., 2B4/CD244/SLAMF4, BLAME/SLAMF8, CD2, CD2F-10/SLAMF9, CD48/SLAMF2, CD58/LFA-3, CD84/SLAMF5, CD229/SLAMF3, CRACC/SLAMF7, NTB-A/SLAMF6, and SLAM/CD150); and any other co-stimulatory molecules, such as CD2, CD7, CD53, CD82/Kai-1, CD90/Thy1, CD96, CD160, CD200, CD300a/LMIR1, HLA Class I, HLA-DR, Ikaros, Integrin alpha 4/CD49d, Integrin alpha 4 beta 1, Integrin alpha 4 beta 7/LPAM-1, LAG-3, TCL1A, TCL1B, CRTAM, DAP12, Dectin-1/CLEC7A, DPPIV/CD26, EphB6, TIM-1/KIM-1/HAVCR, TIM-4, TSLP, TSLP R, lymphocyte function associated antigen-1 (LFA-1), and NKG2C. In some embodiments, the co-stimulatory signaling domain is of 4-1BB, CD28, OX40, ICOS, CD27, GITR, HVEM, TIM1, LFA1 (CD11a) or CD2, or any variant thereof. In other embodiments, the co-stimulatory signaling domain is not derived from 4-1BB.

Also within the scope of the present disclosure are variants of any of the co-stimulatory signaling domains described herein, such that the co-stimulatory signaling domain is capable of modulating the immune response of the immune cell. In some embodiments, the co-stimulatory signaling domains comprises up to 10 amino acid residue variations (e.g., 1, 2, 3, 4, 5, or 8) as compared to a wild-type counterpart. Such co-stimulatory signaling domains comprising one or more amino acid variations may be referred to as variants.

Mutation of amino acid residues of the co-stimulatory signaling domain may result in an increase in signaling transduction and enhanced stimulation of immune responses relative to co-stimulatory signaling domains that do not comprise the mutation. Mutation of amino acid residues of the co-stimulatory signaling domain may result in a decrease in signaling transduction and reduced stimulation of immune responses relative to co-stimulatory signaling domains that do not comprise the mutation. For example, mutation of residues 186 and 187 of the native CD28 amino acid sequence may result in an increase in co-stimulatory activity and induction of immune responses by the co-stimulatory domain of the chimeric receptor. In some embodiments, the mutations are substitution of a lysine at each of positions 186 and 187 with a glycine residue of the CD28 co-stimulatory domain, referred to as a $CD28_{LL \rightarrow GG}$ variant. Additional mutations that can be made in co-stimulatory signaling domains that may enhance or reduce co-stimulatory activity of the domain will be evident to one of ordinary skill in the art. In some embodiments, the co-stimulatory signaling domain is of 4-1BB, CD28, OX40, or $CD28_{LL \rightarrow GG}$ variant. In some embodiments, the co-stimulatory signaling domain is not of 4-1BB.

In some embodiments, the chimeric receptors may comprise more than one co-stimulatory signaling domain (e.g., 2, 3 or more). In some embodiments, the chimeric receptor comprises two or more of the same co-stimulatory signaling domains, for example, two copies of the co-stimulatory signaling domain of CD28. In some embodiments, the chimeric receptor comprises two or more co-stimulatory signaling domains from different co-stimulatory proteins, such as any two or more co-stimulatory proteins described herein. Selection of the type(s) of co-stimulatory signaling domains may be based on factors such as the type of host cells to be used with the chimeric receptors (e.g., immune cells such as T cells, NK cells, macrophages, neutrophils, or eosinophils) and the desired immune effector function. In some embodiments, the chimeric receptor comprises two co-stimulatory signaling domains. In some embodiments, the two co-stimulatory signaling domains are CD28 and 4-1BB. In some embodiments, the two co-stimulatory signaling domains are $CD28_{LL \rightarrow GG}$ variant and 4-1BB.

D. Cytoplasmic Signaling Domain Comprising an Immunoreceptor Tyrosine-Based Activation Motif (ITAM)

Any cytoplasmic signaling domain comprising an immunoreceptor tyrosine-based activation motif (ITAM) can be used to construct the chimeric receptors described herein. An "ITAM," as used herein, is a conserved protein motif that is generally present in the tail portion of signaling molecules expressed in many immune cells. The motif may comprises two repeats of the amino acid sequence YxxL/I separated by 6-8 amino acids, wherein each x is independently any amino acid, producing the conserved motif $YxxL/Ix_{(6-8)}YxxL/I$.

ITAMs within signaling molecules are important for signal transduction within the cell, which is mediated at least in part by phosphorylation of tyrosine residues in the ITAM following activation of the signaling molecule. ITAMs may also function as docking sites for other proteins involved in signaling pathways. In some examples, the cytoplasmic signaling domain comprising an ITAM is of CD3ζ or FcεRIγ. In other examples, the ITAM-containing cytoplasmic signaling domain is not derived from human CD3ζ. In yet other examples, the ITAM-containing cytoplasmic signaling domain is not derived from an Fc receptor, when the extracellular ligand-binding domain of the same chimeric receptor construct is derived from CD16A.

E. Hinge Domain

In some embodiments, the chimeric receptors described herein further comprise a hinge domain that is located between the extracellular ligand-binding domain and the transmembrane domain. A hinge domain is an amino acid segment that is generally found between two domains of a protein and may allow for flexibility of the protein and movement of one or both of the domains relative to one another. Any amino acid sequence that provides such flexibility and movement of the extracellular ligand-binding domain of an Fc receptor relative to the transmembrane domain of the chimeric receptor can be used.

The hinge domain may contain about 10-100 amino acids, e.g., 15-75 amino acids, 20-50 amino acids, or 30-60 amino acids. In some embodiments, the hinge domain may be of 10, 11, 12, 13, 14, 15, 16, 17, 18, 19, 20, 21, 22, 23, 24, 25, 26, 27, 28, 29, 30, 35, 40, 45, 50, 55, 60, 65, 70, or 75 amino acids in length.

In some embodiments, the hinge domain is a hinge domain of a naturally occurring protein. Hinge domains of any protein known in the art to comprise a hinge domain are compatible for use in the chimeric receptors described herein. In some embodiments, the hinge domain is at least a portion of a hinge domain of a naturally occurring protein and confers flexibility to the chimeric receptor. In some embodiments, the hinge domain is of CD8α. In some embodiments, the hinge domain is a portion of the hinge domain of CD8α, e.g., a fragment containing at least 15 (e.g., 20, 25, 30, 35, or 40) consecutive amino acids of the hinge domain of CD8α.

Hinge domains of antibodies, such as an IgG, IgA, IgM, IgE, or IgD antibodies, are also compatible for use in the chimeric receptors described herein. In some embodiments, the hinge domain is the hinge domain that joins the constant domains CH1 and CH2 of an antibody. In some embodiments, the hinge domain is of an antibody and comprises the hinge domain of the antibody and one or more constant regions of the antibody. In some embodiments, the hinge domain comprises the hinge domain of an antibody and the CH3 constant region of the antibody. In some embodiments, the hinge domain comprises the hinge domain of an antibody and the CH2 and CH3 constant regions of the antibody. In some embodiments, the antibody is an IgG, IgA, IgM, IgE, or IgD antibody. In some embodiments, the antibody is an IgG antibody. In some embodiments, the antibody is an IgG1, IgG2, IgG3, or IgG4 antibody. In some embodiments, the hinge region comprises the hinge region and the CH2 and CH3 constant regions of an IgG1 antibody. In some embodiments, the hinge region comprises the hinge region and the CH3 constant region of an IgG1 antibody.

Non-naturally occurring peptides may also be used as hinge domains for the chimeric receptors described herein. In some embodiments, the hinge domain between the C-terminus of the extracellular ligand-binding domain of an Fc receptor and the N-terminus of the transmembrane domain is a peptide linker, such as a $(Gly_4Ser)_n$ linker, wherein x and n, independently can be an integer between 3 and 12, including 3, 4, 5, 6, 7, 8, 9, 10, 11, 12, or more. In some embodiments, the hinge domain is $(Gly_4Ser)_n$ (SEQ ID NO: 76), wherein n can be an integer between 3 and 60, including 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more. In some embodiments, the hinge domain is $(Gly_4Ser)_3$ (SEQ ID NO: 77). In some embodiments, the hinge domain is $(Gly_4Ser)_6$ (SEQ ID NO: 78). In some embodiments, the hinge domain is $(Gly_4Ser)_9$ (SEQ ID NO: 79). In some embodiments, the hinge domain is $(Gly_4Ser)_{12}$ (SEQ ID NO: 80). In some embodiments, the hinge domain is $(Gly_4Ser)_{15}$ (SEQ ID NO: 81). In some embodiments, the hinge domain is $(Gly_4Ser)_{30}$ (SEQ ID NO: 82). In some embodiments, the hinge domain is $(Gly_4Ser)_{45}$ (SEQ ID NO: 83). In some embodiments, the hinge domain is $(Gly_4Ser)_{60}$ (SEQ ID NO: 84).

In other embodiments, the hinge domain is an extended recombinant polypeptide (XTEN), which is an unstructured polypeptide consisting of hydrophilic residues of varying lengths (e.g., 10-80 amino acid residues). Amino acid sequences of XTEN peptides will be evident to one of skill in the art and can be found, for example, in U.S. Pat. No. 8,673,860, which is herein incorporated by reference. In some embodiments, the hinge domain is an XTEN peptide and comprises 60 amino acids. In some embodiments, the hinge domain is an XTEN peptide and comprises 30 amino acids. In some embodiments, the hinge domain is an XTEN peptide and comprises 45 amino acids. In some embodiments, the hinge domain is an XTEN peptide and comprises 15 amino acids.

F. Signal Peptide

In some embodiments, the chimeric receptor also comprises a signal peptide (also known as a signal sequence) at the N-terminus of the polypeptide. In general, signal sequences are peptide sequences that target a polypeptide to the desired site in a cell. In some embodiments, the signal sequence targets the chimeric receptor to the secretory pathway of the cell and will allow for integration and anchoring of the chimeric receptor into the lipid bilayer. Signal sequences including signal sequences of naturally occurring proteins or synthetic, non-naturally occurring signal sequences, that are compatible for use in the chimeric receptors described herein will be evident to one of skill in the art. In some embodiments, the signal sequence from CD8α. In some embodiments, the signal sequence is from CD28. In other embodiments, the signal sequence is from the murine kappa chain. In yet other embodiments, the signal sequence is from CD16.

The chimeric receptors described herein would confer a number of advantages. For example, via the extracellular domain that binds Fc, the chimeric receptor constructs described herein can bind to the Fc portion of antibodies or other Fc-containing molecules, rather than directly binding a specific target antigen (e.g., a cancer antigen). Thus, immune cells expressing the chimeric receptor constructs described herein would be able to induce cell death of any type of cells that are bound by an antibody or another Fc-containing molecule.

Tables 3-5 provide exemplary chimeric receptors described herein. This exemplary constructs have, from N-terminus to C-terminus in order, the signal sequence, the Fc binder (e.g., an extracellular domain of an Fc receptor), the hinge domain, and the transmembrane, while the positions of the co-stimulatory domain and the cytoplasmic signaling domain can be switched.

TABLE 3

Exemplary chimeric receptors.

| Exemplary AA Sequence (SEQ ID NO) | Signal Sequence | Extracellular domain of Fc receptor | Hinge domain | Transmembrane domain | Co-stimulatory domain | Cytoplasmic Signaling domain |
|---|---|---|---|---|---|---|
| 1 | CD8α | CD16A-V158 | CD8α | CD8α | 4-1BB (CD137) | CD3ζ |
| 2 | CD8α | CD16A-V158 | CD8α | 4-1BB (CD137) | 4-1BB (CD137) | CD3ζ |
| 3 | CD8α | CD16A-V158 | CD8α | CD28 | 4-1BB (CD137) | CD3ζ |
| 4 | CD8α | CD16A-V158 | CD8α | CD34 | 4-1BB (CD137) | CD3ζ |
| 5 | CD8α | CD16A-V158 | CD8α | Designed hydrophobic TM domain | 4-1BB (CD137) | CD3ζ |
| 6 | CD8α | CD32A | CD8α | CD8α | 4-1BB (CD137) | CD3ζ |
| 7 | CD8α | CD16A-V158 | CD8α | CD8α | CD28 | CD3ζ |
| 8 | CD8α | CD16A-V158 | CD8α | CD8α | OX40 (CD134) | CD3ζ |
| 9 | CD8α | CD16A-V158 | CD8α | CD8α | CD28 + 4-1BB | CD3ζ |
| 10 | CD8α | CD16A-V158 | None | CD8α | 4-1BB (CD137) | CD3ζ |
| 11 | CD8α | CD16A-V158 | XTEN | CD8α | 4-1BB (CD137) | CD3ζ |

TABLE 4

Exemplary chimeric receptors.

| Exemplary AA Sequence (SEQ ID NO) | Signal Sequence | Extracellular domain of Fc receptor | Hinge domain | Transmembrane domain | Co-stimulatory domain | Cytoplasmic Signaling domain |
|---|---|---|---|---|---|---|
| 12 | CD8α | CD16A-V158 | CD8α | CD8α | CD28 LL to GG mutant | CD3ζ |
| 13 | CD8α | CD16A-V158 | CD8α | CD8α | CD28 LL to GG mutant + 4-1BB | CD3ζ |
| 14 | CD8α | CD16A-V158 | CD8α | CD4 | 4-1BB (CD137) | CD3ζ |
| 15 | CD8α | CD16A-V158 | CD8α | CD4 | CD28 LL to GG mutant + 4-1BB | CD3ζ |
| 16 | CD8α | CD16A-V158 | CD8α | FcεRIγ | 4-1BB (CD137) | CD3ζ |
| 17 | CD8α | CD16A-V158 | CD8α | Designed hydrophobic TM domain, predicted dimerization | 4-1BB (CD137) | CD3ζ |

TABLE 5

Exemplary chimeric receptors.

| Exemplary AA Sequence (SEQ ID NO) | Signal Sequence | Extracellular domain of Fc receptor | Hinge domain | Transmembrane domain | Co-stimulatory domain | Signaling domain |
|---|---|---|---|---|---|---|
| 18 | CD8α | CD16A-V158 | CD8α | CD8β | 4-1BB (CD137) | CD3 ζ |
| 19 | CD8α | CD16A-V158 | CD8α | C16α | 4-1BB (CD137) | CD3 ζ |
| 20 | CD8α | CD16A-V158 | CD8α | OX40 (CD134) | 4-1BB (CD137) | CD3 ζ |
| 21 | CD8α | CD16A-V158 | CD8α | CD3ζ | 4-1BB (CD137) | CD3 ζ |
| 22 | CD8α | CD16A-V158 | CD8α | CD3ε | 4-1BB (CD137) | CD3 ζ |

TABLE 5-continued

Exemplary chimeric receptors.

| Exemplary AA Sequence (SEQ ID NO) | Signal Sequence | Extracellular domain of Fc receptor | Hinge domain | Transmembrane domain | Co-stimulatory domain | Signaling domain |
|---|---|---|---|---|---|---|
| 23 | CD8α | CD16A-V158 | CD8α | CD3γ | 4-1BB (CD137) | CD3 ζ |
| 24 | CD8α | CD16A-V158 | CD8α | CD3δ | 4-1BB (CD137) | CD3 ζ |
| 25 | CD8α | CD16A-V158 | CD8α | TCR-α | 4-1BB (CD137) | CD3 ζ |
| 26 | CD8α | CD16A-V158 | CD8α | CD32 | 4-1BB (CD137) | CD3 ζ |
| 27 | CD8α | CD16A-V158 | CD8α | CD64 | 4-1BB (CD137) | CD3 ζ |
| 28 | CD8α | CD16A-V158 | CD8α | VEGFR2 | 4-1BB (CD137) | CD3 ζ |
| 29 | CD8α | CD16A-V158 | CD8α | FAS | 4-1BB (CD137) | CD3 ζ |
| 30 | CD8α | CD16A-V158 | CD8α | FGFR2B | 4-1BB (CD137) | CD3 ζ |
| 31 | CD8α | CD16A-F158 | CD8α | CD8α | 4-1BB (CD137) | CD3 ζ |
| 32 | CD8α | CD64A | CD8α | CD8α | 4-1BB (CD137) | CD3ζ |
| 33 | CD8α | CD16A-V158 | IgG1 (hinge-CH2-CH3) | CD8α | 4-1BB (CD137) | CD3ζ |
| 34 | CD8α | CD16A-V158 | IgG1 (hinge-CH3) | CD8α | 4-1BB (CD137) | CD3ζ |
| 35 | CD8α | CD16A-V158 | IgG1 (hinge) | CD8α | 4-1BB (CD137) | CD3ζ |
| 36 | CD8α | CD16A-V158 | CD8-alpha fragment 1 (30 amino acids) | CD8α | 4-1BB (CD137) | CD3ζ |
| 37 | CD8α | CD16A-V158 | CD8-alpha fragment 2 (15 amino acids) | CD8α | 4-1BB (CD137) | CD3ζ |
| 38 | CD8α | CD16A-V158 | (Gly4Ser)x3 (60 amino acids) | CD8α | 4-1BB (CD137) | CD3ζ |
| 39 | CD8α | CD16A-V158 | (Gly4Ser)x6 (45 amino acids) | CD8α | 4-1BB (CD137) | CD3ζ |
| 40 | CD8α | CD16A-V158 | (Gly4Ser)x9 (30 amino acids) | CD8α | 4-1BB (CD137) | CD3ζ |
| 41 | CD8α | CD16A-V158 | (Gly4Ser)x12 (15 amino acids) | CD8α | 4-1BB (CD137) | CD3ζ |
| 42 | CD8α | CD16A-V158 | XTEN (60 amino acids) | CD8α | 4-1BB (CD137) | CD3ζ |
| 43 | CD8α | CD16A-V158 | XTEN (30 amino acids) | CD8α | 4-1BB (CD137) | CD3ζ |
| 44 | CD8α | CD16A-V158 | XTEN (15 amino acids) | CD8α | 4-1BB (CD137) | CD3ζ |
| 45 | CD28 | CD16A-V158 | CD8α | CD8α | 4-1BB (CD137) | CD3ζ |
| 46 | Murine kappa chain | CD16A-V158 | CD8α | CD8α | 4-1BB (CD137) | CD3ζ |
| 47 | CD16 | CD16A-V158 | CD8α | CD8α | 4-1BB (CD137) | CD3ζ |
| 48 | CD8α | CD16A-V158 | CD8α | CD8α | ICOS | CD3ζ |
| 49 | CD8α | CD16A-V158 | CD8α | CD8α | CD27 | CD3ζ |
| 50 | CD8α | CD16A-V158 | CD8α | CD8α | GITR | CD3ζ |
| 51 | CD8α | CD16A-V158 | CD8α | CD8α | HVEM | CD3ζ |
| 52 | CD8α | CD16A-V158 | CD8α | CD8α | TIM1 | CD3ζ |
| 53 | CD8α | CD16A-V158 | CD8α | CD8α | LFA1 (CD11a) | CD3ζ |
| 54 | CD8α | CD16A-V158 | CD8α | CD8α | CD2 | CD3ζ |
| 55 | CD8α | CD16A-V158 | CD8α | FcεR1γ | 4-1BB (CD137) | FcεR1γ |
| 56 | CD8α | CD16A-V158 | CD8α | CD8α | 4-1BB (CD137) | FcεR1γ |

Amino acid sequences of the example chimeric receptors are provided below (signal peptide italicized).

SEQ ID NO: 2:
*MALPVTALLLPLALLLHAARP*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDIISFFLALTSTALLFLLFFLTLRFSVVKRGKRGRKKLLYIFKQPFMRPVQTT
QEEDGCSCRFPEEEEGGCELRVKFSRSADAPAYQQGQNQLYNELNLGRREEYDVLDKRRGRD
PEMGGKPRRKNPQEGLYNELQKDKMAEAYSEIGMKGERRRGKGHDGLYQGLSTATKDTYDAL
HMQALPPR

SEQ ID NO: 3:
*MALPVTALLLPLALLLHAARP*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDFWVLVVVGGVLACYSLLVTVAFIIFWVRSKKRGRKKLLYIFKQPFMRPVQTT
QEEDGCSCRFPEEEEGGCELRVKFSRSADAPAYQQGQNQLYNELNLGRREEYDVLDKRRGRD
PEMGGKPRRKNPQEGLYNELQKDKMAEAYSEIGMKGERRRGKGHDGLYQGLSTATKDTYDAL
HMQALPPR

SEQ ID NO: 4:
*MALPVTALLLPLALLLHAARP*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDLIALVTSGALLAVLGITGYFLMNRKRGRKKLLYIFKQPFMRPVQTTQEEDGC
SCRFPEEEEGGCELRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATKDTYDALHMQALP
PR

SEQ ID NO: 5:
*MALPVTALLLPLALLLHAARP*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDLLAALLALLAALLALLAALLARSKKRGRKKLLYIFKQPFMRPVQTTQEEDGC
SCRFPEEEEGGCELRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATKDTYDALHMQALP
PR

SEQ ID NO: 6:
*MALPVTALLLPLALLLHAARP*QAAAPPKAVLKLEPPWINVLQEDSVTLICQGARSPESDSIQ
WFHNGNLIPTHTQPSYRFKANNNDSGEYTCQTGQTSLSDPVHLTVLSEWLVLQTPHLEFQEG
ETIMLRCHSWKDKPLVKVTFFQNGKSQKFSHLDPTFSIPQANHSHSGDYHCTGNIGYTLFSS
KPVTITVQVPSMGSSSPMGTTTPAPRPPTPAPTIASQPLSLRPEACRPAAGGAVHTRGLDFA
CDIYIWAPLAGTCGVLLLSLVITLYCKRGRKKLLYIFKQPFMRPVQTTQEEDGCSCRFPEEE

EGGCELRVKFSRSADAPAYQQGQNQLYNELNLGRREEYDVLDKRRGRDPEMGGKPRRKNPQE

GLYNELQKDKMAEAYSEIGMKGERRRGKGHDGLYQGLSTATKDTYDALHMQALPPR

SEQ ID NO: 7:
MALPVTALLLPLALLLHAARPGMRTEDLPKAVVFLEPQWYRVLEKDSVTLKCQGAYSPEDNS

TQWFHNESLISSQASSYFIDAATVDDSGEYRCQTNLSTLSDPVQLEVHIGWLLLQAPRWVFK

EEDPIHLRCHSWKNTALHKVTYLQNGKGRKYFHHNSDFYIPKATLKDSGSYFCRGLVGSKNV

SSETVNITITQGLAVSTISSFFPPGYQTTTPAPRPPTPAPTIASQPLSLRPEACRPAAGGAV

HTRGLDFACDIYIWAPLAGTCGVLLLSLVITLYCRSKRSRLLHSDYMNMTPRRPGPTRKHYQ

PYAPPRDFAAYRSRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKDTYDALHMQALPP

R

SEQ ID NO: 8:
MALPVTALLLPLALLLHAARPGMRTEDLPKAVVFLEPQWYRVLEKDSVTLKCQGAYSPEDNS

TQWFHNESLISSQASSYFIDAATVDDSGEYRCQTNLSTLSDPVQLEVHIGWLLLQAPRWVFK

EEDPIHLRCHSWKNTALHKVTYLQNGKGRKYFHHNSDFYIPKATLKDSGSYFCRGLVGSKNV

SSETVNITITQGLAVSTISSFFPPGYQTTTPAPRPPTPAPTIASQPLSLRPEACRPAAGGAV

HTRGLDFACDIYIWAPLAGTCGVLLLSLVITLYCALYLLRRDQRLPPDAHKPPGGGSFRTPI

QEEQADAHSTLAKIRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATKDTYDALHMQALP

PR

SEQ ID NO: 9:
MALPVTALLLPLALLLHAARPGMRTEDLPKAVVFLEPQWYRVLEKDSVTLKCQGAYSPEDNS

TQWFHNESLISSQASSYFIDAATVDDSGEYRCQTNLSTLSDPVQLEVHIGWLLLQAPRWVFK

EEDPIHLRCHSWKNTALHKVTYLQNGKGRKYFHHNSDFYIPKATLKDSGSYFCRGLVGSKNV

SSETVNITITQGLAVSTISSFFPPGYQTTTPAPRPPTPAPTIASQPLSLRPEACRPAAGGAV

HTRGLDFACDIYIWAPLAGTCGVLLLSLVITLYCRSKRSRLLHSDYMNMTPRRPGPTRKHYQ

PYAPPRDFAAYRSKRGRKKLLYIFKQPFMRPVQTTQEEDGCSCRFPEEEEGGCELRVKFSRS

ADAPAYQQGQNQLYNELNLGRREEYDVLDKRRGRDPEMGGKPRRKNPQEGLYNELQKDKMAE

AYSEIGMKGERRRGKGHDGLYQGLSTATKDTYDALHMQALPPR

SEQ ID NO: 10:
MALPVTALLLPLALLLHAARPGMRTEDLPKAVVFLEPQWYRVLEKDSVTLKCQGAYSPEDNS

TQWFHNESLISSQASSYFIDAATVDDSGEYRCQTNLSTLSDPVQLEVHIGWLLLQAPRWVFK

EEDPIHLRCHSWKNTALHKVTYLQNGKGRKYFHHNSDFYIPKATLKDSGSYFCRGLVGSKNV

SSETVNITITQGLAVSTISSFFPPGYQIYIWAPLAGTCGVLLLSLVITLYCKRGRKKLLYIF

KQPFMRPVQTTQEEDGCSCRFPEEEEGGCELRVKFSRSADAPAYQQGQNQLYNELNLGRREE

YDVLDKRRGRDPEMGGKPRRKNPQEGLYNELQKDKMAEAYSEIGMKGERRRGKGHDGLYQGL

STATKDTYDALHMQALPPR

SEQ ID NO: 11:
MALPVTALLLPLALLLHAARPGMRTEDLPKAVVFLEPQWYRVLEKDSVTLKCQGAYSPEDNS

TQWFHNESLISSQASSYFIDAATVDDSGEYRCQTNLSTLSDPVQLEVHIGWLLLQAPRWVFK

EEDPIHLRCHSWKNTALHKVTYLQNGKGRKYFHHNSDFYIPKATLKDSGSYFCRGLVGSKNV

SSETVNITITQGLAVSTISSFFPPGYQGGSPAGSPTSTEEGTSESATPESGPGTSTEPSEGS

APGSPAGSPTIYIWAPLAGTCGVLLLSLVITLYCKRGRKKLLYIFKQPFMRPVQTTQEEDGC

SCRFPEEEEGGCELRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATKDTYDALHMQALP
PR

SEQ ID NO: 12:
*MALPVTALLLPLALLLHAARP*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDIYIWAPLAGTCGVLLLSLVITLYCRSKRSRGGHSDYMNMTPRRPGPTRKHYQ
PYAPPRDFAAYRSRVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATKDTYDALHMQALPP
R

SEQ ID NO: 13:
*MALPVTALLLPLALLLHAARP*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDIYIWAPLAGTCGVLLLSLVITLYCRSKRSRGGHSDYMNMTPRRPGPTRKHYQ
PYAPPRDFAAYRSKRGRKKLLYIFKQPFMRPVQTTQEEDGCSCRFPEEEEGGCELRVKFSRS
ADAPAYQQGQNQLYNELNLGRREEYDVLDKRRGRDPEMGGKPRRKNPQEGLYNELQKDKMAE
AYSEIGMKGERRRGKGHDGLYQGLSTATKDTYDALHMQALPPR

SEQ ID NO: 14:
*MALPVTALLLPLALLLHAARP*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDMALIVLGGVAGLLLFIGLGIFFCVRKRGRKKLLYIFKQPFMRPVQTTQEEDG
CSCRFPEEEEGGCELRVKFSRSADAPAYQQGQNQLYNELNLGRREEYDVLDKRRGRDPEMGG
KPRRKNPQEGLYNELQKDKMAEAYSEIGMKGERRRGKGHDGLYQGLSTATKDTYDALHMQAL
PPR

SEQ ID NO: 15:
*MALPVTALLLPLALLLHAARP*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDMALIVLGGVAGLLLFIGLGIFFCVRRSKRSRGGHSDYMNMTPRRPGPTRKHY
QPYAPPRDFAAYRSRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATKDTYDALHMQALP
PR

SEQ ID NO: 16:
*MALPVTALLLPLALLLHAARP*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV

SSETVNITITQGLAVSTISSFFPPGYQTTTPAPRPPTPAPTIASQPLSLRPEACRPAAGGAV

HTRGLDFACDLCYILDAILFLYGIVLTLLYCRLKKRGRKKLLYIFKQPFMRPVQTTQEEDGC

SCRFPEEEEGGCELRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATKDTYDALHMQALP

PR

SEQ ID NO: 17:
MALPVTALLLPLALLLHAARPGMRTEDLPKAVVFLEPQWYRVLEKDSVTLKCQGAYSPEDNS

TQWFHNESLISSQASSYFIDAATVDDSGEYRCQTNLSTLSDPVQLEVHIGWLLLQAPRWVFK

EEDPIHLRCHSWKNTALHKVTYLQNGKGRKYFHHNSDFYIPKATLKDSGSYFCRGLVGSKNV

SSETVNITITQGLAVSTISSFFPPGYQTTTPAPRPPTPAPTIASQPLSLRPEACRPAAGGAV

HTRGLDFACDLLLILLGVLAGVLATLAALLARSKKRGRKKLLYIFKQPFMRPVQTTQEEDGC

SCRFPEEEEGGCELRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATKDTYDALHMQALP

PR

SEQ ID NO: 18:
MALPVTALLLPLALLLHAARPGMRTEDLPKAVVFLEPQWYRVLEKDSVTLKCQGAYSPEDNS

TQWFHNESLISSQASSYFIDAATVDDSGEYRCQTNLSTLSDPVQLEVHIGWLLLQAPRWVFK

EEDPIHLRCHSWKNTALHKVTYLQNGKGRKYFHHNSDFYIPKATLKDSGSYFCRGLVGSKNV

SSETVNITITQGLAVSTISSFFPPGYQTTTPAPRPPTPAPTIASQPLSLRPEACRPAAGGAV

HTRGLDFACDITLGLLVAGVLVLLVSLGVAIHLCKRGRKKLLYIFKQPFMRPVQTTQEEDGC

SCRFPEEEEGGCELRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATKDTYDALHMQALP

PR

SEQ ID NO: 19:
MALPVTALLLPLALLLHAARPGMRTEDLPKAVVFLEPQWYRVLEKDSVTLKCQGAYSPEDNS

TQWFHNESLISSQASSYFIDAATVDDSGEYRCQTNLSTLSDPVQLEVHIGWLLLQAPRWVFK

EEDPIHLRCHSWKNTALHKVTYLQNGKGRKYFHHNSDFYIPKATLKDSGSYFCRGLVGSKNV

SSETVNITITQGLAVSTISSFFPPGYQTTTPAPRPPTPAPTIASQPLSLRPEACRPAAGGAV

HTRGLDFACDVSFCLVMVLLFAVDTGLYFSVKTNKRGRKKLLYIFKQPFMRPVQTTQEEDGC

SCRFPEEEEGGCELRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATKDTYDALHMQALP

PR

SEQ ID NO: 20:
MALPVTALLLPLALLLHAARPGMRTEDLPKAVVFLEPQWYRVLEKDSVTLKCQGAYSPEDNS

TQWFHNESLISSQASSYFIDAATVDDSGEYRCQTNLSTLSDPVQLEVHIGWLLLQAPRWVFK

EEDPIHLRCHSWKNTALHKVTYLQNGKGRKYFHHNSDFYIPKATLKDSGSYFCRGLVGSKNV

SSETVNITITQGLAVSTISSFFPPGYQTTTPAPRPPTPAPTIASQPLSLRPEACRPAAGGAV

HTRGLDFACDVAAILGLGLVLGLLGPLAILLALYKRGRKKLLYIFKQPFMRPVQTTQEEDGC

SCRFPEEEEGGCELRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATKDTYDALHMQALP

PR

SEQ ID NO: 21:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDLCYLLDGILFIYGVILTALFLRVKKRGRKKLLYIFKQPFMRPVQTTQEEDGC
SCRFPEEEEGGCELRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATKDTYDALHMQALP
PR

SEQ ID NO: 22:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDVMSVATIVIVDICITGGLLLLVYYWSKNRKRGRKKLLYIFKQPFMRPVQTTQ
EEDGCSCRFPEEEEGGCELRVKFSRSADAPAYQQGQNQLYNELNLGRREEYDVLDKRRGRDP
EMGGKPRRKNPQEGLYNELQKDKMAEAYSEIGMKGERRRGKGHDGLYQGLSTATKDTYDALH
MQALPPR

SEQ ID NO: 23:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDGFLFAEIVSIFVLAVGVYFIAGQDKRGRKKLLYIFKQPFMRPVQTTQEEDGC
SCRFPEEEEGGCELRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATKDTYDALHMQALP
PR

SEQ ID NO: 24:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDGIIVTDVIATLLLALGVFCFAGHETKRGRKKLLYIFKQPFMRPVQTTQEEDG
CSCRFPEEEEGGCELRVKFSRSADAPAYQQGQNQLYNELNLGRREEYDVLDKRRGRDPEMGG
KPRRKNPQEGLYNELQKDKMAEAYSEIGMKGERRRGKGHDGLYQGLSTATKDTYDALHMQAL
PPR

SEQ ID NO: 25:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDVIGFRILLLKVAGFNLLMTLRLWKRGRKKLLYIFKQPFMRPVQTTQEEDGCS
CRFPEEEEGGCELRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKDTYDALHMQALPP
R

SEQ ID NO: 26:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDIIVAVVIATAVAAIVAAVVALIYCRKKRGRKKLLYIFKQPFMRPVQTTQEED
GCSCRFPEEEEGGCELRVKFSRSADAPAYQQGQNQLYNELNLGRREEYDVLDKRRGRDPEMG
GKPRRKNPQEGLYNELQKDKMAEAYSEIGMKGERRRGKGHDGLYQGLSTATKDTYDALHMQA
LPPR

SEQ ID NO: 27:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDVLFYLAVGIMFLVNTVLWVTIRKEKRGRKKLLYIFKQPFMRPVQTTQEEDGC
SCRFPEEEEGGCELRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATKDTYDALHMQALP
PR

SEQ ID NO: 28:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDIIILVGTAVIAMFFWLLLVIILRTKRGRKKLLYIFKQPFMRPVQTTQEEDGC
SCRFPEEEEGGCELRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATKDTYDALHMQALP
PR

SEQ ID NO: 29:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDLGWLCLLLLPIPLIVWVKRKKRGRKKLLYIFKQPFMRPVQTTQEEDGCSCRF
PEEEEGGCELRVKFSRSADAPAYQQGQNQLYNELNLGRREEYDVLDKRRGRDPEMGGKPRRK
NPQEGLYNELQKDKMAEAYSEIGMKGERRRGKGHDGLYQGLSTATKDTYDALHMQALPPR

SEQ ID NO: 30:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDIAIYCIGVFLIACMVVTVILCRMKKRGRKKLLYIFKQPFMRPVQTTQEEDGC

SCRFPEEEEGGCELRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATKDTYDALHMQALP

PR

SEQ ID NO: 31:
MALPVTALLLPLALLLHAARPGMRTEDLPKAVVFLEPQWYRVLEKDSVTLKCQGAYSPEDNS

TQWFHNESLISSQASSYFIDAATVDDSGEYRCQTNLSTLSDPVQLEVHIGWLLLQAPRWVFK

EEDPIHLRCHSWKNTALHKVTYLQNGKGRKYFHHNSDFYIPKATLKDSGSYFCRGLFGSKNV

SSETVNITITQGLAVSTISSFFPPGYQTTTPAPRPPTPAPTIASQPLSLRPEACRPAAGGAV

HTRGLDFACDIYIWAPLAGTCGVLLLSLVITLYCKRGRKKLLYIFKQPFMRPVQTTQEEDGC

SCRFPEEEEGGCELRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATKDTYDALHMQALP

PR

SEQ ID NO: 32:
MALPVTALLLPLALLLHAARPQVDTTKAVITLQPPWVSVFQEETVTLHCEVLHLPGSSSTQW

FLNGTATQTSTPSYRITSASVNDSGEYRCQRGLSGRSDPIQLEIHRGWLLLQVSSRVFTEGE

PLALRCHAWKDKLVYNVLYYRNGKAFKFFHWNSNLTILKTNISHNGTYHCSGMGKHRYTSAG

ISVTVKELFPAPVLNASVTSPLLEGNLVTLSCETKLLLQRPGLQLYFSFYMGSKTLRGRNTS

SEYQILTARREDSGLYWCEAATEDGNVLKRSPELELQVLGLQLPTPVWFHIYIWAPLAGTCG

VLLLSLVITLYCKRGRKKLLYIFKQPFMRPVQTTQEEDGCSCRFPEEEEGGCELRVKFSRSA

DAPAYQQGQNQLYNELNLGRREEYDVLDKRRGRDPEMGGKPRRKNPQEGLYNELQKDKMAEA

YSEIGMKGERRRGKGHDGLYQGLSTATKDTYDALHMQALPPR

SEQ ID NO: 33:
MALPVTALLLPLALLLHAARPGMRTEDLPKAVVFLEPQWYRVLEKDSVTLKCQGAYSPEDNS

TQWFHNESLISSQASSYFIDAATVDDSGEYRCQTNLSTLSDPVQLEVHIGWLLLQAPRWVFK

EEDPIHLRCHSWKNTALHKVTYLQNGKGRKYFHHNSDFYIPKATLKDSGSYFCRGLVGSKNV

SSETVNITITQGLAVSTISSFFPPGYQEPKSCDKTHTCPPCPAPELLGGPSVFLFPPKPKDT

LMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFSCSVMHEALHNHY

TQKSLSLSPGKIYIWAPLAGTCGVLLLSLVITLYCKRGRKKLLYIFKQPFMRPVQTTQEEDG

CSCRFPEEEEGGCELRVKFSRSADAPAYQQGQNQLYNELNLGRREEYDVLDKRRGRDPEMGG

KPRRKNPQEGLYNELQKDKMAEAYSEIGMKGERRRGKGHDGLYQGLSTATKDTYDALHMQAL

PPR

SEQ ID NO: 34:
MALPVTALLLPLALLLHAARPGMRTEDLPKAVVFLEPQWYRVLEKDSVTLKCQGAYSPEDNS

TQWFHNESLISSQASSYFIDAATVDDSGEYRCQTNLSTLSDPVQLEVHIGWLLLQAPRWVFK

EEDPIHLRCHSWKNTALHKVTYLQNGKGRKYFHHNSDFYIPKATLKDSGSYFCRGLVGSKNV

SSETVNITITQGLAVSTISSFFPPGYQEPKSCDKTHTCPGQPREPQVYTLPPSRDELTKNQV

SLTCLVKGFYPSDIAVEWESNGQPENNYKTTPPVLDSDGSFFLYSKLTVDKSRWQQGNVFSC

SVMHEALHNHYTQKSLSLSPGKIYIWAPLAGTCGVLLLSLVITLYCKRGRKKLLYIFKQPFM

RPVQTTQEEDGCSCRFPEEEEGGCELRVKFSRSADAPAYQQGQNQLYNELNLGRREEYDVLD
KRRGRDPEMGGKPRRKNPQEGLYNELQKDKMAEAYSEIGMKGERRRGKGHDGLYQGLSTATK
DTYDALHMQALPPR

SEQ ID NO: 35:
*MALPVTALLLPLALLLHAARP*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQEPKSCDKTHTCPIYIWAPLAGTCGVLLLSLVITLY
CKRGRKKLLYIFKQPFMRPVQTTQEEDGCSCRFPEEEEGGCELRVKFSRSADAPAYQQGQNQ
LYNELNLGRREEYDVLDKRRGRDPEMGGKPRRKNPQEGLYNELQKDKMAEAYSEIGMKGERR
RGKGHDGLYQGLSTATKDTYDALHMQALPPR

SEQ ID NO: 36:
*MALPVTALLLPLALLLHAARP*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEAFACDIYIWA
PLAGTCGVLLLSLVITLYCKRGRKKLLYIFKQPFMRPVQTTQEEDGCSCRFPEEEEGGCELR
VKFSRSADAPAYQQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPR

SEQ ID NO: 37:
*MALPVTALLLPLALLLHAARP*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPFACDIYIWAPLAGTCGVLLLSLVI
TLYCKRGRKKLLYIFKQPFMRPVQTTQEEDGCSCRFPEEEEGGCELRVKFSRSADAPAYQQG
QNQLYNELNLGRREEYDVLDKRRGRDPEMGGKPRRKNPQEGLYNELQKDKMAEAYSEIGMKG
ERRRGKGHDGLYQGLSTATKDTYDALHMQALPPR

SEQ ID NO: 38:
*MALPVTALLLPLALLLHAARP*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQGGGGSGGGGSGGGGSIYIWAPLAGTCGVLLLSLVI
TLYCKRGRKKLLYIFKQPFMRPVQTTQEEDGCSCRFPEEEEGGCELRVKFSRSADAPAYQQG
QNQLYNELNLGRREEYDVLDKRRGRDPEMGGKPRRKNPQEGLYNELQKDKMAEAYSEIGMKG
ERRRGKGHDGLYQGLSTATKDTYDALHMQALPPR

SEQ ID NO: 39:
*MALPVTALLLPLALLLHAARP*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQGGGGSGGGGSGGGGSGGGGSGGGGSGGGGSIYIWA
PLAGTCGVLLLSLVITLYCKRGRKKLLYIFKQPFMRPVQTTQEEDGCSCRFPEEEEGGCELR
VKFSRSADAPAYQQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPR

SEQ ID NO: 40:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQGGGGSGGGGSGGGGSGGGGSGGGGSGGGGSGGGGS
GGGGSGGGGSIYIWAPLAGTCGVLLLSLVITLYCKRGRKKLLYIFKQPFMRPVQTTQEEDGC
SCRFPEEEEGGCELRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATKDTYDALHMQALP
PR

SEQ ID NO: 41:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQGGGGSGGGGSGGGGSGGGGSGGGGSGGGGSGGGGS
GGGGSGGGGSGGGGSGGGGSGGGGSIYIWAPLAGTCGVLLLSLVITLYCKRGRKKLLYIFKQ
PFMRPVQTTQEEDGCSCRFPEEEEGGCELRVKFSRSADAPAYQQGQNQLYNELNLGRREEYD
VLDKRRGRDPEMGGKPRRKNPQEGLYNELQKDKMAEAYSEIGMKGERRRGKGHDGLYQGLST
ATKDTYDALHMQALPPR

SEQ ID NO: 42:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQGGSPAGSPTSTEEGTSESATPESGPGTSTEPSEGS
APGSPAGSPTSTEEGTSTEPSEGSAIYIWAPLAGTCGVLLLSLVITLYCKRGRKKLLYIFKQ
PFMRPVQTTQEEDGCSCRFPEEEEGGCELRVKFSRSADAPAYQQGQNQLYNELNLGRREEYD
VLDKRRGRDPEMGGKPRRKNPQEGLYNELQKDKMAEAYSEIGMKGERRRGKGHDGLYQGLST
ATKDTYDALHMQALPPR

SEQ ID NO: 43:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQGGSPAGSPTSTEEGTSESATPESGPGTSTEIYIWA
PLAGTCGVLLLSLVITLYCKRGRKKLLYIFKQPFMRPVQTTQEEDGCSCRFPEEEEGGCELR
VKFSRSADAPAYQQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPR

SEQ ID NO: 44:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQGGSPAGSPTSTEEGTIYIWAPLAGTCGVLLLSLVI
TLYCKRGRKKLLYIFKQPFMRPVQTTQEEDGCSCRFPEEEEGGCELRVKFSRSADAPAYQQG
QNQLYNELNLGRREEYDVLDKRRGRDPEMGGKPRRKNPQEGLYNELQKDKMAEAYSEIGMKG
ERRRGKGHDGLYQGLSTATKDTYDALHMQALPPR

SEQ ID NO: 45:
*MLRLLLALNLFPSIQVTGG*MRTEDLPKAVVFLEPQWYRVLEKDSVILKCQGAYSPEDNSTQW
FHNESLISSQASSYFIDAATVDDSGEYRCQTNLSTLSDPVQLEVHIGWLLLQAPRWVFKEED
PIHLRCHSWKNTALHKVTYLQNGKGRKYFHHNSDFYIPKATLKDSGSYFCRGLVGSKNVSSE
TVNITITQGLAVSTISSFFPPGYQTTTPAPRPPTPAPTIASQPLSLRPEACRPAAGGAVHTR
GLDFACDIYIWAPLAGTCGVLLLSLVITLYCKRGRKKLLYIFKQPFMRPVQTTQEEDGCSCR
FPEEEEGGCELRVKFSRSADAPAYQQGQNQLYNELNLGRREEYDVLDKRRGRDPEMGGKPRR
KNPQEGLYNELQKDKMAEAYSEIGMKGERRRGKGHDGLYQGLSTATKDTYDALHMQALPPR

SEQ ID NO: 46:
*METDTLLLWVLLLWVPGSTGD*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDIYIWAPLAGTCGVLLLSLVITLYCKRGRKKLLYIFKQPFMRPVQTTQEEDGC
SCRFPEEEEGGCELRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATKDTYDALHMQALP
PR

SEQ ID NO: 47:
*MWQLLLPTALLLLLVSA*GMRTEDLPKAVVFLEPQWYRVLEKDSVTLKCQGAYSPEDNSTQWFH
NESLISSQASSYFIDAATVDDSGEYRCQTNLSTLSDPVQLEVHIGWLLLQAPRWVFKEEDPI
HLRCHSWKNTALHKVTYLQNGKGRKYFHHNSDFYIPKATLKDSGSYFCRGLVGSKNVSSETV
NITITQGLAVSTISSFFPPGYQTTTPAPRPPTPAPTIASQPLSLRPEACRPAAGGAVHTRGL
DFACDIYIWAPLAGTCGVLLLSLVITLYCKRGRKKLLYIFKQPFMRPVQTTQEEDGCSCRFP
EEEEGGCELRVKFSRSADAPAYQQGQNQLYNELNLGRREEYDVLDKRRGRDPEMGGKPRRKN
PQEGLYNELQKDKMAEAYSEIGMKGERRRGKGHDGLYQGLSTATKDTYDALHMQALPPR

SEQ ID NO: 48:
*MALPVTALLLPLALLLHAARP*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDIYIWAPLAGTCGVLLLSLVITLYCCWLTKKKYSSSVHDPNGEYMFMRAVNTA
KKSRLTDVTLRVKFSRSADAPAYQQGQNQLYNELNLGRREEYDVLDKRRGRDPEMGGKPRRK
NPQEGLYNELQKDKMAEAYSEIGMKGERRRGKGHDGLYQGLSTATKDTYDALHMQALPPR

SEQ ID NO: 49:
*MALPVTALLLPLALLLHAARP*GMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDIYIWAPLAGTCGVLLLSLVITLYCQRRKYRSNKGESPVEPAEPCRYSCPREE
EGSTIPIQEDYRKPEPACSPRVKFSRSADAPAYQQGQNQLYNELNLGRREEYDVLDKRRGRD
PEMGGKPRRKNPQEGLYNELQKDKMAEAYSEIGMKGERRRGKGHDGLYQGLSTATKDTYDAL
HMQALPPR

SEQ ID NO: 50:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDIYIWAPLAGTCGVLLLSLVITLYCQLGLHIWQLRSQCMWPRETQLLLEVPPS
TEDARSCQFPEEERGERSAEEKGRLGDLWVRVKFSRSADAPAYQQGQNQLYNELNLGRREEY
DVLDKRRGRDPEMGGKPRRKNPQEGLYNELQKDKMAEAYSEIGMKGERRRGKGHDGLYQGLS
TATKDTYDALHMQALPPR

SEQ ID NO: 51:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDIYIWAPLAGTCGVLLLSLVITLYCCVKRRKPRGDVVKVIVSVQRKRQEAEGE
ATVIEALQAPPDVTTVAVEETIPSFTGRSPNHRVKFSRSADAPAYQQGQNQLYNELNLGRRE
EYDVLDKRRGRDPEMGGKPRRKNPQEGLYNELQKDKMAEAYSEIGMKGERRRGKGHDGLYQG
LSTATKDTYDALHMQALPPR

SEQ ID NO: 52:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDIYIWAPLAGTCGVLLLSLVITLYCKKYFFKKEVQQLSVSFSSLQIKALQNAV
EKEVQAEDNIYIENSLYATDRVKFSRSADAPAYQQGQNQLYNELNLGRREEYDVLDKRRGRD
PEMGGKPRRKNPQEGLYNELQKDKMAEAYSEIGMKGERRRGKGHDGLYQGLSTATKDTYDAL
HMQALPPR

SEQ ID NO: 53:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDIYIWAPLAGTCGVLLLSLVITLYCYKVGFFKRNLKEKMEAGRGVPNGIPAED
SEQLASGQEAGDPGCLKPLHEKDSESGGGKDRVKFSRSADAPAYQQGQNQLYNELNLGRREE
YDVLDKRRGRDPEMGGKPRRKNPQEGLYNELQKDKMAEAYSEIGMKGERRRGKGHDGLYQGL
STATKDTYDALHMQALPPR

SEQ ID NO: 54:
MALPVTALLLPLALLLHAARPGMRTEDLPKAVVFLEPQWYRVLEKDSVTLKCQGAYSPEDNS
TQWFHNESLISSQASSYFIDAATVDDSGEYRCQTNLSTLSDPVQLEVHIGWLLLQAPRWVFK
EEDPIHLRCHSWKNTALHKVTYLQNGKGRKYFHHNSDFYIPKATLKDSGSYFCRGLVGSKNV
SSETVNITITQGLAVSTISSFFPPGYQTTTPAPRPPTPAPTIASQPLSLRPEACRPAAGGAV
HTRGLDFACDIYIWAPLAGTCGVLLLSLVITLYCKRKKQRSRRNDEELETRAHRVATEERGR
KPHQIPASTPQNPATSQHPPPPPGHRSQAPSHRPPPPGHRVQHQPQKRPPAPSGTQVHQQKG

-continued

PPLPRPRVQPKPPHGAAENSLSPSSNRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATK

DTYDALHMQALPPR

SEQ ID NO: 55:
MALPVTALLLPLALLLHAARPGMRTEDLPKAVVFLEPQWYRVLEKDSVTLKCQGAYSPEDNS

TQWFHNESLISSQASSYFIDAATVDDSGEYRCQTNLSTLSDPVQLEVHIGWLLLQAPRWVFK

EEDPIHLRCHSWKNTALHKVTYLQNGKGRKYFHHNSDFYIPKATLKDSGSYFCRGLVGSKNV

SSETVNITITQGLAVSTISSFFPPGYQTTTPAPRPPTPAPTIASQPLSLRPEACRPAAGGAV

HTRGLDFACDPQLCYILDAILFLYGIVLTLLYCRLKIQVRKAAITSYEKSDGVYTGLSTRNQ

ETYETLKHEKPPQKRGRKKLLYIFKQPFMRPVQTTQEEDGCSCRFPEEEEGGCEL

SEQ ID NO: 56:
MALPVTALLLPLALLLHAARPGMRTEDLPKAVVFLEPQWYRVLEKDSVILKCQGAYSPEDNS

TQWFHNESLISSQASSYFIDAATVDDSGEYRCQTNLSTLSDPVQLEVHIGWLLLQAPRWVFK

EEDPIHLRCHSWKNTALHKVTYLQNGKGRKYFHHNSDFYIPKATLKDSGSYFCRGLVGSKNV

SSETVNITITQGLAVSTISSFFPPGYQTTTPAPRPPTPAPTIASQPLSLRPEACRPAAGGAV

HTRGLDFACDIYIWAPLAGTCGVLLLSLVITLYCKRGRKKLLYIFKQPFMRPVQTTQEEDGC

SCRFPEEEEGGCELRLKIQVRKAAITSYEKSDGVYTGLSTRNQETYETLKHEKPPQ

It would be appreciated by a skilled person that the signal peptide of any of the above exemplary chimeric receptors may be removed or replaced with another suitable signal peptide without affecting the function of the chimeric receptor. Such variants of the exemplary chimeric receptors are also within the scope of the present disclosure.

Any of the chimeric receptors described herein can be prepared by a routine method, such as recombinant technology. Methods for preparing the chimeric receptors herein involve generation of a nucleic acid that encodes a polypeptide comprising each of the domains of the chimeric receptors, including the extracellular ligand-binding domain of an Fc receptor, the transmembrane domain, at least one co-stimulatory signaling domain, and the cytoplasmic signaling domain comprising an ITAM. In some embodiments, the nucleic acid also encodes a hinge domain between the extracellular ligand-binding domain of an Fc receptor and the transmembrane domain. The nucleic acid encoding the chimeric receptor may also encode a signal sequence. In some embodiments, the nucleic acid sequence encodes any one of the exemplary chimeric receptors provided by SEQ ID NO: 2-56.

Sequences of each of the components of the chimeric receptors may be obtained via routine technology, e.g., PCR amplification from any one of a variety of sources known in the art. In some embodiments, sequences of one or more of the components of the chimeric receptors are obtained from a human cell. Alternatively, the sequences of one or more components of the chimeric receptors can be synthesized. Sequences of each of the components (e.g., domains) can be joined directly or indirectly (e.g., using a nucleic acid sequence encoding a peptide linker) to form a nucleic acid sequence encoding the chimeric receptor, using methods such as PCR amplification or ligation. Alternatively, the nucleic acid encoding the chimeric receptor may be synthesized. In some embodiments, the nucleic acid is DNA. In other embodiments, the nucleic acid is RNA.

Any of the chimeric receptor proteins, nucleic acid encoding such, and expression vectors carrying such nucleic acid can be mixed with a pharmaceutically acceptable carrier to form a pharmaceutical composition, which is also within the scope of the present disclosure. "Acceptable" means that the carrier is compatible with the active ingredient of the composition (e.g., the nucleic acids, vectors, cells, or therapeutic antibodies) and does not negatively affect the subject to which the composition(s) are administered. Any of the pharmaceutical compositions to be used in the present methods can comprise pharmaceutically acceptable carriers, excipients, or stabilizers in the form of lyophilized formations or aqueous solutions.

Pharmaceutically acceptable carriers, including buffers, are well known in the art, and may comprise phosphate, citrate, and other organic acids; antioxidants including ascorbic acid and methionine; preservatives; low molecular weight polypeptides; proteins, such as serum albumin, gelatin, or immunoglobulins; amino acids; hydrophobic polymers; monosaccharides; disaccharides; and other carbohydrates; metal complexes; and/or non-ionic surfactants. See, e.g. Remington: The Science and Practice of Pharmacy 20$^{th}$ Ed. (2000) Lippincott Williams and Wilkins, Ed. K. E. Hoover.

II. Immune Cells Expressing Chimeric Receptors

Host cells expressing the chimeric receptors described herein provide a specific population of cells that can recognize target cells bound by antibodies (e.g., therapeutic antibodies) or Fc-fusion proteins. Engagement of the extracellular ligand-binding domain of a chimeric receptor construct expressed on such host cells (e.g., immune cells) with the Fc portion of an antibody or an Fc-fusion protein transmits an activation signal to the co-stimulatory signaling domain(s) and the ITAM-containing cytoplasmic signaling domain of the chimeric receptor construct, which in turn activates cell proliferation and/or effector functions of the host cell, such as ADCC effects triggered by the host cells. The combination of co-stimulatory signaling domain(s) and the cytoplasmic signaling domain comprising an ITAM may allow for robust activation of multiple signaling pathways within the cell. In some embodiments, the host cells are immune cells, such as T cells, NK cells, macrophages, neutrophils, eosinophils, or any combination thereof. In some embodiments, the immune cells are T cells. In some embodiments, the immune cells are NK cells. In other embodiments, the immune cells can be established cell lines, for example, NK-92 cells.

The population of immune cells can be obtained from any source, such as peripheral blood mononuclear cells (PB-MCs), bone marrow, tissues such as spleen, lymph node, thymus, or tumor tissue. A source suitable for obtaining the type of host cells desired would be evident to one of skill in the art. In some embodiments, the population of immune cells is derived from PBMCs. The type of host cells desired (e.g., immune cells such as T cells, NK cells, macrophages, neutrophils, eosinophils, or any combination thereof) may be expanded within the population of cells obtained by co-incubating the cells with stimulatory molecules, for example, anti-CD3 and anti-CD28 antibodies may be used for expansion of T cells.

To construct the immune cells that express any of the chimeric receptor constructs described herein, expression vectors for stable or transient expression of the chimeric receptor construct may be constructed via conventional methods as described herein and introduced into immune host cells. For example, nucleic acids encoding the chimeric receptors may be cloned into a suitable expression vector, such as a viral vector in operable linkage to a suitable promoter. The nucleic acids and the vector may be contacted, under suitable conditions, with a restriction enzyme to create complementary ends on each molecule that can pair with each other and be joined with a ligase. Alternatively, synthetic nucleic acid linkers can be ligated to the termini of the nucleic acid encoding the chimeric receptors. The synthetic linkers may contain nucleic acid sequences that correspond to a particular restriction site in the vector. The selection of expression vectors/plasmids/viral vectors would depend on the type of host cells for expression of the chimeric receptors, but should be suitable for integration and replication in eukaryotic cells.

A variety of promoters can be used for expression of the chimeric receptors described herein, including, without limitation, cytomegalovirus (CMV) intermediate early promoter, a viral LTR such as the Rous sarcoma virus LTR, HIV-LTR, HTLV-1 LTR, the simian virus 40 (SV40) early promoter, herpes simplex tk virus promoter. Additional promoters for expression of the chimeric receptors include any constitutively active promoter in an immune cell. Alternatively, any regulatable promoter may be used, such that its expression can be modulated within an immune cell.

Additionally, the vector may contain, for example, some or all of the following: a selectable marker gene, such as the neomycin gene for selection of stable or transient transfectants in host cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; T7 and SP6 RNA promoters for in vitro transcription of sense and antisense RNA; a "suicide switch" or "suicide gene" which when triggered causes cells carrying the vector to die (e.g., HSV thymidine kinase, an inducible caspase such as iCasp9), and reporter gene for assessing expression of the chimeric receptor. See section VI below. Suitable vectors and methods for producing vectors containing transgenes are well known and available in the art. Examples of the preparation of vectors for expression of chimeric receptors can be found, for example, in US2014/0106449, herein incorporated in its entirety by reference.

Any of the vectors comprising a nucleic acid sequence that encodes a chimeric receptor construct described herein is also within the scope of the present disclosure. Such a vector may be delivered into host cells such as host immune cells by a suitable method. Methods of delivering vectors to immune cells are well known in the art and may include DNA electroporation, RNA electroporation, transfection reagents such as liposomes, or viral transduction. In some embodiments, the vectors for expression of the chimeric receptors are delivered to host cells by viral transduction. Exemplary viral methods for delivery include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors, and adeno-associated virus (AAV) vectors (see, e.g., PCT Publication Nos. WO 94/12649, WO 93/03769; WO 93/19191; WO 94/28938; WO 95/11984 and WO 95/00655). In some embodiments, the vectors for expression of the chimeric receptors are retroviruses. In some embodiments, the vectors for expression of the chimeric receptors are lentiviruses.

In examples in which the vectors encoding chimeric receptors are introduced to the host cells using a viral vector, viral particles that are capable of infecting the immune cells and carry the vector may be produced by any method known in the art and can be found, for example in PCT Application No. WO 1991/002805A2, WO 1998/009271 A1, and U.S. Pat. No. 6,194,191. The viral particles are harvested from the cell culture supernatant and may be isolated and/or purified prior to contacting the viral particles with the immune cells.

Following introduction into the host cells a vector encoding any of the chimeric receptors provided herein, the cells are cultured under conditions that allow for expression of the chimeric receptor. In examples in which the nucleic acid encoding the chimeric receptor is regulated by a regulatable promoter, the host cells are cultured in conditions wherein the regulatable promoter is activated. In some embodiments, the promoter is an inducible promoter and the immune cells are cultured in the presence of the inducing molecule or in conditions in which the inducing molecule is produced. Determining whether the chimeric receptor is expressed will be evident to one of skill in the art and may be assessed by any known method, for example, detection of the chimeric receptor-encoding mRNA by quantitative reverse transcriptase PCR (qRT-PCR) or detection of the chimeric receptor protein by methods including Western blotting, fluorescence microscopy, and flow cytometry. Alternatively, expression of the chimeric receptor may take place in vivo after the immune cells are administered to a subject.

Alternatively, expression of a chimeric receptor construct in any of the immune cells disclosed herein can be achieved by introducing RNA molecules encoding the chimeric receptor constructs. Such RNA molecules can be prepared by in vitro transcription or by chemical synthesis. The RNA molecules can then introduced into suitable host cells such as immune cells (e.g., T cells, NK cells, macrophages, neutrophils, eosinophils, or any combination thereof) by, e.g., electroporation. For example, RNA molecules can be synthesized and introduced into host immune cells following the methods described in Rabinovich et al., Human Gene Therapy, 17:1027-1035 and WO WO2013/040557.

Methods for preparing host cells expressing any of the chimeric receptors described herein may also comprise activating the host cells ex vivo. Activating a host cell means stimulating a host cell into an activate state in which the cell may be able to perform effector functions (e.g., ADCC). Methods of activating a host cell will depend on the type of host cell used for expression of the chimeric receptors. For example, T cells may be activated ex vivo in the presence of one or more molecule such as an anti-CD3 antibody, an anti-CD28 antibody, IL-2, or phytohemoagglutinin. In other examples, NK cells may be activated ex vivo in the presence of one or molecules such as a 4-1BB ligand, an anti-4-1BB antibody, IL-15, an anti-IL-15 receptor antibody, IL-2, IL12, IL-21, and K562 cells. In some embodiments, the host cells expressing any of the chimeric receptors described herein are activated ex vivo prior to administration to a subject. Determining whether a host cell is activated will be evident to one of skill in the art and may include assessing expression of one or more cell surface markers associated with cell activation, expression or secretion of cytokines, and cell morphology.

The methods of preparing host cells expressing any of the chimeric receptors described herein may comprise expanding the host cells ex vivo. Expanding host cells may involve any method that results in an increase in the number of cells expressing chimeric receptors, for example, allowing the host cells to proliferate or stimulating the host cells to proliferate. Methods for stimulating expansion of host cells will depend on the type of host cell used for expression of the chimeric receptors and will be evident to one of skill in the art. In some embodiments, the host cells expressing any of the chimeric receptors described herein are expanded ex vivo prior to administration to a subject.

In some embodiments, the host cells expressing the chimeric receptors are expanded and activated ex vivo prior to administration of the cells to the subject.

IV. Application of Immune Cells Expressing Chimeric Receptor in Immunotherapy

Host cells (e.g., immune cells) expressing chimeric receptors (the encoding nucleic acids or vectors comprising such) described herein are useful for enhancing ADCC in a subject and/or for enhancing the efficacy of an antibody-based immunotherapy. In some embodiments, the subject is a mammal, such as a human, monkey, mouse, rabbit, or domestic mammal. In some embodiments, the subject is a human. In some embodiments, the subject is a human cancer patient. In some embodiments, the subject has been treated or is being treated with any of the therapeutic antibodies described herein.

The immune cells can be mixed with a pharmaceutically acceptable carrier to form a pharmaceutical composition, which is also within the scope of the present disclosure.

To perform the methods described herein, an effective amount of the immune cells expressing any of the chimeric receptor constructs described herein can be administered into a subject in need of the treatment. The immune cells may be autologous to the subject, i.e., the immune cells are obtained from the subject in need of the treatment, genetically engineered for expression of the chimeric receptor constructs, and then administered to the same subject. Administration of autologous cells to a subject may result in reduced rejection of the host cells as compared to administration of non-autologous cells. Alternatively, the host cells are allogeneic cells, i.e., the cells are obtained from a first subject, genetically engineered for expression of the chimeric receptor construct, and administered to a second subject that is different from the first subject but of the same species. For example, allogeneic immune cells may be derived from a human donor and administered to a human recipient who is different from the donor.

In some embodiments, the immune cells are administered to a subject in an amount effective in enhancing ADCC activity by least 20%, e.g., 50%, 80%, 100%, 2-fold, 5-fold, 10-fold, 20-fold, 50-fold, 100-fold or more.

In some embodiments, the immune cells are co-used with a therapeutic Fc-containing therapeutic agent (e.g., an antibody or Fc fusion molecule such as Fc fusion protein) so as to enhance the efficacy of the anti-based immunotherapy. Antibody-based immunotherapy is used to treat, alleviate, or reduce the symptoms of any disease or disorder for which the immunotherapy is considered useful in a subject. In such therapy, a therapeutic antibody may bind to a cell surface antigen that is differentially expressed on cancer cells (i.e., not expressed on non-cancer cells or expressed at a lower level on non-cancer cells). Examples of antigens or target molecules that are bound by therapeutic antibodies and indicate that the cell expressing the antigen or target molecule should be subjected to ADCC include, without limitation, CD17/L1-CAM, CD19, CD20, CD22, CD30, CD33, CD37, CD52, CD56, CD70, CD79b, CD138, CEA, DS6, EGFR, EGFRvIII, ENPP3, FR, GD2, GPNMB, HER2, IL-13Rα2, Mesothelin, MUC1, MUC16, Nectin-4, PSMA, and SCL44A4.

The efficacy of an antibody-based immunotherapy may be assessed by any method known in the art and would be evident to a skilled medical professional. For example, the efficacy of the antibody-based immunotherapy may be assessed by survival of the subject or tumor or cancer burden in the subject or tissue or sample thereof. In some embodiments, the immune cells are administered to a subject in need of the treatment in an amount effective in enhancing the efficacy of an antibody-based immunotherapy by at least 20%, e.g., 50%, 80%, 100%, 2-fold, 5-fold, 10-fold, 20-fold, 50-fold, 100-fold or more, as compared to the efficacy in the absence of the immune cells.

In some embodiments, the immune cells expressing any of the chimeric receptors disclosed herein are administered to a subject who has been treated or is being treated with an Fc-containing therapeutic agent (e.g., an Fc-containing therapeutic protein). The immune cells expressing any one of the chimeric receptors disclosed herein may be co-administered with an Fc-containing therapeutic agent. For example, the immune cells may be administered to a human subject simultaneously with a therapeutic antibody. Alternatively, the immune cells may be administered to a human subject during the course of an antibody-based immunotherapy. In some examples, the immune cells and an therapeutic antibody can be administered to a human subject at least 4 hours apart, e.g., at least 12 hours apart, at least 1 day apart, at least 3 days apart, at least one week apart, at least two weeks apart, or at least one month apart.

Examples of therapeutic Fc-containing therapeutic protein include, without limitation, Adalimumab, Ado-Trastuzumab emtansine, Alemtuzumab, Basiliximab, Bevacizumab, Belimumab, Brentuximab, Canakinumab, Cetuximab, Daclizumab, Denosumab, Dinoutuzimab, Eculizumab, Efalizumab, Epratuzumab, Gemtuzumab, Golimumab, Infliximab, Ipilimumab, Labetuzumab, Natalizumab, Obinutuzumab, Ofatumumab, Omalizumab, Palivizumab, Panitumumab, Pertuzumab, Ramucirumab, Ritutimab, Tocilizumab, Tratuzumab, Ustekinumab, and Vedolizumab.

To practice the method disclosed herein, an effective amount of the immune cells expressing chimeric receptors, Fc-containing therapeutic agents (e.g., Fc-containing therapeutic proteins such as Fc fusion proteins and therapeutic antibodies), or compositions thereof can be administered to a subject (e.g., a human cancer patient) in need of the treatment via a suitable route, such as intravenous administration. Any of the immune cells expressing chimeric receptors, Fc-containing therapeutic agents, or compositions thereof may be administered to a subject in an effective amount. As used herein, an effective amount refers to the amount of the respective agent (e.g., the host cells expressing chimeric receptors, Fc-containing therapeutic agents, or compositions thereof) that upon administration confers a therapeutic effect on the subject. Determination of whether an amount of the cells or compositions described herein achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. In some embodiments, the effective amount alleviates, relieves, ameliorates, improves, reduces the symptoms, or delays the progression of any disease or disorder in the subject. In some embodiments, the subject is a human. In some embodiments, the subject is a human cancer patient.

In some embodiments, the subject is a human patient suffering from a cancer, which can be carcinoma, lymphoma, sarcoma, blastoma, or leukemia. Examples of cancers for which administration of the cells and compositions disclosed herein may be suitable include, for example, lymphoma, breast cancer, gastric cancer, neuroblastoma, osteosarcoma, lung cancer, skin cancer, prostate cancer, colon cancer, renal cell carcinoma, ovarian cancer, rhabdomyosarcoma, leukemia, mesothelioma, pancreatic cancer, head and neck cancer, retinoblastoma, glioma, glioblastoma, and thyroid cancer.

V. Kits for Therapeutic Use

The present disclosure also provides kits for use of the chimeric receptors in enhancing antibody-dependent cell-mediated cytotoxicity and enhancing an antibody-based immunotherapy. Such kits may include one or more containers comprising a first pharmaceutical composition that comprises any nucleic acid or host cells (e.g., immune cells such as those described herein), and a pharmaceutically acceptable carrier, and a second pharmaceutical composition that comprises a therapeutic antibody and a pharmaceutically acceptable carrier.

In some embodiments, the kit can comprise instructions for use in any of the methods described herein. The included instructions can comprise a description of administration of the first and second pharmaceutical compositions to a subject to achieve the intended activity, e.g., enhancing ADCC activity, and/or enhancing the efficacy of an antibody-based immunotherapy, in a subject. The kit may further comprise a description of selecting a subject suitable for treatment based on identifying whether the subject is in need of the treatment. In some embodiments, the instructions comprise a description of administering the first and second pharmaceutical compositions to a subject who is in need of the treatment.

The instructions relating to the use of the chimeric receptors and the first and second pharmaceutical compositions described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the pharmaceutical compositions are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device, such as an inhaler, nasal administration device, or an infusion device. A kit may have a sterile access port (for example, the container may be an intravenous solution bag or a vial having a stopper pierceable by a hypodermic injection needle). The container may also have a sterile access port. At least one active agent in the pharmaceutical composition is a chimeric receptor as described herein.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

VI. Chimeric Receptor CD16/CD8α/4-1BB/CD3ζ

Exemplary chimeric receptors disclosed herein include those that comprise an extracellular ligand-binding domain of CD16 (CD16F or CD16V, also known as F158 FCGR3A and V158 FCGR3A variant), hinge and transmembrane domains of CD8α, a co-stimulatory signaling domain of 4-1BB, and a cytoplasmic signaling domain of CD3ζ, e.g., the CD16F-BB-ζ and CD16V-BB-ζ disclosed herein. Like other chimeric receptors disclosed herein, expression of these exemplary chimeric receptors in immune cells such as T cells and NK cells, would confer ADCC capability to these cells and, therefore, would significantly augment the anti-tumor potential of monoclonal antibodies (as well as other anti-tumor molecules comprising the Fc portion, such as, e.g., a composite molecule constituted by a ligand (e.g., cytokine, immune cell receptor) binding a tumor surface receptor combined with the Fc-portion of an immunoglobulin or Fc-containing DNA or RNA), regardless of the targeted tumor-antigen.

These exemplary chimeric receptors (as well as others disclosed herein) are universal chimeric receptors with potential for augmenting significantly the efficacy of antibody therapy against multiple tumors. As discussed in Example 1 below, when expressed in human T cells by retroviral transduction, the V158 receptor of the disclosure has a significantly higher affinity for human IgG including humanized antibodies such as the anti-CD20 antibody Rituximab as compared to an identical chimeric receptor containing the common F158 variant (also provided herein). Engagement of the chimeric receptor provokes T-cell activation, exocytosis of lytic granules and proliferation. CD16V-BB-ζ expressing T cells specifically kill lymphoma cell lines and primary chronic lymphocytic leukemia (CLL) cells in the presence of Rituximab at low effector:target ratio, even when CLL cultures are performed on bone marrow-derived mesenchymal cells. The anti-HER2 antibody Trastuzumab trigger chimeric receptor-mediated antibody-dependent cell cytotoxicity (ADCC) against breast and gastric cancer cells, and the anti-GD2 antibody hu14.18K322A against neuroblastoma and osteosarcoma cells. As further disclosed in the Examples section, T cells expressing the chimeric receptor and Rituximab in combination eradicated human lymphoma cells in immunodeficient mice, while T cells or antibody alone did not. To facilitate clinical translation of this technology, a method based on electroporation of the chimeric receptor mRNA was developed, leading to efficient and transient receptor expression without the use of viral vectors.

The disclosures of the exemplary chimeric receptors disclosed in this section are merely illustrative and are equally applicable to other chimeric receptors disclosed in the present disclosure.

(i) Chimeric Receptors CD16V-BB-ζ

The present disclosure provides an exemplary chimeric receptor comprising: (a) an extracellular ligand-binding domain of the V158 FCGR3A variant; (b) the hinge and transmembrane domains of CD8α; and (c) a cytoplasmic domain comprising a 4-1BB co-stimulatory signaling domain and a CD3 signaling domain. In one specific embodiment, the V158 FCGR3A variant consists of the amino acid sequence of SEQ ID NO: 57. In one specific embodiment, the hinge and transmembrane domains of CD8c consist of the amino acid sequence of SEQ ID NO: 58. In one specific embodiment, the 4-1BB signaling domain consists of the amino acid sequence of SEQ ID NO: 59. In one specific embodiment, the CD3ζ signaling domain consists of the amino acid sequence of SEQ ID NO: 60. In one embodiment, the extracellular ligand-binding domain of the chimeric receptor further comprises a signal peptide of CD8α. In one specific embodiment, the signal peptide of CD8c consists of the amino acid sequence of SEQ ID NO: 61. In one specific embodiment, the chimeric receptor comprises the amino acid sequence of SEQ ID NO: 1. In one specific embodiment, the chimeric receptor (CD16V-BB-ζ) consists of the amino acid sequence of SEQ ID NO: 1.

The present disclosure also provides a chimeric receptor comprising: (a) an extracellular ligand-binding domain comprising F158 FCGR3A variant; (b) the hinge and transmembrane domains of CD8α; and (c) a cytoplasmic domain comprising a 4-1BB signaling domain and a CD3ζ signaling domain. In one specific embodiment, the F158 FCGR3A variant consists of the amino acid sequence of SEQ ID NO: 70. In one specific embodiment, the hinge and transmembrane domains of CD8α consist of the amino acid sequence of SEQ ID NO: 58. In one specific embodiment, the 4-1BB signaling domain consists of the amino acid sequence of SEQ ID NO: 59. In one specific embodiment, the CD3ζ signaling domain consists of the amino acid sequence of SEQ ID NO: 60. In one specific embodiment, the extracellular ligand-binding domain of the chimeric receptor further comprises a signal peptide of CD8α. In one specific embodiment, such signal peptide of CD8α consists of the amino acid sequence of SEQ ID NO: 61. In one specific embodiment, the chimeric receptor comprises the amino acid sequence of SEQ ID NO: 31. In one specific embodiment, the chimeric receptor consists of the amino acid sequence of SEQ ID NO: 31.

In one embodiment, the chimeric receptors of the disclosure contain one or more signaling domains in addition to the two signaling domains described herein, i.e. CD3ζ and 4-1BB/CD137. In one specific embodiment, several signaling domains are fused together for additive or synergistic effect. Non-limiting examples of useful additional signaling domains include part or all of one or more of TCR Zeta chain, CD28, OX40/CD134, 4-1BB/CD137, FcεRIγ, ICOS/CD278, ILRB/CD122, IL-2RG/CD132, and CD40.

The present disclosure also provides polynucleotides encoding the chimeric receptors disclosed above. In one specific embodiment, the polynucleotide encoding the V158 FCGR3A variant comprises the sequence of SEQ ID NO: 65. In one specific embodiment, the polynucleotide encoding the F158 FCGR3A variant comprises the sequence of SEQ ID NO: 72. In one specific embodiment, the polynucleotide encoding the hinge and transmembrane domains of CD8α comprises of SEQ ID NO: 66. In one specific embodiment, the polynucleotide encoding the 4-1BB signaling domain comprises of SEQ ID NO: 67. In one specific embodiment, the polynucleotide encoding the CD3ζ signaling domain comprises SEQ ID NO: 68. In one specific embodiment, the polynucleotide encoding the signal peptide of CD8α comprises of SEQ ID NO: 69. In one specific embodiment, the polynucleotide encoding the chimeric receptor (CD16V-BB-ζ) comprises the sequence of SEQ ID NO: 64. In one specific embodiment, the polynucleotide encoding the chimeric receptor (CD16F-BB-ζ) comprises the sequence of SEQ ID NO: 71.

TABLE 6

Exemplary sequences

| SEQ ID NO | SEQUENCE | DESCRIPTION |
|---|---|---|
| 1 | MALPVTALLLPLALLLHAARPGMRTEDLPKAVVFLEPQWYRVLEKDSVTLKCQGAYS PEDNSTQWFHNESLISSQASSYFIDAATVDDSGEYRCQTNLSTLSDPVQLEVHIGWL LLQAPRWVFKEEDPIHLRCHSWKNTALHKVTYLQNGKGRKYFHHNSDFYIPKATLKD SGSYFCRGLVGSKNVSSETVNITITQGLAVSTISSFFPPGYQTTTPAPRPPTPAPTI ASQPLSLRPEACRPAAGGAVHTRGLDFACDIYIWAPLAGTCGVLLLSLVITLYCKRG RKKLLYIFKQPFMRPVQTTQEEDGCSCRFPEEEEGGCELRVKFSRSADAPAYQQGQN QLYNELNLGRREEYDVLDKRRGRDPEMGGKPRRKNPQEGLYNELQKDKMAEAYSEIG MKGERRRGKGHDGLYQGLSTATKDTYDALHMQALPPR | CD16V-BB-ζ |
| 57 | GMRTEDLPKAVVFLEPQWYRVLEKDSVTLKCQGAYSPEDNSTQWFHNESLISSQASS YFIDAATVDDSGEYRCQTNLSTLSDPVQLEVHIGWLLLQAPRWVFKEEDPIHLRCHS WKNTALHKVTYLQNGKGRKYFHHNSDFYIPKATLKDSGSYFCRGLVGSKNVSSETVN ITITQGLAVSTISSFFPPGYQ | V158 FCGR3A variant |
| 58 | TTTPAPRPPTPAPTIASQPLSLRPEACRPAAGGAVHTRGLDFACDIYIWAPLAGTCG VLLLSLVITLYC | hinge and transmembrane domains of CD8alpha |

TABLE 6-continued

Exemplary sequences

| SEQ ID NO | SEQUENCE | DESCRIPTION |
|---|---|---|
| 59 | KRGRKKLLYIFKQPFMRPVQTTQEEDGCSCRFPEEEEGGCEL | 4-1BB signaling domain |
| 60 | RVKFSRSADAPAYQQGQNQLYNELNLGRREEYDVLDKRRGRDPEMGGKPRRKNPQEG LYNELQKDKMAEAYSEIGMKGERRRGKGHDGLYQGLSTATKDTYDALHMQALPPR | CD3zeta signaling domain |
| 61 | MALPVTALLLPLALLLHAARP | signal peptide of CD8alpha |
| 62 | CTTCTGCAGGGGGCTTGTTGGGAGTAAAAATGTGTC | synthetic/ primer |
| 63 | GACACATTTTTACTCCCAACAAGCCCCCTGCAGAAG | synthetic/ primer |
| 64 | ATGGCCTTACCAGTGACCGCCTTGCTCCTGCCGCTGGCCTTGCTGCTCCACGCCGCC AGGCCGGGCATGCGGACTGAAGATCTCCCAAAGGCTGTGGTGTTCCTGGAGCCTCAA TGGTACAGGGTGCTCGAGAAGGACAGTGTGACTCTGAAGTGCCAGGGAGCCTACTCC CCTGAGGACAATTCCACACAGTGGTTTCACAATGAGAGCCTCATCTCAAGCCAGGCC TCGAGCTACTTCATTGACGCTGCCACAGTCGACGACAGTGGAGAGTACAGGTGCCAG ACAAACCTCTCCACCCTCAGTGACCCGGTGCAGCTAGAAGTCCATATCGGCTGGCTG TTGCTCCAGGCCCCTCGGTGGGTGTTCAAGGAGGAAGACCCTATTCACCTGAGGTGT CACAGCTGGAAGAACACTGCTCTGCATAAGGTCACATATTTACAGAATGGCAAAGGC AGGAAGTATTTTCATCATAATTCTGACTTCTACATTCCAAAAGCCACACTCAAAGAC AGCGGCTCCTACTTCTGCAGGGGGCTTGTTGGGAGTAAAAATGTGTCTTCAGAGACT GTGAACATCACCATCACTCAAGGTTTGGCAGTGTCAACCATCTCATCATTCTTTCCA CCTGGGTACCAAACCACGACGCCAGCGCCGCGACCACCAACACCGGCGCCCACCATC GCGTCGCAGCCCCTGTCCCTGCGCCCAGAGGCGTGCCGGCCAGCGGCGGGGGGCGCA GTGCACACGAGGGGGCTGGACTTCGCCTGTGATATCTACATCTGGGCGCCCTTGGCC GGGACTTGTGGGGTCCTTCTCCTGTCACTGGTTATCACCCTTTACTGCAAACGGGGC AGAAAGAAACTCCTGTATATATTCAAACAACCATTTATGAGACCAGTACAAACTACT CAAGAGGAAGATGGCTGTAGCTGCCGATTTCCAGAAGAAGAAGAAGGAGGATGTGAA CTGAGAGTGAAGTTCAGCAGGAGCGCAGACGCCCCCGCGTACCAGCAGGGCCAGAAC CAGCTCTATAACGAGCTCAATCTAGGACGAAGAGAGGAGTACGATGTTTTGGACAAG AGACGTGGCCGGGACCCTGAGATGGGGGGAAAGCCGAGAAGGAAGAACCCTCAGGAA GGCCTGTACAATGAACTGCAGAAAGATAAGATGGCGGAGGCCTACAGTGAGATTGGG ATGAAAGGCGAGCGCCGGAGGGGCAAGGGGCACGATGGCCTTTACCAGGGTCTCAGT ACAGCCACCAAGGACACCTACGACGCCCTTCACATGCAGGCCCTGCCCCCTCGCTAA | CD16V-BB-ζ |
| 65 | GGCATGCGGACTGAAGATCTCCCAAAGGCTGTGGTGTTCCTGGAGCCTCAATGGTAC AGGGTGCTCGAGAAGGACAGTGTGACTCTGAAGTGCCAGGGAGCCTACTCCCCTGAG GACAATTCCACACAGTGGTTTCACAATGAGAGCCTCATCTCAAGCCAGGCCTCGAGC TACTTCATTGACGCTGCCACAGTCGACGACAGTGGAGAGTACAGGTGCCAGACAAAC CTCTCCACCCTCAGTGACCCGGTGCAGCTAGAAGTCCATATCGGCTGGCTGTTGCTC CAGGCCCCTCGGTGGGTGTTCAAGGAGGAAGACCCTATTCACCTGAGGTGTCACAGC TGGAAGAACACTGCTCTGCATAAGGTCACATATTTACAGAATGGCAAAGGCAGGAAG TATTTTCATCATAATTCTGACTTCTACATTCCAAAAGCCACACTCAAAGACAGCGGC TCCTACTTCTGCAGGGGGCTTGTTGGGAGTAAAAATGTGTCTTCAGAGACTGTGAAC ATCACCATCACTCAAGGTTTGGCAGTGTCAACCATCTCATCATTCTTTCCACCTGGG TACCAA | V158 FCGR3A variant |
| 66 | ACCACGACGCCAGCGCCGCGACCACCAACACCGGCGCCCACCATCGCGTCGCAGCCC CTGTCCCTGCGCCCAGAGGCGTGCCGGCCAGCGGCGGGGGGCGCAGTGCACACGAGG GGGCTGGACTTCGCCTGTGATATCTACATCTGGGCGCCCTTGGCCGGGACTTGTGGG GTCCTTCTCCTGTCACTGGTTATCACCCTTTACTGC | hinge and trans- membrane domains of CD8alpha |
| 67 | AAACGGGGCAGAAAGAAACTCCTGTATATATTCAAACAACCATTTATGAGACCAGTA CAAACTACTCAAGAGGAAGATGGCTGTAGCTGCCGATTTCCAGAAGAAGAAGAAGGA GGATGTGAACTG | 4-1BB signaling domain |
| 68 | AGAGTGAAGTTCAGCAGGAGCGCAGACGCCCCCGCGTACCAGCAGGGCCAGAACCAG CTCTATAACGAGCTCAATCTAGGACGAAGAGAGGAGTACGATGTTTTGGACAAGAGA CGTGGCCGGGACCCTGAGATGGGGGGAAAGCCGAGAAGGAAGAACCCTCAGGAAGGC CTGTACAATGAACTGCAGAAAGATAAGATGGCGGAGGCCTACAGTGAGATTGGGATG AAAGGCGAGCGCCGGAGGGGCAAGGGGCACGATGGCCTTTACCAGGGTCTCAGTACA GCCACCAAGGACACCTACGACGCCCTTCACATGCAGGCCCTGCCCCCTCGCTAA | CD3zeta signaling domain |
| 69 | ATGGCCTTACCAGTGACCGCCTTGCTCCTGCCGCTGGCCTTGCTGCTCCACGCCGCC AGGCCG | signal peptide of CD8alpha |

TABLE 6-continued

Exemplary sequences

| SEQ ID NO | SEQUENCE | DESCRIPTION |
|---|---|---|
| 31 | MALPVTALLLPLALLLHAARPGMRTEDLPKAVVFLEPQWYRVLEKDSVTLKCQGAYS PEDNSTQWFHNESLISSQASSYFIDAATVDDSGEYRCQTNLSTLSDPVQLEVHIGWL LLQAPRWVFKEEDPIHLRCHSWKNTALHKVTYLQNGKGRKYFHHNSDFYIPKATLKD SGSYFCRGLFGSKNVSSETVNITITQGLAVSTISSFFPPGYQTTTPAPRPPTPAPTI ASQPLSLRPEACRPAAGGAVHTRGLDFACDIYIWAPLAGTCGVLLLSLVITLYCKRG RKKLLYIFKQPFMRPVQTTQEEDGCSCRFPEEEEGGCELRVKFSRSADAPAYQQGQN QLYNELNLGRREEYDVLDKRRGRDPEMGGKPRRKNPQEGLYNELQKDKMAEAYSEIG MKGERRRGKGHDGLYQGLSTATKDTYDALHMQALPPR | CD16F-BB-ζ |
| 70 | GMRTEDLPKAVVFLEPQWYRVLEKDSVTLKCQGAYSPEDNSTQWFHNESLISSQASS YFIDAATVDDSGEYRCQTNLSTLSDPVQLEVHIGWLLLQAPRWVFKEEDPIHLRCHS WKNTALHKVTYLQNGKGRKYFHHNSDFYIPKATLKDSGSYFCRGLFGSKNVSSETVN ITITQGLAVSTISSFFPPGYQ | F158 FCGR3A |
| 71 | ATGGCCTTACCAGTGACCGCCTTGCTCCTGCCGCTGGCCTTGCTGCTCCACGCCGCC AGGCCGGGCATGCGGACTGAAGATCTCCCAAAGGCTGTGGTGTTCCTGGAGCCTCAA TGGTACAGGGTGCTCGAGAAGGACAGTGTGACTCTGAAGTGCCAGGGAGCCTACTCC CCTGAGGACAATTCCACACAGTGGTTTCACAATGAGAGCCTCATCTCAAGCCAGGCC TCGAGCTACTTCATTGACGCTGCCACAGTCGACGACAGTGGAGAGTACAGGTGCCAG ACAAACCTCTCCACCCTCAGTGACCCGGTGCAGCTAGAAGTCCATATCGGCTGGCTG TTGCTCCAGGCCCCTCGGTGGGTGTTCAAGGAGGAAGACCCTATTCACCTGAGGTGT CACAGCTGGAAGAACACTGCTCTGCATAAGGTCACATATTTACAGAATGGCAAAGGC AGGAAGTATTTTCATCATAATTCTGACTTCTACATTCCAAAAGCCACACTCAAAGAC AGCGGCTCCTACTTCTGCAGGGGGCTTTTTGGGAGTAAAAATGTGTCTTCAGAGACT GTGAACATCACCATCACTCAAGGTTTGGCAGTGTCAACCATCTCATCATTCTTTCCA CCTGGGTACCAAACCACGACGCCAGCGCCGCGACCACCAACACCGGCGCCCACCATC GCGTCGCAGCCCCTGTCCCTGCGCCCAGAGGCGTGCCGGCCAGCGGCGGGGGGCGCA GTGCACACGAGGGGGCTGGACTTCGCCTGTGATATCTACATCTGGGCGCCCTTGGCC GGGACTTGTGGGGTCCTTCTCCTGTCACTGGTTATCACCCTTTACTGCAAACGGGGC AGAAAGAAACTCCTGTATATATTCAAACAACCATTTATGAGACCAGTACAAACTACT CAAGAGGAAGATGGCTGTAGCTGCCGATTTCCAGAAGAAGAAGAAGGAGGATGTGAA CTGAGAGTGAAGTTCAGCAGGAGCGCAGACGCCCCCGCGTACCAGCAGGGCCAGAAC CAGCTCTATAACGAGCTCAATCTAGGACGAAGAGAGGAGTACGATGTTTTGGACAAG AGACGTGGCCGGGACCCTGAGATGGGGGGAAAGCCGAGAAGGAAGAACCCTCAGGAA GGCCTGTACAATGAACTGCAGAAAGATAAGATGGCGGAGGCCTACAGTGAGATTGGG ATGAAAGGCGAGCGCCGGAGGGGCAAGGGGCACGATGGCCTTTACCAGGGTCTCAGT ACAGCCACCAAGGACACCTACGACGCCCTTCACATGCAGGCCCTGCCCCCTCGCTAA | CD16F-BB-ζ |
| 72 | GGCATGCGGACTGAAGATCTCCCAAAGGCTGTGGTGTTCCTGGAGCCTCAATGGTAC AGGGTGCTCGAGAAGGACAGTGTGACTCTGAAGTGCCAGGGAGCCTACTCCCCTGAG GACAATTCCACACAGTGGTTTCACAATGAGAGCCTCATCTCAAGCCAGGCCTCGAGC TACTTCATTGACGCTGCCACAGTCGACGACAGTGGAGAGTACAGGTGCCAGACAAAC CTCTCCACCCTCAGTGACCCGGTGCAGCTAGAAGTCCATATCGGCTGGCTGTTGCTC CAGGCCCCTCGGTGGGTGTTCAAGGAGGAAGACCCTATTCACCTGAGGTGTCACAGC TGGAAGAACACTGCTCTGCATAAGGTCACATATTTACAGAATGGCAAAGGCAGGAAG TATTTTCATCATAATTCTGACTTCTACATTCCAAAAGCCACACTCAAAGACAGCGGC TCCTACTTCTGCAGGGGGCTTTTTGGGAGTAAAAATGTGTCTTCAGAGACTGTGAAC ATCACCATCACTCAAGGTTTGGCAGTGTCAACCATCTCATCATTCTTTCCACCTGGG TACCAA | F158 FCGR3A variant |

In conjunction with the polynucleotides, the present disclosure also provides vectors comprising such polynucleotides (including vectors in which such polynucleotides are operatively linked to at least one regulatory element for expression of a chimeric receptor). Non-limiting examples of useful vectors of the disclosure include viral vectors such as, e.g., retroviral vectors and lentiviral vectors.

In one specific embodiment, such vectors also include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, nitroreductase and caspases such as caspase 8.

The present disclosure also provides host cells comprising the chimeric receptors disclosed above. Non-limiting examples of useful host cells include T lymphocytes and NK cells, which can be either autologous or allogeneic (with endogenous T-cell receptor either removed or retained). In one specific embodiment, the host cell is an autologous T lymphocyte isolated from a patient having cancer. In one specific embodiment, such autologous T lymphocyte is activated and expanded ex vivo.

The chimeric receptors of the disclosure can be introduced into the host cell by any method known in the art. Non-limiting examples of particularly useful methods include retroviral transduction, lentiviral transduction, and DNA and mRNA electroporation. As demonstrated in the Examples below, mRNA electroporation, results in effective expression of the chimeric receptors of the disclosure in T lymphocytes. Examples of references describing retroviral transduction include Anderson et al., U.S. Pat. No. 5,399,346; Mann et al., Cell 33:153 (1983); Temin et al., U.S. Pat. No. 4,650,764; Temin et al., U.S. Pat. No. 4,980,289; Markowitz et al., J. Virol. 62:1120 (1988); Temin et al., U.S. Pat. No. 5,124,263; International Patent Publication No. WO 95/07358, published Mar. 16, 1995, by Dougherty et al.; and Kuo et al., Blood 82:845 (1993). International Patent Publication No. WO 95/07358 describes high efficiency transduction of primary B lymphocytes. See also the Examples section, below, for examples of specific techniques for retroviral transduction and mRNA electroporation which can be used.

Host cell activation and expansion is usually used to allow integration of a viral vector into the genome and expression of the gene encoding the chimeric receptor of the disclosure. However, if mRNA electroporation is used, no activation and expansion is required (although electroporation is more effective when performed on activated cells). As a result of viral transduction, host cells (T lymphocytes or NKT cells) express the chimeric receptors for a long time potentially producing a stronger effect than upon mRNA electroporation when the receptor is expressed transiently (typically for 3-5 days). However, viral transduction is complex, expensive and difficult to implement, while mRNA electroporation is much simpler and more easily implementable. In addition, transient expression is useful if there is a potential toxicity and should be helpful in the initial phases of clinical testing for possible side effects.

(ii) Pharmaceutical Compositions of the CD16F-BB-ζ and CD16V-BB-ζ Chimeric Receptors A further aspect of the disclosure provides pharmaceutical compositions. In one embodiment, the disclosure provides a pharmaceutical composition comprising (i) a polynucleotide encoding a chimeric receptor CD16F-BB-ζ or CD16V-BB-ζ, or a vector comprising such polynucleotide and (ii) a pharmaceutically acceptable carrier or excipient.

In another embodiment, the disclosure provides a pharmaceutical composition comprising (i) a host cell comprising the chimeric receptor noted above and (ii) a pharmaceutically acceptable carrier or excipient. In one specific embodiment, such pharmaceutical composition further comprises a monoclonal antibody which can exert cytotoxicity to cancer cells (e.g., Rituximab, Trastuzumab, hu14.18K322A, etc.) or another anti-tumor molecule comprising the Fc portion (e.g., a composite molecule constituted by a ligand (e.g., cytokine, immune cell receptor) binding a tumor surface receptor combined with the Fc-portion of an immunoglobulin or Fc-containing DNA or RNA).

Suitable excipients for use in the pharmaceutical compositions of the disclosure will be well known to those of skill in the art and may, for example, comprise tissue culture medium (e.g., for cells to survive ex vivo) or a saline solution (e.g., when cells are being injected in patients). A thorough discussion of pharmaceutically acceptable excipients is available in Remington's Pharmaceutical Sciences (Mack Pub. Co., N.J. 1991).

The pharmaceutical compositions of the disclosure may also contain one or more additional active compounds as necessary for the particular indication being treated, preferably those with complementary activities that do not adversely affect each other. Non-limiting examples of possible additional active compounds include, e.g., IL2 as well as various agents listed in the discussion of combination treatments, below.

(iii) Therapeutic Methods Involving CD16F-BB-z or CD16F-BB-z Chimeric Receptor

The exemplary chimeric receptors of the present disclosure confer antibody-dependent cell cytotoxicity (ADCC) capacity to T lymphocytes and enhance ADCC in NK cells. When the receptor is engaged by an antibody (or another anti-tumor molecule comprising the Fc portion) bound to tumor cells, it triggers T-cell activation, sustained proliferation and specific cytotoxicity against cancer cells targeted by the antibody (or such other anti-tumor molecule comprising the Fc portion). As disclosed in the Examples section, below, T lymphocytes comprising the chimeric receptors of the disclosure were highly cytotoxic against a wide range of tumor cell types, including B-cell lymphoma, breast and gastric cancer, neuroblastoma and osteosarcoma, as well as primary chronic lymphocytic leukemia (CLL). Cytotoxicity was entirely dependent on the presence of a specific antibody bound to target cells: soluble antibodies did not induce exocytosis of cytolytic granules and did not provoke non-specific cytotoxicity.

The degree of affinity of CD16 for the Fc portion of Ig is a critical determinant of ADCC and thus to clinical responses to antibody immunotherapy. The CD16 with the V158 polymorphism which has a high binding affinity for Ig and mediates superior ADCC was selected as an example. Although the F158 receptor has lower potency than the V158 receptor in induction of T cell proliferation and ADCC, the F158 receptor may have lower in vivo toxicity than the V158 receptor making it useful in some clinical contexts.

The chimeric receptors of the present disclosure facilitate T-cell therapy by allowing one single receptor to be used for multiple cancer cell types. It also allows the targeting of multiple antigens simultaneously, a strategy that may ultimately be advantageous given immunoescape mechanism exploited by tumors. Grupp et al., *N Engl J Med.* 2013. Antibody-directed cytotoxicity could be stopped whenever required by simple withdrawal of antibody administration. Because the T cells expressing the chimeric receptors of the disclosure are only activated by antibody bound to target cells, unbound immunoglobulin should not exert any stimulation on the infused T cells. Clinical safety can be further enhanced by using mRNA electroporation to express the chimeric receptors transiently, to limit any potential autoimmune reactivity.

The results disclosed in the Examples section, below, suggest that the infusion of autologous T cells, activated and expanded ex vivo and re-infused after genetic modification with the chimeric receptors of the disclosure should significantly boost ADCC. Because the combined CD3ζ/4-1BB signaling also causes T-cell proliferation, there should be an accumulation of activated T cells at the tumor site which may further potentiate their activity.

Thus, in one embodiment, the disclosure provides a method for enhancing efficacy of an antibody-based immunotherapy of a cancer in a subject in need thereof, which subject is being treated with an antibody which can bind to cancer cells and has a humanized Fc portion which can bind to human CD16, said method comprising introducing into the subject a therapeutically effective amount of T lymphocytes or NK cells, which T lymphocytes or NK cells comprise a chimeric receptor of the disclosure.

In another embodiment, the disclosure provides a method of enhancing T lymphocyte or NK cell ADCC activity in a subject comprising administering to the subject a T lymphocyte or NK cell, which T lymphocyte or NK cell comprises a chimeric receptor of the disclosure. In one embodiment, the subject has cancer. In one specific embodiment, such subject is being treated with an antibody which can bind to cancer cells.

In one embodiment of the above methods, the T lymphocytes or NK cells are autologous T lymphocytes or NK cells isolated from the subject. In one specific embodiment, prior to re-introduction into the subject, the autologous T lymphocytes or NK cells are activated and/or expanded ex vivo. In another embodiment, the T lymphocytes or NK cells are allogeneic T lymphocytes or NK cells. In one specific embodiment, the T lymphocytes are allogeneic T lymphocytes in which the expression of the endogenous T cell receptor has been inhibited or eliminated. In one specific embodiment, prior to introduction into the subject, the allogeneic T lymphocytes are activated and/or expanded ex vivo. T lymphocytes can be activated by any method known in the art, e.g., in the presence of anti-CD3/CD28, IL-2, and/or phytohemoagglutinin. NK cells can be activated by any method known in the art, e.g., in the presence of one or more agents selected from the group consisting of CD137 ligand protein, CD137 antibody, IL-15 protein, IL-15 receptor antibody, IL-2 protein, IL-12 protein, IL-21 protein, and K562 cell line. See, e.g., U.S. Pat. Nos. 7,435,596 and 8,026,097 for the description of useful methods for expanding NK cells.

In one embodiment of the above methods, the chimeric receptors of the disclosure are introduced into the T lymphocytes or the NK cells (e.g., after ex vivo activation and/or expansion) by retroviral transduction, lentiviral transduction, or DNA or RNA electroporation.

In one embodiment of the above methods, introduction (or re-introduction) of T lymphocytes or NK cells to the subject is followed by administering to the subject a therapeutically effective amount of IL-2.

The chimeric receptors of the disclosure may be used for treatment of any cancer, including, without limitation, carcinomas, lymphomas, sarcomas, blastomas, and leukemias, for which a specific antibody with an Fc portion that binds to CD16 exists or is capable of being generated. Specific non-limiting examples of cancers, which can be treated by the chimeric receptors of the disclosure include, e.g., cancers of B-cell origin (e.g., B-lineage acute lymphoblastic leukemia, B-cell chronic lymphocytic leukemia and B-cell non-Hodgkin's lymphoma), breast cancer, gastric cancer, neuroblastoma, and osteosarcoma.

Non-limiting examples of anti-cancer antibodies containing an Fc portion that can bind to human CD16, whose efficacy can be enhanced by the method of the disclosure, include, for example, Rituximab, Trastuzumab, hu14.18K322A, Epratuzumab, Cetuximab, and Labetuzumab.

The appropriate dosage of the antibody used will depend on the type of cancer to be treated, the severity and course of the disease, previous therapy, the patient's clinical history and response to the antibody, and the discretion of the attending physician. The antibody can be administered to the patient at one time or over a series of treatments. The progress of the therapy of the disclosure can be easily monitored by conventional techniques and assays.

The administration of antibodies can be performed by any suitable route, including systemic administration as well as administration directly to the site of the disease (e.g., to primary tumor).

The T lymphocytes used in the methods of the disclosure are most preferably patient's own cells (i.e., autologous cells) that were earlier isolated from a blood sample and preferably activated and expanded ex vivo (e.g., for 3-5 days) with standard methods, such as, e.g., anti-CD3/CD28 beads, IL-2, or phytohemoagglutinin. Alternatively, allogeneic T lymphocytes can be used (preferably allogeneic T lymphocytes in which the expression of the endogenous T cell receptor has been inhibited or eliminated). See Torikai et al., Blood, 2012 119: 5697-5705. Following isolation (and optionally activation and/or expansion), T lymphocytes and NK cells from a patient are transduced (or electroporated) with the polynucleotide encoding a chimeric receptor of the disclosure (or a vector comprising such polynucleotide) so that the chimeric receptor is expressed on the cell surface of the T cell or NK cell. The modified cells can then be administered into the patient (e.g., 1 day after infusion of a therapeutic antibody).

In accordance with the present disclosure, patients can be treated by infusing therapeutically effective doses of T lymphocytes or NK cells comprising a chimeric receptor of the disclosure in the range of about $10^5$ to $10^{10}$ or more cells per kilogram of body weight (cells/Kg). The infusion can be repeated as often and as many times as the patient can tolerate until the desired response is achieved. The appropriate infusion dose and schedule will vary from patient to patient, but can be determined by the treating physician for a particular patient. Typically, initial doses of approximately $10^6$ cells/Kg will be infused, escalating to $10^8$ or more cells/Kg. IL-2 can be co-administered to expand infused cells post-infusion. The amount of IL-2 can about $1-5\times10^6$ international units per square meter of body surface.

NK cells used in the methods of the disclosure may be preferentially expanded by exposure to cells that lack or poorly express major histocompatibility complex I and/or II molecules and which have been genetically modified to express membrane bound IL-15 and 4-1BB ligand (CDI37L). Such cell lines include, but are not necessarily limited to, K562 [ATCC, CCL 243; Lozzio et al., *Blood* 45(3): 321-334 (1975); Klein et al., *Int. J. Cancer* 18: 421-431 (1976)], and the Wilms tumor cell line HFWT (Fehniger et al., *Int Rev Immunol* 20(3-4):503-534 (2001); Harada H, et al., *Exp Hematol* 32(7):614-621 (2004)), the uterine endometrium tumor cell line HHUA, the melanoma cell line HMV-II, the hepatoblastoma cell line HuH-6, the lung small cell carcinoma cell lines Lu-130 and Lu-134-A, the neuroblastoma cell lines NB19 and N1369, the embryonal carcinoma cell line from testis NEC 14, the cervix carcinoma cell line TCO-2, and the bone marrow-metastasized neuroblastoma cell line TNB1 [Harada, et al., *Jpn. J. Cancer Res* 93: 313-319 (2002)]. Preferably the cell line used lacks or poorly expresses both MHC I and II molecules, such as the K562 and HFWT cell lines. A solid support may be used instead of a cell line. Such support should preferably have attached on its surface at least one molecule capable of binding to NK cells and inducing a primary activation event and/or a proliferative response or capable of binding a molecule having such an affect thereby acting as a scaffold. The support may have attached to its surface the CD137 ligand protein, a CD137 antibody, the IL-15 protein or an IL-15 receptor antibody. Preferably, the support will have IL-15 receptor antibody and CD137 antibody bound on its surface.

(iv) Combination Treatments

The compositions and methods described in the present disclosure may be utilized in conjunction with other types of therapy for cancer, such as chemotherapy, surgery, radiation, gene therapy, and so forth. Such therapies can be administered simultaneously or sequentially (in any order) with the immunotherapy according to the present disclosure.

When co-administered with an additional therapeutic agent, suitable therapeutically effective dosages for each agent may be lowered due to the additive action or synergy.

The treatments of the disclosure can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 41BB, OX40, etc.).

Non-limiting examples of other therapeutic agents useful for combination with the immunotherapy of the disclosure include: (i) anti-angiogenic agents (e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000)); (ii) a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof; and (iii) chemotherapeutic compounds such as, e.g., pyrimidine analogs (5-fluorouracil, floxuridine, capecitabine, gemcitabine and cytarabine), purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

For examples of additional useful agents see also Physician's Desk Reference, 59.sup.th edition, (2005), Thomson P D R, Montvale N.J.; Gennaro et al., Eds. Remington's The Science and Practice of Pharmacy 20.sup.th edition, (2000), Lippincott Williams and Wilkins, Baltimore Md.; Braunwald et al., Eds. Harrison's Principles of Internal Medicine, 15.sup.th edition, (2001), McGraw Hill, N.Y.; Berkow et al., Eds. The Merck Manual of Diagnosis and Therapy, (1992), Merck Research Laboratories, Rahway N.J.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introuction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. T Lymphocytes Expressing a CD16 Signaling Receptor Exert Antibody Dependent Cancer Cell Killing Materials and Methods
Cells The human B-lineage lymphoma cell lines Daudi and Ramos, the T-cell acute lymphoblastic leukemia cell line Jurkat, and the neuroblastoma cell lines CHLA-255, NB1691 and SK—N—SH were available at St. Jude Children's Research Hospital. The breast carcinoma cell lines MCF-7 (ATCC HTB-22) and SK-BR-3 (ATCC HTB-30), and the osteosarcoma cell line U-2 OS (ATCC HTB-96) were obtained from the American Type Culture Collection (ATCC; Rockville, Md.); the gastric carcinoma cell line MKN7 was from National Institute of Biomedical Innovation (Osaka, Japan). Daudi, CHLA-255, NB1691, SK-N-SH, SK-BR-3, MCF-7, U-2 OS and MKN7 were also transduced with a murine stem cell virus (MSCV)-internal ribosome entry site (IRES)-green fluorescent protein (GFP) retroviral vector containing the firefly luciferase gene.[34] Transduced cells were selected for their expression of GFP with a FACSAria cell sorter (BD Biosciences, San Jose, Calif.). Peripheral blood or bone marrow samples from newly diagnosed and untreated patients with B-chronic lymphocytic leukemia (CLL) were obtained following informed consent and approval from the Domain Specific Ethics Board governing Singapore's National University Hospital.

Peripheral blood samples were obtained from de-identified by-products of platelet donations from healthy adult donors. Mononuclear cells were enriched by centrifugation on Accu-Prep Human Lymphocytes Cell Separation Media (Accurate Chemical & Scientific Corp., Westbury, N.Y.), and cultured with anti-CD3/CD28 beads (Invitrogen, Carlsbad, Calif.) in RPMI-1640 with 10% fetal bovine serum (FBS), antibiotics, 100 IU interleukin (IL)-2 (Roche, Mannheim, Germany) for 3 days. On day 4, T cells were purified by negative selection with a mixture of CD14, CD16, CD19, CD36, CD56, CD123 and CD235a antibodies and magnetic beads (Pan T Cell Isolation Kit II; Miltenyi Biotec, Bergisch Gladbach, Germany) (purity, >98%). Purified T cells were maintained in the above medium, with the addition of 100 IU IL-2 every other day.

Plasmids, Virus Production and Gene Transduction

The pMSCV-IRES-GFP, pEQ-PAM3(-E), and pRDF were obtained from the St. Jude Children's Research Hospital Vector Development and Production Shared Resource (Memphis, Tenn.).[10] The FCRG3A cDNA was obtained from Origene (Rockville, Md.) and its V158F variant was generated using site-directed mutagenesis by PCR using primers "F" CTTCTGCAGGGGGCTTGTTGGGAG-TAAAAATGTGTC (SEQ ID NO: 73) and "R" GACA-CATTTTTACTCCCAACAAGCCCCCTGCAGAAG (SEQ ID NO: 74). The polynucleotides encoding CD8α hinge and transmembrane domain (SEQ ID NO: 66), and the intracellular domains of 4-1BB (SEQ ID NO: 67) and CD3ζ (SEQ ID NO: 68) were subcloned from an anti-CD19-41BB-CD3ζ cDNA previously made. Imai et al., 2004. These molecules were assembled using splicing by overlapping extension by PCR. The constructs ("CD16F-BB-ζ" and "CD16V-BB-ζ") and the expression cassette were subcloned into EcoRI and MLu1 sites of the MSCV-IRES-GFP vector.

To generate RD114-pseudotyped retrovirus, fuGENE 6 or X-tremeGENE 9 (Roche, Indianapolis, Ind.) was used to transfect $3\times10^6$ 293T cells with 3.5 µg of cDNA encoding CD16V-BB-ζ, 3.5 µg of pEQ-PAM3(-E), and 3 µg of pRDF. Imai et al., 2004. After replacing the medium with RPMI-1640 with 10% FBS at 24 hours, the medium containing retrovirus was harvested after 48-96 hours and added to RetroNectin (TakaRa, Otsu, Japan)-coated polypropylene tubes, which were centrifugated at 1400 g for 10 min and incubated at 37° C. for 6 hours. After additional centrifugation, and removal of the supernatant, T cells ($1\times10^5$) were added to the tubes and left in at 37° C. for 24 hours. Cells were then maintained in RPMI-1640 with FBS, antibiotics and 100 IU/mL IL-2 until the time of the experiments, 7-21 days after transduction.

Surface expression of CD16 was analyzed by flow cytometry using R-Phycoerythrin conjugated anti-human CD16 (clone B73.1, BD Biosciences Pharmingen, San Diego, Calif.). For western blotting, $2\times10^7$ T cells were lysed in Cellytic M lysis Buffer (Sigma, St Louis, Mo.) containing 1% protease inhibitor cocktail (Sigma) and 1% phosphatase inhibitor cocktail 2 (Sigma). After centrifugation, lysate supernatants were boiled with an equal volume of LDS buffer (Invitrogen, Carlsbad, Calif.) with or without reducing buffer (Invitrogen) and then separated by NuPAGE Novex 12% Bis-Tris Gel (Invitrogen). The proteins were transferred to a polyvinylidene fluoride (PVDF) membrane, which was incubated with a mouse anti-human CD3ζ (clone 8D3; BD eBioscience Pharmingen) and then with a goat anti-mouse IgG horseradish peroxidase-conjugated secondary antibody (Cell Signaling Technology, Danvers, Mass.). Antibody binding was revealed by using the Amersham ECL Prime detection reagent (GE Healthcare).

mRNA Electroporation

The pVAX1 vector (Invitrogen, Carlsbad, Calif.) was used as a template for in vitro mRNA transcription. The CD16V-BB-ζ cDNA was subcloned into EcoRI and XbaI sites of pVAX1. The corresponding mRNA was transcribed in vitro with T7 mScript mRNA production system (CellScript, Madison, Wis.). Shimasaki et al., *Cytotherapy*. 2012; 14(7):830-40.

For electroporation, the Amaxa Nucleofector (Lonza, Walkersville, Md.) was used; $1\times10^7$ of purified T cells activated with 200 IU/mL IL-2 overnight were mixed with 200 µg/mL mRNA in Cell Line Nucleofector Kit V (Lonza), transferred into the processing chamber, and transfected using the program X-001. Immediately after electroporation, cells were transferred from the processing chamber into a 24-well plate and then cultured in RPMI-1640 with FBS, antibiotics and 100 IU/mL IL-2 (Roche, Mannheim, Germany). See also Shimasaki et al., *Cytotherapy*, 2012, 1-11.

Antibody Binding, Cell Conjugation and Cell Proliferation Assays

To measure the chimeric receptors' antibody-binding capacity, T lymphocytes ($5\times10^5$) transduced with chimeric receptors or a vector containing GFP only were incubated with Rituximab (Rituxan, Roche; 0.1-1 µg/mL), Trastuzumab (Herceptin; Roche; 0.1-1 µg/mL) and/or purified human IgG (R&D Systems, Minneapolis, Minn.; 0.1-1 µg/mL) for 30 minutes at 4° C. After washing twice with phosphate buffered saline (PBS), cells were incubated with goat anti-human IgG-PE (Southern Biotechnology Associates, Birmingham, Ala.) for 10 minutes at room temperature and cell staining was measured using an Accuri C6 flow cytometer (BD Biosciences).

To determine whether antibody binding to the receptor promoted cell aggregation, CD20-positive Daudi cells were labeled with CellTrace calcein red-orange AM (Invitrogen) and then incubated with Rituximab (0.1 µg/mL) for 30 minutes at 4° C. After washing twice in PBS, cells with Jurkat cells transduced with the chimeric receptor or mock-transduced at 1:1 E:T ratio in 96 round bottom plates (Costar, Corning, N.Y.) for 60 min at 37° C. The proportion of cells forming heterologous cell aggregates (calcein AM-GFP double positive) was determined by flow cytometry.

To measure cell proliferation, $1 \times 10^6$ of T cells transduced with the chimeric receptor or mock-transduced were placed in the wells of a 24-well plate (Costar, Corning, N.Y.) in RPMI-1640 with FBS, antibiotics and 50 IU/mL IL-2. Daudi cells were treated with Streck cell preservative (Streck Laboratories, Omaha, Nebr.) to stop proliferation and labeled with Rituximab (0.1 µg/mL) for 30 min at 4° C. They were added to the wells, at 1:1 ratio with T cells, on days 0, 7, 14 and 21. The n number of viable T cells after culture was measured by flow cytometry.

CD107 Degranulation and Cytotoxicity Assays

To determine whether CD16 cross-linking caused exocytosis of lytic granules, chimeric receptor- and mock transduced T cells ($1 \times 10^5$) were placed into each well of a Rituximab-coated 96-well flat bottom plate and cultured for 4 hours at 37° C. In other experiments, T cells were co-cultured with Daudi cells pre-incubated with Rituximab. An anti-human CD107a antibody conjugated to phycoerythrin (BD Biosciences) was added at the beginning of the cultures and one hour later GolgiStop (0.154 BD Biosciences) was added. CD107a positive T cells were analyzed by flow cytometry.

To test cytotoxicity, target cells were suspended in RPMI-1640 with 10% FBS, labeled with calcein AM (Invitrogen) and plated into 96-well round bottom plates (Costar). T cells were added at various E:T ratio as indicated in Results, and co-cultured with target cells for 4 hours, with or without the antibodies Rituximab (Rituxan, Roche), Trastuzumab (Herceptin, Roche), or hu14.18K322A (obtained from Dr. James Allay, St Jude Children's GMP, Memphis, Tenn.; at 1 µg/mL). At the end of the cultures, cells were collected, resuspended in an identical volume of PBS, propidium iodide was added. The number of viable target cells (calcein AM-positive, propidium-iodide negative) was counted using the Accuri C6 flow cytometer.[34] For adherent cell lines, cytotoxicity was tested using luciferase-labeled target cells. To measure cytotoxicity against the adherent cell lines NB1691, CHLA-255, SK-BR-3, MCF-7, U-2 OS and MKN7, their luciferase-labeled derivatives were used. After plating for at least 4 hours, T cells were added as described above. After 4 hours of co-culture, the Promega Bright-Glo luciferase reagent (Promega, Madison, Wis.) was added to each well; 5 minutes later, luminescence was measured using a plate reader Biotek FLx800 (BioTek, Tucson, Ariz.) and analyzed with the Gen5 2.0 Data Analysis Software.

Xenograft Experiments

Daudi cells expressing luciferase were injected intraperitoneally (i.p.; $0.3 \times 10^6$ cells per mouse) in NOD.Cg-Prkdc$^{scid}$ IL2rg$^{tm1Wjl}$/SzJ (NOD/scid IL2RGnull) mice (Jackson Laboratory, Bar Harbor). Some mice received Rituximab (100 µg) i.p. 4 days after Daudi inoculation, with or without i.p. injection of human primary T cells on days 5 and 6. T cells had been activated with anti-CD3/CD28 beads for 3 days, transduced with the CD16V-BB-ζ receptor, resuspended in RPMI-1640 plus 10% FBS and then injected at $1 \times 10^7$ cells per mouse. Rituximab injection was repeated weekly for 4 weeks, with no further T lymphocyte injection. All mice received i.p. injections of 1000-2000 IU of IL-2 twice a week for 4 weeks. A group of mice received tissue culture medium instead of Rituximab or T cells.

Tumor engraftment and growth was measured using a Xenogen IVIS-200 system (Caliper Life Sciences, Hopkinton, Mass.). Imaging commenced 5 minutes after i.p. injection of an aqueous solution of D-luciferin potassium salt (3 mg/mouse) and photons emitted from luciferase-expressing cells were quantified using the Living Image 3.0 software.

Results

Expression of the CD16V-BB-ζ Receptor

Figure 2:
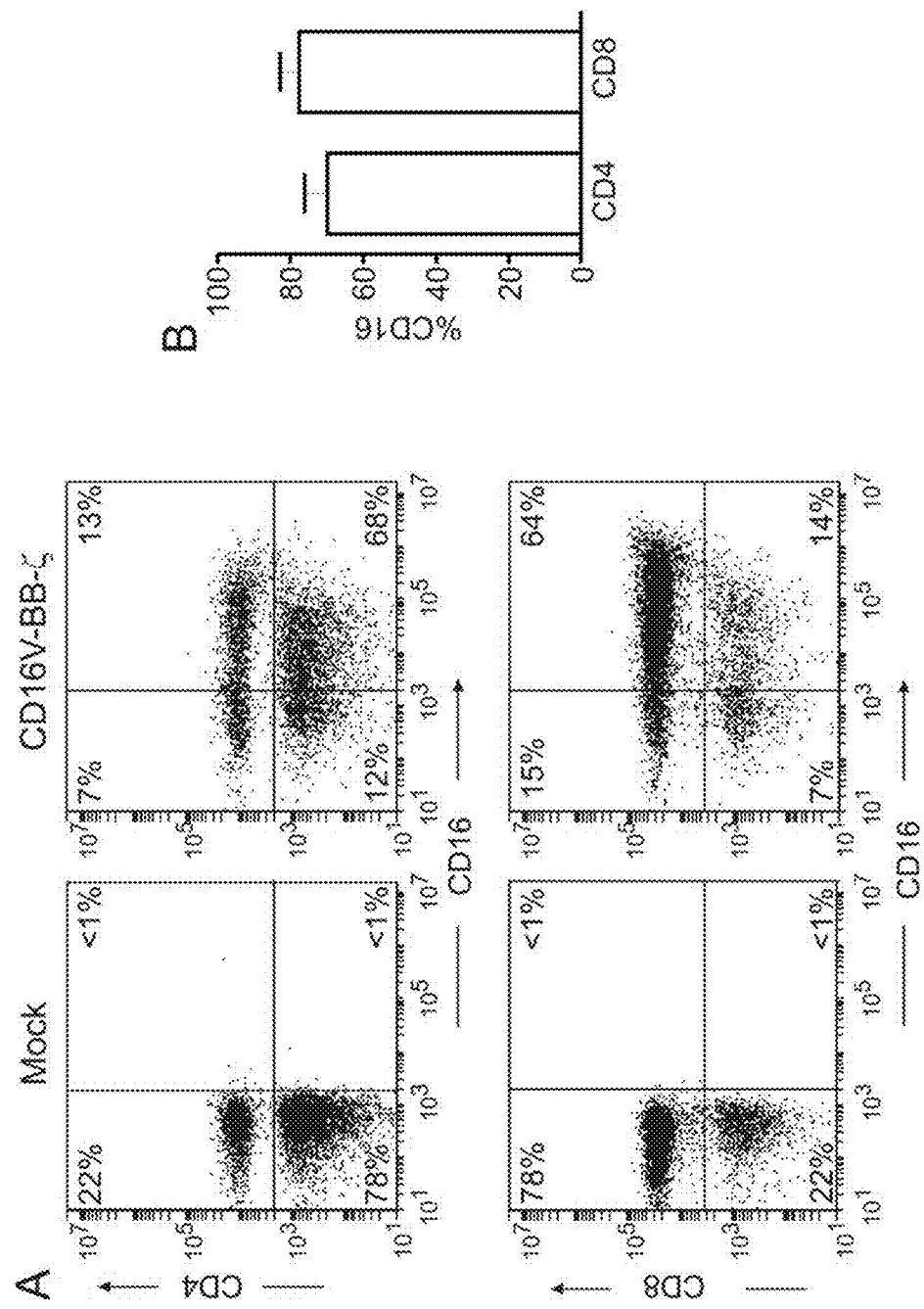
FIG. 2 shows expression of CD16V-BB-ζ receptor in T-cell subsets. A: activated CD3+ T lymphocytes were transduced with a vector containing GFP alone (Mock) and with a vector containing the CD16V-BB-ζ construct. Expression of CD16 was tested in CD4+ and CD8+ cells by flow cytometry. Dot plots show results of one representative experiment. B: a summary of results (mean±SD) obtained with T lymphocytes from 3 donors (P=N.S.).

The V158 polymorphism of FCGR3A (CD16), expressed in about one-fourth of individuals, encodes a high-affinity immunoglobulin Fc receptor and is associated with favorable responses to antibody therapy. A V158 variant of the FCGR3A gene was combined with the hinge and transmembrane domain of CD8α, the T-cell stimulatory molecule CD3ζ, and the co-stimulatory molecule 4-1BB (FIG. 1A). An MCSV retroviral vector containing the CD16V-BB-ζ construct and GFP was used to transduce peripheral blood T lymphocytes from 12 donors: median GFP expression in CD3+ cells was 89.9% (range, 75.3%-97.1%); in the same cells, median chimeric receptor surface expression as assessed by anti-CD16 staining was 83.0% (67.5%-91.8%) (FIG. 1B). T lymphocytes from the same donors transduced with a vector containing only GFP had a median GFP expression of 90.3% (67.8%-98.7%) but only 1.0% (0.1%-2.7%) expressed CD16 (FIG. 1B). Expression of the receptor did not differ significantly between CD4+ and CD8+ T cells: 69.8%±10.8% CD4+ cells were CD16+ after transduction with CD16V-BB-ζ, as compared to 77.6%±9.2% CD8+ cells (FIG. 2).

To ensure that the other components of the chimeric receptor were expressed, levels of expression of CD3 were measured by flow cytometry. As shown in FIG. 1B, CD16V-BB-ζ-transduced T lymphocytes expressed CD3ζ at levels much higher than those expressed by mock-transduced cells: mean (±SD) of the mean fluorescence intensity was 45,985±16,365 in the former versus 12,547±4,296 in the latter (P=0.027 by t test; n=3; FIG. 1B). The presence of the chimeric protein was also determined by western blotting probed with the anti-CD3ζ antibody. As shown in FIG. 1C, CD16V-BB-ζ-transduced T lymphocytes expressed a chimeric protein of approximately 25 kDa under reducing conditions, in addition to the endogenous CD3ζ of 16 kDa. Under non-reducing conditions, the CD16V-BB-ζ protein was shown to be expressed as either a monomer or a dimer of 50 kDa.

Antibody-Binding Capacity of V158 Versus F158 CD16 Receptors

Figure 3:
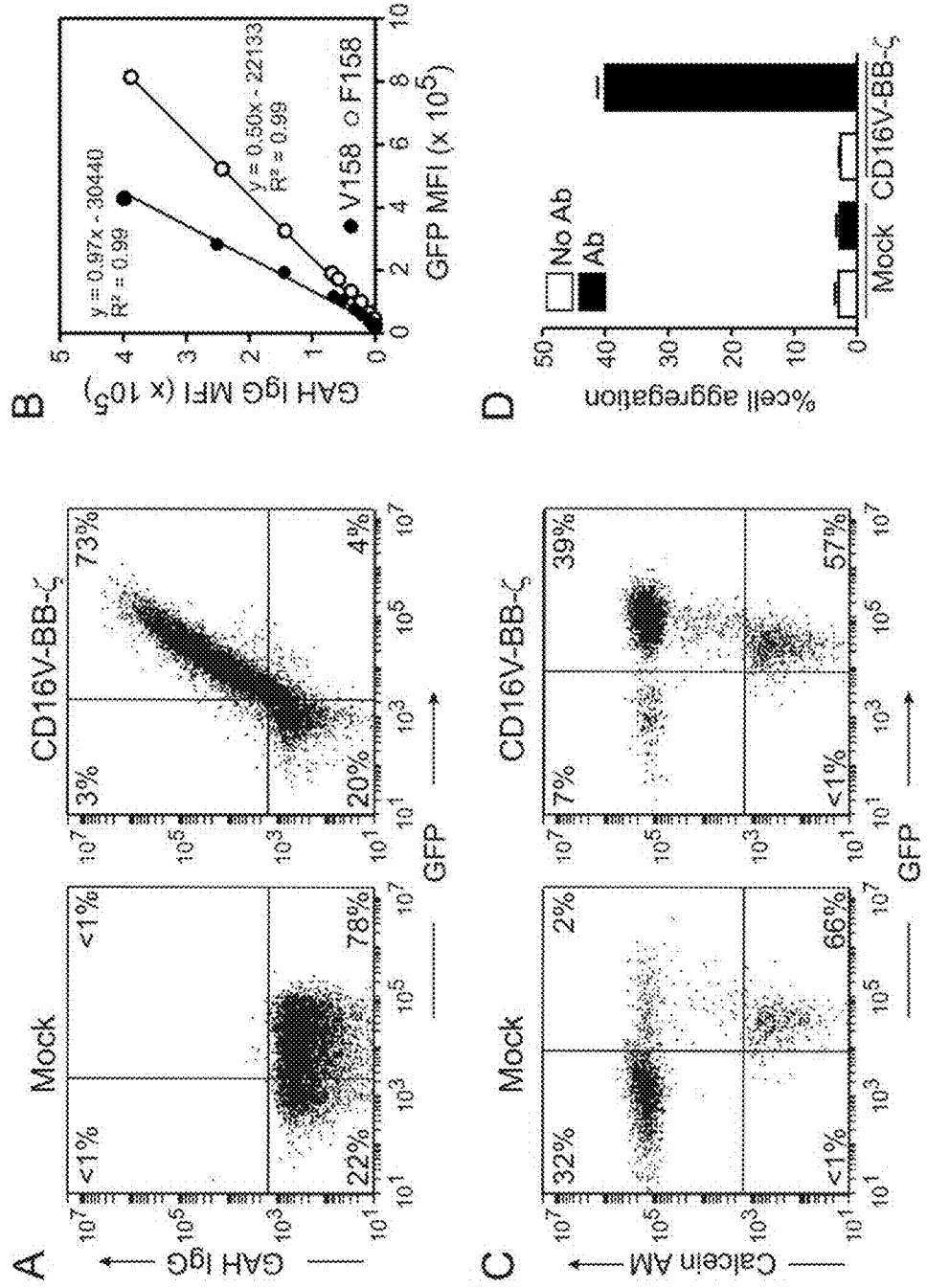
FIG. 3 demonstrates antibody-binding capacity of CD16V-BB-ζ receptors. A: T lymphocytes transduced with a vector containing GFP (Mock) or GFP and CD16V-BB-ζ and incubated with Rituximab for 30 minutes; the amount of antibody bound to the cell surface was visualized with a goat-anti human IgG antibody conjugated to phycoerythrin (GAH IgG) and flow cytometry. B: Jurkat cells transduced with CD16V-BB-ζ (V158) or CD16F-BB-ζ (F158) incubated with Rituximab for 30 minutes. The plot compares the relationship between mean fluorescence intensity (MFI) of GFP and MFI of GAH IgG obtained with cells expressing the two receptors. C: Jurkat cells mock-transduced or transduced with CD16V-BB-ζ co-cultured with Daudi cells labeled with calcein AM orange-red in the presence of Rituximab. Cell aggregates are quantified in the upper right quadrants of each dot plot. D: a summary of the aggregation assays illustrated in panel C. Bars show mean±SD of 3 experiments. Aggregation measured with Jurkat cells transduced with CD16V-BB-ζ in the presence of Rituximab ("Ab") was significantly higher than that measured in the 3 other culture conditions (P<0.001 by t test).

To test the capacity of the CD16V-BB-ζ chimeric receptor to bind immunoglobulin (Ig), peripheral blood T lymphocytes from 3 donors were transduced. As shown in FIG. 3A, CD16V-BB-ζ-expressing T lymphocytes were coated with the antibody after incubation with Rituximab. Similar results were obtained with Trastuzumab and human IgG.

Figure 4:
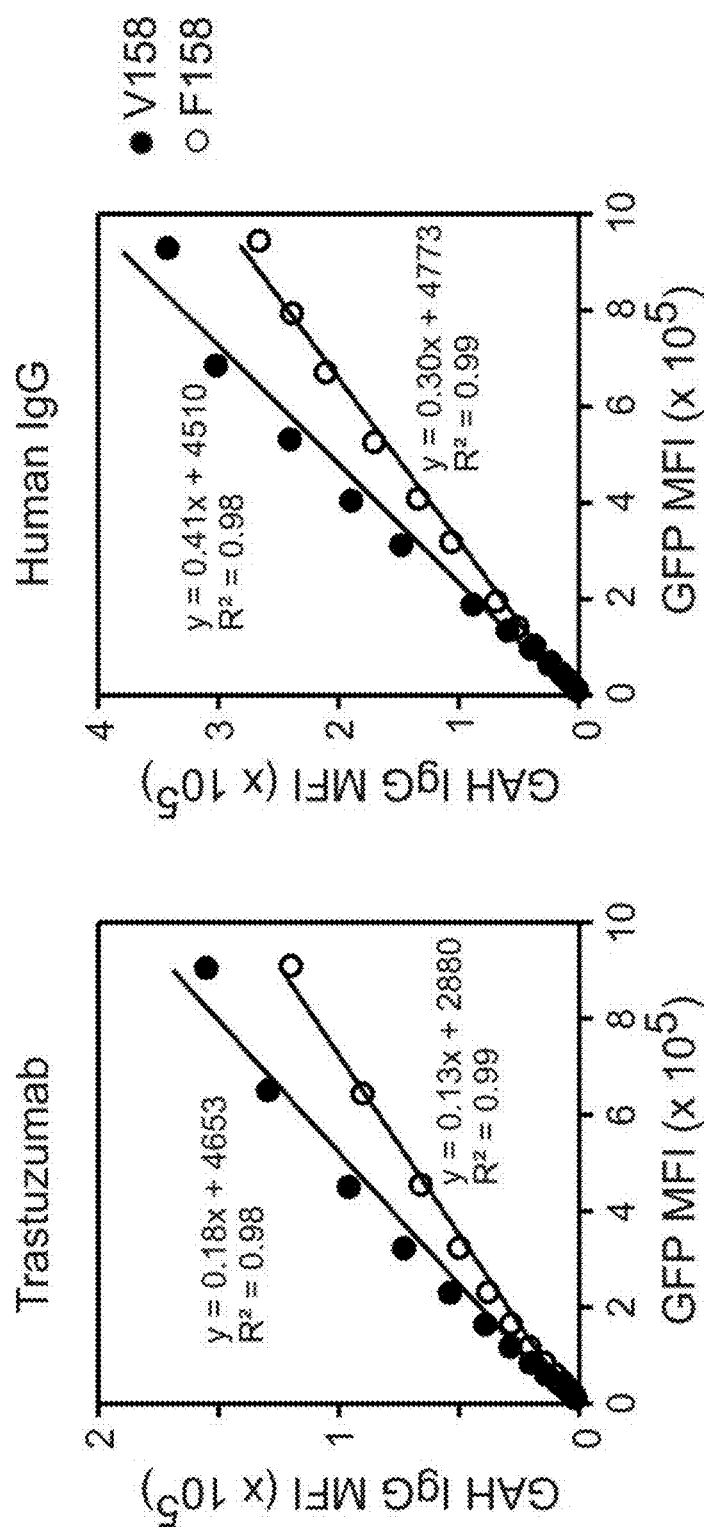
FIG. 4 shows the relative capacity of CD16V-BB-ζ and CD16F-BB-ζ receptors to bind Trastuzumab and human IgG. Jurkat cells transduced with CD16V-BB-ζ (V158; black symbols) or CD16F-BB-ζ (F158; white symbols) were incubated with Trastuzumab or human IgG for 30 minutes. The plots compare the relation between mean fluorescence intensity (MFI) of GFP and MFI of goat-anti human (GAH) IgG conjugated to PE obtained with cells expressing either receptor (P<0.0001 for both Trastuzumab and IgG).

The Ig-binding capacity of the CD16V-BB-ζ receptor, which contained the high-affinity V158 polymorphism of FCGR3A (CD16), was then compared to that of an identical receptor containing the F158 variant instead ("CD16F-BB-ζ"). After transducing Jurkat cells with either receptor, they were incubated with Rituximab and an anti-human Ig PE antibody (binding Rituximab) and the PE fluorescence intensity was related to that of GFP. As shown in FIG. 3B, at any given level of GFP, cells transduced with the CD16V-BB-ζ receptor had a higher PE fluorescence intensity than that of cells transduced with the CD16F-BB-ζ receptor, indicating that the former had a significantly higher antibody-binding affinity. Trastuzumab and human IgG were also bound by CD16V-BB-ζ receptors with a higher affinity (FIG. 4).

To determine whether antibody binding to the CD16-BB-ζ receptor could promote aggregation of effector and target cells, Jurkat cells expressing CD16V-BB-ζ (and GFP) were mixed at a 1:1 ratio with the CD20$^+$ Daudi cell line (labeled with Calcein AM red-orange) for 60 minutes, and the formation of GFP-Calcein doublets was measured with or without addition of Rituximab. In 3 experiments, 39.0%±1.9% of events in the coculture were doublets if Jurkat cells expressed CD16V-BB-ζ receptors and Rituximab was present (FIGS. 3C and D). By contrast, there were <5% doublets with human IgG instead of Rituximab, or with mock-transduced Jurkat cells regardless of whether Rituximab was present.

Figure 5:
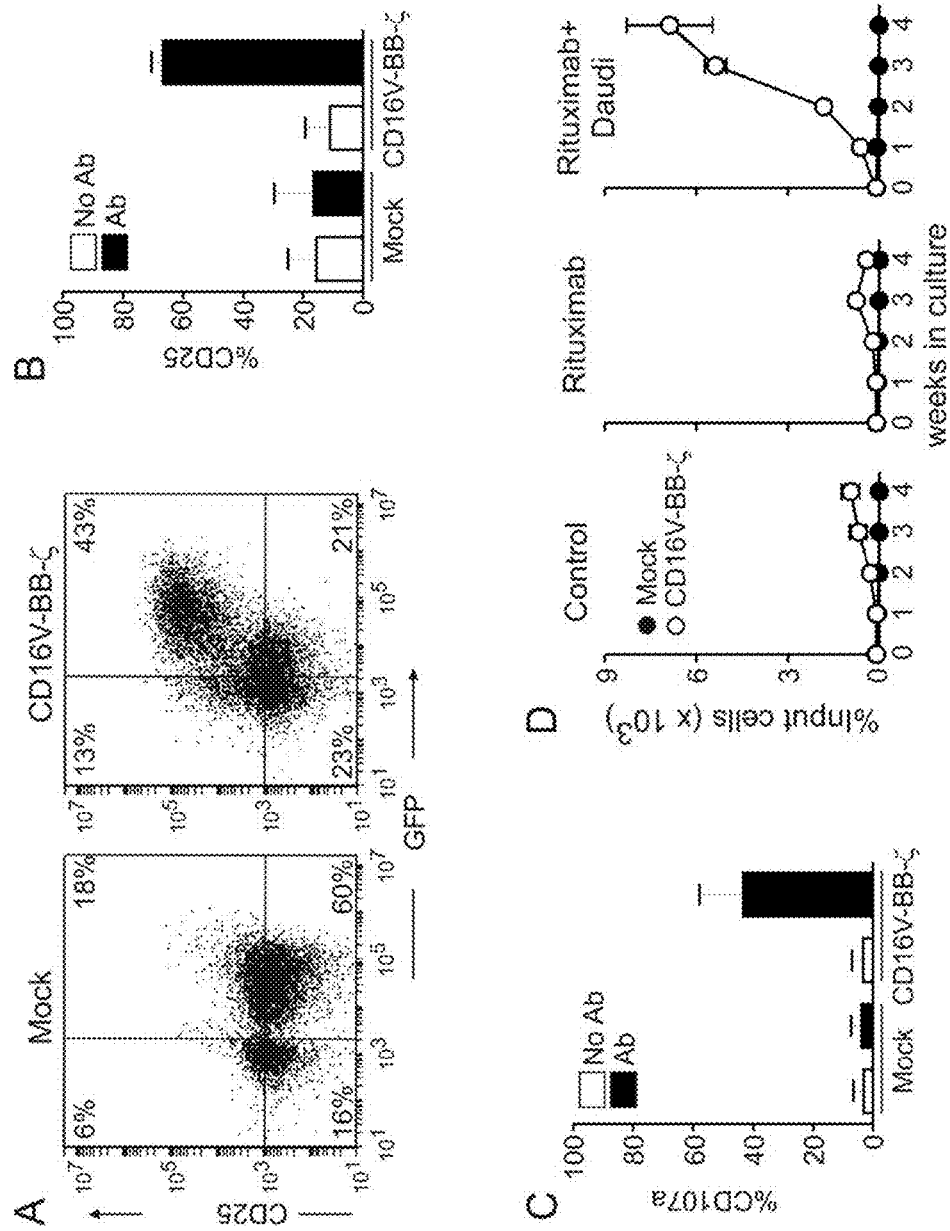
FIG. 5 demonstrates that immunoglobulin binding to CD16V-BB-ζ receptors induces T cell activation, exocytosis of lytic granules, and cell proliferation. A: T lymphocytes transduced with a vector containing GFP (Mock) or GFP and CD16V-BB-ζ were cultured in microtiter plates coated with Rituximab for 48 hours without IL-2; expression of CD25 was measured by flow cytometry. B: a summary of the results of the test illustrated in A, bars show CD25 expression in GFP+ cells (mean±SD of experiments with T cells from 3 donors); CD25 expression was significantly higher in T lymphocytes transduced with CD16V-BB-ζ in the presence of Rituximab ("Ab") than in the other experimental conditions (P≤0.003). C: T lymphocytes from 4 donors transduced with a vector containing GFP (Mock) or GFP and CD16V-BB-ζ were cultured as in A (n=3) or with Daudi cells (n=3) for 4 hours; CD107a staining was measured by flow cytometry. Bars show mean±SD of the 6 experiments; CD107a expression was significantly higher in T lymphocytes transduced with CD16V-BB-ζ in the presence of Rituximab ("Ab") than in the other experimental conditions (P<0.0001). D: mock- or CD16V-BB-ζ-transduced T lymphocytes cultured alone, or with Rituximab with or without Daudi cells for up to 4 weeks. Symbols indicate percentage of cell recovery as compared to the number of input cells (mean±SD of experiments with T cells from 3 donors).

Binding of Ig to CD16V-BB-ζ Induces T Cell Activation, Degranulation and Cell Proliferation It was assessed whether CD16V-BB-ζ receptor cross-linking by an immobilized antibody could induce activation signals in T lymphocytes. Indeed, T lymphocytes transduced with CD16V-BB-ζ markedly increased IL-2 receptor expression (CD25) when cultured on plates coated with Rituximab whereas no changes were detected in the absence of antibody, or in mock-transduced cells regardless of whether the antibody was present (FIGS. 5A and B).

In addition to expression of IL-2 receptors, CD16V-BB-ζ receptor cross-linking triggered exocytosis of lytic granules in T lymphocytes, as detected by CD107a staining. Thus, in 6 experiments in which T lymphocytes from 4 donors were either seeded onto microtiter plates coated with Rituximab (n=3) or cocultured with Daudi cells in the presence of Rituximab (n=3), T lymphocytes expressing CD16V-BB-ζ became CD107a positive (FIG. 5C).

Finally, it was determined whether receptor cross-linking could induce cell proliferation. As shown in FIG. 5D, T lymphocytes expressing CD16V-BB-ζ expanded in the presence of Rituximab and Daudi cells (at a 1:1 ratio with T lymphocytes): in 3 experiments, mean T cell recovery after 7 days of culture was 632%(±97%) of input cells; after 4 weeks of culture, it was 6877% (±1399%). Of note, unbound Rituximab, even at a very high concentration (1-10 μg/mL), had no significant effect on cell proliferation in the absence of target cells, and no cell growth occurred without Rituximab, or in mock-transduced T cells regardless of the presence of the antibody and/or target cells (FIG. 5D). Thus, CD16V-BB-ζ receptor cross-linking induces signals that result in sustained proliferation.

T Lymphocytes Expressing CD16V-BB-ζ Mediate ADCC In Vitro and In Vivo

Figure 6:
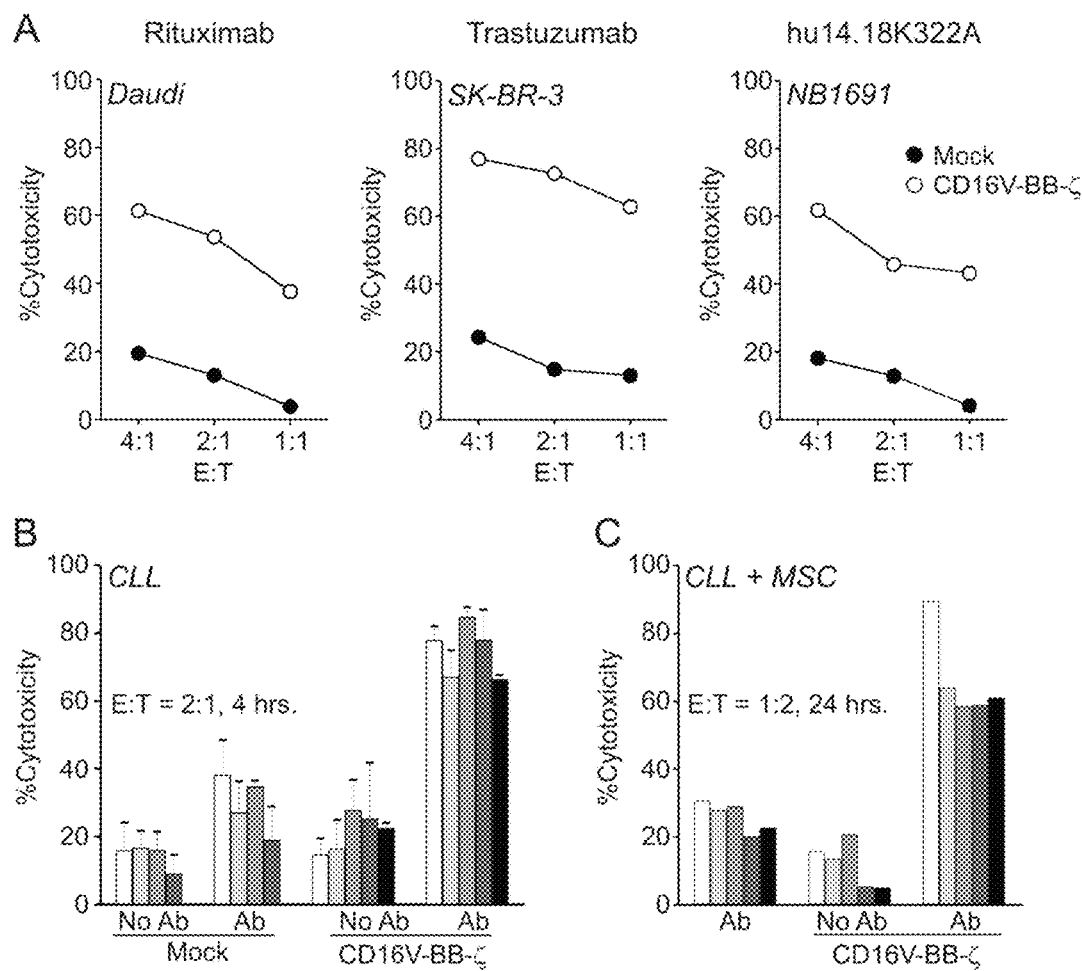
FIG. 6 demonstrates antibody-dependent cell cytotoxicity mediated by CD16V-BB-ζ T lymphocytes in vitro. A: representative examples of cytotoxicity against cancer cell lines mediated by mock- or CD16V-BB-ζ-transduced T lymphocytes in the presence of the corresponding antibody. Each symbol indicates the mean of triplicate cultures (P<0.01 by paired t test for all 3 comparisons). The full set of data is shown in FIG. 7. B: Cytotoxicity of mock- or CD16V-BB-ζ-transduced T lymphocytes, with or without Rituximab ("Ab"), against primary cells from patients with chronic lymphocytic leukemia (CLL). Each bar (with a different shade for each patient) corresponds to mean (±SD) cytotoxicity as determined in triplicate 4-hour assays at 2:1 E:T ratio. Cytotoxicity with CD16V-BB-ζ T cells and antibody was significantly higher than that measured in any of the other 3 conditions (P<0.0001 by t test); with mock-transduced T cells, the addition of antibody increased cytotoxicity (P=0.016); all other comparisons: P>0.05. C: cytotoxicity against the same CLL samples tested in panel B after 24 hours at 1:2 E:T in the presence of mesenchymal stromal cells (MSC). Each bar corresponds to the average of two tests. Cytotoxicity with CD16V-BB-ζ T cells plus antibody was significantly higher than that with antibody alone (P=0.0002) or cells alone (P<0.0001); cytotoxicity with antibody alone was significantly higher than that with cells alone (P=0.0045).
Figure 7:
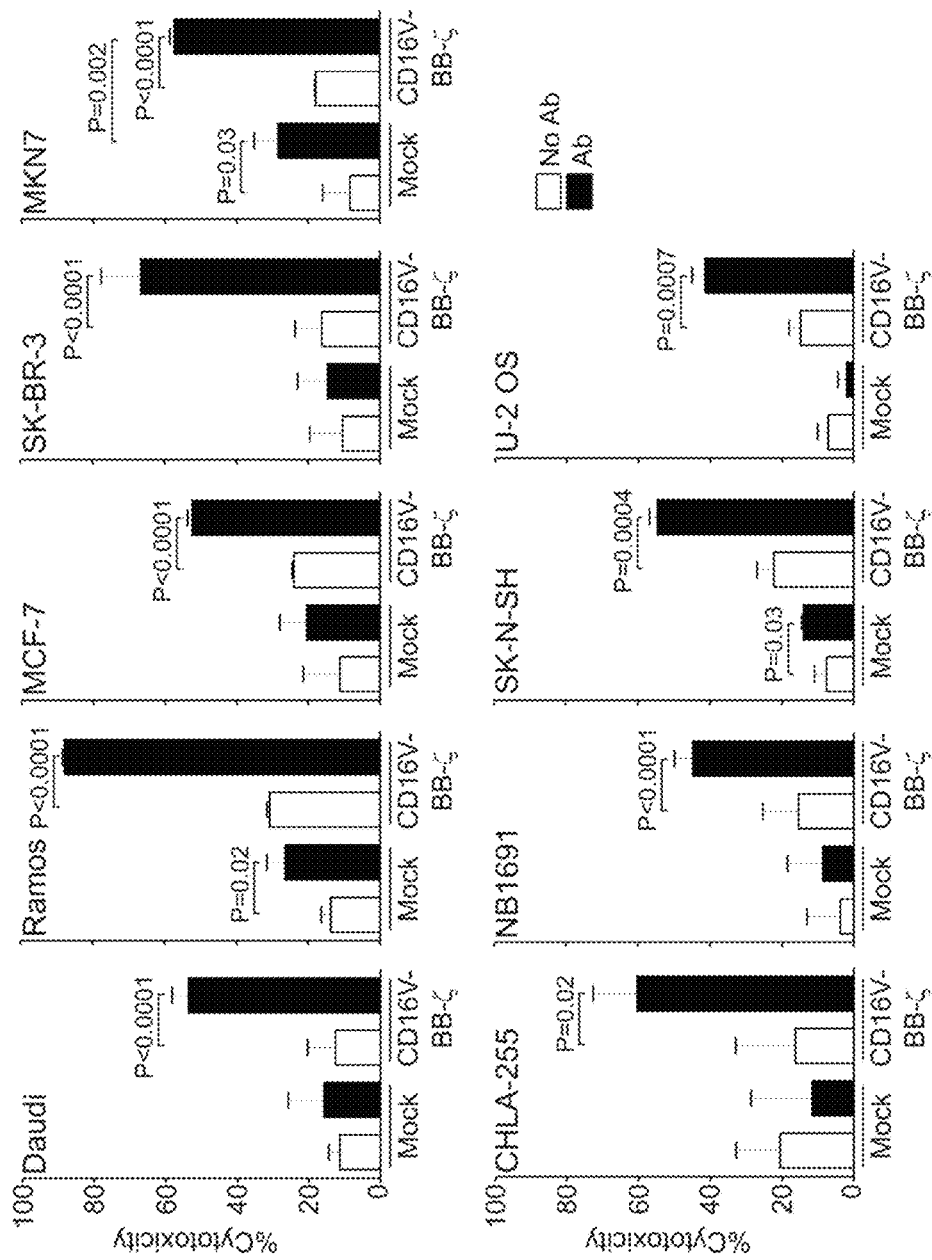
FIG. 7 shows the collective results of 4-hour in vitro cytotoxicity assays. Mock- or CD16V-BB-ζ T lymphocytes were cocultured with the cell lines shown and either non-reactive human immunoglobulin ("No Ab") or the corresponding antibody ("Ab"). This was Rituximab for Daudi and Ramos, Trastuzumab for MCF-7, SKBR-3, and MKN-7, and hu14.18K322A for CHLA-255, NB1691, SK-N-SH and U-2 OS. Shown are cytotoxicities at 2:1 ratio (4:1 for CHLA-255) as compared to tumor cells cultured without T cells and/or antibody. Results correspond to mean (±SD) cytotoxicity of triplicate experiments performed with T lymphocytes of 3 donors for NB1691 and SK-BR-3, and of 1 donor for the remaining cell lines; results of Daudi are mean (±SD) cytotoxicity of triplicate measurements from 2 donors and single measurements with T lymphocytes from 4 additional donors. Mean cytotoxicity of Rituximab, Trastuzumab or hu14.18K322A when added to cultures in the absence of T cells was <10%.

The observation that CD16V-BB-ζ cross-linking provoked exocytosis of lytic granules implied that CD16V-BB-ζ T lymphocytes should be capable of killing target cells in the presence of specific antibodies. Indeed, in 4-hour in vitro cytotoxicity assays, CD16V-BB-ζ T lymphocytes were highly cytotoxic against the B-cell lymphoma cell lines Daudi and Ramos in the presence of Rituximab: more than 50% target cells were typically lysed after 4 hours of co-culture at a 2:1 E:T ratio (FIG. 6 and FIG. 7). By contrast, target cell killing was low in the absence of the antibody or with mock-transduced T cells (FIG. 6 and FIG. 7). Notably, the effector cells used in these experiments were highly enriched with CD3+ T lymphocytes (>98%) and contained no detectable CD3-CD56+ NK cells. Rituximab-mediated cytotoxicity of CD16V-BB-ζ T lymphocytes was also clear with CD20+ primary CLL cells (n=5); as shown in FIG. 6B, cytotoxicity typically exceeded 70% after 4 hours of coculture at a 2:1 E:T ratio. Bone marrow mesenchymal stromal cells have been shown to exert immunosuppressive effects. To test whether this would affect the cytotoxic capacity of CD16V-BB-ζ T lymphocytes, they were co-cultured with CLL cells in the presence of bone marrow-derived mesenchymal stromal cells for 24 hours at a 1:2 E:T. As shown in FIG. 6C, mesenchymal cells did not diminish the killing capacity of the ADCC-mediating lymphocytes.

Figure 8:
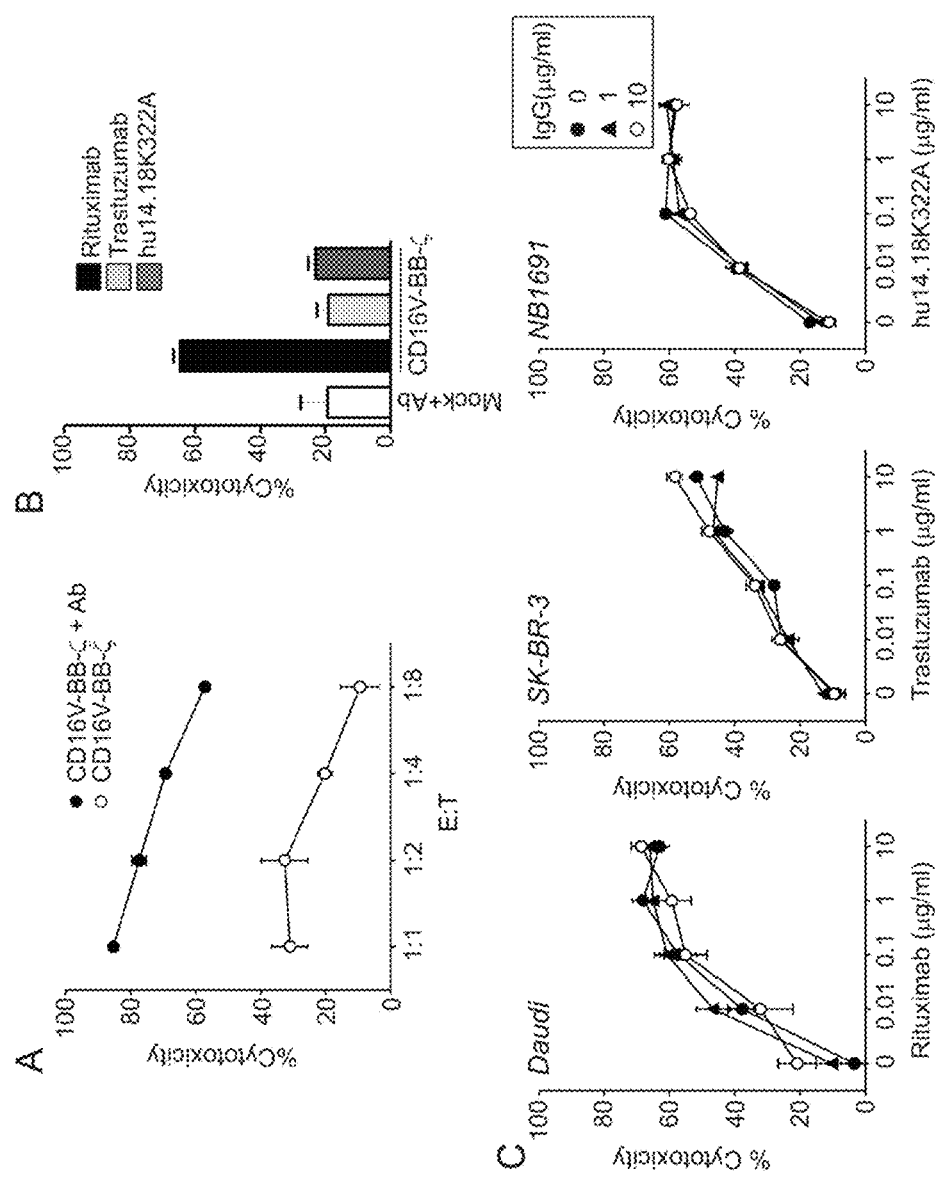
FIG. 8 demonstrates that cytotoxicity of CD16V-BB-ζ T lymphocytes is powerful, specific and is not affected by unbound IgG. A: CD16V-BB-ζ T lymphocytes cocultured with the neuroblastoma cell line NB1691 with either non-reactive human immunoglobulin ("No Ab") or the hu14.18K322A antibody ("Ab") for 24 hours. Results correspond to mean (±SD) cytotoxicity of triplicate experiments. Cytotoxicity remained significantly higher with CD16V-BB-ζ cells plus hu14.18K322A antibody as compared to CD16V-BB-ζ T cells alone even at 1:8 E:T (P=0.0002). B: mock- or CD16V-BB-ζ-transduced T lymphocytes cocultured with the B-cell lymphoma cell line Daudi for 4 hours at 2:1 E:T in the presence of Rituximab or the non-reactive antibodies Trastuzumab or hu14.18K322A. Results correspond to mean (±SD) cytotoxicity of triplicate experiments ("Mock" results are the aggregate of triplicate experiments with each antibody). Cytotoxicity with Rituximab was significantly higher than those in all other experimental conditions (P<0.0001 for all comparisons). C: cytotoxicity of T lymphocytes expressing CD16V-BB-ζ against tumor cell lines at 8:1 E:T in the presence of various concentrations of immunotherapeutic antibodies and competing unbound IgG (added simultaneously to the antibody). Symbols correspond to mean (±SD) of at least triplicate measurement for each antibody concentration. For each cell line, cytotoxicities were not statistically different, regardless of the amount of unbound IgG present.

Next, it was investigated as to whether different immunotherapeutic antibodies could trigger similar cytotoxicities against tumor cells expressing the corresponding antigen. Thus, the cytotoxicity of CD16V-BB-ζ T lymphocytes was tested against solid tumor cells expressing HER2 (the breast cancer cell lines MCF-7 and SK-BR-3 and the gastric cancer cell line MKN7) or GD2 (the neuroblastoma cell lines CHLA-255, NB1691 and SK—N—SH, and the osteosarcoma cell line U2-OS). The antibodies Trastuzumab were used to target HER2 and hu14.18K322A were used to target GD2. CD16V-BB-ζ T lymphocytes were highly cytotoxic against these cells in the presence of the corresponding antibody (FIG. 6 and FIG. 7). In experiments with NB1691, it was also tested whether cytotoxicity could be achieved at even lower E:T ratios by prolonging the culture to 24 hours. As shown in FIG. 8, cytotoxicity exceeded 50% at 1:8 ratio in the presence of hu14.18K322A. To further test the specificity of the CD16V-BB-ζ-mediated cell killing, the CD20+ Daudi cells were cultured with CD16V-BB-ζ T lymphocytes and antibodies of different specificity: only Rituximab mediated cytotoxicity, while there was no increase in cytotoxicity in the presence of Trastuzumab or hu14.18K322A (FIG. 8). Finally, it was determined whether CD16V-BB-ζ-mediated cell killing in the presence of immunotherapeutic antibodies could be inhibited by unbound monomeric IgG. As shown in FIG. 8, T cell cytotoxicity was not affected even if IgG was present at up to 1000 times higher concentration than the cell-bound immunotherapeutic antibody.

Figure 9:
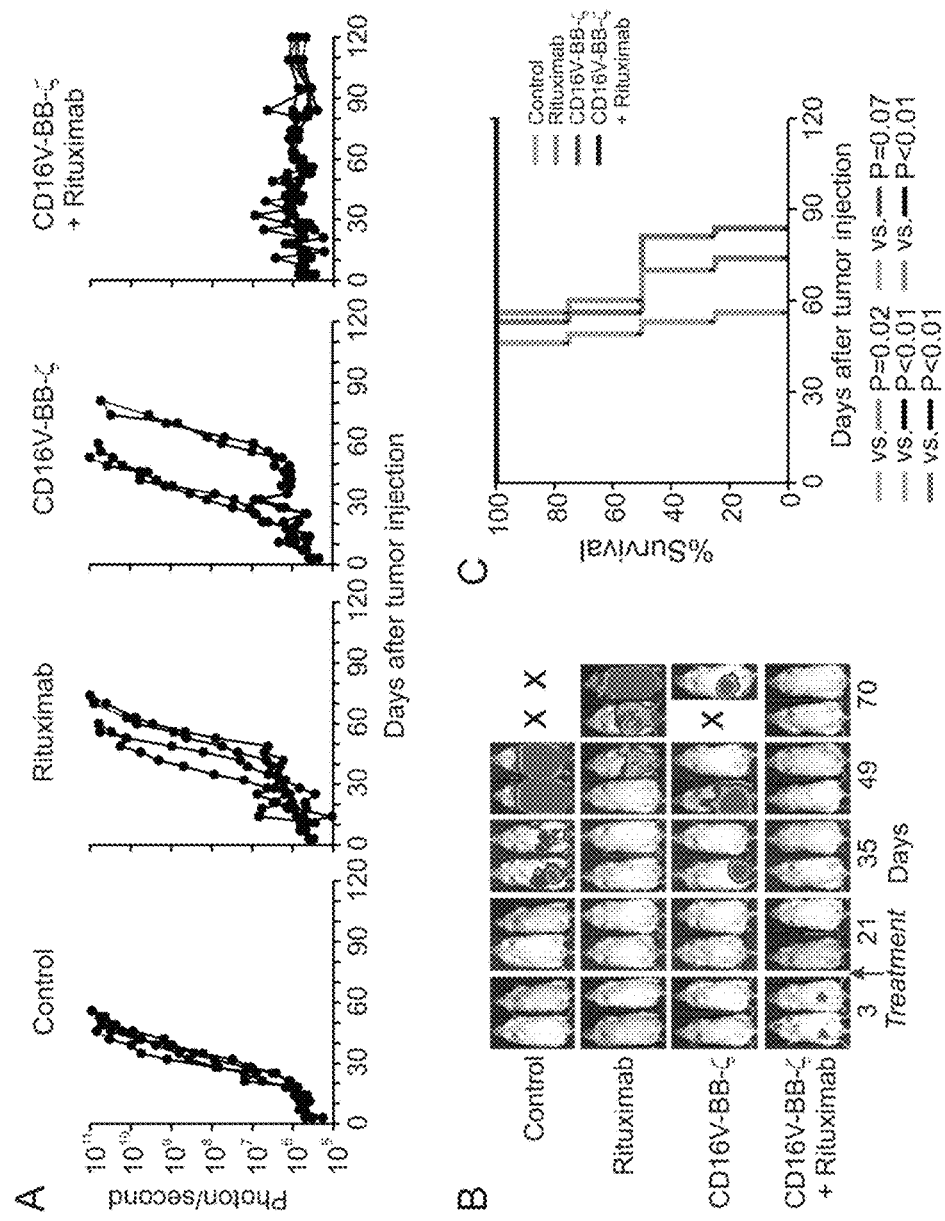
FIG. 9 demonstrates that T lymphocytes expressing CD16V-BB-ζ receptors exert anti-tumor activity in vivo. NOD-SCID-IL2RGnull mice were injected i.p. with $3 \times 10^5$ Daudi cells labeled with luciferase. Rituximab (150 μg) was injected i.p. once weekly for 4 weeks starting on day 4. In 4 mice, no other treatment was given, while in 5 other mice, the first Rituximab injection was followed by T lymphocytes expressing CD16V-BB-ζ receptors ($1 \times 10^7$ i.p.; n=5) on days 5 and 6; other 2 groups of 4 mice each received CD16V-BB-ζ T lymphocytes preceded by i.p. injection of RPMI-1640 instead of Rituximab, or i.p. injection of RPMI-1640 medium only ("Control"). A: results of in vivo imaging of tumor growth. Each symbol corresponds to one bioluminescence measurement; lines connect all measurements in one mouse. B: representative mice (2 per group) are shown for each experimental condition. Ventral images on day 3 were processed with enhanced sensitivity to demonstrate the presence of tumors in mice of the CD16V-BB-ζ+Rituximab group. Mice were euthanized when bioluminescence reached $5 \times 10^{10}$ photons/second. C: overall survival comparisons of mice in the different treatment groups.
Figure 10:
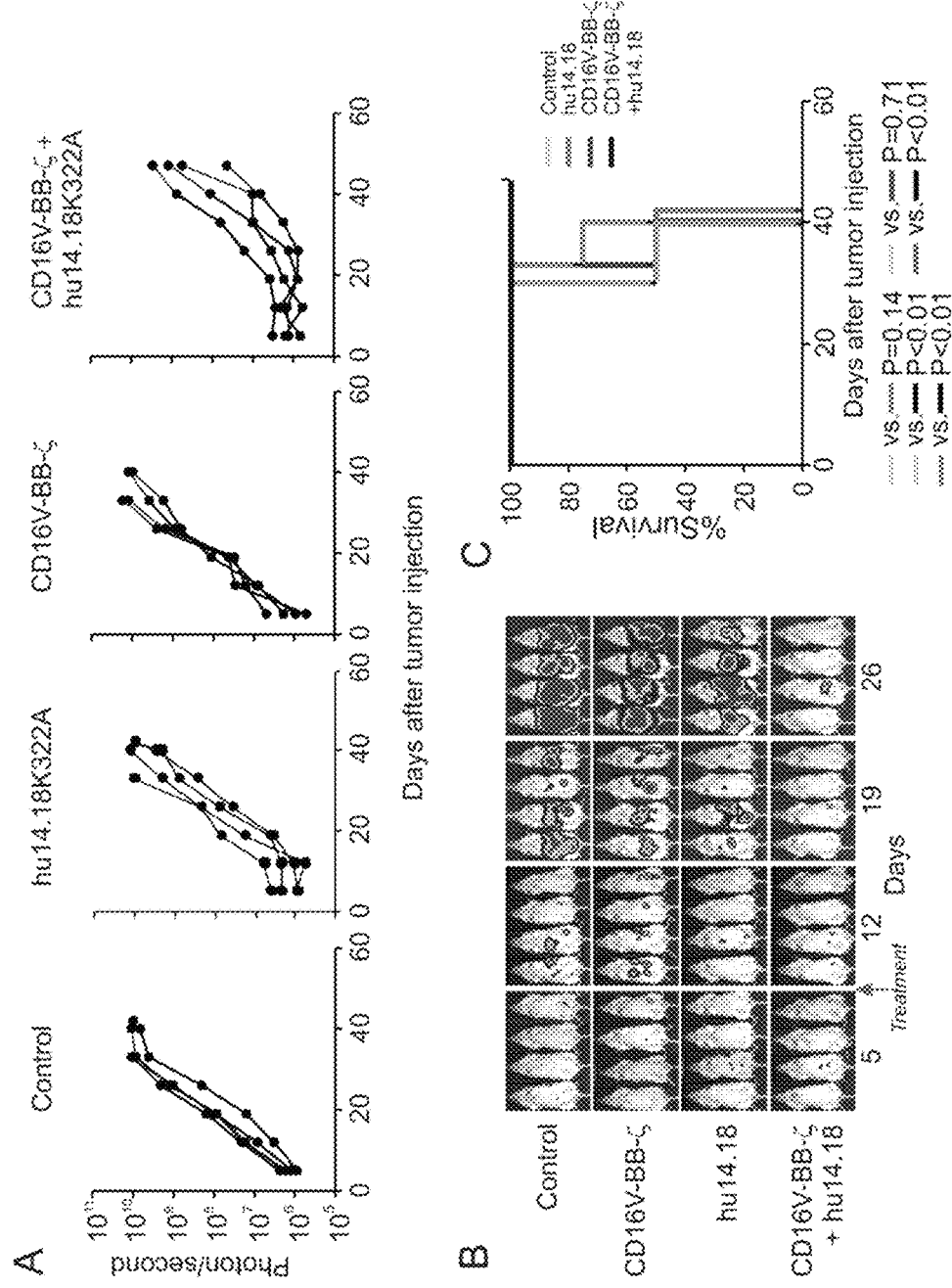
FIG. 10 confirms that T lymphocytes expressing CD16V-BB-ζ receptors exert anti-tumor activity in vivo. NOD-SCID-IL2RGnull mice were injected i.p. with $3 \times 10^5$ NB1691 cells labeled with luciferase. Hu14.18K322A antibody (25 μg) was injected i.p. once weekly for 4 weeks starting on day 5. In 4 mice, no other treatment was given, while in 4 other mice, the first antibody injection was followed by T lymphocytes expressing CD16V-BB-ζ receptors ($1 \times 10^7$ i.p.; n=4) on days 6 and 7; other 2 groups of 4 mice each received CD16V-BB-ζ T lymphocytes preceded by i.p. injection of RPMI-1640 instead of antibody, or i.p. injection of RPMI-1640 medium only ("Control"). A: results of in vivo imaging of tumor growth. Each symbol corresponds to one bioluminescence measurement; lines connect all measurements in one mouse. B: images of all mice for each experimental condition. Mice were euthanized when bioluminescence reached $1 \times 10^{10}$ photons/second. C: overall survival comparisons of mice in the different treatment groups.

To gauge the anti-tumor capacity of CD16V-BB-ζ T lymphocytes in vivo, experiments were performed with NOD/scid IL2RGnull mice engrafted with luciferase-labeled Daudi cells. Tumor growth was measured by live imaging in mice receiving CD16V-BB-ζ T lymphocytes plus Rituximab, and their outcome was compared to mice receiving either Rituximab or T lymphocytes alone, or no treatment. As shown in FIG. 9, tumor cells expanded in all mice except those that received Rituximab followed by CD16V-BB-ζ T lymphocytes. All 5 mice treated with this combination were still in remission >120 days after tumor injection, in contrast to 0 of 12 mice that were untreated or received antibody or cells alone. A strong anti-tumor activity was also observed in mice engrafted with the neuroblastoma cell line NB1691 and treated with hu14.18K322A and CD16V-BB-ζ T lymphocytes (FIG. 10).

Comparison of CD16V-BB-ζ with Other Receptors

Figure 11:
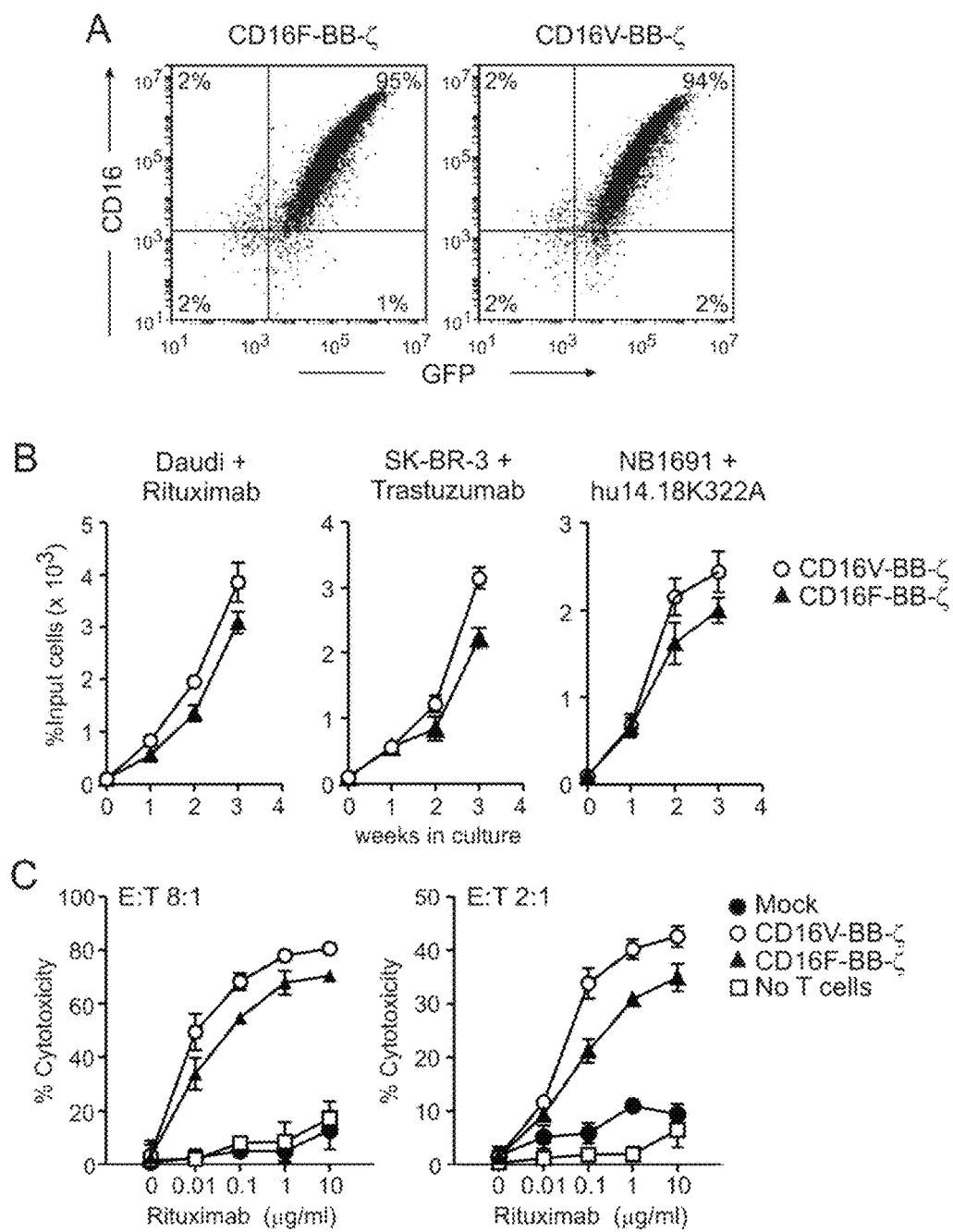
FIG. 11 demonstrates functional differences between T lymphocytes expressing CD16V-BB-ζ and CD16F-BB-ζ receptors. A: flow cytometric dot plots show expression of CD16 (detected with the B73.1 antibody) and green fluorescent protein (GFP) in T lymphocytes transduced with CD16V-BB-ζ or CD16F-BB-ζ. Percentage of positive cells in each quadrant is shown. B: T lymphocytes transduced with either CD16V or CD16F receptor were cultured with Daudi, SK-BR-3 or NB1691 cells in the presence of Rituximab, Trastuzumab and hu14.18K322A, respectively. All antibodies were used at 0.1 µg/mL. Symbols indicate percentage of cell recovery as compared to the number of input cells (mean±SD of 3 experiments); cell counts for weeks 1-3 of culture were significantly different by paired t test for all 3 cultures (Daudi, P=0.0007; SK-BR-3, P=0.0164; NB1691, P=0.022). C: antibody-dependent cell cytotoxicity mediated by T lymphocytes expressing either CD16V-BB-ζ or CD16F-BB-ζ receptors against Daudi cells in the presence of various concentrations of Rituximab. Each symbol indicates the mean±SD of triplicate cultures at 8:1 (left) or 2:1 (right) E:T. Cytotoxicities of T cells with CD16V-BB-ζ were significantly higher than those of T cells with CD16F-BB-ζ (P<0.001 for either E:T).

It was first compared the function of T cells bearing either CD16V-BB-ζ or CD16F-BB-ζ receptors. CD16F-BB-ζ receptors induced T cell proliferation and ADCC which was higher than that measured in mock-transduced T cells. Nevertheless, in line with their higher affinity for Ig, CD16V-BB-ζ receptors induced significantly higher T cell proliferation and ADCC than that triggered by the lower affinity CD16F-BB-ζ receptors (FIG. 11).

Figure 12:
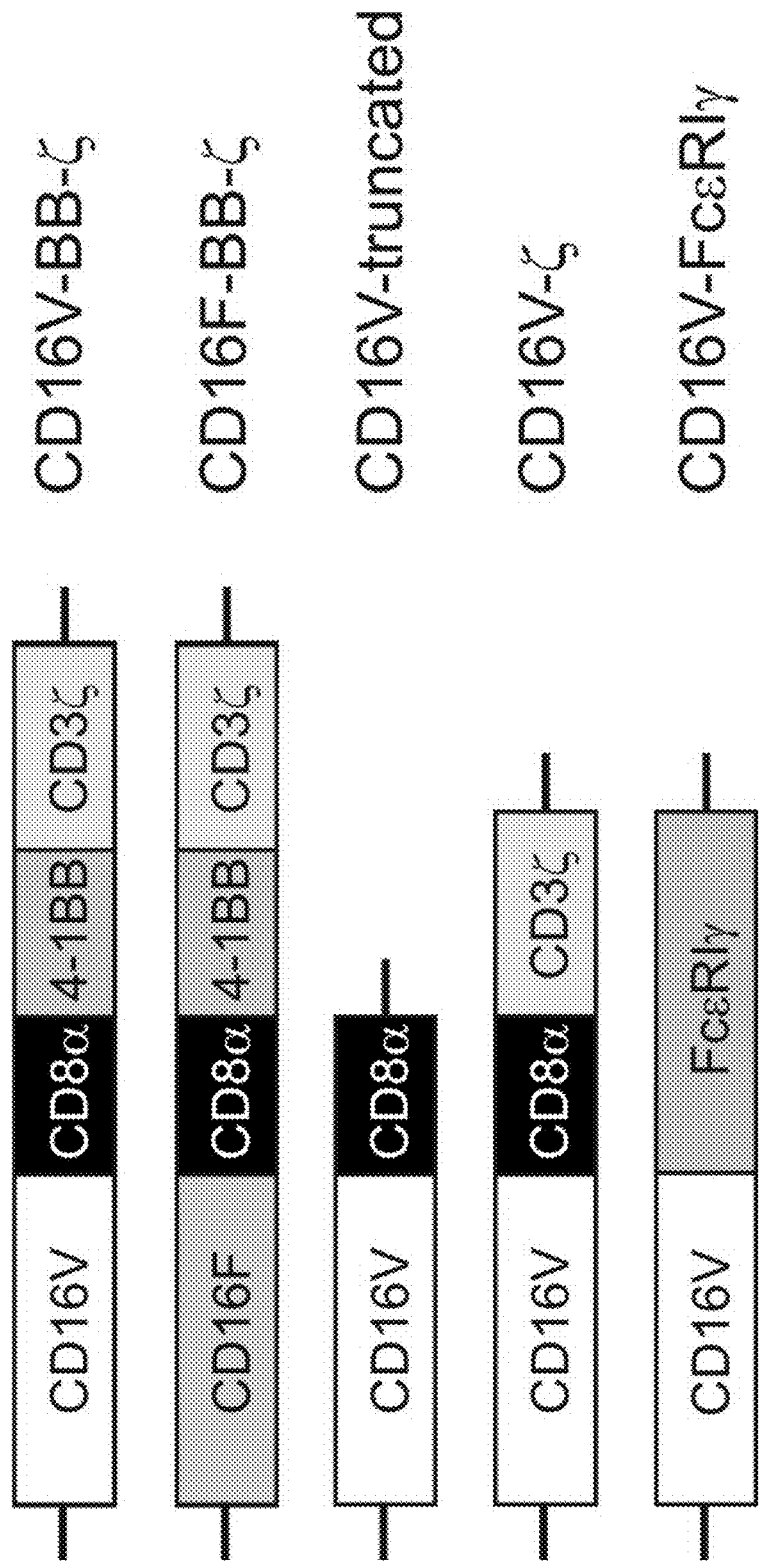
FIG. 12 shows a schematic representation of CD16 chimeric receptors used in this study.
Figure 13:
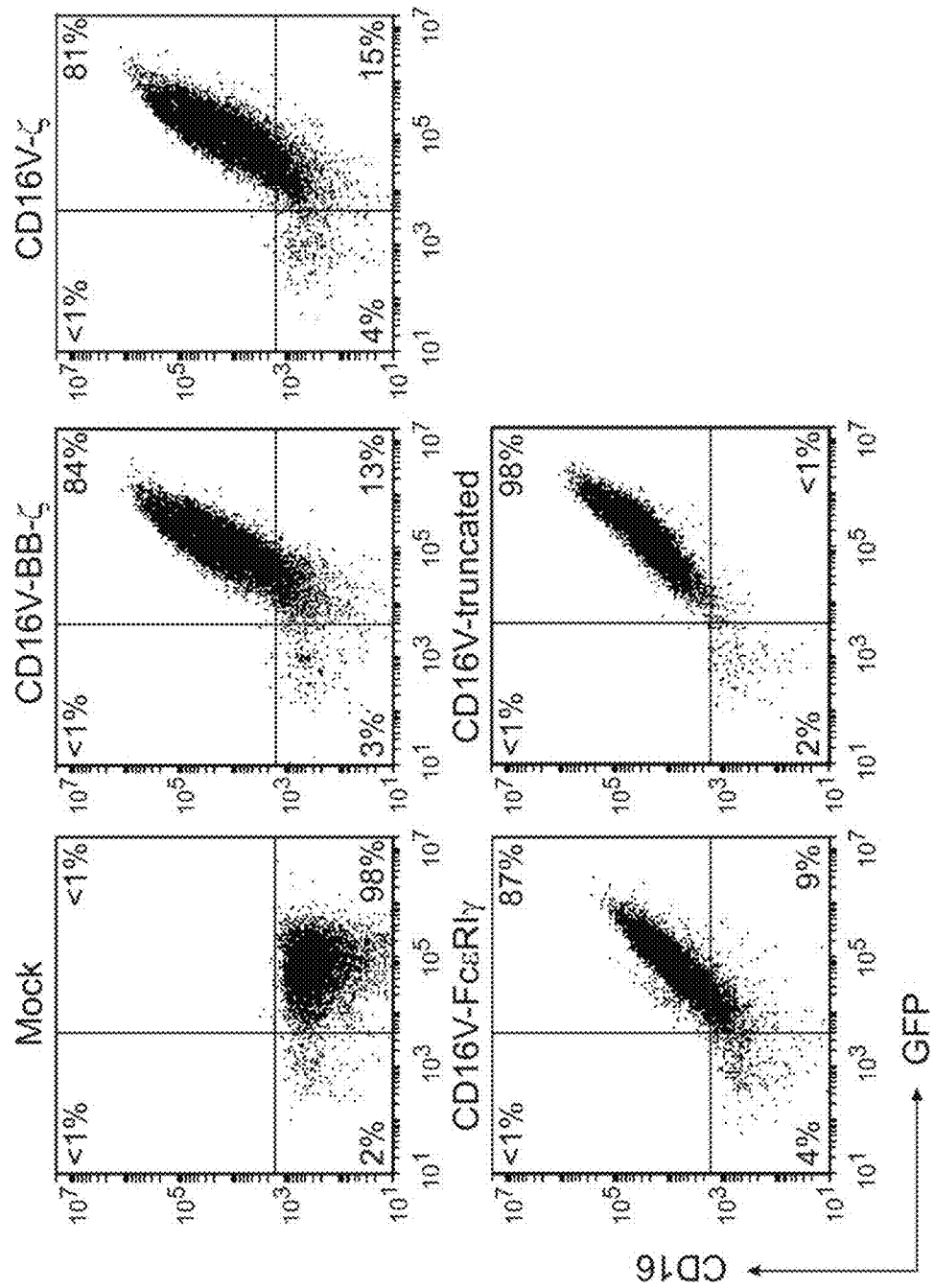
FIG. 13 shows expression of CD16V receptors with different signaling domains. Flow cytometric dot plots illustrate expression of CD16 (detected with the 3G8 antibody) in combination with GFP in activated T lymphocytes transduced with a vector containing green fluorescent protein (GFP) alone (Mock) or different CD16V constructs. Percentage of positive cells in each quadrant is shown.
Figure 14:
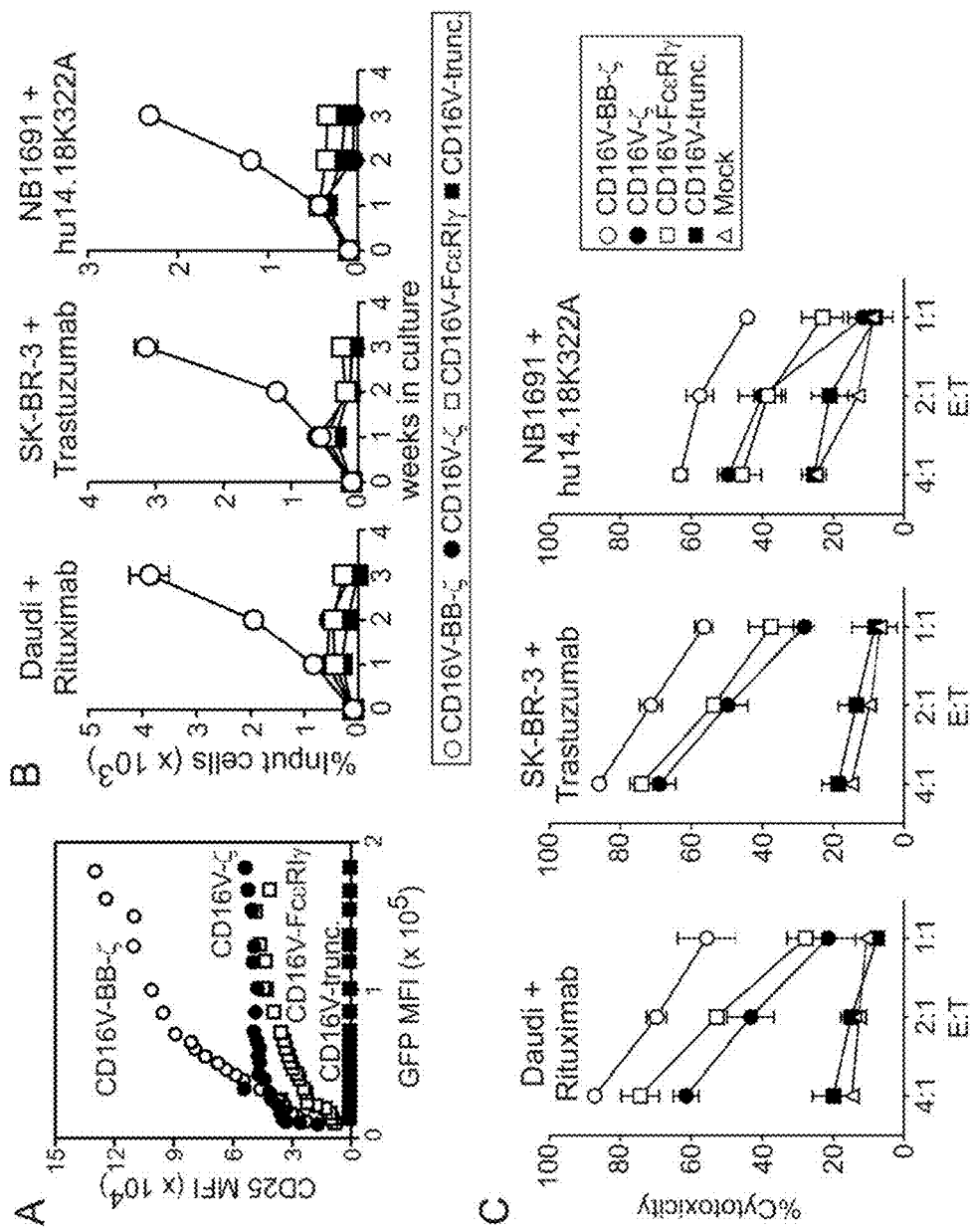
FIG. 14 demonstrates that CD16V-BB-ζ induces higher T cell activation, proliferation and cytotoxicity than CD16V receptors with different signaling properties. A: CD25 mean fluorescence intensity (MFI) by flow cytometry plotted against green fluorescent protein (GFP) MFI in T lymphocytes expressing different chimeric receptors after 48-hour co-culture with Daudi cells and Rituximab (0.1 µg/mL). CD25 expression with CD16V-BB-ζ was significantly higher than that triggered by CD16V-ζ, CD16V-FcεRIγ or CD16V with no signaling capacity ("CD16V-trunc.") (P<0.0001 by linear regression analysis). B: T lymphocytes transduced with various CD16V receptors were cultured with Daudi, SK-BR-3 or NB1691 cells in the presence of Rituximab, Trastuzumab and hu14.18K322A, respectively. All antibodies were used at 0.1 µg/mL. Symbols indicate percentage of cell recovery as compared to number of input cells (mean±SD of 3 experiments); cell counts for weeks 1-3 of culture were significantly higher with CD16V-BB-ζ receptors that with all other receptors by paired t test for all 3 cultures (P<0.0001). C: ADCC of T lymphocytes expressing various CD16V receptors or mock-transduced T cells against Daudi, SK-BR-3 and NB1691 in the presence of Rituximab, Trastuzumab and hu14.18K322A, respectively. Symbols are mean±SD of triplicate cultures at the E:T shown. Cytotoxicities with CD16V-BB-ζ receptors were significantly higher than those with all other receptors (P<0.0001 by t test in all comparisons) while cytotoxicities of lymphocytes mock-transduced or transduced with the CD16V-truncated receptor were not significantly different (P>0.05) from each other; cytotoxicity with CD16V-FcεRIγ was significantly higher than that with CD3-ζ against Daudi (P=0.006) and SK-BR-3 (P=0.019); lymphocytes expressing either receptor had higher cytotoxicities than those mock-transduced or transduced with CD16V-truncated (P<0.01 for all comparisons).

Next, the function of T cells bearing CD16V-BB-ζ was compared to that of T cells expressing other receptors with different signaling properties. These included a receptor with no signaling capacity ("CD16V-truncated"), one with CD3ζ but no 4-1BB ("CD16V-κ"), and a previously described receptor that combined CD16V with the transmembrane and cytoplasmic domains of FcεRIγ ("CD16V-FcεRIγ") (FIG. 12). After retroviral transduction in activated T cells, all receptors were highly expressed (FIG. 13). As shown in FIG. 14, CD16V-BB-ζ induced significantly higher activation, proliferation and specific cytotoxicity than all other constructs.

Expression of CD16V-BB-ζ Receptors by mRNA Electroporation

Figure 15:
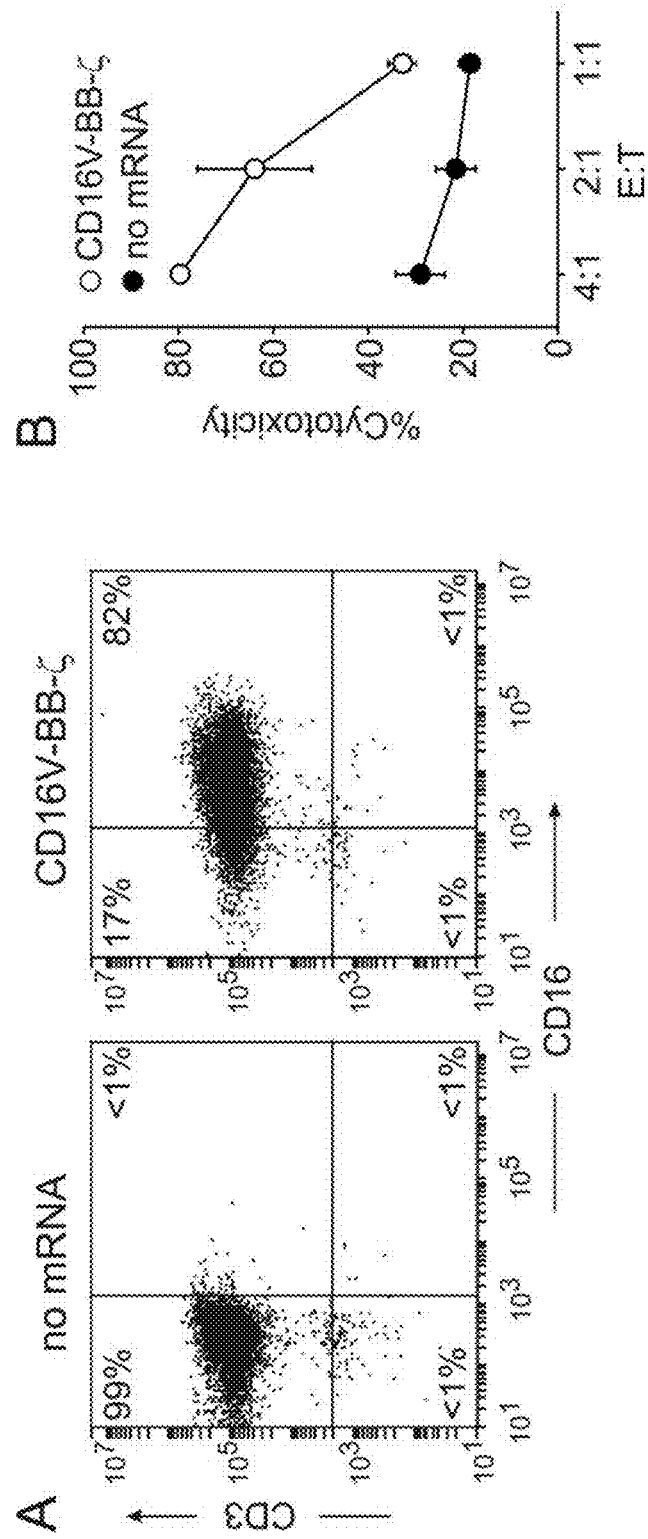
FIG. 15 demonstrates expression of CD16V-BB-ζ receptors by mRNA electroporation. A: activated T lymphocytes were electroporated with CD16V-BB-ζ mRNA or without mRNA (Mock); expression of CD16 was tested 24 hours later by flow cytometry. B: cytotoxicity of mock or CD16V-BB-ζ electroporated T cells was tested against the Ramos cell line in the presence of Rituximab. Symbols show mean±SD percent cytotoxicity (n=3; P<0.01 for comparisons at all E:T ratios).

In all the above experiments, CD16V-BB-ζ expression was enforced by retroviral transduction. It was tested whether an alternative method, electroporation of mRNA, could also confer ADCC capacity to T lymphocytes. Activated T lymphocytes from 2 donors were electroporated and high expression efficiencies were obtained: 55% and 82% of T lymphocytes became CD16+ 24 hours after electroporation (FIG. 15A). In the second donor, receptor expression was also tested on day 3, when it was 43%, a result similar to those of previous experiments with another receptor where expression persisted for 72 to 96 hours. ADCC was activated in T lymphocytes electroporated with CD16V-BB-ζ mRNA: in the presence of Rituximab, 80% Ramos cells were killed after 4 hours at a 2:1 E:T ratio, while cells electroporated without mRNAs were ineffective (FIG. 15B).

See also Kudo et al., Cancer Res. 2014 Jan. 1; 74(1):93-103, the entire content of which is incorporated by reference herein.

Discussion

Described herein is the development of chimeric receptors which endow T lymphocytes with the capacity to exert ADCC. When the CD16V-BB-ζ receptor is engaged by an antibody bound to tumor cells, it triggers T-cell activation, sustained proliferation and specific cytotoxicity against cancer cells targeted by antibody. CD16V-BB-ζ T lymphocytes were highly cytotoxic against a wide range of tumor cell types, including B-cell lymphoma, breast and gastric cancer, neuroblastoma and osteosarcoma, as well as primary CLL cells. Cytotoxicity was entirely dependent on the presence of a specific antibody bound to target cells; unbound antibodies did not provoke non-specific cytotoxicity nor affected cytotoxicity with cell-bound antibodies. CD16V-BB-ζ T cells also killed CLL cells when these were cultured on mesenchymal cell layers, regardless of the known immunosuppressive effects of this microenvironment. Moreover, CD16V-BB-ζ T lymphocytes infused after Rituximab eradicated B-cell lymphoma cells engrafted in immunodeficient mice, and had considerable anti-tumor activity in mice engrafted with neuroblastoma cells in the presence of an anti-GD2 antibody. In sum, T cells expressing CD16V-BB-ζ effected strong ADCC in vitro and in vivo.

The affinity of CD16 for the Fc portion of Ig is a critical determinant of ADCC and, thus, influences clinical responses to antibody immunotherapy. Hence, considerable efforts are being made to further enhance the affinity of Fc fragments for FcγR, for example by glycoengineering. To construct the chimeric receptor of the disclosure, the FCGR3A (CD16) gene with the V158 polymorphism (SEQ ID NO: 65) was selected as an example. This variant encodes a receptor with higher binding affinity for Ig and has been shown to mediate superior ADCC. Indeed, in side-to-side comparisons with an identical chimeric receptor containing the more common F158 variant, the CD16V-BB-ζ had a significantly higher capacity to bind human Ig Fc, and induced more vigorous proliferation and cytotoxicity, evoking results of recent studies addressing the role of affinity in chimeric antigen receptor function. Current "second generation" chimeric receptors combine a stimulatory molecule with a co-stimulatory one to augment signaling and prevent activation-induced apoptosis. Therefore, CD16 V158 was combined with a stimulatory molecular tandem constituted by CD3ζ and 4-1BB (CD137). Indeed, the CD16V-BB-ζ receptor induced a markedly superior T cell activation, proliferation and cytotoxicity than did receptors acting through CD3ζ alone, or of FcεRIγ.

The clinical potential of genetically modified T cells expressing receptors that recognize antigens of the surface of tumor cells and can transduce stimulatory signals is being increasingly demonstrated by results of clinical trials. Most notably, significant tumor reductions and/or complete remissions have been reported in patients with B-cell malignancies who received autologous T lymphocytes expressing chimeric antigen receptors against CD19 or CD20 by viral transduction. Expanding this strategy to other tumors involves considerable effort, including the development of another chimeric antigen receptor construct, and the optimization of large-scale transduction conditions in compliance with regulatory requirements. In this regard, the CD16V-BB-ζ receptor described herein should facilitate the implementation of T-cell therapy by allowing one single receptor to be used for multiple cancer cell types. It should also allow the targeting of multiple antigens simultaneously, a strategy that may ultimately be advantageous given immunoescape mechanisms exploited by tumors, as illustrated by the recent report of a leukemia relapse driven by a subclone lacking the marker targeted by a chimeric receptor with single specificity. Antibody-directed cytotoxicity could be stopped whenever required by simple withdrawal of antibody administration. Because the T cells expressing CD16V-BB-ζ are only activated by antibody bound to target cells, soluble immunoglobulin should not exert any stimulation on the infused T cells. As demonstrated herein, mRNA electroporation can express the receptor very effectively.

Antibody therapy has become standard-of-care for many cancer subtypes; its clinical efficacy is mostly determined by its capacity to trigger ADCC through the engagement of Fc receptors. The main effectors of ADCC are NK cells but their function can be impaired in patients with cancer. For example, it was reported that Trastuzumab-mediated ADCC of gastric cancer cells overexpressing HER2 was significantly lower with peripheral blood mononuclear cells from gastric cancer patients and advanced disease as compared to that obtained with samples from patients with early disease or healthy donors. Moreover, responses are likely to be influenced by other factors, including the genotype of NK-cell inhibitory receptors and their ligands. The results presented herein suggest that the infusion of autologous T cells genetically engineered with the CD16V-BB-ζ receptor should significantly boost ADCC. Because the combined CDζ/4-1BB signaling also causes T-cell proliferation, there should be an accumulation of activated T cells at the tumor site which may further potentiate their activity. CD16V-BB-ζ receptors can be expressed by mRNA electroporation not only in activated T lymphocytes but also in resting peripheral blood mononuclear cells, a procedure that would take only a few hours from blood collection to infusion of CD16V-BB-ζ-expressing cells and is therefore well suited for clinical application.

Example 2. Construction of Various Chimeric Receptors

Nucleic acid sequences encoding chimeric receptors SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 14 were cloned into the HindIII and XbaI sites of vector pVAX1. The DNA vectors were linearized by digestion with restriction endonuclease XbaI and transcribed into RNA with T7 RNA polymerase. The RNA was subsequently enzymatically capped at its 5'-end with ScriptCap Capping Enzyme and ScriptCap 2'-O-Methyltransferase from Cellscript to give a Cap 1 structure and then polyadenylated at its 3'-end with poly-A polymerase. The resulting mRNA was electroporated into Jurkat cells using an Invitrogen Neon electroporation system and grown in RPMI-1640 media with 10% fetal bovine serum at 37° C. for 6 hr.

Electroporated cells in media were then incubated with the CD20-specific antibody Rituxan (10 μg/mL) at 37° C. for 30 min. Cells were harvested, washed twice with flow cytometry buffer (FC buffer; DPBS without Ca2+ and Mg2+, 0.2% bovine serum albumin, 0.2% NaN3) and stained with a PE-labeled anti-CD16 antibody or anti-CD32 antibody (for SEQ ID NO: 6) to detect chimeric receptor expression or a PE-labeled goat-anti-human antibody to detect bound Rituxan. Stained cells were analyzed by flow cytometry. Chimeric receptor proteins from all constructs were detected with the PE-labeled anti-CD16 or anti-CD32 antibodies with mean fluorescence values that ranged from 36,000 to 537,000. Uconstruct 1 (SEQ ID NO: 1) showed the highest expression level.

Figure 16:
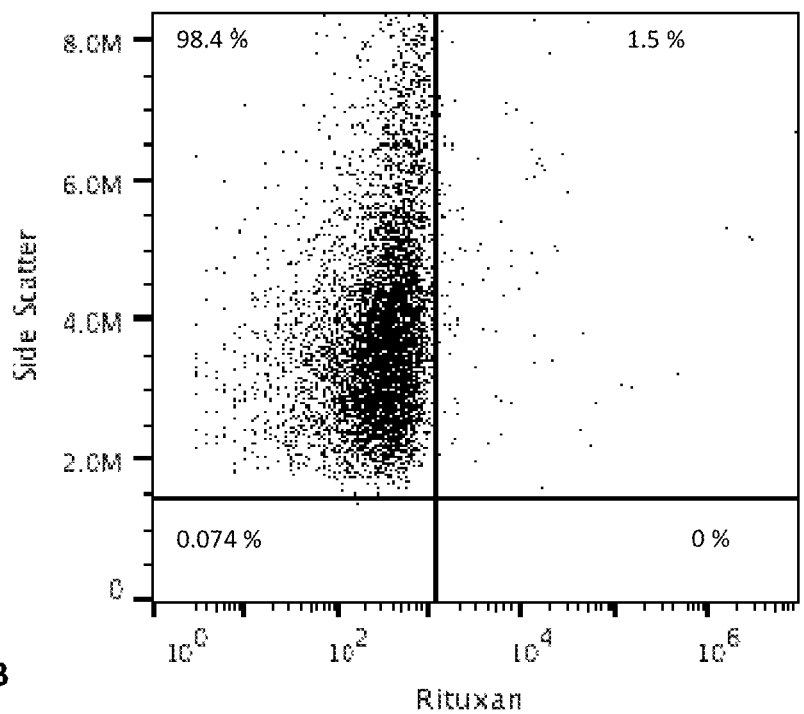
FIG. 16 shows binding of Rituxan to Jurkat cells with and without expression of the chimeric receptor SEQ ID NO: 1. Jurkat cells were electroporated in the presence of no mRNA (panel A) or mRNA encoding chimeric receptor SEQ ID NO: 1 (panel B), incubated with Rituxan, stained with a PE-labeled goat-anti-human antibody to detect bound Rituxan, and analyzed by flow cytometry. In panels A and B, the same quadrant gate was applied to each set of data and the percentage of cells in each quadrant is shown, with the top right quadrant representing Rituxan-positive cells. In panel C, cell number is plotted as a function of Rituxan staining for mock-electroporated cells (no fill) and cells electroporated with mRNA encoding chimeric receptor SEQ ID NO: 1 (gray).
Figure 16:
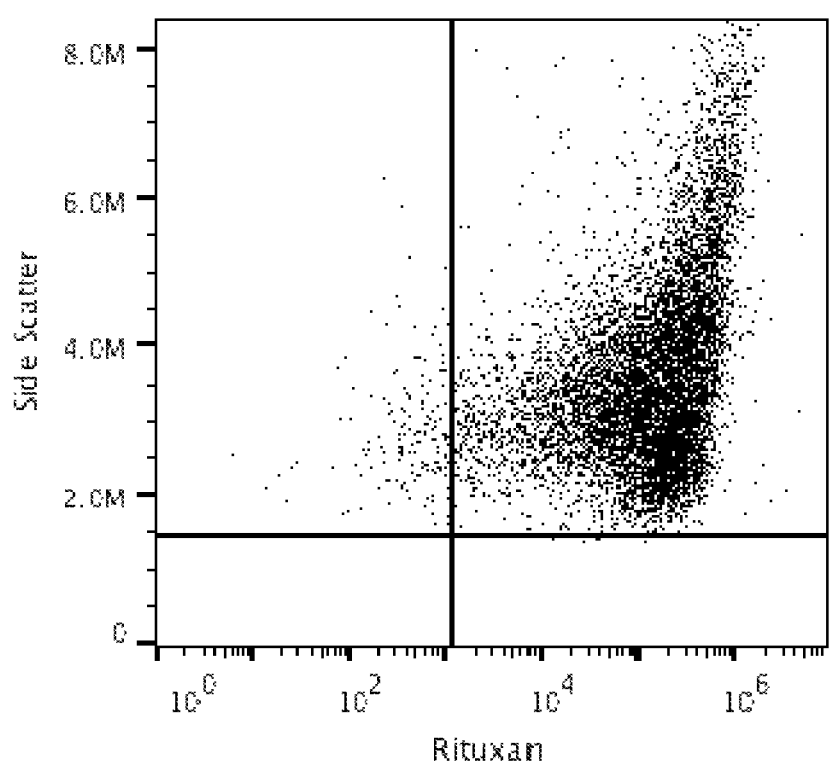
Figure 16:
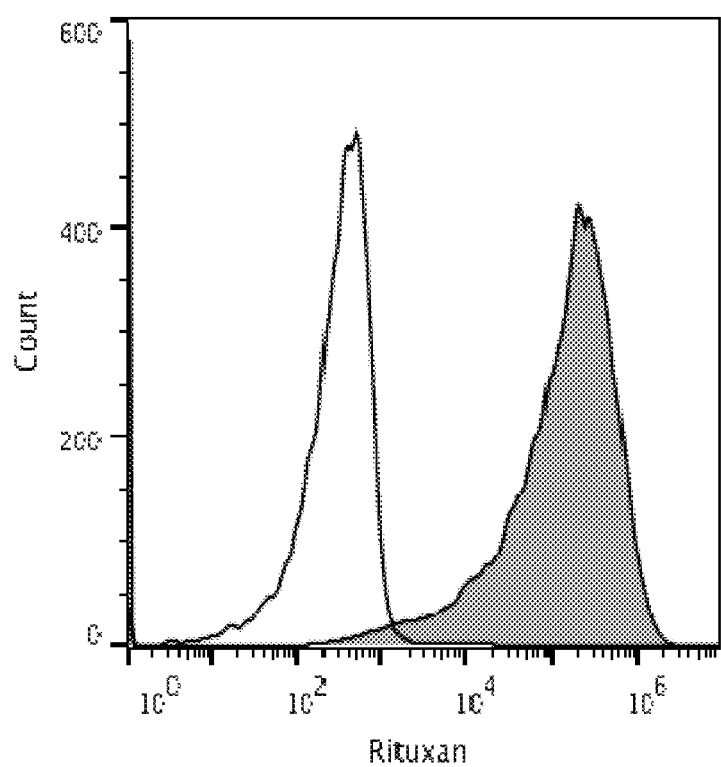

FIG. 16 (panels A to C) shows flow cytometry data for Rituxan binding to cells electroporated with SEQ ID NO: 1 mRNA and mock-electroporated cells. Greater than 95% of the cells electroporated with mRNA encoding SEQ ID NO: 1 were stained with the goat-anti-human antibody, as compared to less than 2% of mock-electroporated cells, indicating the chimeric receptor expressed on the surface of Jurkat cells was able to bind to Rituxan (FIGS. 16A and 16B). The median fluorescence value of SEQ ID NO: 1 mRNA-electroporated cells was approximately 700-fold higher than the median fluorescence value of mock-electroporated cells when stained with PE-labeled goat-anti-human antibody (FIG. 16C, Table 7). A similar analysis was carried out for SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9), SEQ ID NO: 10, SEQ ID NO: 11, and SEQ ID NO: 14. The median fluorescence values for cells electroporated with chimeric receptor mRNA for these constructs were approximately 14- to 680-fold higher than the median fluorescence value of mock-electroporated cells when stained with PE-labeled goat-anti-human antibody (Table 7), indicating that all of these chimeric receptor proteins that were expressed on the surface of Jurkat cells were able to bind to Rituxan.

These experiments indicated that chimeric receptors SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 14 were all expressed in Jurkat cells and all bound the CD20-specific antibody Rituxan.

TABLE 7

Relative median fluorescence for chimeric receptor binding to Rituxan, and CD25 and CD69 expression in activity experiments for chimeric receptor constructs.

| mRNA electroporated into Jurkat cells | SEQ ID | variation relative to SEQ ID NO: 1 | Rituxan binding relative median fluorescence | CD25 expression relative median fluorescence | CD69 expression relative median fluorescence |
|---|---|---|---|---|---|
| none | — | — | 1 | 1 | 1 |
| SEQ ID NO: 1 | 1 | — | 694.7 | 6.7 | 69.1 |
| SEQ ID NO: 2 | 2 | 4-1BB TM domain | 22.4 | 2.3 | 10.9 |
| SEQ ID NO: 3 | 3 | CD28 TM domain | 77.7 | 5.1 | 25.0 |
| SEQ ID NO: 4 | 4 | CD34 TM domain | 25.8 | 3.0 | 10.6 |
| SEQ ID NO: 5 | 5 | generic TM domain | 14.2 | 2.4 | 10.2 |
| SEQ ID NO: 6 | 6 | CD32 Fc receptor | 682.4 | 5.4 | 64.1 |
| SEQ ID NO: 7 | 7 | CD28 costimulatory domain | 232.7 | 4.7 | 35.2 |
| SEQ ID NO: 8 | 8 | OX40 costimulatory domain | 322.7 | 5.3 | 37.6 |
| SEQ ID NO: 9 | 9 | CD28 + 4-1BB costimulatory domains | 102.4 | 5.3 | 25.7 |
| SEQ ID NO: 10 | 10 | no hinge | 24.0 | 5.8 | 13.0 |
| SEQ ID NO: 11 | 11 | XTEN hinge | 55.4 | 7.6 | 20.6 |
| SEQ ID NO: 14 | 14 | CD4 TM domain | 32.1 | 4.8 | 13.0 |

Example 3. Cells Expressing Chimeric Receptors Display T Cell Activation Markers Jurkat cells expressing the chimeric receptors disclosed in Example 2 above were evaluated for activity by monitoring for the presence of the cell-surface activity markers CD25 and CD69. For these experiments, Jurkat cells were electroporated without mRNA (mock) or with mRNA encoding the chimeric receptor constructs described in Example 2 above, using an Invitrogen Neon electroporation system and grown in RPMI-1640 media with 10% FBS at 37° C. for 8-9 hr. Cells were harvested, washed with RPMI-1640 media with 10% fetal bovine serum, 50 U/mL penicillin, and 50 μg/mL streptomycin. These cells were mixed at a one to one ratio with Daudi target cells, which have cell-surface-expressed CD20, that had been fixed with Streck's cell preservative, and the CD20-specific antibody Rituxan (10 μg/mL). This mixture was incubated at 37° C. for 18-20 hr in RPMI-1640 media with 10% fetal bovine serum, 50 U/mL penicillin, and 50 μg/mL streptomycin. Cells were harvested and stained with a PE-labeled anti-CD7 antibody to detect Jurkat cells and an APC-labeled anti-CD25 antibody or an APC-labeled anti-CD69 antibody to detect CD25 and CD69 expression, respectively, on Jurkat cells. Stained cells were evaluated by flow cytometry.

Figure 17:
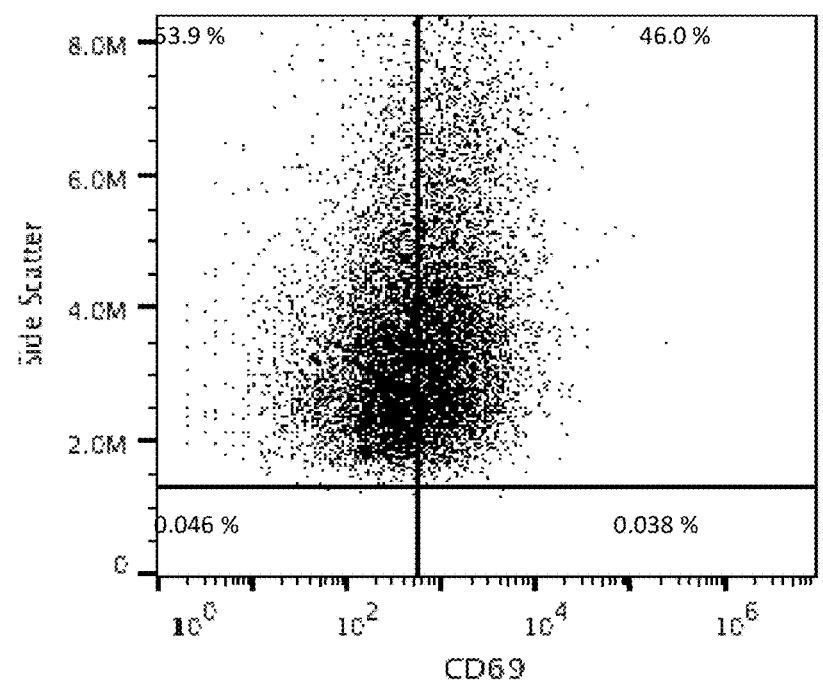
FIG. 17 shows the presence of CD25 on Jurkat cells, with or without expression of chimeric receptor SEQ ID NO: 1, in the presence of Rituxan and target Daudi cells. Jurkat cells were electroporated in the presence of no mRNA (panel A) or mRNA encoding chimeric receptor SEQ ID NO: 1 (panel 17B), and subsequently incubated with Rituxan and target Daudi cells. Cells were stained with a PE-labeled anti-CD7 antibody to isolate Jurkat cells and APC-labeled anti-C25 antibody to detect CD25 expression, and analyzed by flow cytometry. CD7-positive cells are shown in panels A and B, and the same quadrant gate was applied to each set of data. The percentage of cells in each quadrant is shown, with the top right quadrant representing CD25-positive cells. Panel C shows a histogram of data from the same experiment. The number of CD7-positive cells is plotted as a function of CD25 staining for mock-electroporated cells (no fill) and cells electroporated with mRNA encoding chimeric receptor SEQ ID NO: 1 (gray) are plotted as a function of CD25 staining.
Figure 17:
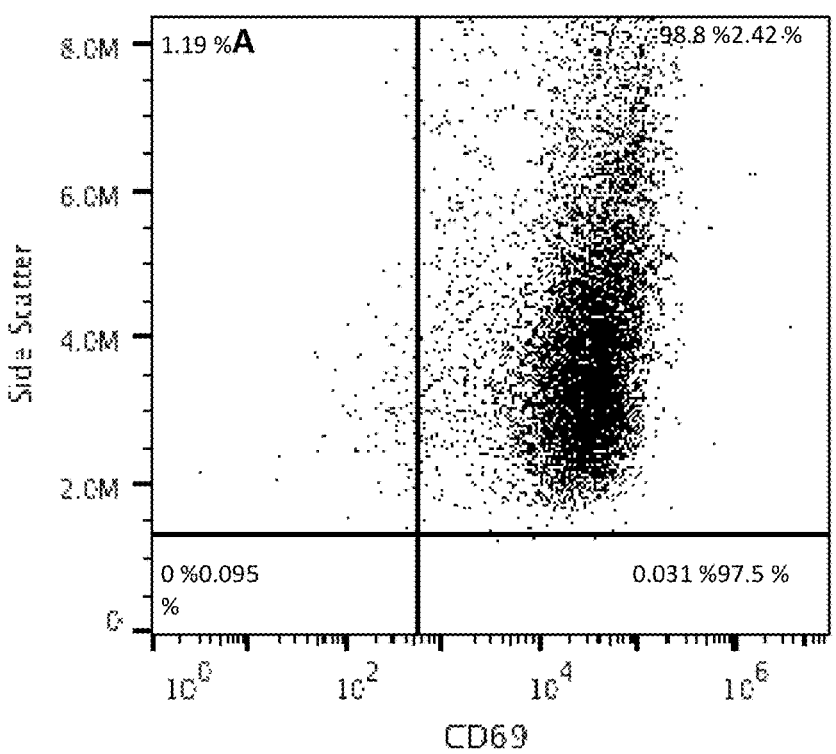
Figure 17:
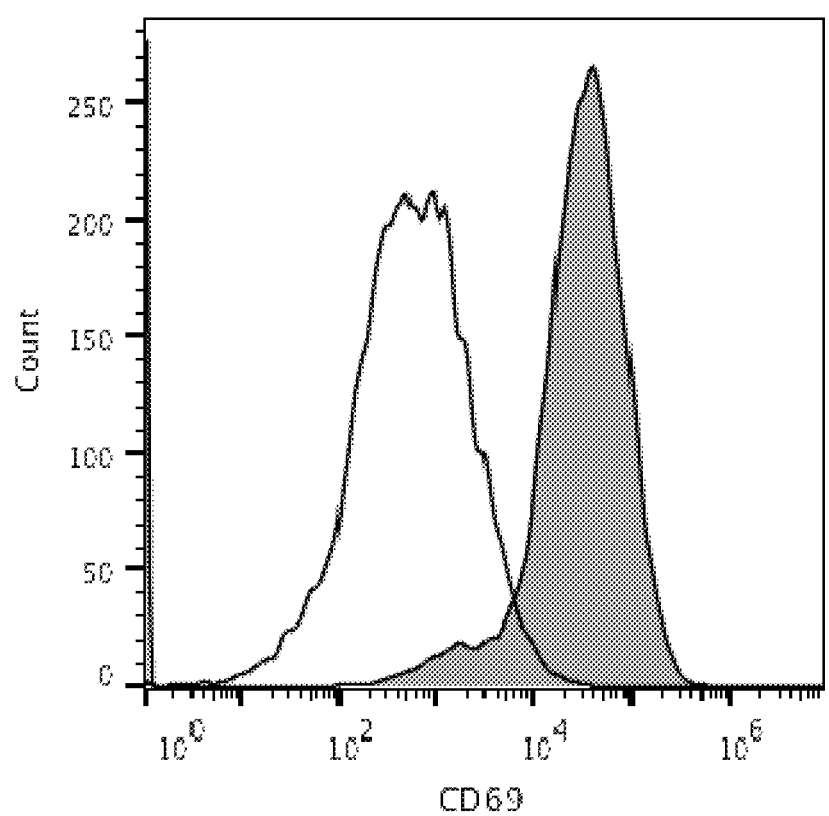
Figure 18:
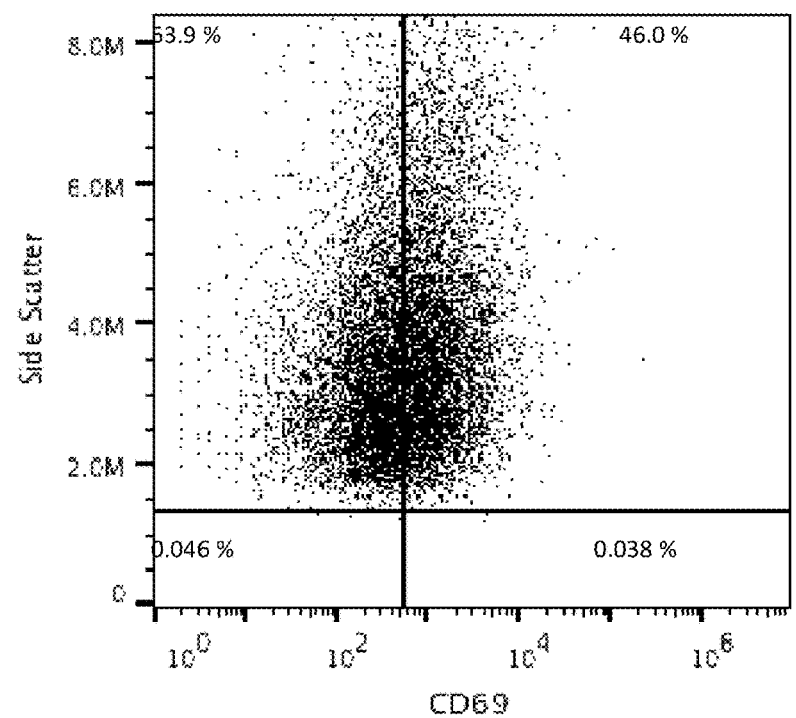
FIG. 18 shows the presence of CD69 on Jurkat cells, with or without expression of chimeric receptor SEQ ID NO: 1, in the presence of Rituxan and target Daudi cells. Jurkat cells were electroporated in the presence of no mRNA (panel A) or mRNA encoding SEQ ID NO: 1 (panel B), and subsequently incubated with Rituxan and target Daudi cells. Cells were stained with a PE-labeled anti-CD7 antibody to isolate Jurkat cells and APC-labeled anti-CD69 antibody to detect CD69 expression, and analyzed by flow cytometry. CD7-positive cells are shown in panels A and B, and the same quadrant gate was applied to each set of data. The percentage of cells in each quadrant is shown, with the top right quadrant representing CD69-positive cells. Panel C shows a histogram of data from the same experiment. The number of CD7-positive cells is plotted as a function of CD69 staining for mock-electroporated cells (no fill) and cells electroporated with mRNA encoding chimeric receptor SEQ ID NO: 1 (gray).
Figure 18:
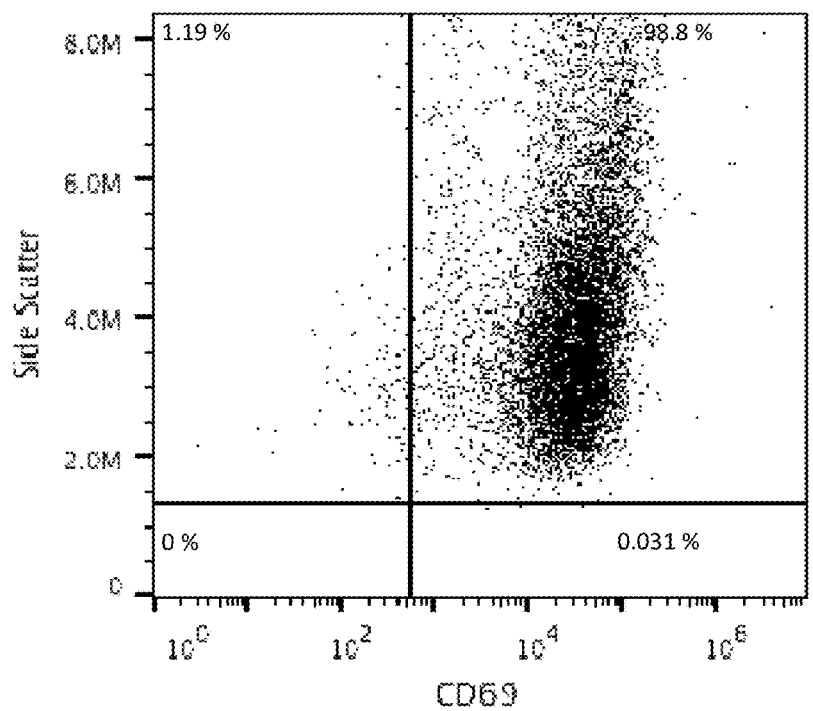
Figure 18:
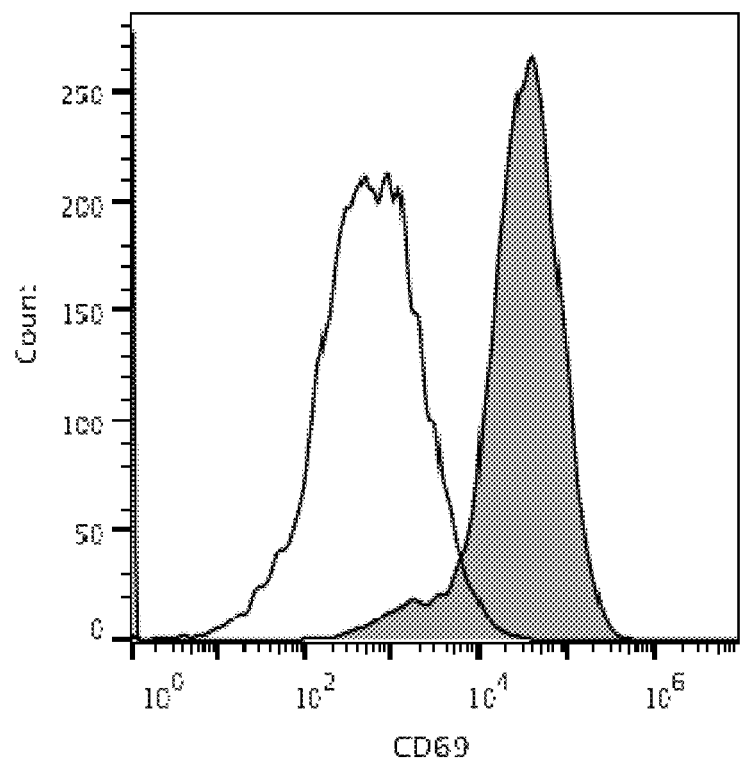

CD7 positive cells were evaluated for expression of both CD25 and CD69. Greater than 45% of the CD7-positive cells in the condition with mRNA encoding SEQ ID NO: 1 were stained with the APC-labeled anti-CD25 antibody, as compared to less than 3% of CD7-positive cells in the mock-electroporation condition, indicating increased expression of the CD25 activity marker on Jurkat cells expressing chimeric receptor versus cells that do not express the receptor under the conditions of these experiments (FIGS. 17A and 17B). The median fluorescence value in the SEQ ID NO: 1 mRNA condition was approximately 6.7-fold higher than the median fluorescence value of mock-electroporated cells when CD7-positive cells were evaluated for staining with APC-labeled anti-CD25 antibody (FIG. 17C, Table 7). Greater than 98% of the CD7-positive cells in the condition with mRNA encoding SEQ ID NO: 1 were stained with the APC-labeled anti-CD69 antibody, as compared to approximately 46% of CD7-positive cells in the mock-electroporation condition, indicating increased expression of the CD69 activity marker on Jurkat cells expressing chimeric receptor versus cells that do not express the receptor under the conditions of these experiments (FIGS. 18A and 18B). The median fluorescence value in the SEQ ID NO: 1 mRNA condition was approximately 69-fold higher than the median fluorescence value of mock-electroporated cells when CD7-positive cells were evaluated for staining with APC-labeled anti-CD69 antibody (FIG. 18C, Table 7).

A similar analysis was carried out for SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 14. The median fluorescence values for conditions in which cells were expressing chimeric receptors for these constructs were approximately 2.3- to 7.6-fold higher than the median fluorescence value of mock-electroporated cells when CD7-positive cells were evaluated for staining with APC-labeled anti-CD25 antibody (Table 7), indicating increased expression of the CD25 activity marker on Jurkat cells expressing each of these chimeric receptor versus cells that do not express the receptor under the conditions of these experiments (Table 7). The median fluorescence values for conditions in which cells were expressing chimeric receptors for these constructs were approximately 10- to 64-fold higher than the median fluorescence value of mock-electroporated cells when CD7-positive cells were evaluated for staining with APC-labeled anti-CD69 antibody (Table 7), indicating increased expression of the CD69 activity marker on Jurkat cells expressing each of these chimeric receptor versus cells that do not express the receptor under the conditions of these experiments (Table 7).

These experiments indicate that Jurkat cells expressing these chimeric receptors show an increase in the activity markers CD25 and CD69 relative to Jurkat cells that do not express a chimeric receptor under conditions where these receptors interact with the CD20-specific antibody Rituxan and CD20-expressing Daudi target cells.

Example 4. Chimeric Receptors are Expressed on Jurkat Cells

Jurkat cells electroporated with mRNA encoding chimeric receptors were analyzed for chimeric receptor expression by Western blot analysis with an anti-CDζ antibody. For these experiments, Jurkat cells were electroporated without mRNA (mock) or with mRNA encoding the constructs disclosed in Example 2 above, using an Invitrogen Neon electroporation system and grown in RPMI-1640 media with 10% FBS at 37° C. for 8-9 hr. Cells were harvested and lysed with RIPA buffer (50 mM Tris-HCl, 150 mM NaCl, 1 mM EDTA, 1% NP-40, 0.5% sodium deoxycholate, pH 7.4) in the presence of phosphatase and protease inhibitors. For each lysate, 25 μg of total protein was loaded onto one lane of a 4-12% Bis-Tris polyacrylamide gel. Proteins were transferred to a PVDF membrane and the membrane was blocked with 5% milk in TBST buffer (500 mM Tris-HCl, 1.5M NaCl, 1% Tween-20, pH 7.4) for 1 hr at room temperature. The membrane was probed with an anti-CDζ antibody overnight at 4° C., washed 3 times with TBST buffer, and probed with a horseradish-peroxidase-linked goat-anti-human secondary antibody. Protein bands were visualized using a horseradish peroxidase chemiluminescent substrate.

Figure 19:
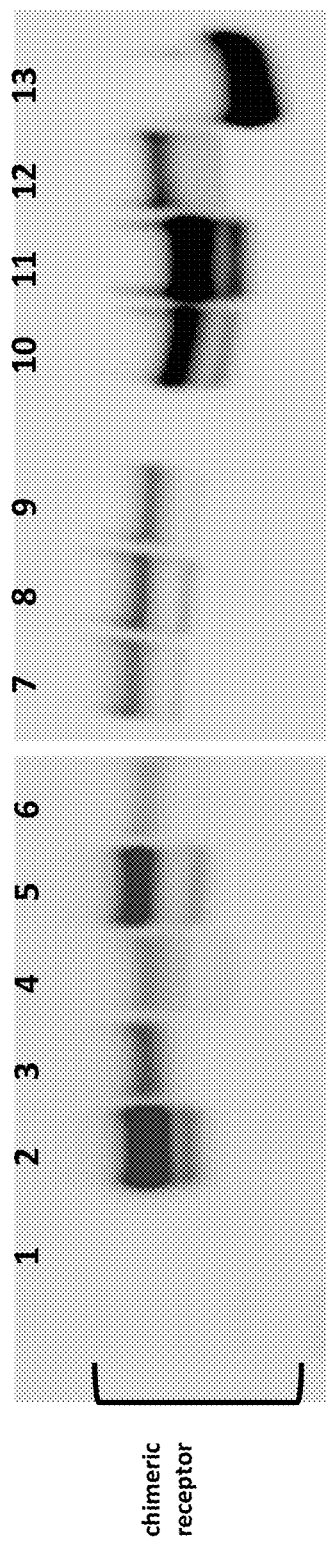
FIG. 19 shows a representative anti-CD3ζ western blot analysis of chimeric receptors. Jurkat cells were electroporated without mRNA (lane 1) or with mRNA encoding chimeric receptor SEQ ID NO: 1 (lane 2), SEQ ID NO: 3 (lane 3), SEQ ID NO: 10 (lane 4), SEQ ID NO: 11 (lane 5), SEQ ID NO: 14 (lane 6), SEQ ID NO: 2 (lane 7), SEQ ID NO: 4 (lane 8), SEQ ID NO: 5 (lane 9), SEQ ID NO: 7 (lane 10), SEQ ID NO: 8 (lane 11), SEQ ID NO: 9 (lane 12), or SEQ ID NO: 6 (lane 13). Cells were harvested, lysed, and analyzed by Western blot analysis with an anti-CD3ζ antibody. Chimeric receptor proteins were detected in lysates from all cells that were electroporated with chimeric receptor mRNA.

The results of the Western blot experiments are shown in FIG. 19. The anti-CDζ antibody detects the C-terminal region of the chimeric receptor proteins that contain the CDζ intracellular protein sequence. For all chimeric receptor constructs, bands corresponding to the full-length receptor protein were detected (lanes 2-13). The mobility of the chimeric receptor proteins varies in a manner that is consistent with the different molecular weights of the proteins.

These results demonstrate that these chimeric receptors were all expressed in Jurkat cells after electroporation with the corresponding mRNA.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one of skill in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A chimeric receptor, comprising:
   (a) an extracellular ligand-binding domain of an Fc receptor;
   (b) a transmembrane domain;
   (c) at least one co-stimulatory signaling domain, which is from a co-stimulatory protein involved in immune cell co-stimulation; and
   (d) a cytoplasmic signaling domain comprising an immunoreceptor tyrosine-based activation motif (ITAM);
   wherein either (c) or (d) is located at the C-terminus of the chimeric receptor; wherein (c) and (d) are different signaling domains; and wherein if (a) is an extracellular ligand-binding domain of CD16A, (d) does not comprise an ITAM domain of an Fc receptor.

2. The chimeric receptor of claim 1, wherein (d) is located at the C-terminus of the chimeric receptor.

3. The chimeric receptor of claim 1, further comprising (e) a hinge domain which is located at the C-terminus of (a) and the N-terminus of (b).

4. The chimeric receptor of claim 1, wherein the chimeric receptor comprises:
   (a) an extracellular ligand-binding domain of F158 FCGR3A or V158 FCGR3A variant,
   (b) a hinge and transmembrane domain of CD8α,
   (c) a co-stimulatory signaling domain of 4-1BB, and
   (d) a cytoplasmic signaling domain of CD3ζ.

5. The chimeric receptor of claim 4, wherein the chimeric receptor further comprises a signal peptide of CD8α.

6. The chimeric receptor of claim 4, wherein the extracellular domain of F158 FCGR3A and V158 FCGR3A variant consist of the amino acid sequences of SEQ ID NO:70 and SEQ ID NO:57, respectively.

7. The chimeric receptor of claim 4, wherein the hinge and transmembrane domains of CD8α consist of the amino acid sequence of SEQ ID NO: 58.

8. The chimeric receptor of claim 4, wherein the co-stimulatory signaling domain of 4-1BB consists of the amino acid sequence of SEQ ID NO: 59.

9. The chimeric receptor of claim 4, wherein the cytoplasmic signaling domain of CD3ζ consists of the amino acid sequence of SEQ ID NO: 60.

10. The chimeric receptor of claim 5, wherein the signal peptide of CD8a consists of the amino acid sequence of SEQ ID NO: 61.

11. The chimeric receptor of claim 4, which comprises the amino acid sequence of residues 22 to 436 of SEQ ID NO: 1, or residues 22 to 436 of SEQ ID NO: 31.

12. The chimeric receptor of claim 5, which comprises the amino acid sequence of SEQ ID NO: 1 or SEQ ID NO:31.

13. A nucleic acid comprising a nucleotide sequence encoding a chimeric receptor of claim 1.

14. A host cell comprising the chimeric receptor of claim 1.

15. The host cell of claim 14, wherein the chimeric receptor comprises:
  (a) an extracellular ligand-binding domain of F158 FCGR3A or V158 FCGR3A variant,
  (b) a hinge and transmembrane domain of CD8a,
  (c) a co-stimulatory signaling domain of 4-1BB, and
  (d) a cytoplasmic signaling domain of CD3ζ.

16. The host cell of claim 14, which is a T lymphocyte or an NK cell.

17. The host cell of claim 16, wherein the T lymphocyte or the NK cell is activated and/or expanded ex vivo.

18. The host cell of claim 16, wherein the T lymphocyte or NK cell is an autologous T lymphocyte or an autologous NK cell isolated from a patient having a cancer.

19. The host cell of claim 16, wherein the T lymphocyte or NK cell is an allogenic T lymphocyte or an allogenic NK cell.

20. A pharmaceutical composition comprising the host cell of claim 14 and a pharmaceutically acceptable carrier or excipient.

21. A method for enhancing efficacy of an antibody-based immunotherapy of a cancer in a subject being treated with an anti-cancer antibody, the method comprising administering to the subject a therapeutically effective amount of T lymphocytes or NK cells that express the chimeric receptor of claim 1.

22. The method of claim 21, wherein the chimeric receptor comprises:
  (a) an extracellular ligand-binding domain of F158 FCGR3A or V158 FCGR3A variant,
  (b) a hinge and transmembrane domain of CD8a,
  (c) a co-stimulatory signaling domain of 4-1BB, and
  (d) a cytoplasmic signaling domain of CD3ζ.

23. The method of claim 21, wherein the antibody has a humanized Fc portion, which bind to human CD16.

24. The method of claim 21, wherein the antibody is selected from the group consisting of Rituximab, Trastuzumab, hu14.18K322A, Epratuzumab, Cetuximab, and Labetuzumab.

25. The method of claim 21, wherein the T lymphocytes or NK cells are autologous T lymphocytes or autologous NK cells isolated from the subject, or wherein the T lymphocytes or NK cells are allogenic cells.

26. The method of claim 25, wherein, prior to the administration step, the autologous T lymphocytes or autologous NK cells are activated and/or expanded ex vivo.

27. The method of claim 25, wherein the allogeneic T lymphocytes are T lymphocytes, in which the expression of the endogenous T cell receptor has been inhibited or eliminated.

28. The method of claim 21, wherein the chimeric receptor is introduced into the T lymphocytes or the NK cells by a method selected from the group consisting of retroviral transduction, lentiviral transduction, DNA electroporation, and RNA electroporation.

29. A method of enhancing a T lymphocyte or an NK cell antibody-dependent cell cytotoxicity (ADCC) in a subject, the method comprising administering to the subject a therapeutically effective amount of T lymphocytes or NK cells that express the chimeric receptor of claim 1.

30. The method of claim 29, wherein the chimeric receptor comprising:
  (a) an extracellular ligand-binding domain of F158 FCGR3A or V158 FCGR3A variant,
  (b) the hinge and transmembrane domain of CD8a,
  (c) a co-stimulatory signaling domain of 4-1BB, and
  (d) a cytoplasmic signaling domain of CD3ζ.

31. A method for preparing immune cells expressing a chimeric receptor, comprising:
  (i) providing a population of immune cells;
  (ii) introducing into the immune cells a nucleic acid encoding a chimeric receptor of claim 1; and
culturing the immune cells under conditions allowing for expression of the chimeric receptor.

\* \* \* \* \*

UNITED STATES PATENT AND TRADEMARK OFFICE
CERTIFICATE OF CORRECTION

PATENT NO. : 10,144,770 B2
APPLICATION NO. : 14/516880
DATED : December 4, 2018
INVENTOR(S) : Dario Campana et al.

Page 1 of 1

It is certified that error appears in the above-identified patent and that said Letters Patent is hereby corrected as shown below:

In the Claims

Claim 10, at Column 235, Line 5, should read:
--peptide of CD28α consists of the amino acid sequence of SEQ--

Signed and Sealed this
Twenty-sixth Day of February, 2019

Andrei Iancu
*Director of the United States Patent and Trademark Office*